(12) United States Patent
Koike et al.

(10) Patent No.: US 8,901,309 B2
(45) Date of Patent: Dec. 2, 2014

(54) FUSED TRIAZOLES FOR THE TREATMENT OR PROPHYLAXIS OF MILD COGNITIVE IMPAIRMENT

(75) Inventors: Tatsuki Koike, Kanagawa (JP); Minoru Nakamura, Kanagawa (JP); Takafumi Takai, Kanagawa (JP); Yuichi Kajita, Kanagawa (JP); Makoto Kamata, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/819,239

(22) PCT Filed: Sep. 1, 2011

(86) PCT No.: PCT/JP2011/070419
§ 371 (c)(1),
(2), (4) Date: Mar. 19, 2013

(87) PCT Pub. No.: WO2012/029991
PCT Pub. Date: Mar. 8, 2012

(65) Prior Publication Data
US 2013/0178497 A1    Jul. 11, 2013

(30) Foreign Application Priority Data

Sep. 2, 2010   (JP) .................................. 2010-197064
Jun. 28, 2011  (JP) .................................. 2011-143548

(51) Int. Cl.
*C07D 471/04*    (2006.01)

(52) U.S. Cl.
CPC .................................. *C07D 471/04* (2013.01)
USPC ....................................... 546/272.4; 514/303

(58) Field of Classification Search
USPC ....................................... 546/272.4; 514/303
See application file for complete search history.

(56) References Cited

U.S. PATENT DOCUMENTS

| | | | |
|---|---|---|---|
| 6,525,044 B2 | 2/2003 | Olson et al. | |
| 7,244,739 B2 | 7/2007 | Cheng et al. | |
| 7,667,041 B2 | 2/2010 | Kimura et al. | |
| 7,687,640 B2 | 3/2010 | Kimura et al. | |
| 7,713,993 B2 | 5/2010 | Kimura et al. | |
| 7,781,442 B2 | 8/2010 | Cheng et al. | |
| 7,799,808 B2 | 9/2010 | Cheng et al. | |
| 7,880,009 B2 | 2/2011 | Kimura et al. | |
| 7,897,632 B2 | 3/2011 | Kimura et al. | |
| 7,923,563 B2 | 4/2011 | Kushida et al. | |
| 7,973,033 B2 | 7/2011 | Kimura et al. | |
| 8,017,629 B2 | 9/2011 | Cheng et al. | |
| 8,119,680 B2 | 2/2012 | Cheng et al. | |
| 8,183,276 B2 | 5/2012 | Fischer et al. | |
| 8,349,880 B2 | 1/2013 | Marcin et al. | |
| 2002/0055501 A1 | 5/2002 | Olson et al. | |
| 2005/0070538 A1 | 3/2005 | Cheng et al. | |
| 2006/0004013 A1 | 1/2006 | Kimura et al. | |
| 2007/0219181 A1 | 9/2007 | Kimura et al. | |
| 2007/0249833 A1 | 10/2007 | Cheng et al. | |
| 2007/0259860 A1 | 11/2007 | Wallberg et al. | |
| 2007/0260058 A1 | 11/2007 | Cheng et al. | |
| 2008/0070902 A1 | 3/2008 | Kimura et al. | |
| 2009/0203916 A1 | 8/2009 | Kushida et al. | |
| 2009/0221611 A1 | 9/2009 | DeVita et al. | |
| 2009/0281310 A1 | 11/2009 | Kimura et al. | |
| 2010/0004221 A1 | 1/2010 | Hasegawa et al. | |
| 2010/0168095 A1 | 7/2010 | Kimura et al. | |
| 2010/0324029 A1 | 12/2010 | Fischer et al. | |
| 2010/0324032 A1 | 12/2010 | Cheng et al. | |
| 2010/0331551 A1 | 12/2010 | Cheng et al. | |
| 2011/0015175 A1 | 1/2011 | Marcin et al. | |
| 2011/0015190 A1 | 1/2011 | Huang et al. | |
| 2011/0086860 A1 | 4/2011 | Kimura et al. | |
| 2011/0112138 A1 | 5/2011 | Kimura et al. | |
| 2011/0212937 A1 | 9/2011 | Boy et al. | |
| 2012/0028994 A1 | 2/2012 | Boy et al. | |
| 2012/0053171 A1 | 3/2012 | Kitazawa et al. | |
| 2012/0059030 A1* | 3/2012 | Koike et al. ................... 514/303 |
| 2012/0135981 A1 | 5/2012 | Wu et al. | |
| 2012/0142672 A1 | 6/2012 | Koike et al. | |
| 2012/0295891 A1 | 11/2012 | Van Brandt et al. | |
| 2012/0295901 A1 | 11/2012 | De Cleyn et al. | |

FOREIGN PATENT DOCUMENTS

| | | |
|---|---|---|
| EP | 1 992 618 | 11/2008 |
| WO | 01/60826 | 8/2001 |
| WO | 2004/110350 | 12/2004 |
| WO | 2005/115990 | 12/2005 |
| WO | 2007/081897 | 7/2007 |
| WO | 2007/130824 | 11/2007 |
| WO | 2008/078725 | 7/2008 |
| WO | 2008/097538 | 8/2008 |

(Continued)

OTHER PUBLICATIONS

Silverman; The Organic Chemistry of Drug Design and Drug Action, 2nd Ed, 2004, Elsevier, pp. 29-34.*
International Search Report issued Jan. 31, 2012 in International (PCT) Application No. PCT/JP2011/070419.
Richard E. Olson et al., "Secretase Inhibitors and Modulators for the Treatment of Alzheimer's Disease", Annual Reports in Medicinal Chemistry, vol. 42, pp. 24-47, 2007.
Taisuke Tomita, "At the frontline of Alzheimer's disease treatment: γ-secretase inhibitor/modulator mechanism", Naunyn-Schmiedeberg's Arch. Pharmacol., vol. 377, pp. 295-300, 2008.
Michael S. Wolfe, "Inhibition ad Modulation of γ-Secretase for Alzheimer's Disease", Neurotherapeutics, vol. 5, pp. 391-398, 2008.

*Primary Examiner* — John Mabry
*Assistant Examiner* — Daniel Carcanague
(74) *Attorney, Agent, or Firm* — Wenderoth, Lind & Ponack, L.L.P.

(57) ABSTRACT

The present invention provides a heterocycle derivative having a superior amyloid β production inhibitory activity and/or a superior γ-secretase modulation activity, and use thereof. A compound represented by the formula (I): wherein each symbol is as defined in the present specification, or a salt thereof.

1 Claim, No Drawings

(56) References Cited

FOREIGN PATENT DOCUMENTS

| WO | 2009/073777 | 6/2009 |
| WO | 2010/083141 | 7/2010 |
| WO | 2010/098487 | 9/2010 |
| WO | 2010/098488 | 9/2010 |
| WO | 2010/098495 | 9/2010 |
| WO | 2011/002067 | 1/2011 |
| WO | 2011/006903 | 1/2011 |
| WO | 2011/007756 | 1/2011 |
| WO | 2011/014535 | 2/2011 |
| WO | 2011/016559 | 2/2011 |
| WO | 2011/086098 | 7/2011 |

* cited by examiner

FUSED TRIAZOLES FOR THE TREATMENT OR PROPHYLAXIS OF MILD COGNITIVE IMPAIRMENT

TECHNICAL FIELD

The present invention relates to a heterocyclic compound having a superior amyloid β production inhibitory activity and/or a superior γ-secretase modulation activity, and useful as an agent for the treatment or prophylaxis of mild cognitive impairment, Alzheimer's disease and the like.

BACKGROUND OF THE INVENTION

The major symptoms of dementia are Alzheimer's disease and mild cognitive impairment, and the patient number is drastically increasing with the advent of aging society. The sole therapeutic drugs therefor are symptomatic improvement drugs such as acetylcholinesterase inhibitors and the like, and the development of a drug capable of halting or delaying the progression of pathology, or a drug having a prophylactic effect has been desired.

The etiology of Alzheimer's disease is considered to be senile plaque formed by accumulation of a peptide consisting of about 40 amino acids, which is called amyloid β (hereinafter sometimes to be simply referred to as Aβ), or nerve cell death. Aβ is a peptide produced by processing a single transmembrane protein amyloid precursor (hereinafter sometimes to be simply referred to as APP), which is a precursor protein, with a degrading enzyme called secretase, and the main molecule species are Aβ40 consisting of 40 amino acids and Aβ42 consisting of 42 amino acids. Of these, Aβ42 aggregates easily and is considered to play a key role in senile plaque formation or nerve cell death (non-patent document 1).

On the other hand, secretase, which is an excision enzyme, is known to include β-secretase for cutting out amino terminal and γ-secretase for cutting out carboxy terminal. γ-Secretase is constituted with presenilin (PS) and 3 kinds of cofactor proteins (nicastrin: NCT, APH-1, PEN-2) etc. (non-patent document 2). A radical treatment drug for Alzheimer's disease, which is based on inhibition of these secretases and suppression of production or secretion of Aβ, has been investigated (non-patent document 1). In the meantime, since γ-secretase is involved not only in the processing of APP but also functions such as activation of Notch receptor playing an important role in cell differentiation by intramembranous cleavage and the like, the development of a drug capable of specifically inhibiting Aβ production alone without influencing other than APP processing has been desired (non-patent document 3).

Patent document 1 describes, as an amyloid β production inhibitor, a compound represented by the following formula:

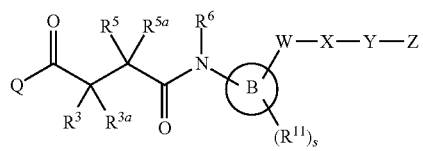

wherein each symbol is as defined in patent document 1, and the following compound.

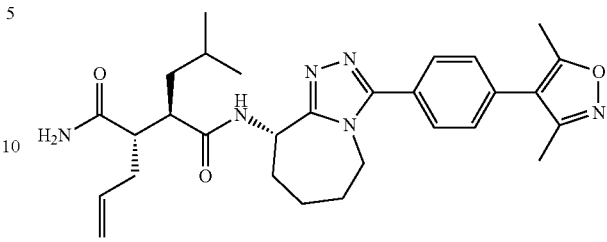

Patent document 2 describes, as a compound having an amyloid β level regulating action (use: neurodegenerative disease), a compound represented by the following formula:

(A)-L$_A$-(B)-L$_B$-(C)-L$_C$-(D)

wherein each symbol is as defined in patent document 2.

Patent document 3 describes, as a cinnamide compound (use: neurodegenerative diseases caused by amyloid β, such as Alzheimer's disease, Down's disease and the like), a compound represented by the following formula:

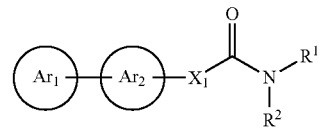

wherein each symbol is as defined in patent document 3.

Patent document 4 describes, as a polycyclic cinnamide compound (use: neurodegenerative diseases caused by amyloid β, such as Alzheimer's disease, Down's disease and the like), a compound represented by the following formula:

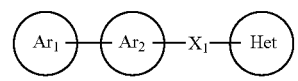

wherein each symbol is as defined in patent document 4, and the following compound.

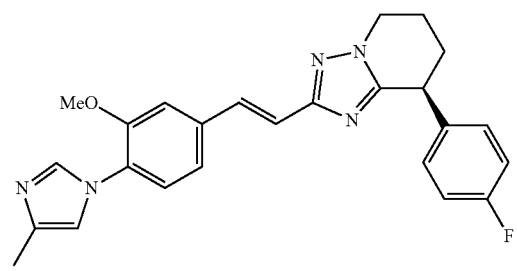 [SMILES: COc1cc(/C=C/c2nc3n(n2)CCC[C@H]3c2ccc(F)cc2)ccc1-n1cnc(C)c1]

Patent document 5 describes, as an imidazolyl-phenyl-vinyl-heterocycle derivative (use: Alzheimer's disease), a compound represented by the following formula:

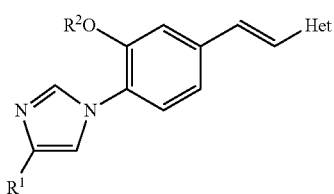

wherein each symbol is as defined in patent document 5.

Patent document 6 describes, as a γ-secretase modulator, a compound represented by the following formula:

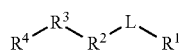

wherein each symbol is as defined in patent document 6, and the following compounds.

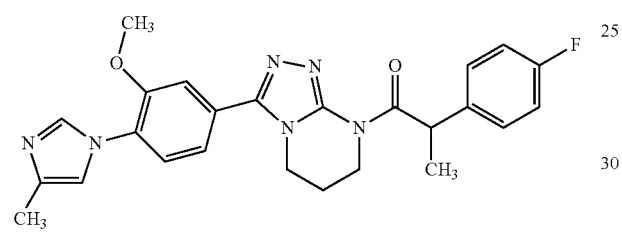

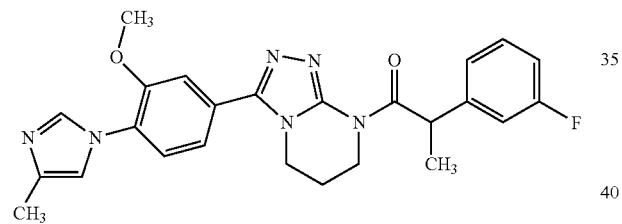

Patent document 7 describes, as an amyloid β production inhibitor, a compound represented by the following formula:

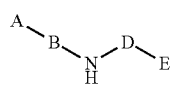

-D- shows the following structures.

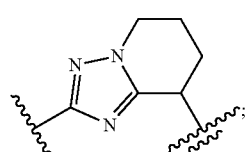

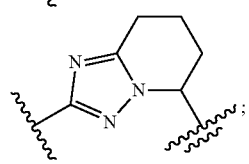

-continued

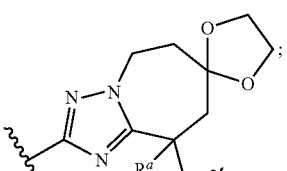

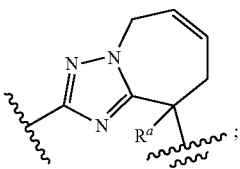

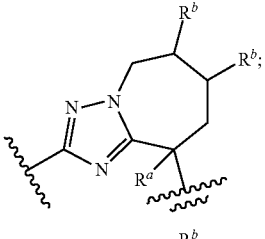

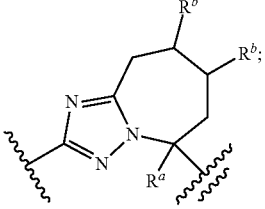

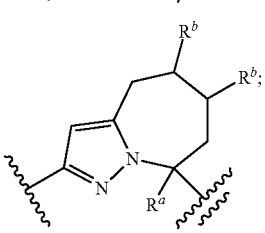

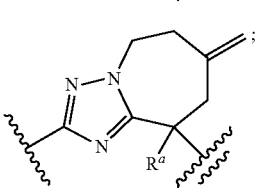

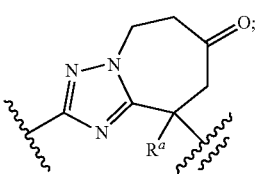

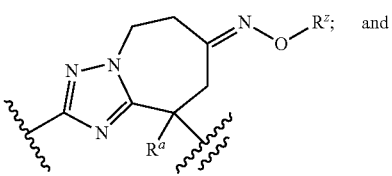

-continued

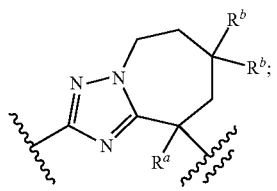

wherein each symbol is as defined in patent document 7, and the following compounds.

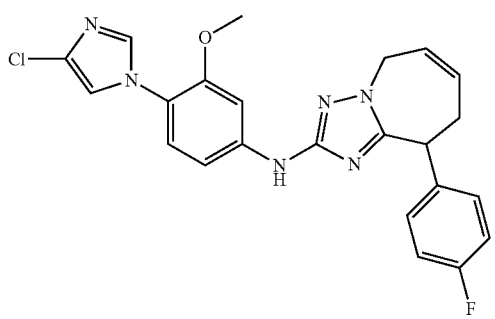

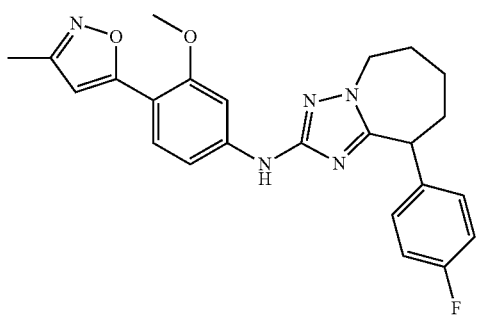

Patent document 8 describes, as various heterocyclic compounds, a tachykinin receptor antagonist represented by the following formula:

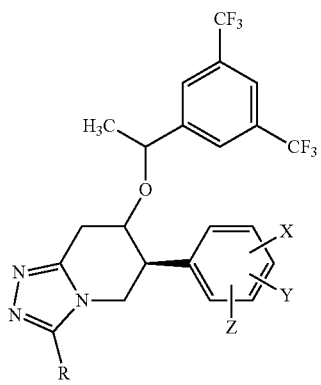

wherein each symbol is as defined in patent document 8.

Patent document 9 describes a mGluR5 regulator represented by the following formula:

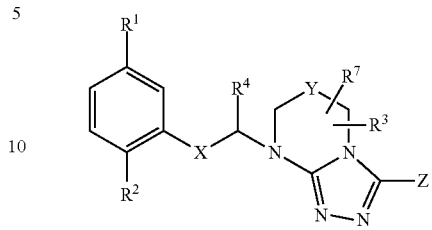

wherein each symbol is as defined in patent document 9.

Patent document 10 describes a 11β-hydroxysteroid dehydrogenase type 1 inhibitor represented by the following formula:

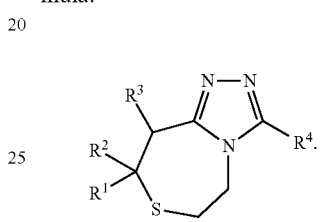

wherein each symbol is as defined in patent document 10.

Patent document 11 describes, as an amyloid β production inhibitor, a compound represented by the following formula:

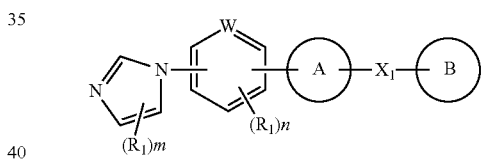

wherein each symbol is as defined in patent document 11, and the following compounds.

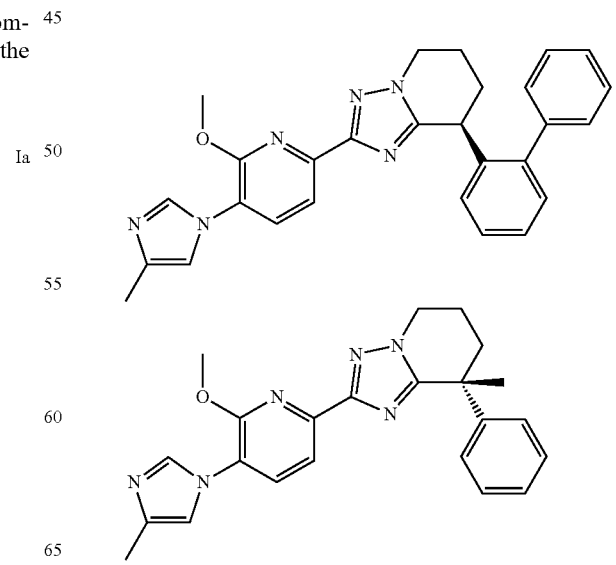

Patent document 12 describes, as an amyloid β production inhibitor, a compound represented by the following formula:

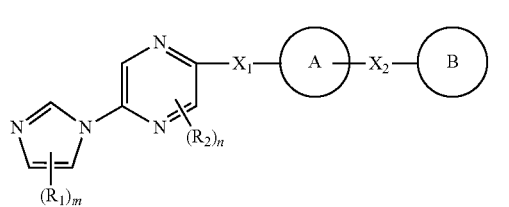

[I]

wherein each symbol is as defined in patent document 12, and the following compound.

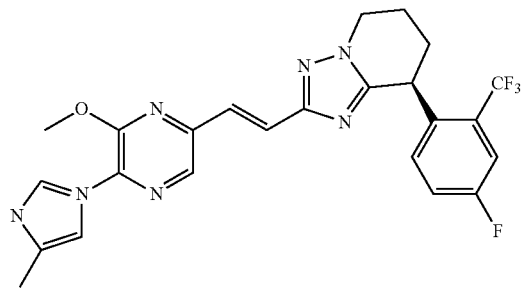

A-1

Patent document 13 describes, as a compound having an amyloid β production inhibitory action, a compound represented by the following formula:

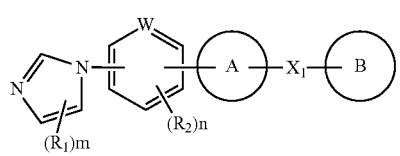

[I]

wherein each symbol is as defined in patent document 13.

Patent document 14 describes, as a γ-secretase modulator, a compound represented by the following formula:

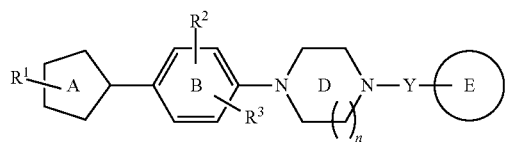

(I)

wherein each symbol is as defined in patent document 14.

Patent document 15 describes, as a γ-secretase modulator, a compound represented by the following formula:

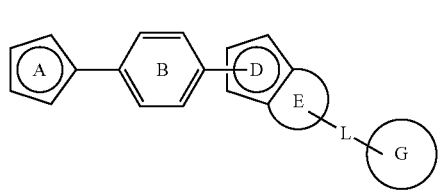

(I)

wherein each symbol is as defined in patent document 15, and the following compound.

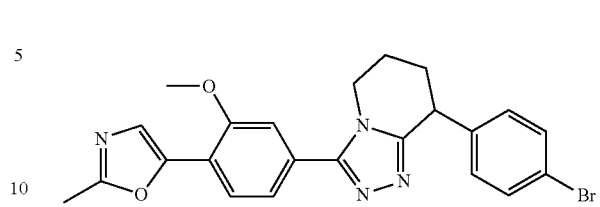

Patent document 16 describes, as a γ-secretase modulator, a compound represented by the following formula:

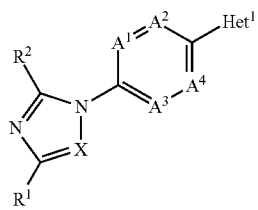

(I)

wherein each symbol is as defined in patent document 16, and the following compound.

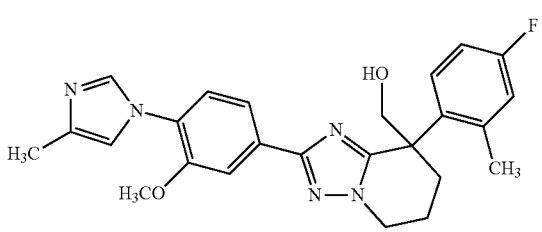 [SMILES: COc1cc(-c2nc3n(n2)CCCC3(CO)c2ccc(F)cc2C)ccc1-n1cnc(C)c1]

Patent document 17 describes, as an amyloid β production inhibitor, a compound represented by the following formula:

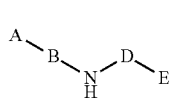

wherein each symbol is as defined in patent document 17, and the following compound.

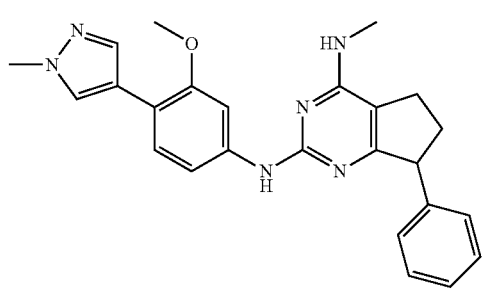 [SMILES: CNc1nc(Nc2ccc(-c3cnn(C)c3)c(OC)c2)nc2c1CCC2c1ccccc1]

Patent document 18 describes, as a γ-secretase modulator, a compound represented by the following formula:

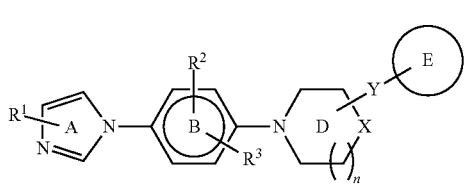

wherein each symbol is as defined in patent document 18.

Patent document 19 describes, as a γ-secretase modulator, a compound represented by the following formula:

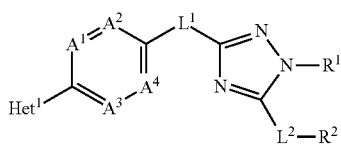

wherein each symbol is as defined in patent document 19.

DOCUMENT LIST

Patent Documents patent document 1: WO2001/60826
patent document 2: WO2004/110350
patent document 3: WO2005/115990
patent document 4: WO2007/102580
patent document 5: WO2008/097538
patent document 6: WO2009/073777
patent document 7: WO2010/083141
patent document 8: WO2007/081897
patent document 9: WO2007/130824
patent document 10: WO2008/078725
patent document 11: WO2010/098487
patent document 12: WO2010/098495
patent document 13: WO2010/098488
patent document 14: WO2011/002067
patent document 15: WO2011/007756
patent document 16: WO2011/006903
patent document 17: WO2011/014535
patent document 18: WO2011/016559
patent document 19: WO2011/086098

Non-Patent Documents non-patent document 1: Annual Reports in Medicinal Chemistry, 2007, vol. 42, p. 27-47
non-patent document 2: Naunyn-Schmiedeberg's Arch. Pharmacol., 2008, vol. 377, p. 295-300
non-patent document 3: Neurotherapeutics (2008), vol. 5, p. 391-398

SUMMARY OF THE INVENTION

Problems to be Solved by the Invention

The development of a compound having a superior amyloid β production inhibitory activity and/or a superior γ-secretase modulation activity, useful as an agent for the treatment or prophylaxis of mild cognitive impairment, Alzheimer's disease and the like, and having superior properties in terms of efficacy, low toxicity, stability, pharmacokinetics and the like has been desired.

The present invention aims to provide a heterocyclic compound having a chemical structure different from that of known compounds (including the aforementioned compounds) and having an amyloid β production inhibitory activity and/or a superior γ-secretase modulation activity, and a prophylactic drug or a therapeutic drug for diseases such as mild cognitive impairment, Alzheimer's disease and the like, which contains the heterocyclic compound.

Means of Solving the Problems

The present inventors have conducted intensive studies in an attempt to solve the aforementioned problems and found that a compound represented by the following formula (I) or a salt thereof has a superior amyloid β production inhibitory activity and/or a superior γ-secretase modulation activity and conducted further studies, which resulted in the completion of the present invention.

Accordingly, the present invention provides the following.

[1] A compound represented by the formula (I):

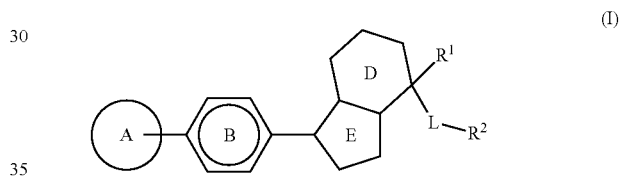

wherein ring A is an optionally substituted oxazole ring, an optionally substituted triazole ring, an optionally substituted imidazole ring, an optionally substituted pyridine ring, or an optionally substituted pyrazole ring, ring B is an optionally substituted benzene ring, an optionally substituted pyridine ring, or an optionally substituted pyrimidine ring, and partial structure (1):

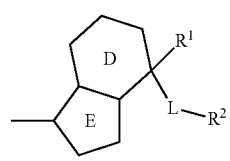

is

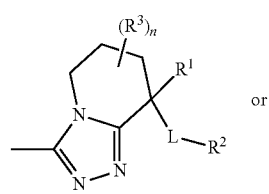

-continued

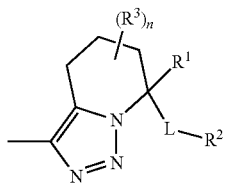
(1-2)

wherein
R¹ and R² are the same or different and each is a substituent,
L is a bond, —Y—, —O—, —YO—, —OY—, —S—, —SO—, —SO₂—, —CONR$^a$—, —NR$^a$CO—, —NR$^a$—, —YNR$^a$—, —NR$^a$Y—, —YCONR$^a$—, —NR$^a$COY—, —OCONR$^a$—, —NR$^a$COO— or —NR$^b$CONR$^a$—
wherein
Y is an optionally substituted $C_{1-6}$ alkylene group,
$R^a$ is a hydrogen atom or an optionally substituted $C_{1-6}$ alkyl group,
$R^b$ is a hydrogen atom or an optionally substituted $C_{1-6}$ alkyl group,
R³ is a substituent, and
n is an integer of 0-6,
or a salt thereof;
[2] the compound of the above-mentioned [1], wherein R¹ is a hydroxy group, an optionally substituted $C_{1-6}$ alkyl group, an optionally substituted $C_{1-6}$ alkoxy group, an optionally substituted aminocarbonyl group, a carboxy group, a $C_{1-6}$ alkyl-carbonyl group or an optionally substituted $C_{1-6}$ alkoxy-carbonyl group,
R² is a halogen atom, an optionally substituted hydrocarbon ring group or an optionally substituted heterocyclic group, or a salt thereof;
[3] the compound of the above-mentioned [1], wherein ring A is an optionally substituted oxazole ring, or a salt thereof;
[4] the compound of the above-mentioned [1], wherein ring A is an optionally substituted imidazole ring, or a salt thereof;
[5] the compound of the above-mentioned [1], wherein ring B is an optionally substituted benzene ring or an optionally substituted pyridine ring, or a salt thereof;
[6] the compound of the above-mentioned [1], wherein the partial structure (1):

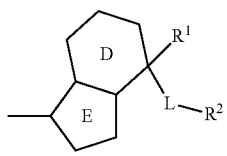
(1)

is

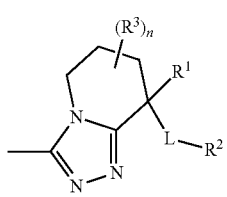
(1-1)

wherein each symbol is the same as the above-mentioned [1], or a salt thereof;
[7] the compound of the above-mentioned [1], wherein R¹ is a $C_{1-6}$ alkyl group substituted by a hydroxy group, or a salt thereof;
[8] the compound of the above-mentioned [1], wherein R² is an optionally substituted $C_{6-14}$ aryl group or an optionally substituted aromatic heterocyclic group, or a salt thereof;
[9] the compound of the above-mentioned [1], wherein L is —O—, or a salt thereof;
[10] 2-{8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol or a salt thereof;
[11] 2-{(8R)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol or a salt thereof;
[12] 2-{3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol or a salt thereof;
[13] 2-{3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl}propan-2-ol or a salt thereof;
[14] 2-{8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol or a salt thereof;
[15] 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol or a salt thereof;
[16] a medicament containing the compound of the above-mentioned [1] or a salt thereof;
[17] the medicament of the above-mentioned [16], which is for the prophylaxis or therapy of mild cognitive impairment or Alzheimer's disease;
[18] an amyloid β production inhibitor containing the compound of the above-mentioned [1] or a salt thereof;
[19] a γ-secretase modulator containing the compound of the above-mentioned [1] or a salt thereof;
[20] a method of inhibiting amyloid β production in a mammal, comprising administering an effective amount of the compound of the above-mentioned [1] or a salt thereof to the mammal;
[21] a method of modulating γ-secretase in a mammal, comprising administering an effective amount of the compound of the above-mentioned [1] or a salt thereof to the mammal;
[22] a method of preventing or treating mild cognitive impairment or Alzheimer's disease in a mammal, comprising administering an effective amount of the compound of the above-mentioned [1] or a salt thereof to the mammal;
[23] the compound of the above-mentioned [1] or a salt thereof for inhibiting amyloid β production;
[24] the compound of the above-mentioned [1] or a salt thereof for modulating γ-secretase;
[25] the compound of the above-mentioned [1] or a salt thereof for the prophylaxis or treatment of mild cognitive impairment or Alzheimer's disease;
[26] use of the compound of the above-mentioned [1] or a salt thereof for the inhibition of amyloid β production;
[27] use of the compound of the above-mentioned [1] or a salt to thereof for the modulation of γ-secretase;
[28] use of the compound of the above-mentioned [1] or a salt thereof for the prophylaxis or treatment of mild cognitive impairment or Alzheimer's disease;
[29] use of the compound of the above-mentioned [1] or a salt thereof for the production of an agent for the prophylaxis or treatment of mild cognitive impairment or Alzheimer's disease; and the like.

Effect of the Invention

Since a compound represented by the formula (I) (hereinafter sometimes to be referred to as compound (I)) or a salt thereof, or a prodrug thereof has a superior amyloid β production inhibitory activity and/or a superior γ-secretase modulation activity, it is useful as a safe prophylactic or therapeutic drug for diseases possibly relating to abnormality of amyloid β production and/or γ-secretase, such as mild cognitive impairment, Alzheimer's disease and the like. Compound (I) or a salt thereof, or a prodrug thereof exhibits low toxicity (e.g., acute toxicity, chronic toxicity, genetic toxicity, reproductive toxicity, cardiotoxicity, drug interaction, carcinogenicity etc.) and shows superior stability and disposition (absorbability, distribution, metabolism, excretion etc.), and therefore, is useful as a pharmaceutical product. Furthermore, it has been found that compound (I) wherein a ring constituting atom on a fused ring represented by

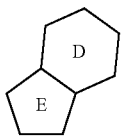

contains a quaternary carbon atom shows a particularly superior amyloid β production inhibitory activity and/or γ-secretase modulation activity. It has also been found that compound (I) wherein $R^1$ is a $C_{1-6}$ alkyl group substituted by a hydroxyl group shows a more desireble ADME/Tox profiles, a more superior amyloid β production inhibitory activity and/or a more superior γ-secretase modulation activity.

DESCRIPTION OF EMBODIMENTS

The present invention is explained in detail in the following.

In the present specification, unless particularly limited, examples of the "halogen atom" include a fluorine atom, a chlorine atom, a bromine atom, and an iodine atom.

In the present specification, unless particularly limited, examples of the "$C_{1-6}$ alkyl group" and the "$C_{1-6}$ alkyl" in the substituent include methyl, ethyl, propyl, isopropyl, butyl, isobutyl, sec-butyl, tert-butyl, pentyl, isopentyl, neopentyl, 1-ethylpropyl, 1,1-dimethylpropyl, 2-methylbutyl, hexyl, isohexyl, 1,1-dimethylbutyl, 2,2-dimethylbutyl, 3,3-dimethylbutyl, 2-ethylbutyl and the like.

In the present specification, unless particularly limited, examples of the "$C_{1-6}$ alkoxy group" and the "$C_{1-6}$ alkoxy" in the substituent include methoxy, ethoxy, propoxy, isopropoxy, butoxy, isobutoxy, sec-butoxy, tert-butoxy, 2-methylbutyloxy, pentyloxy, hexyloxy and the like.

In the present specification, unless particularly limited, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

In the present specification, unless particularly limited, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl, heptanoyl and the like.

In the present specification, unless particularly limited, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like.

In the present specification, unless particularly limited, examples of the "$C_{2-6}$ alkenyloxy group" include ethenyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy and the like.

In the present specification, unless particularly limited, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

In the present specification, unless particularly limited, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

In the present specification, unless particularly limited, examples of the "$C_{3-10}$ cycloalkyloxy group" include cyclopropyloxy, cyclobutyloxy, cyclopentyloxy, cyclohexyloxy, cycloheptyloxy, cyclooctyloxy, bicyclo[2.2.1]heptyloxy, bicyclo[2.2.2]octyloxy, bicyclo[3.2.1]octyloxy, bicyclo[3.2.2]nonyloxy, bicyclo[3.3.1]nonyloxy, bicyclo[4.2.1]nonyloxy, bicyclo[4.3.1]decyloxy, adamantyloxy and the like.

In the present specification, unless particularly limited, examples of the "$C_{6-14}$ aryl group" and the "$C_{6-14}$ aryl" in the substituent include phenyl, naphthyl, anthryl, phenanthryl, acenaphthyl, biphenylyl and the like.

In the present specification, examples of the "$C_{6-10}$ aryl group" and the "$C_{6-10}$ aryl" in the substituent include phenyl, naphthyl (1-naphthyl, 2-naphthyl) and the like.

In the present specification, unless particularly limited, examples of the "$C_{6-10}$ aryloxy group" include phenyloxy, naphthyloxy (1-naphthyloxy, 2-naphthyloxy) and the like.

In the present specification, unless particularly limited, examples of the "hydrocarbon ring group" include the above-mentioned "$C_{3-10}$ cycloalkyl group" and "$C_{6-14}$ aryl group" and the like.

In the present specification, examples of the "$C_{7-13}$ aralkyl group" and the "$C_{7-13}$ aralkyl" in the substituent include benzyl, phenethyl, naphthylmethyl (1-naphthylmethyl, 2-naphthylmethyl), biphenylylmethyl and the like.

In the present specification, examples of the "$C_{7-13}$ aralkyloxy group" include benzyloxy, phenethyloxy, naphthylmethyloxy (1-naphthylmethyloxy, 2-naphthylmethyloxy), biphenylylmethyloxy and the like.

In the present specification, unless particularly limited, examples of the "$C_{1-6}$ alkyl-carbonyloxy group" include acetyloxy, propanoyloxy, butanoyloxy, 2-methylpropanoyloxy, pentanoyloxy, 3-methylbutanoyloxy, 2-methylbutanoyloxy, 2,2-dimethylpropanoyloxy, hexanoyloxy, heptanoyloxy and the like.

In the present specification, unless particularly limited, examples of the "$C_{1-6}$ alkyl-carbonylamino group" include acetylamino, propanoylamino, butanoylamino, 2-methylpropanoylamino, pentanoylamino, 3-methylbutanoylamino, 2-methylbutanoylamino, 2,2-dimethylpropanoylamino, hexanoylamino, heptanoylamino and the like.

In the present specification, examples of the "$C_{1-6}$ alkylthio group" include methylthio, ethylthio, propylthio, isopropylthio, butylthio, isobutylthio, sec-butylthio, tert-butylthio, pentylthio, hexylthio and the like.

In the present specification, examples of the "$C_{7-13}$ aralkylthio group" include benzylthio, phenethylthio, naphthylmethylthio (1-naphthylmethylthio, 2-naphthylmethylthio), biphenylylmethylthio and the like.

In the present specification, examples of the "$C_{6-14}$ arylthio group" include phenylthio, naphthylthio, anthrylthio, phenanthrylthio, acenaphthylthio, biphenylylthio and the like.

In the present specification, examples of the "$C_{1-6}$ alkylsulfonyl group" include methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl and the like.

In the present specification, unless particularly limited, examples of the aromatic heterocyclic group include a 4- to 7-membered (preferably 5- or 6-membered) monocyclic aromatic heterocyclic group containing 1 to 4 heteroatoms selected from an oxygen atom, a sulfur atom (the sulfur atom is optionally oxidized) and a nitrogen atom as a ring-constituting atom besides carbon atoms, and a fused aromatic heterocyclic group. Examples of the fused aromatic heterocyclic group include a group derived from a fused ring wherein the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,5-oxadiazol-3-yl, 1,3,4-oxadiazol-2-yl), thiadiazolyl (e.g., 1,2,3-thiadiazol-4-yl, 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-3-yl, 1,2,4-triazin-5-yl, 1,2,4-triazin-6-yl) and the like; condensed aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl, 4-benzofuranyl, 5-benzofuranyl, 6-benzofuranyl, 7-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl, 6-benzothiazolyl), benzimidazolyl (e.g., benzimidazol-1-yl, benzimidazol-2-yl, benzimidazol-5-yl), benzotriazolyl (e.g., 1H-1,2,3-benzotriazol-1-yl, 1H-1,2,3-benzotriazol-5-yl), indolyl (e.g., indol-1-yl, indol-2-yl, indol-3-yl, indol-5-yl), indazolyl (e.g., 2H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), thienopyrazolyl (e.g., 1H-thieno[2,3-c]pyrazol-5-yl), pyrazolotriazinyl (e.g., pyrazolo[5,1-c][1,2,4]triazin-3-yl), triazolopyrimidinyl (e.g., [1,2,4]triazolo[1,5-a]pyrimidin-2-yl), phthalazinyl and the like; and the like.

In the present specification, unless particularly limited, examples of the non-aromatic heterocyclic group include a 4- to 7-membered (preferably 5- or 6-membered) monocyclic non-aromatic heterocyclic group containing 1 to 4 heteroatoms selected from an oxygen atom, a sulfur atom (the sulfur atom is optionally oxidized) and a nitrogen atom as a ring-constituting atom besides carbon atoms, and a fused non-aromatic heterocyclic group. Examples of the fused non-aromatic heterocyclic group include a group derived from a fused ring wherein the 4- to 7-membered monocyclic non-aromatic heterocyclic group and 1 or 2 rings selected from a 5- or 6-membered aromatic or non-aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the non-aromatic heterocyclic group include monocyclic non-aromatic heterocyclic groups such as pyrrolidinyl (e.g., 1-pyrrolidinyl, 2-pyrrolidinyl, 3-pyrrolidinyl), piperidinyl (e.g., piperidino, 2-piperidinyl, 3-piperidinyl, 4-piperidinyl), homopiperidinyl (e.g., homopiperidino, 2-homopiperidinyl, 3-homopiperidinyl, 4-homopiperidinyl), tetrahydropyridyl (e.g., 1,2,3,6-tetrahydropyridin-1-yl), dihydropyridyl (e.g., 2,3-dihydropyridin-4-yl), morpholinyl (e.g., morpholino, 2-morpholinyl), thiomorpholinyl (e.g., thiomorpholino), 1,1-dioxidethiomorpholinyl (e.g., 1,1-dioxidethiomorpholino), piperazinyl (e.g., 1-piperazinyl, 2-piperazinyl), hexamethyleniminyl (e.g., 1-hexamethyleniminyl), oxazolidinyl (e.g., 2-oxazolidinyl), thiazolidinyl (e.g., 3-thiazolidinyl, 2-thiazolidinyl), imidazolidinyl (e.g., 2-imidazolidinyl, 3-imidazolidinyl), oxazolinyl (e.g., 2-oxazolinyl), thiazolinyl (e.g., 2-thiazolinyl), imidazolinyl (e.g., 2-imidazolinyl, 3-imidazolinyl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidetetrahydrothiopyranyl (e.g., 1-oxidetetrahydrothiopyran-4-yl), 1,1-dioxidetetrahydrothiopyranyl (e.g., 1,1-dioxidetetrahydrothiopyran-4-yl), tetrahydrofuryl (e.g., tetrahydrofuran-3-yl, tetrahydrofuran-2-yl), pyrazolidinyl (e.g., 1-pyrazolidinyl, 3-pyrazolidinyl), pyrazolinyl (e.g., 1-pyrazolinyl), tetrahydropyrimidinyl (e.g., 1-tetrahydropyrimidinyl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), dihydrooxadiazolyl (e.g., 4,5-dihydro-1,2,4-oxadiazol-3-yl), thiazinyl (e.g., 1,4-thiazin-2-yl), 1,1-dioxidethiazinanyl (e.g., 1,1-dioxide-1,2-thiazinan-2-yl), dihydropyridazinyl (e.g., 1,6-dihydropyridazin-3-yl), tetrahydropyridazinyl (e.g., 1,4,5,6-tetrahydropyridazin-3-yl), dihydrothioxazinyl (e.g., 2,3- dihydro-1,4-thioxazin-3-yl), dihydrothiazinyl (e.g., 3,4-dihydro-2H-1,4-thiazin-5-yl) and the like; condensed non-aromatic heterocyclic groups such as dihydroindolyl (e.g., 2,3-dihydro-1H-indol-1-yl), dihydroisoindolyl (e.g., 2,3-dihydro-1H-isoindol-1-yl, 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepin-7-yl), tetrahydrobenzofuranyl (e.g., 4,5,6,7-tetrahydro-1-benzofuran-3-yl), chromenyl (e.g., 4H-chromen-2-yl, 2H-chromen-3-yl, 2H-chromen-7-yl), dihydroquinolinyl (e.g., 1,2-dihydroquinolin-4-yl, 3,4-dihydroquinolin-1(2H)-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl, 1,2,3,4-tetrahydroisoquinolin-2-yl), dihydrophthalazinyl (e.g., 3,4-dihydrophthalazin-1-yl, 1,4-dihydrophthalazin-4-yl), tetrahydrobenzoazepinyl (e.g., 2,3,4,5-tetrahydro-1H-benzo[c]azepin-1-yl), benzodioxolyl (e.g., 1,3-benzodioxol-5-yl), benzothiazinyl (e.g., 3,4-dihydro-2H-1,4-benzothiazin-2-yl) and the like;
and the like.

In the present specification, unless particularly limited, examples of the "heterocyclic group" include those exemplified as the above-mentioned "aromatic heterocyclic group", and those exemplified as the above-mentioned "non-aromatic heterocyclic group".

In the present specification, unless particularly limited, examples of the "$C_{1-6}$ alkylene group" include methylene, ethylene, propylene, —CH(CH$_3$)—CH$_2$—, —CH$_2$—CH(CH$_3$)—, —C(CH$_3$)$_2$—, —(CH$_2$)$_4$—, —CH(CH$_3$)—(CH$_2$)$_2$—, —CH$_2$—CH(CH$_3$)—CH$_2$—, —(CH$_2$)$_2$—CH(CH$_3$)—, —C(CH$_3$)$_2$—CH$_2$—, —CH$_2$—(CH$_3$)$_2$—, —CH(CH$_3$)—CH(CH$_3$)—, —C(C$_2$H$_5$)(CH$_3$)—, —(CH$_2$)$_5$—, —CH(CH$_3$)—(CH$_2$)$_3$—, —CH$_2$—CH(CH$_3$)—(CH$_2$)$_2$—, —(CH$_2$)$_2$—CH(CH$_3$)—CH$_2$—, —(CH$_2$)$_3$—CH(CH$_3$)—, —CH(CH$_3$)—(CH$_2$)$_3$—, —CH$_2$—CH(CH$_3$)—(CH$_2$)$_2$—, —(CH$_2$)$_2$—CH(CH$_3$)—CH$_2$—, —(CH$_2$)$_3$—CH(CH$_3$)—, —C(CH$_3$)$_2$—(CH$_2$)$_2$—, —CH(CH$_3$)—CH(CH$_3$)—CH$_2$—, —CH(CH$_3$)—CH$_2$—CH(CH$_3$)—, —CH$_2$—C(CH$_3$)$_2$—CH$_2$—, —CH$_2$—CH(CH$_3$)—CH(CH$_3$)—, —(CH$_2$)$_2$—C(CH$_3$)$_2$—, —C(CH$_3$)$_2$—CH(CH$_3$)—, —CH(CH$_3$)—C(CH$_3$)$_2$—, —C(C$_2$H$_5$)(CH$_3$)—CH$_2$—, —CH(C$_2$H$_5$)—CH(CH$_3$)—, —CH(CH$_3$)—CH(C$_2$H$_5$)—, —CH$_2$—C(C$_2$H$_5$)(CH$_3$)—, —CH(C$_3$H$_7$)—CH$_2$—, —CH$_2$—CH(C$_3$H$_7$)—, —CH(C$_4$H$_9$)—, —(CH$_2$)$_6$— and the like.

In the present specification, unless particularly limited, examples of the "$C_{1-3}$ alkylene group" include methylene, ethylene, propylene, —CH(CH$_3$)—CH$_2$—, —CH$_2$—CH(CH$_3$)—, —C(CH$_3$)$_2$— and the like.

The definition of each symbol in the formula (I) is described in detail in the following.

Ring A is an optionally substituted oxazole ring, an optionally substituted triazole ring, an optionally substituted imidazole ring, an optionally substituted pyridine ring, or an optionally substituted pyrazole ring.

The "oxazole ring", "triazole ring", "imidazole ring", "pyridine ring" and "pyrazole ring" of the "optionally substituted oxazole ring", "optionally substituted triazole ring", "optionally substituted imidazole ring", "optionally substituted pyridine ring" and "optionally substituted pyrazole ring" for ring A may have 1-4 (preferably 1-3, more preferably 1 or 2) substituents at substitutable position(s).

Examples of such substituent include
(1) a $C_{3-10}$ cycloalkyl group (e.g., cyclopropyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group,
    (d) a halogen atom, and
    (e) an oxo group;
(2) a $C_{6-14}$ aryl group (e.g., phenyl) optionally substituted by 1 to 4 substituents selected from
    (a) a $C_{1-6}$ alkyl group (e.g., methyl) optionally substituted by 1 to 3 substituents selected from a halogen atom (e.g., a fluorine atom) and a $C_{1-6}$ alkoxy-carbonyl group (e.g., ethoxycarbonyl),
    (b) a hydroxy group,
    (c) a $C_{1-6}$ alkoxy group (e.g., methoxy),
    (d) a halogen atom (e.g., a chlorine atom, a fluorine atom),
    (e) a $C_{1-6}$ alkylthio group (e.g., methylthio),
    (f) a $C_{1-6}$ alkylsulfonyl group (e.g., methylsulfonyl), and
    (g) a cyano group;
(3) an aromatic heterocyclic group (e.g., pyridyl, oxadiazolyl) optionally substituted by 1 to 3 substituents selected from
    (a) a $C_{1-6}$ alkyl group (e.g., methyl) optionally substituted by 1 to 3 halogen atoms (e.g., a fluorine atom),
    (b) a hydroxy group,
    (c) a $C_{1-6}$ alkoxy group,
    (d) a halogen atom, and
    (e) a $C_{6-14}$ aryl group (e.g., phenyl) optionally substituted by 1 to 3 halogen atoms (e.g., a chlorine atom);
(4) a non-aromatic heterocyclic group (e.g., tetrahydropyranyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group,
    (d) a halogen atom, and
    (e) an oxo group;
(5) an amino group optionally mono- or di-substituted by substituent(s) selected from
    (a) a $C_{1-6}$ alkyl group optionally substituted by 1 to 3 halogen atoms,
    (b) a hydroxy group,
    (c) a $C_{1-6}$ alkoxy group, and
    (d) a halogen atom;
(6) an aminocarbonyl group optionally mono- or di-substituted by substituent(s) selected from
    (a) a $C_{1-6}$ alkyl group (e.g., methyl, ethyl) optionally substituted by 1 to 3 halogen atoms (e.g., a fluorine atom),
    (b) a hydroxy group,
    (c) a $C_{1-6}$ alkoxy group, and
    (d) a halogen atom;
(7) a hydroxy group;
(8) a $C_{1-6}$ alkoxy group (e.g., methoxy, ethoxy, 2-methylbutyloxy) optionally substituted by 1 to 3 substituents selected from
    (a) a hydroxy group,
    (b) a $C_{1-6}$ alkoxy group,
    (c) a halogen atom,
    (d) a $C_{6-14}$ aryl group (e.g., phenyl) optionally substituted by 1 to 3 halogen atoms (e.g., a chlorine atom), and
    (e) a $C_{3-10}$ cycloalkyl group (e.g., cyclopropyl);
(9) a $C_{2-6}$ alkenyloxy group optionally substituted by 1 to 3 substituents selected from
    (a) a hydroxy group,
    (b) a $C_{1-6}$ alkoxy group, and
    (c) a halogen atom;

(10) a $C_{3-10}$ cycloalkyloxy group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group,
  (d) a halogen atom, and
  (e) an oxo group;
(11) a $C_{7-13}$ aralkyloxy group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(12) a $C_{6-10}$ aryloxy group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(13) a $C_{1-6}$ alkyl-carbonyloxy group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(14) a $C_{1-6}$ alkylthio group optionally substituted by 1 to 3 substituents selected from
  (a) a hydroxy group,
  (b) a $C_{1-6}$ alkoxy group, and
  (c) a halogen atom;
(15) a $C_{7-13}$ aralkylthio group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(16) a $C_{6-14}$ arylthio group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(17) a sulfonate group;
(18) a cyano group;
(19) an azide group;
(20) a nitro group;
(21) a nitroso group;
(22) a halogen atom (e.g., a chlorine atom, a fluorine atom);
(23) a mono- or di-$C_{1-6}$ alkylphosphoryl group;
(24) a $C_{1-6}$ alkoxy-carbonyl group (e.g., ethoxycarbonyl) optionally substituted by 1 to 3 substituents selected from
  (a) a hydroxy group,
  (b) a $C_{1-6}$ alkoxy group, and
  (c) a halogen atom;
(25) a $C_{1-6}$ alkyl-carbonyl group (e.g., acetyl, propionyl) optionally substituted by 1 to 3 substituents selected from
  (a) a hydroxy group,
  (b) a $C_{1-6}$ alkoxy group, and
  (c) a halogen atom;
(26) a $C_{1-6}$ alkyl group (e.g., methyl, ethyl, propyl, isopropyl, 1-ethylpropyl, 2-methylbutyl) optionally substituted by 1 to 4 substituents selected from
  (a) a halogen atom,
  (b) a carboxy group,
  (c) a hydroxy group,
  (d) a $C_{1-6}$ alkoxy group (e.g., methoxy),
  (e) an amino group optionally mono- or di-substituted by $C_{1-6}$ alkyl group(s),
  (f) a $C_{6-14}$ aryl group (e.g., phenyl) optionally substituted by 1 to 3 halogen atoms (e.g., a fluorine atom),
  (g) a $C_{3-10}$ cycloalkyl group (e.g., cyclopropyl),
  (h) a $C_{1-6}$ alkyl-carbonyloxy group (e.g., acetyloxy),
  (i) a $C_{1-6}$ alkyl-carbonylamino group (e.g., acetylamino),
  (j) an aromatic heterocyclic group,
  (k) a non-aromatic heterocyclic group, and
  (l) a cyano group;
(27) a $C_{2-6}$ alkenyl group optionally substituted by 1 to 3 substituents selected from
  (a) a halogen atom,
  (b) a carboxy group,
  (c) a $C_{1-6}$ alkoxy-carbonyl group, and
  (d) an aminocarbonyl group;
(28) a $C_{2-6}$ alkynyl group optionally substituted by 1 to 3 substituents selected from
  (a) a halogen atom,
  (b) a carboxyl group,
  (c) a $C_{1-6}$ alkoxy-carbonyl group, and
  (d) an aminocarbonyl group;
(29) a $C_{7-13}$ aralkyl group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(30) a carboxy group;

and the like. When the number of the substituents is two or more, the respective substituents may be the same or different.

When the "amino group" and "aminocarbonyl group" as the above-mentioned substituent are disubstituted, said two substituents may form, together with the nitrogen atom bonded thereto, an optionally substituted nitrogen-containing heterocycle.

Examples of the "nitrogen-containing heterocycle" of the "optionally substituted nitrogen-containing heterocycle" include a 5- to 7-membered nitrogen-containing heterocycle containing, as a ring constituting atom besides carbon atom, at least one nitrogen atom, and further optionally containing 1 or 2 hetero atoms selected from an oxygen atom, a sulfur atom (the sulfur atom may be oxidized) and a nitrogen atom. Preferable examples of the nitrogen-containing heterocycle include pyrrolidine, imidazolidine, pyrazolidine, piperidine, piperazine, morpholine, thiomorpholine, oxopiperazine and the like.

The "nitrogen-containing heterocycle" may have 1-5 (preferably 1-4) substituents at substitutable position(s). Example of the substituent include
  (a) a $C_{1-6}$ alkyl group optionally substituted by 1 to 3 halogen atoms,
  (b) a hydroxy group,
  (c) a $C_{1-6}$ alkoxy group,
  (d) a halogen atom (e.g., a fluorine atom),
  (e) an oxo group and the like. When the number of the substituents is two or more, the respective substituents may be the same or different.

Ring A is preferably an oxazole ring, an imidazole ring, a triazole ring, a pyridine ring or a pyrazole ring, each of which is optionally substituted by 1-3 (preferably 1 or 2, more preferably 1) substituents selected from a $C_{1-6}$ alkyl group (preferably, methyl) and a halogen atom (preferably, a chlorine atom), more preferably an oxazole ring, an imidazole ring, a triazole ring or a pyrazole ring, each of which is optionally substituted by 1-3 (preferably 1 or 2, more preferably 1) $C_{1-6}$ alkyl group(s) (preferably, methyl).

In another embodiment, Ring A is preferably an optionally substituted oxazole ring, an optionally substituted triazole ring, an optionally substituted imidazole ring, more preferably an oxazole ring, a triazole ring or an imidazole ring, each of which is optionally substituted by 1-3 (preferably 1 or 2, more preferably 1) $C_{1-6}$ alkyl groups (preferably, methyl).

In another embodiment, ring A is preferably an optionally substituted imidazole ring or an optionally substituted oxazole ring. As the substituent(s), $C_{1-6}$ alkyl groups (preferably, methyl) is preferable.

Ring B is an optionally substituted benzene ring, an optionally substituted pyridine ring, or an optionally substituted pyrimidine ring.

The "benzene ring", "pyridine ring" and "pyrimidine ring" of the "optionally substituted benzene ring", "optionally substituted pyridine ring" and "optionally substituted pyrimidine ring" for ring B may have, besides ring A, 1-4 (preferably 1-3, more preferably 1 or 2) substituents at substitutable position(s).

Examples of such substituent include the groups exemplified as the substituents the aforementioned "oxazole ring", "triazole ring", "imidazole ring", "pyridine ring" and "pyrazole ring" of the "optionally substituted oxazole ring", "optionally substituted triazole ring", "optionally substituted imidazole ring", "optionally substituted pyridine ring" and "optionally substituted pyrazole ring" for ring A optionally have. When the number of the substituents is two or more, the respective substituents may be the same or different.

Ring B is preferably an optionally substituted benzene ring, an optionally substituted pyridine ring, more preferably a benzene ring or a pyridine ring, each of which is optionally substituted by 1-3 (preferably 1 or 2, more preferably 1) substituents selected from (1) a hydroxy group, (2) a $C_{1-6}$ alkoxy group (preferably, methoxy, ethoxy) optionally substituted by 1-3 halogen atoms (preferably, a fluorine atom), (3) a halogen atom (preferably, a fluorine atom) and (4) a $C_{7-13}$ aralkyloxy group (preferably, benzyloxy), further preferably a benzene ring or a pyridine ring, each of which is optionally substituted by 1-3 (preferably 1 or 2, more preferably 1) substituents selected from (1) a $C_{1-6}$ alkoxy group (preferably, methoxy, ethoxy) optionally substituted by 1-3 halogen atoms (preferably, a fluorine atom), and (2) a halogen atom (preferably, a fluorine atom), particularly preferably a benzene ring or a pyridine ring, each of which is optionally substituted by 1-3 (preferably 1 or 2, more preferably 1) $C_{1-6}$ alkoxy groups (preferably, methoxy).

Partial structure (1):

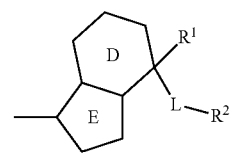

(1)

is

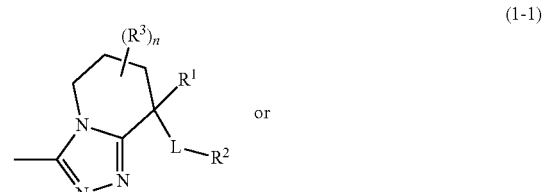

(1-1)

or

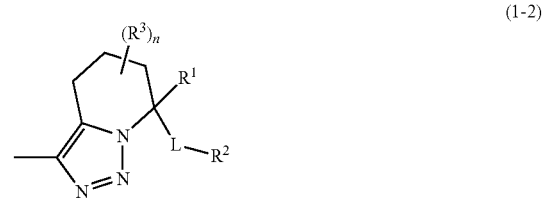

(1-2)

wherein
$R^1$ and $R^2$ are the same or different and each is a substituent,
L is a bond, —Y—, —O—, —YO—, —OY—, —S—, —SO—, —SO$_2$—, —CONR$^a$—, —NR$^a$CO—, —NR$^a$—, —YNR$^a$—, —NR$^a$Y—, —YCONR$^a$—, —NR$^a$COY—, —OCONR$^a$—, —NR$^a$COO— or —NR$^b$CONR$^a$—
wherein
Y is an optionally substituted $C_{1-6}$ alkylene group,
$R^a$ is a hydrogen atom or an optionally substituted $C_{1-6}$ alkyl group, and
$R^b$ is a hydrogen atom or an optionally substituted $C_{1-6}$ alkyl group,
$R^3$ is a substituent respectively, and
n is an integer of 0-6.

$R^1$ and $R^2$ are the same or different and each is a substituent.

Examples of the "substituent" for $R^1$ or $R^2$ include the groups exemplified as the substituents the aforementioned "oxazole ring", "triazole ring", "imidazole ring", "pyridine ring" and "pyrazole ring" of the "optionally substituted oxazole ring", "optionally substituted triazole ring", "optionally substituted imidazole ring", "optionally substituted pyridine ring" and "optionally substituted pyrazole ring" for ring A optionally have.

$R^1$ is preferably a hydroxy group, an optionally substituted $C_{1-6}$ alkyl group, an optionally substituted $C_{1-6}$ alkoxy group, an optionally substituted aminocarbonyl group, a carboxy group, an optionally substituted $C_{1-6}$ alkyl-carbonyl group, or an optionally substituted $C_{1-6}$ alkoxy-carbonyl group, more preferably
(1) a hydroxy group,
(2) a $C_{1-6}$ alkyl group (preferably, methyl, ethyl, propyl, isopropyl, 1-ethylpropyl, 2-methylbutyl) optionally substituted by 1 to 4 substituents selected from
 (a) a halogen atom (preferably, a fluorine atom),
 (b) a hydroxy group,
 (c) a $C_{1-6}$ alkoxy group (preferably, methoxy),
 (d) an amino group, (e) a $C_{6-14}$ aryl group (preferably, phenyl) optionally substituted by 1 to 3 halogen atoms (preferably, a fluorine atom),
(f) a $C_{3-10}$ cycloalkyl group (preferably, cyclopropyl),
(g) a $C_{1-6}$ alkyl-carbonyloxy group (preferably, acetyloxy), and
(h) a $C_{1-6}$ alkyl-carbonylamino group (preferably, acetylamino);
(3) a $C_{1-6}$ alkoxy group (preferably, methoxy, ethoxy, 2-methylbutyloxy) optionally substituted by 1 to 3 substituents selected from
  (a) a $C_{6-14}$ aryl group (preferably, phenyl) optionally substituted by 1 to 3 halogen atoms (preferably, a chlorine atom), and
  (b) a $C_{3-10}$ cycloalkyl group (preferably, cyclopropyl);
(4) an aminocarbonyl group optionally mono- or di-substituted by $C_{1-6}$ alkyl group(s) (preferably, methyl, ethyl) optionally substituted by 1 to 3 halogen atoms (preferably, a fluorine atom) (two substituents of the aminocarbonyl group may form, together with the nitrogen atom bonded thereto, a pyrrolidine ring optionally substituted by 1-4 halogen atoms (preferably, a fluorine atom));
(5) a carboxy group;
(6) a $C_{1-6}$ alkyl-carbonyl group (preferably, acetyl, propionyl); or
(7) a $C_{1-6}$ alkoxy-carbonyl group (preferably, ethoxycarbonyl), further preferably
(1) a hydroxy group,
(2) a $C_{1-6}$ alkyl group (preferably, methyl, ethyl, propyl, isopropyl, 1-ethylpropyl, 2-methylbutyl) optionally substituted by 1 to 3 substituents selected from
  (a) a hydroxy group,
  (b) a $C_{1-6}$ alkoxy group (preferably, methoxy),
  (c) an amino group,
  (d) a $C_{6-14}$ aryl group (preferably, phenyl) optionally substituted by 1 to 3 halogen atoms (preferably, a fluorine atom),
  (e) a $C_{3-10}$ cycloalkyl group (preferably, cyclopropyl),
  (f) a $C_{1-6}$ alkyl-carbonyloxy group (preferably, acetyloxy), and
  (g) a $C_{1-6}$ alkyl-carbonylamino group (preferably, acetylamino);
(3) a $C_{1-6}$ alkoxy group (preferably, methoxy, ethoxy, 2-methylbutyloxy) optionally substituted by 1 to 3 substituents selected from
  (a) a $C_{6-14}$ aryl group (preferably, phenyl) optionally substituted by 1 to 3 halogen atoms (preferably, a chlorine atom), and
  (b) a $C_{3-10}$ cycloalkyl group (preferably, cyclopropyl);
(4) an aminocarbonyl group optionally mono- or di-substituted by $C_{1-6}$ alkyl group(s) (preferably, methyl, ethyl) optionally substituted by 1 to 3 halogen atoms (preferably, a fluorine atom) (two substituents of the aminocarbonyl group may form, together with the nitrogen atom bonded thereto, a pyrrolidine ring optionally substituted by 1-4 halogen atoms (preferably, a fluorine atom));
(5) a carboxy group;
(6) a $C_{1-6}$ alkyl-carbonyl group (preferably, acetyl, propionyl); or
(7) a $C_{1-6}$ alkoxy-carbonyl group (preferably, ethoxycarbonyl).

In another embodiment, $R^1$ is preferably
(1) a hydroxy group,
(2) a $C_{1-6}$ alkyl group (preferably, methyl, ethyl, propyl, isopropyl, 1-ethylpropyl, 2-methylbutyl) optionally substituted by 1 to 4 substituents selected from
  (a) a halogen atom (preferably, a fluorine atom),
  (b) a hydroxy group,
  (c) a $C_{1-6}$ alkoxy group (preferably, methoxy),
  (d) an amino group,
  (e) a $C_{6-14}$ aryl group (preferably, phenyl) optionally substituted by 1 to 3 halogen atoms (preferably, a fluorine atom),
  (f) a $C_{3-10}$ cycloalkyl group (preferably, cyclopropyl),
  (g) a $C_{1-6}$ alkyl-carbonyloxy group (preferably, acetyloxy), and
  (h) a $C_{1-6}$ alkyl-carbonylamino group (preferably, acetylamino);
(3) a $C_{1-6}$ alkoxy group (preferably, methoxy, ethoxy, 2-methylbutyloxy) optionally substituted by 1 to 3 substituents selected from
  (a) a $C_{6-14}$ aryl group (preferably, phenyl) optionally substituted by 1 to 3 halogen atoms (preferably, a chlorine atom), and
  (b) a $C_{3-10}$ cycloalkyl group (preferably, cyclopropyl);
(4) an aminocarbonyl group optionally mono- or di-substituted by $C_{1-6}$ alkyl group(s) (preferably, methyl, ethyl) optionally substituted by 1 to 3 halogen atoms (preferably, a fluorine atom) (two substituents of the aminocarbonyl group may form, together with the nitrogen atom bonded thereto, a pyrrolidine ring optionally substituted by 1-4 halogen atoms (preferably, a fluorine atom));
(5) a $C_{1-6}$ alkyl-carbonyl group (preferably, acetyl, propionyl); or
(6) a $C_{1-6}$ alkoxy-carbonyl group (preferably, ethoxycarbonyl), more preferably
(1) a $C_{1-6}$ alkyl group (preferably, methyl, isopropyl, 1-ethylpropyl) optionally substituted by 1 to 3 substituents selected from
  (a) a hydroxy group, and
  (b) a $C_{3-10}$ cycloalkyl group (preferably, cyclopropyl), or
(2) an aminocarbonyl group optionally mono- or di-substituted by $C_{1-6}$ alkyl group(s) (preferably, methyl, ethyl) optionally substituted by 1 to 3 halogen atoms (preferably, a fluorine atom),
further preferably
a $C_{1-6}$ alkyl group (preferably, methyl, isopropyl, 1-ethylpropyl) optionally substituted by 1 to 3 substituents selected from
  (a) a hydroxy group, and
  (b) a $C_{3-10}$ cycloalkyl group (preferably, cyclopropyl).

In another embodiment, $R^1$ is preferably a $C_{1-6}$ alkyl group (preferably, methyl, ethyl, propyl, isopropyl, 1-ethylpropyl, 2-methylbutyl) substituted by a hydroxyl group.

$R^2$ is preferably a halogen atom, an optionally substituted $C_{3-10}$ cycloalkyl group, an optionally substituted $C_{6-14}$ aryl group, an optionally substituted aromatic heterocyclic group, or an optionally substituted non-aromatic heterocyclic group, more preferably
(1) a halogen atom (e.g., a chlorine atom, a fluorine atom);
(2) a $C_{3-10}$ cycloalkyl group (e.g., cyclopropyl);
(3) a $C_{6-14}$ aryl group (e.g., phenyl) optionally substituted by 1 to 4 substituents selected from
  (a) a $C_{1-6}$ alkyl group (e.g., methyl) optionally substituted by 1 to 3 substituents selected from a halogen atom (e.g., a fluorine atom) and a $C_{1-6}$ alkoxy-carbonyl group (e.g., ethoxycarbonyl),
  (b) a $C_{1-6}$ alkoxy group (e.g., methoxy),
  (c) a halogen atom (e.g., a chlorine atom, a fluorine atom, a bromine atom),
  (d) a $C_{1-6}$ alkylthio group (e.g., methylthio),
  (e) a $C_{1-6}$ alkylsulfonyl group (e.g., methylsulfonyl), and
  (f) a cyano group;

(4) an aromatic heterocyclic group (e.g., pyridyl, oxadiazolyl) optionally substituted by 1 to 3 substituents selected from
  (a) a $C_{1-6}$ alkyl group (e.g., methyl) optionally substituted by 1 to 3 halogen atoms (e.g., a fluorine atom), and
  (b) a $C_{6-14}$ aryl group (e.g., phenyl) optionally substituted by 1 to 3 halogen atoms (e.g., a chlorine atom); or
(5) a non-aromatic heterocyclic group (e.g., tetrahydropyranyl), further preferably
(1) a halogen atom (e.g., a chlorine atom, a fluorine atom);
(2) a $C_{3-10}$ cycloalkyl group (e.g., cyclopropyl);
(3) a $C_{6-14}$ aryl group (e.g., phenyl) optionally substituted by 1 to 3 substituents selected from
  (a) a $C_{1-6}$ alkyl group (e.g., methyl) optionally substituted by 1 to 3 halogen atoms (e.g., a fluorine atom),
  (b) a $C_{1-6}$ alkoxy group (e.g., methoxy),
  (c) a halogen atom (e.g., a chlorine atom, a fluorine atom, a bromine atom),
  (d) a $C_{1-6}$ alkylthio group (e.g., methylthio),
  (e) a $C_{1-6}$ alkylsulfonyl group (e.g., methylsulfonyl), and
  (f) a cyano group;
(4) an aromatic heterocyclic group (e.g., pyridyl, oxadiazolyl) optionally substituted by 1 to 3 substituents selected from
  (a) a $C_{1-6}$ alkyl group (e.g., methyl) optionally substituted by 1 to 3 halogen atoms (e.g., a fluorine atom), and
  (b) a $C_{6-14}$ aryl group (e.g., phenyl) optionally substituted by 1 to 3 halogen atoms (e.g., a chlorine atom); or
(5) a non-aromatic heterocyclic group (e.g., tetrahydropyranyl).

In another embodiment, $R^2$ is preferably a halogen atom, an optionally substituted hydrocarbon ring group, or an optionally substituted heterocyclic group.

In another embodiment, $R^2$ is preferably
(1) a $C_{6-14}$ aryl group (e.g., phenyl) optionally substituted by 1 to 4 (preferably 1 to 3) substituents selected from
  (a) a $C_{1-6}$ alkyl group (e.g., methyl) optionally substituted by 1 to 3 substituents selected from a halogen atom (e.g., a fluorine atom) and a $C_{1-6}$ alkoxy-carbonyl group (e.g., ethoxycarbonyl), and
  (b) a halogen atom (e.g., a chlorine atom, a fluorine atom); or
(2) an aromatic heterocyclic group (e.g., pyridyl) optionally substituted by 1 to 3 $C_{1-6}$ alkyl group (e.g., methyl) optionally substituted by 1 to 3 halogen atoms (e.g., a fluorine atom), more preferably
(1) a $C_{6-14}$ aryl group (e.g., phenyl) optionally substituted by 1 to 4 (preferably 1 to 3) substituents selected from
  (a) a $C_{1-6}$ alkyl group (e.g., methyl) optionally substituted by 1 to 3 halogen atoms (e.g., a fluorine atom), and
  (b) a halogen atom (e.g., a chlorine atom, a fluorine atom); or
(2) an aromatic heterocyclic group (e.g., pyridyl) optionally substituted by 1 to 3 $C_{1-6}$ alkyl group (e.g., methyl) optionally substituted by 1 to 3 halogen atoms (e.g., a fluorine atom), further preferably a $C_{6-14}$ aryl group (e.g., phenyl) optionally substituted by 1 to 4 (preferably 1 to 3) substituents selected from
  (a) a $C_{1-6}$ alkyl group (e.g., methyl) optionally substituted by 1 to 3 halogen atoms (e.g., a fluorine atom), and
  (b) a halogen atom (e.g., a chlorine atom, a fluorine atom).

In another embodiment, $R^2$ is preferably an optionally substituted $C_{6-14}$ aryl group, or an optionally substituted heterocyclic group.

L is a bond, —Y—, —O—, —YO—, —OY—, —S—, —SO—, —SO$_2$—, —CONR$^a$—, —NR$^a$CO—, —NR$^a$—, —YNR$^a$—, —NR$^a$Y—, —YCONR$^a$—, —NR$^a$COY—, —OCONR$^a$—, —NR$^a$COO— or —NR$^b$CONR$^a$— wherein
Y is an optionally substituted $C_{1-6}$ alkylene group,
$R^a$ is a hydrogen atom or an optionally substituted $C_{1-6}$ alkyl group, and
$R^b$ is a hydrogen atom or an optionally substituted $C_{1-6}$ alkyl group.

The "$C_{1-6}$ alkylene group" of the "optionally substituted $C_{1-6}$ alkylene group" for Y may have 1-3 (preferably 1 or 2) substituents at substitutable position(s).

Examples of such substituent include
(1) a $C_{3-10}$ cycloalkyl group (e.g., cyclopropyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group,
  (d) a halogen atom, and
  (e) an oxo group;
(2) a $C_{6-14}$ aryl group (e.g., phenyl) optionally substituted by 1 to 3 substituents selected from
  (a) a $C_{1-6}$ alkyl group (e.g., methyl) optionally substituted by 1 to 3 halogen atoms (e.g., a fluorine atom),
  (b) a hydroxy group,
  (c) a $C_{1-6}$ alkoxy group (e.g., methoxy),
  (d) a halogen atom (e.g., a chlorine atom, a fluorine atom),
  (e) a $C_{1-6}$ alkylthio group (e.g., methylthio),
  (f) a $C_{1-6}$ alkylsulfonyl group (e.g., methylsulfonyl), and
  (g) a cyano group;
(3) an aromatic heterocyclic group (e.g., pyridyl, oxadiazolyl) optionally substituted by 1 to 3 substituents selected from
  (a) a $C_{1-6}$ alkyl group (e.g., methyl) optionally substituted by 1 to 3 halogen atoms (e.g., a fluorine atom),
  (b) a hydroxy group,
  (c) a $C_{1-6}$ alkoxy group,
  (d) a halogen atom, and
  (e) a $C_{6-14}$ aryl group (e.g., phenyl) optionally substituted by 1 to 3 halogen atoms (e.g., a chlorine atom);
(4) a non-aromatic heterocyclic group (e.g., tetrahydropyranyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group,
  (d) a halogen atom, and
  (e) an oxo group;
(5) an amino group optionally mono- or di-substituted by substituent(s) selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(6) an aminocarbonyl group optionally mono- or di-substituted by substituent(s) selected from
  (a) a $C_{1-6}$ alkyl group (e.g., methyl, ethyl) optionally substituted by 1 to 3 halogen atoms (e.g., a fluorine atom),
  (b) a hydroxy group,
  (c) a $C_{1-6}$ alkoxy group, and
  (d) a halogen atom;
(7) a hydroxy group;
(8) a $C_{1-6}$ alkoxy group (e.g., methoxy, ethoxy, 2-methylbutyloxy) optionally substituted by 1 to 3 substituents selected from (a) a hydroxy group,
(b) a $C_{1-6}$ alkoxy group,
(c) a halogen atom,
(d) a $C_{6-14}$ aryl group (e.g., phenyl) optionally substituted by 1 to 3 halogen atoms (e.g., a chlorine atom), and
(e) a $C_{3-10}$ cycloalkyl group (e.g., cyclopropyl);
(9) a $C_{2-6}$ alkenyloxy group optionally substituted by 1 to 3 substituents selected from
(a) a hydroxy group,
(b) a $C_{1-6}$ alkoxy group, and
(c) a halogen atom;
(10) a $C_{3-10}$ cycloalkyloxy group optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group,
(d) a halogen atom, and
(e) an oxo group;
(11) a $C_{7-13}$ aralkyloxy group optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;
(12) a $C_{6-10}$ aryloxy group optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;
(13) a $C_{1-6}$ alkyl-carbonyloxy group optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;
(14) a $C_{1-6}$ alkylthio group optionally substituted by 1 to 3 substituents selected from
(a) a hydroxy group,
(b) a $C_{1-6}$ alkoxy group, and
(c) a halogen atom;
(15) a $C_{7-13}$ aralkylthio group optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;
(16) a $C_{6-14}$ arylthio group optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;
(17) a sulfonate group;
(18) a cyano group;
(19) an azide group;
(20) a nitro group;
(21) a nitroso group;
(22) a halogen atom (e.g., a chlorine atom, a fluorine atom);
(23) a mono- or di-$C_{1-6}$ alkylphosphoryl group;
(24) a $C_{1-6}$ alkoxy-carbonyl group (e.g., ethoxycarbonyl) optionally substituted by 1 to 3 substituents selected from
(a) a hydroxy group,
(b) a $C_{1-6}$ alkoxy group, and
(c) a halogen atom;
(25) a $C_{1-6}$ alkyl-carbonyl group (e.g., acetyl, propionyl) optionally substituted by 1 to 3 substituents selected from
(a) a hydroxy group,
(b) a $C_{1-6}$ alkoxy group, and
(c) a halogen atom;
(26) a carboxy group;
and the like. When the number of the substituents is two or more, the respective substituents may be the same or different.

Y is preferably an optionally substituted $C_{1-3}$ alkylene group (preferably, methylene), more preferably a $C_{1-3}$ alkylene group (preferably, methylene).

The "$C_{1-6}$ alkyl group" of the "optionally substituted $C_{1-6}$ alkyl group" for $R^a$ may have 1-3 (preferably 1 or 2) substituents at substitutable position(s).

Examples of such substituent include the groups exemplified as the substituents the aforementioned "$C_{1-6}$ alkylene group" of the "optionally substituted $C_{1-6}$ alkylene group" for Y optionally has. When the number of the substituents is two or more, the respective substituents may be the same or different.

$R^a$ is preferably a hydrogen atom.

The "$C_{1-6}$ alkyl group" of the "optionally substituted $C_{1-6}$ alkyl group" for $R^b$ optionally has 1-3 (preferably 1 or 2) substituents at substitutable position(s).

Examples of such substituent include the groups exemplified as the substituents the aforementioned "$C_{1-6}$ alkylene group" of the "optionally substituted $C_{1-6}$ alkylene group" for Y optionally has. When the number of the substituents is two or more, the respective substituents may be the same or different.

L is preferably a bond, —Y—, —O—, —YO—, —OY—, —S—, —CONR$^a$—, —NR$^a$— wherein Y is an optionally substituted $C_{1-3}$ alkylene group (preferably a $C_{1-3}$ alkylene group, more preferably methylene), and $R^a$ is a hydrogen atom, more preferably a bond, —Y—, —O—, —YO—, —OY—, —CONR$^a$— wherein Y is an optionally substituted $C_{1-3}$ alkylene group (preferably a $C_{1-3}$ alkylene group, more preferably methylene), and $R^a$ is a hydrogen atom, further preferably a bond, —Y—, —O—, —YO—, —OY—, —CONR$^a$— wherein Y is a $C_{1-3}$ alkylene group (preferably, methylene), and $R^a$ is a hydrogen atom.

In another embodiment, L is preferably a bond, —Y—, —O—, —YO—, —OY—, —S—, —NR$^a$— wherein Y is an optionally substituted $C_{1-3}$ alkylene group (preferably a $C_{1-3}$ alkylene group, more preferably methylene), and $R^a$ is a hydrogen atom, more preferably a bond, —O—, —YO— wherein Y is an optionally substituted $C_{1-3}$ alkylene group (preferably a $C_{1-3}$ alkylene group, more preferably methylene), further preferably —O—.

$R^3$ is a substituent.

Examples of the "substituent" for $R^3$ include the groups exemplified as the substituents the aforementioned "oxazole ring", "triazole ring", "imidazole ring", "pyridine ring" and "pyrazole ring" of the "optionally substituted oxazole ring", "optionally substituted triazole ring", "optionally substituted imidazole ring", "optionally substituted pyridine ring" and "optionally substituted pyrazole ring" for ring A optionally have.

When the number of $R^3$ is two or more (that is, when n is an integer of 2 or more), the respective substituents may be the same or different.

In partial structure (1-1) or (1-2), when two R³ are adjacent to one carbon atom constituting a ring, said two R³ may form, together with the adjacent carbon atom, an optionally substituted ring.

The "ring" of such "optionally substituted ring" may be any of a ring constituting the above-mentioned "hydrocarbon ring group" and a ring constituting the above-mentioned "heterocyclic group", which is preferably a 3- to 6-membered ring.

Preferable examples of the "3- to 6-membered ring" include $C_{3-6}$ cycloalkane (e.g., cyclopropane, cyclobutane, cyclopentane, cyclohexane), pyrrolidine, imidazolidine, pyrazolidine, piperidine, piperazine, morpholine, thiomorpholine, oxopiperazine and the like. More preferred is $C_{3-6}$ cycloalkane (e.g., cyclopropane, cyclobutane, cyclopentane, cyclohexane).

The "ring" may have 1-5 (preferably 1-4) substituents at substitutable position(s). Examples of such substituent include the groups exemplified as the substituents the aforementioned "oxazole ring", "triazole ring", "imidazole ring", "pyridine ring" and "pyrazole ring" of the "optionally substituted oxazole ring", "optionally substituted triazole ring", "optionally substituted imidazole ring", "optionally substituted pyridine ring" and "optionally substituted pyrazole ring" for ring A optionally have. When the number of the substituents is two or more, the respective substituents may be the same or different.

R³ is preferably a hydroxy group or a $C_{1-6}$ alkyl group (preferably, methyl), more preferably a $C_{1-6}$ alkyl group (preferably, methyl).

n is preferably 0, 1 or 2, more preferably 0 or 1, particularly preferably 0.

The partial structure (1):

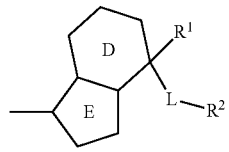

(1)

is preferably

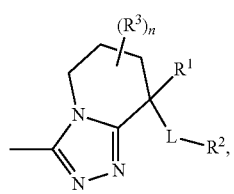

(1-1)

wherein preferable embodiment of each group is as shown above for each of the above-mentioned groups.

Also, it is preferable that a ring constituting atom on a fused ring represented by

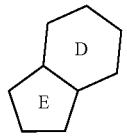

preferably contains a quaternary carbon atom.

A compound represented by the formula (I) is preferably a compound wherein ring A is an optionally substituted oxazole ring, an optionally substituted triazole ring, an optionally substituted imidazole ring, an optionally substituted pyridine ring, or an optionally substituted pyrazole ring, ring B is an optionally substituted benzene ring, or an optionally substituted pyridine ring, and partial structure (1):

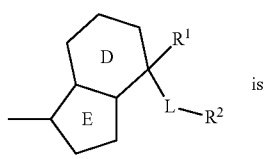

(1)

is

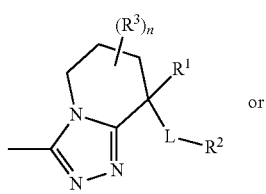

(1-1)

or

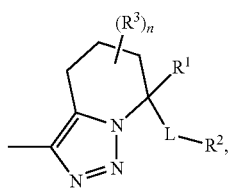

(1-2)

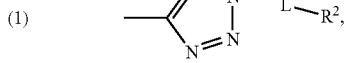

R¹ is a hydroxy group, an optionally substituted $C_{1-6}$ alkyl group, an optionally substituted $C_{1-6}$ alkoxy group, an optionally substituted aminocarbonyl group, a carboxy group, an optionally substituted $C_{1-6}$ alkyl-carbonyl group, or an optionally substituted $C_{1-6}$ alkoxy-carbonyl group, R² is a halogen atom, an optionally substituted $C_{3-10}$ cycloalkyl group, an optionally substituted $C_{6-14}$ aryl group, an optionally substituted aromatic heterocyclic group, or an optionally substituted non-aromatic heterocyclic group, L is a bond, —Y—, —O—, —YO—, —OY—, —S—, —CONR$^a$— or —NR$^a$— wherein Y is an optionally substituted $C_{1-3}$ alkylene group (preferably a $C_{1-3}$ alkylene group, more preferably methylene), and R$^a$ is a hydrogen atom, R³ is hydroxyl or a $C_{1-6}$ alkyl group (preferably, methyl), and n is 0, 1 or 2.

A compound represented by the formula (I) is more preferably a compound wherein ring A is an oxazole ring, a triazole ring, an imidazole ring, a pyridine ring or a pyrazole ring, each of which is optionally substituted by 1-3 (preferably 1 or 2, more preferably 1) substituents selected form a $C_{1-6}$ alkyl group (preferably, methyl) and a halogen atom (preferably, a chlorine atom), ring B is a benzene ring or a pyridine ring, each of which is optionally substituted by 1-3 (preferably 1 or 2, more preferably 1) substituents selected from (1) a hydroxy group, (2) a C$_{1-6}$ alkoxy group (preferably, methoxy, ethoxy) optionally substituted by 1-3 halogen atoms (preferably, a fluorine atom), (3) a halogen atom (preferably, a fluorine atom) and (4) a C$_{7-13}$ aralkyloxy group (preferably, benzyloxy), and
partial structure (1):

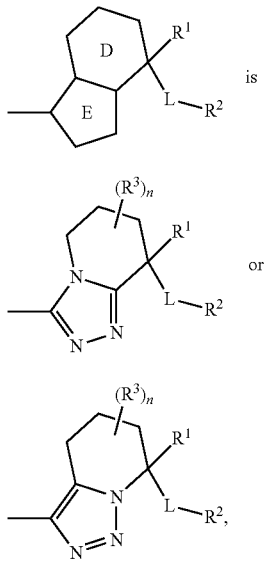

R$^1$ is
(1) a hydroxy group,
(2) a C$_{1-6}$ alkyl group (preferably, methyl, ethyl, propyl, isopropyl, 1-ethylpropyl, 2-methylbutyl) optionally substituted by 1 to 4 substituents selected from
  (a) a halogen atom (preferably, a fluorine atom)
  (b) a hydroxy group,
  (c) a C$_{1-6}$ alkoxy group (preferably, methoxy),
  (d) an amino group,
  (e) a C$_{6-14}$ aryl group (preferably, phenyl) optionally substituted by 1 to 3 halogen atoms (preferably, a fluorine atom),
  (f) a C$_{3-10}$ cycloalkyl group (preferably, cyclopropyl),
  (g) a C$_{1-6}$ alkyl-carbonyloxy group (preferably, acetyloxy), and
  (h) a C$_{1-6}$ alkyl-carbonylamino group (preferably, acetylamino);
(3) a C$_{1-6}$ alkoxy group (preferably, methoxy, ethoxy, 2-methylbutyloxy) optionally substituted by 1 to 3 substituents selected from
  (a) a C$_{6-14}$ aryl group (preferably, phenyl) optionally substituted by 1 to 3 halogen atoms (preferably, a chlorine atom), and
  (b) a C$_{3-10}$ cycloalkyl group (preferably, cyclopropyl);
(4) an aminocarbonyl group optionally mono- or di-substituted by C$_{1-6}$ alkyl group(s) (preferably, methyl, ethyl) optionally substituted by 1 to 3 halogen atoms (preferably, a fluorine atom) (two substituents of the aminocarbonyl group may form, together with the nitrogen atom bonded thereto, a pyrrolidine ring optionally substituted by 1-4 halogen atoms (preferably, a fluorine atom));
(5) a carboxy group;
(6) a C$_{1-6}$ alkyl-carbonyl group (preferably, acetyl, propionyl); or
(7) a C$_{1-6}$ alkoxy-carbonyl group (preferably, ethoxycarbonyl), R$^2$ is
(1) a halogen atom (e.g., a chlorine atom, a fluorine atom);
(2) a C$_{3-10}$ cycloalkyl group (e.g., cyclopropyl);
(3) a C$_{6-14}$ aryl group (e.g., phenyl) optionally substituted by 1 to 4 substituents selected from
  (a) a C$_{1-6}$ alkyl group (e.g., methyl) optionally substituted by 1 to 3 substituents selected from a halogen atom (e.g., a fluorine atom) and a C$_{1-6}$ alkoxy-carbonyl group (e.g., ethoxycarbonyl),
  (b) a C$_{1-6}$ alkoxy group (e.g., methoxy),
  (c) a halogen atom (e.g., a chlorine atom, a fluorine atom, a bromine atom),
  (d) a C$_{1-6}$ alkylthio group (e.g., methylthio),
  (e) a C$_{1-6}$ alkylsulfonyl group (e.g., methylsulfonyl), and
  (f) a cyano group;
(4) an aromatic heterocyclic group (e.g., pyridyl, oxadiazolyl) optionally substituted by 1 to 3 substituents selected from
  (a) a C$_{1-6}$ alkyl group (e.g., methyl) optionally substituted by 1 to 3 halogen atoms (e.g., a fluorine atom), and
  (b) a C$_{6-14}$ aryl group (e.g., phenyl) optionally substituted by 1 to 3 halogen atoms (e.g., a chlorine atom); or
(5) a non-aromatic heterocyclic group (e.g., tetrahydropyranyl), L is a bond, —Y—, —O—, —YO—, —OY—, —S—, —CONR$^a$— or —NR$^a$— wherein Y is an optionally substituted C$_{1-3}$ alkylene group (preferably a C$_{1-3}$ alkylene group, more preferably methylene), and R$^a$ is a hydrogen atom, R$^3$ is hydroxyl or a C$_{1-6}$ alkyl group (preferably, methyl), and n is 0 or 1.

In another embodiment, a compound represented by the formula (I) is preferably a compound wherein ring A is an optionally substituted oxazole ring, an optionally substituted triazole ring, or an optionally substituted imidazole ring, ring B is an optionally substituted benzene ring, or an optionally substituted pyridine ring, and partial structure (1):

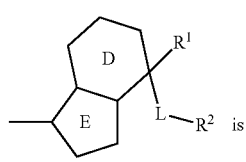

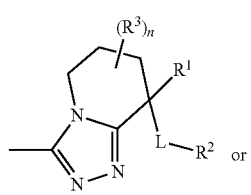

-continued

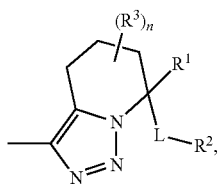
(1-2)

R¹ is a hydroxy group, an optionally substituted $C_{1-6}$ alkyl group, an optionally substituted $C_{1-6}$ alkoxy group, an optionally substituted aminocarbonyl group, a carboxy group, an optionally substituted $C_{1-6}$ alkyl-carbonyl group, or an optionally substituted $C_{1-6}$ alkoxy-carbonyl group, R² is a halogen atom, an optionally substituted $C_{3-10}$ cycloalkyl group, an optionally substituted $C_{6-14}$ aryl group, an optionally substituted aromatic heterocyclic group, or an optionally substituted non-aromatic heterocyclic group, L is a bond, —Y—, —O—, —YO—, —OY—, or —CONR$^a$— wherein Y is an optionally substituted $C_{1-3}$ alkylene group (preferably, methylene), and R$^a$ is a hydrogen atom, R³ is hydroxyl, and n is 0, 1 or 2.

A compound represented by the formula (I) is more preferably a compound wherein ring A is an oxazole ring, a triazole ring or an imidazole ring, each of which is optionally substituted by 1-3 (preferably 1 or 2, more preferably 1) $C_{1-6}$ alkyl groups (preferably, methyl), ring B is a benzene ring or a pyridine ring, each of which is optionally substituted by 1-3 (preferably 1 or 2, more preferably 1) $C_{1-6}$ alkoxy groups (preferably, methoxy), and partial structure (1):

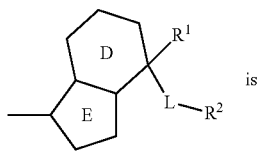
(1)

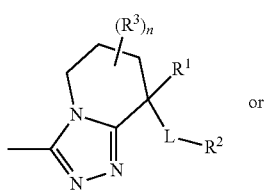
(1-1)

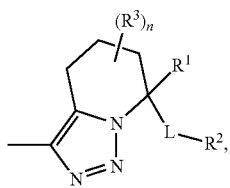
(1-2)

R¹ is
(1) a hydroxy group,
(2) a $C_{1-6}$ alkyl group (preferably, methyl, ethyl, propyl, isopropyl, 1-ethylpropyl, 2-methylbutyl) optionally substituted by 1 to 3 substituents selected from
    (a) a hydroxy group,
    (b) a $C_{1-6}$ alkoxy group (preferably, methoxy),
    (c) an amino group,
    (d) a $C_{6-14}$ aryl group (preferably, phenyl) optionally substituted by 1 to 3 halogen atoms (preferably, a fluorine atom),
    (e) a $C_{3-10}$ cycloalkyl group (preferably, cyclopropyl),
    (f) a $C_{1-6}$ alkyl-carbonyloxy group (preferably, acetyloxy), and
    (g) a $C_{1-6}$ alkyl-carbonylamino group (preferably, acetylamino);
(3) a $C_{1-6}$ alkoxy group (preferably, methoxy, ethoxy, 2-methylbutyloxy) optionally substituted by 1 to 3 substituents selected from
    (a) a $C_{6-14}$ aryl group (preferably, phenyl) optionally substituted by 1 to 3 halogen atoms (preferably, a chlorine atom), and
    (b) a $C_{3-10}$ cycloalkyl group (preferably, cyclopropyl);
(4) an aminocarbonyl group optionally mono- or di-substituted by $C_{1-6}$ alkyl group(s) (preferably, methyl, ethyl) optionally substituted by 1 to 3 halogen atoms (preferably, a fluorine atom) (two substituents of the aminocarbonyl group may form, together with the nitrogen atom bonded thereto, a pyrrolidine ring optionally substituted by 1-4 halogen atoms (preferably, a fluorine atom));
(5) a carboxy group;
(6) a $C_{1-6}$ alkyl-carbonyl group (preferably, acetyl, propionyl); or
(7) a $C_{1-6}$ alkoxy-carbonyl group (preferably, ethoxycarbonyl), R² is
(1) a halogen atom (e.g., a chlorine atom, a fluorine atom);
(2) a $C_{3-10}$ cycloalkyl group (e.g., cyclopropyl);
(3) a $C_{6-44}$ aryl group (e.g., phenyl) optionally substituted by 1 to 3 substituents selected from
    (a) a $C_{1-6}$ alkyl group (e.g., methyl) optionally substituted by 1 to 3 halogen atoms (e.g., a fluorine atom),
    (b) a $C_{1-6}$ alkoxy group (e.g., methoxy),
    (c) a halogen atom (e.g., a chlorine atom, a fluorine atom, a bromine atom),
    (d) a $C_{1-6}$ alkylthio group (e.g., methylthio),
    (e) a $C_{1-6}$ alkylsulfonyl group (e.g., methylsulfonyl), and
    (f) a cyano group;
(4) an aromatic heterocyclic group (e.g., pyridyl, oxadiazolyl) optionally substituted by 1 to 3 substituents selected from
    (a) a $C_{1-6}$ alkyl group (e.g., methyl) optionally substituted by 1 to 3 halogen atoms (e.g., a fluorine atom), and
    (b) a $C_{6-14}$ aryl group (e.g., phenyl) optionally substituted by 1 to 3 halogen atoms (e.g., a chlorine atom); or
(5) a non-aromatic heterocyclic group (e.g., tetrahydropyranyl), L is a bond, —Y—, —O—, —YO—, —OY— or —CONR$^a$— wherein Y is a $C_{1-3}$ alkylene group (preferably, methylene), and R$^a$ is a hydrogen atom, R³ is hydroxy, and n is 0 or 1.

In another embodiment, a compound represented by the formula (I) is preferably a compound wherein ring A is an optionally substituted oxazole ring, an optionally substituted triazole ring, or an optionally substituted imidazole ring, ring B is an optionally substituted benzene ring, or an optionally substituted pyridine ring, and partial structure:

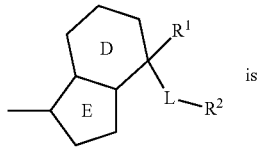

(1)

is

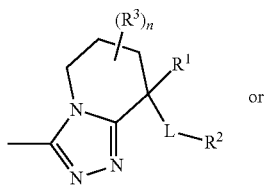

(1-1)

or

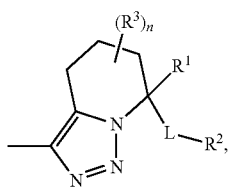

(1-2)

R¹ is a hydroxy group, an optionally substituted $C_{1-6}$ alkyl group, an optionally substituted $C_{1-6}$ alkoxy group, an optionally substituted aminocarbonyl group, a carboxy group, or an optionally substituted $C_{1-6}$ alkoxy-carbonyl group, R² is a halogen atom, an optionally substituted hydrocarbon ring group, or an optionally substituted heterocyclic group, L is a bond, —Y—, —O—, —YO—, —OY— or —CONR$^a$— wherein Y is an optionally substituted $C_{1-3}$ alkylene group (preferably, methylene), and R$^a$ is a hydrogen atom, R³ is hydroxy, and n is 0, 1 or 2.

In another embodiment, a compound represented by the formula (I) is preferably a compound (W-1) wherein ring A is an oxazole ring, a triazole ring, an imidazole ring, a pyridine ring or a pyrazole ring, each of which is optionally substituted by 1-3 (preferably 1 or 2, more preferably 1) substituents selected form a $C_{1-6}$ alkyl group (preferably, methyl) and a halogen atom (preferably, a chlorine atom), ring B is a benzene ring or a pyridine ring, each of which is optionally substituted by 1-3 (preferably 1 or 2, more preferably 1) substituents selected from (1) a hydroxy group, (2) a $C_{1-6}$ alkoxy group (preferably, methoxy, ethoxy) optionally substituted by 1-3 halogen atoms (preferably, a fluorine atom), (3) a halogen atom (preferably, a fluorine atom) and (4) a $C_{7-13}$ aralkyloxy group (preferably, benzyloxy), partial structure (1):

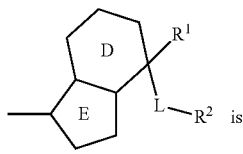

(1)

is

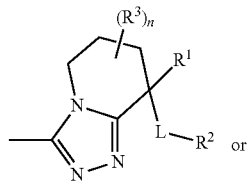

(1-1)

or

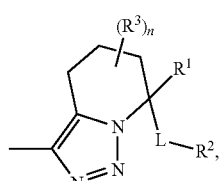

(1-2)

R¹ is
(1) a hydroxy group,
(2) a $C_{1-6}$ alkyl group (preferably, methyl, ethyl, propyl, isopropyl, 1-ethylpropyl, 2-methylbutyl) optionally substituted by 1 to 4 substituents selected from
  (a) a halogen atom (preferably, a fluorine atom)
  (b) a hydroxy group,
  (c) a $C_{1-6}$ alkoxy group (preferably, methoxy),
  (d) an amino group,
  (e) a $C_{6-14}$ aryl group (preferably, phenyl) optionally substituted by 1 to 3 halogen atoms (preferably, a fluorine atom),
  (f) a $C_{3-10}$ cycloalkyl group (preferably, cyclopropyl),
  (g) a $C_{1-6}$ alkyl-carbonyloxy group (preferably, acetyloxy), and
  (h) a $C_{1-6}$ alkyl-carbonylamino group (preferably, acetylamino);
(3) a $C_{1-6}$ alkoxy group (preferably, methoxy, ethoxy, 2-methylbutyloxy) optionally substituted by 1 to 3 substituents selected from
  (a) a $C_{6-14}$ aryl group (preferably, phenyl) optionally substituted by 1 to 3 halogen atoms (preferably, a chlorine atom), and
  (b) a $C_{3-10}$ cycloalkyl group (preferably, cyclopropyl);
(4) an aminocarbonyl group optionally mono- or di-substituted by $C_{1-6}$ alkyl group(s) (preferably, methyl, ethyl) optionally substituted by 1 to 3 halogen atoms (preferably, a fluorine atom) (two substituents of the aminocarbonyl group may form, together with the nitrogen atom bonded thereto, a pyrrolidine ring optionally substituted by 1-4 halogen atoms (preferably, a fluorine atom));
(5) a $C_{1-6}$ alkyl-carbonyl group (preferably, acetyl, propionyl); or
(6) a $C_{1-6}$ alkoxy-carbonyl group (preferably, ethoxycarbonyl), R² is
(1) a halogen atom (e.g., a chlorine atom, a fluorine atom);
(2) a $C_{3-10}$ cycloalkyl group (e.g., cyclopropyl);
(3) a $C_{6-14}$ aryl group (e.g., phenyl) optionally substituted by 1 to 4 substituents selected from
  (a) a $C_{1-6}$ alkyl group (e.g., methyl) optionally substituted by 1 to 3 substituents selected from a halogen atom (e.g., a fluorine atom) and a $C_{1-6}$ alkoxy-carbonyl group (e.g., ethoxycarbonyl),
  (b) a $C_{1-6}$ alkoxy group (e.g., methoxy),
  (c) a halogen atom (e.g., a chlorine atom, a fluorine atom, a bromine atom),
  (d) a $C_{1-6}$ alkylthio group (e.g., methylthio),
  (e) a $C_{1-6}$ alkylsulfonyl group (e.g., methylsulfonyl), and
  (f) a cyano group;

(4) an aromatic heterocyclic group (e.g., pyridyl, oxadiazolyl) optionally substituted by 1 to 3 substituents selected from
(a) a $C_{1-6}$ alkyl group (e.g., methyl) optionally substituted by 1 to 3 halogen atoms (e.g., a fluorine atom), and
(b) a $C_{6-14}$ aryl group (e.g., phenyl) optionally substituted by 1 to 3 halogen atoms (e.g., a chlorine atom); or
(5) a non-aromatic heterocyclic group (e.g., tetrahydropyranyl),
L is a bond, —Y—, —O—, —YO—, —OY—, —S—, —CONR$^a$— or —NR$^a$— wherein Y is an optionally substituted $C_{1-3}$ alkylene group (preferably a $C_{1-3}$ alkylene group, more preferably methylene), and R$^a$ is a hydrogen atom,
R$^3$ is hydroxyl or a $C_{1-6}$ alkyl group (preferably, methyl), and
n is 0 or 1,
more preferably is a compound (W-2) wherein
ring A is an oxazole ring, a triazole ring, an imidazole ring, a pyridine ring or a pyrazole ring, each of which is optionally substituted by 1-3 (preferably 1 or 2, more preferably 1) substituents selected form a $C_{1-6}$ alkyl group (preferably, methyl) and a halogen atom (preferably, a chlorine atom),
ring B is a benzene ring or a pyridine ring, each of which is optionally substituted by 1-3 (preferably 1 or 2, more preferably 1) substituents selected from (1) a $C_{1-6}$ alkoxy group (preferably, methoxy, ethoxy) optionally substituted by 1-3 halogen atoms (preferably, a fluorine atom) and (2) a halogen atom (preferably, a fluorine atom), and
partial structure (1):

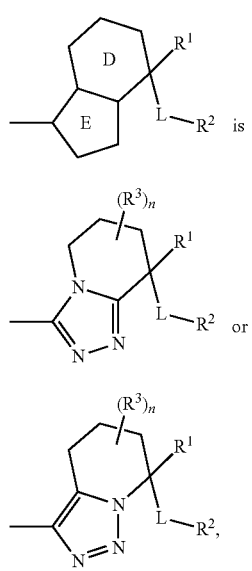

R$^1$ is
(1) a $C_{1-6}$ alkyl group (preferably, methyl, isopropyl, 1-ethylpropyl) optionally substituted by 1 to 3 substituents selected from
(a) a hydroxy group, and
(b) a $C_{3-10}$ cycloalkyl group (preferably, cyclopropyl); or
(2) an aminocarbonyl group optionally mono- or di-substituted by $C_{1-6}$ alkyl group(s) (preferably, methyl, ethyl) optionally substituted by 1 to 3 halogen atoms (preferably, a fluorine atom);

R$^2$ is
(1) a $C_{6-14}$ aryl group (e.g., phenyl) optionally substituted by 1 to 4 (preferably 1 to 3) substituents selected from
(a) a $C_{1-6}$ alkyl group (e.g., methyl) optionally substituted by 1 to 3 substituents selected from a halogen atom (e.g., a fluorine atom) and a $C_{1-6}$ alkoxy-carbonyl group (e.g., ethoxycarbonyl), and
(b) a halogen atom (e.g., a chlorine atom, a fluorine atom); or
(2) an aromatic heterocyclic group (e.g., pyridyl) optionally substituted by 1 to 3 $C_{1-6}$ alkyl group (e.g., methyl) optionally substituted by 1 to 3 halogen atoms (e.g., a fluorine atom),
L is a bond, —Y—, —O—, —YO—, —OY—, —S—, or —NR$^a$— wherein Y is an optionally substituted $C_{1-3}$ alkylene group (preferably a $C_{1-3}$ alkylene group, more preferably methylene), and R$^a$ is a hydrogen atom,
R$^3$ is a $C_{1-6}$ alkyl group (preferably, methyl), and
n is 0 or 1;
and further preferably is a compound (W-3) wherein ring A is an oxazole ring, a triazole ring, an imidazole ring or a pyrazole ring, each of which is optionally substituted by 1-3 (preferably 1 or 2, more preferably 1) $C_{1-6}$ alkyl group(s) (preferably, methyl),
ring B is a benzene ring or a pyridine ring, each of which is optionally substituted by 1-3 (preferably 1 or 2, more preferably 1) substituents selected from (1) a $C_{1-6}$ alkoxy group (preferably, methoxy, ethoxy) optionally substituted by 1-3 halogen atoms (preferably, a fluorine atom) and (2) a halogen atom (preferably, a fluorine atom), and
partial structure (1):

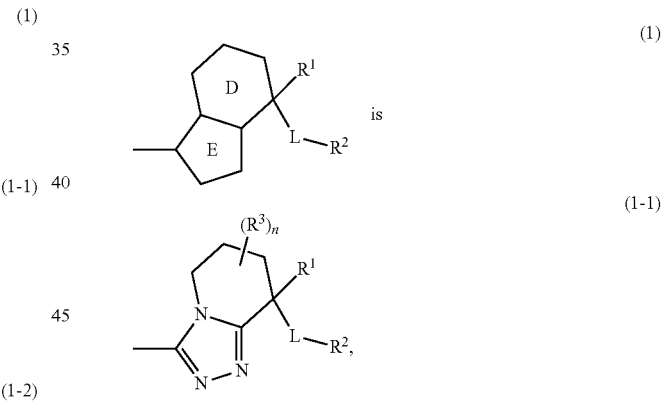

R$^1$ is a $C_{1-6}$ alkyl group (preferably, methyl, isopropyl, 1-ethylpropyl) optionally substituted by 1 to 3 substituents selected from
(a) a hydroxy group, and
(b) a $C_{3-10}$ cycloalkyl group (preferably, cyclopropyl);
R$^2$ is a $C_{6-14}$ aryl group (e.g., phenyl) optionally substituted by 1 to 4 (preferably 1 to 3) substituents selected from
(a) a $C_{1-6}$ alkyl group (e.g., methyl) optionally substituted by 1 to 3 halogen atoms (e.g., a fluorine atom), and
(b) a halogen atom (e.g., a chlorine atom, a fluorine atom);
L is a bond, —O—, or —YO—, wherein Y is an optionally substituted $C_{1-3}$ alkylene group (preferably a $C_{1-3}$ alkylene group, more preferably methylene), and
n is 0.
As compound (1),
2-{8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol or a salt thereof;

2-{(8R)-8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol or a salt thereof;

2-{(8S)-8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol or a salt thereof;

2-{(8R)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol or a salt thereof;

2-{3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol or a salt thereof;

2-{(8R)-3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol or a salt thereof;

2-{(8S)-3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol or a salt thereof;

2-{3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl}propan-2-ol or a salt thereof;

2-{(8R)-3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl}propan-2-ol or a salt thereof;

2-{(8S)-3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl}propan-2-ol or a salt thereof;

2-{8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol or a salt thereof;

2-{(8R)-8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol or a salt thereof;

2-{(8S)-8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol or a salt thereof; and 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol or a salt thereof;

are particularly preferable.

When compound (I) is a salt, examples of such salt include metal salts, ammonium salt, salts with organic base, salts with inorganic acid, salts with organic acid, salts with basic or acidic amino acid and the like. Preferable examples of metal salts include alkali metal salts such as sodium salt, potassium salt and the like; alkaline earth metal salts such as calcium salt, magnesium salt, barium salt and the like; aluminum salt and the like. Preferable examples of salts with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acid include salts with hydrochloric acid, hydrobromic acid, nitric acid, sulfuric acid, phosphoric acid and the like. Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, (+)-mandelic acid, gentisic acid and the like. Preferable examples of salts with basic amino acid include salts with arginine, lysine, ornithine and the like, and preferable examples of salts with acidic amino acid include salts with aspartic acid, glutamic acid and the like.

Of these, pharmaceutically acceptable salts are preferable. When a compound has an acidic functional group, preferable examples thereof include inorganic salts such as an alkali metal salts (e.g., sodium salt, potassium salt etc.), an alkaline earth metal salts (e.g., calcium salt, magnesium salt etc.) and the like, ammonium salts and the like. When the compound has an basic functional group, preferable examples thereof include salts with inorganic acid such as hydrochloric acid, hydrobromic acid, nitric acid, sulfuric acid, phosphoric acid and the like; and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic, (+)-mandelic acid, gentisic acid and the like.

In the following, compound (1) and a salt thereof are also generically referred to as the compound of the present invention.

[Production Methods]

Compound (I) and starting compounds thereof can be produced according to a method known per se, for example, a method shown in the following schemes and the like. Compound (I) can be produced according to the method described in production method A, B, D, E or F.

In the following, the "room temperature" generally shows 10 to 30° C., and each symbol in the chemical structures described in the schemes is as defined above unless otherwise specified.

The compound in the formula also includes the form of a salt, and examples of such salt include those similar to the salts of compound (I) and the like. In addition, while the compound obtained in each step can be used for the next reaction as a reaction mixture or a crude product, it can also be isolated from a reaction mixture according to a conventional method, or can be easily purified by a separation means such as recrystallization, distillation, chromatography and the like. When the compound in the formula is commercially available, a commercially available product can be directly used. In addition, when each ring in the formula (I) has a substituent, the corresponding precursor is considered to also have a similar substituent.

When the starting compound has amino, carboxy, hydroxy or heterocyclic group, these groups may be protected by a protecting group generally used in the peptide chemistry and the like. In this case, the object compound can be obtained by removing the protecting group as necessary after the reaction. Introduction and removal of these protecting groups can be performed by a method known per se, for example, the method described in "Protective Groups in Organic Synthesis, 3$^{rd}$ Ed." (Theodora W. Greene, Peter G. M. Wuts, Wiley-Interscience, 1999) and the like. In the formula, $P^1$ and $P^2$ are each a protecting group of a nitrogen atom in amine or amide, a protecting group of a hydroxy group, or a hydrogen atom, and those known per se can be used. For example, $P^1$ and $P^2$ are preferably a tert-butyl carbamate group, a benzyl carbamate group, a benzyl group, a methyl group, an ethyl group, a tert-butyl group and the like.

As the "leaving group" for $LG^1$-$LG^{13}$, for example, a halogen atom (e.g., a chlorine atom, a bromine atom, an iodine atom etc.), $C_{1-6}$ alkylsulfonyloxy (e.g., methanesulfonyloxy, ethanesulfonyloxy, trifluoromethanesulfonyloxy etc.), $C_{6-10}$ arylsulfonyloxy (e.g., benzenesulfonyloxy, p-toluenesulfonyloxy etc.), $C_{1-6}$ alkylsulfonyl (e.g., methanesulfonyl, ethanesulfonyl etc.) and the like are used. In addition, $LG^1$-$LG^{13}$ also include a substituent that can be converted to a leaving group, and can be converted to a leaving group in a desired step by a reaction known per se. For example, when $LG^1$-$LG^{13}$ are methylthio groups, they can be converted to methanesulfonyl groups by oxidation reaction.

Each step described below can be performed without solvent, or by dissolving or suspending in an appropriate solvent, where two or more kinds of solvents may be used by mixing them at an appropriate ratio. Of those recited as examples of the solvent to be used in the production method of the compound (I), the following solvents are specifically used.

alcohols:
methanol, ethanol, 1-propanol, 2-propanol, tert-butyl alcohol, 2-methoxyethanol etc.

ethers:
diethyl ether, diisopropyl ether, diphenylether, tetrahydrofuran, 1,4-dioxane, 1,2-dimethoxyethane, etc.

aromatic hydrocarbons:
benzene, chlorobenzene, toluene, xylene, etc.

saturated hydrocarbons:
cyclohexane, hexane, etc.

amides:
N,N-dimethylformamide, N,N-dimethylacetamide, hexamethylphosphoric triamide, etc.

halogenated hydrocarbons:
dichloromethane, chloroform, carbon tetrachloride, 1,2-dichloroethane, etc.

nitriles:
acetonitrile, propionitrile, etc.

sulfoxides:
dimethylsulfoxide, etc.

aromatic organic bases:
pyridine, lutidine, etc.

acid anhydrides:
acetic anhydride, etc.

organic acids:
formic acid, acetic acid, propionic acid, trifluoroacetic acid, methanesulfonic acid, etc.

inorganic acids:
hydrochloric acid, sulfuric acid, etc.

esters:
methyl acetate, ethyl acetate, butyl acetate, etc.

ketones:
acetone, methylethylketone, etc.

Of those recited as examples of the base or deoxidizer to be used in the production method of the compound (I), the following bases and deoxidizers are specifically used.

inorganic bases:
sodium hydroxide, potassium hydroxide, magnesium hydroxide, etc.

basic salts:
sodium carbonate, potassium carbonate, cesium carbonate, calcium carbonate, sodium hydrogen carbonate, etc.

organic bases:
triethylamine, diethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole, etc. metal alkoxides:
sodium methoxide, sodium ethoxide, potassium tert-butoxide, etc.

alkali metal hydrides:
sodium hydride, potassium hydride, etc.

metal amides:
sodium amide, lithium diisopropylamide, lithium hexamethyldisilazide, etc.

organic lithiums:
methyl lithium, n-butyl lithium, sec-butyl lithium, tert-butyl lithium, etc.

Of those recited as examples of the acid or acidic catalyst to be used in the production method of compound (1), the following acid and acidic catalyst are specifically used.

inorganic acids:
hydrochloric acid, sulfuric acid, nitric acid, hydrobromic acid, phosphoric acid, etc.

organic acids:
acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, trifluoromethanesulfonic acid, etc.

Lewis acids:
boron trifluoride-diethyl ether complex, zinc iodide, anhydrous aluminum chloride, anhydrous zinc chloride, anhydrous iron chloride, etc.

Production Method A:

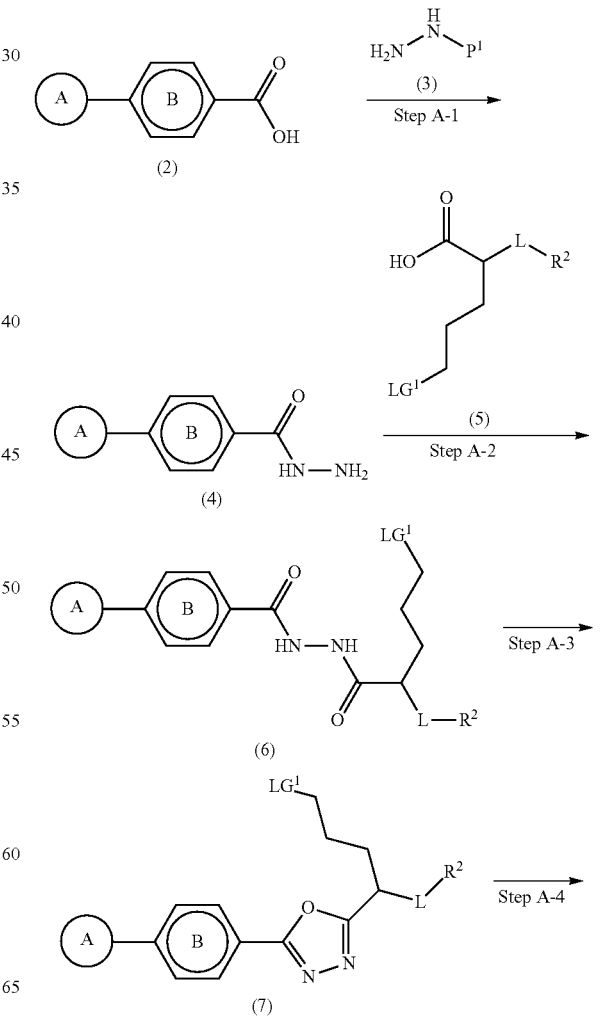

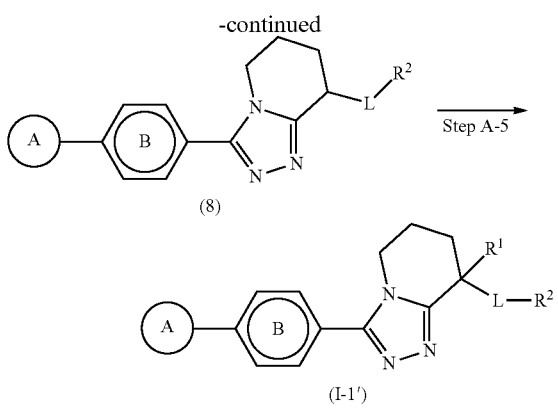

(8)

(I-1')

wherein each symbol is as defined above.

In compounds (I), a compound (to be referred to as compound (I-1)) wherein partial structure (1):

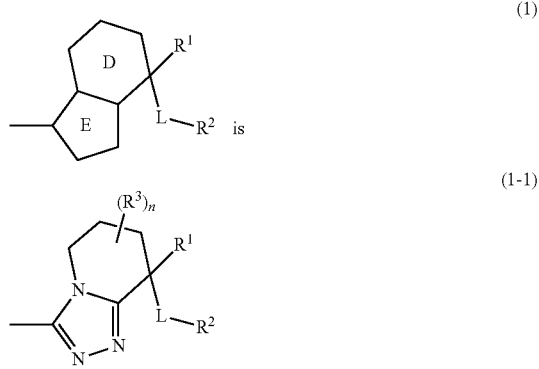

(1)

(1-1)

can be produced according to a series of reaction steps from step A-1 to step A-5. In the above-mentioned reaction scheme, a structure wherein n is 0 is shown as an example. When n is 1-6, the corresponding starting compound wherein $R^3$ in the number of n has been introduced can be used, or $R^3$ in the number of n may be introduced into predetermined positions during the production step.

(Step A-1)

Compound (4) can be produced by reacting carboxylic acid (2) or a reactive derivative thereof with compound (3), followed by removal of the protecting group $P^1$. When $P^1$ is a hydrogen atom, removal of the protecting group can be omitted. Examples of the reactive derivative of carboxylic acid include acid halides such as acid chloride, acid bromide and the like, acid amides with pyrazole, imidazole, benzotriazole and the like, mixed acid anhydride with acetic acid, propionic acid, butyric acid and the like, acid azide, active esters such as diethoxy phosphate ester, diphenoxy phosphate ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone and the like, active thioesters such as 2-pyridyl thioester, 2-benzothiazolyl thioester and the like, and the like. Instead of using a reactive derivative, carboxylic acid (2) may be directly reacted with compound (3) in the presence of a suitable condensing agent. Examples of the condensing agent include N,N'-disubstituted carbodiimides such as N,N'-dicyclohexylcarbodiimide, 1-ethyl-3-(3dimethylaminopropyl)carbodiimide (WSC) hydrochloride and the like, azolides such as N,N'-carbonyldiimidazole and the like, dehydrating agents such as N-ethoxycarbonyl-2-ethoxy-1,2-dihydroquinoline, phosphorus oxychloride, alkoxyacetylene and the like, 2-halogenopyridinium salts such as 2-chloromethylpyridinium iodide, 2-fluoro-1-methylpyridinium iodide and the like, phosphoryl cyanides such as diethylphosphoryl cyanide and the like, 2-(7-azabenzotriazol-1-yl)-1,1,3,3-tetramethyluronium hexafluorophosphate (HATU), O-(7-azabenzotriazol-1-yl)-N,N,N',N'-tetramethyluronium tetrafluoroborate (TATU) and the like. When these condensing agents are used, the reaction is considered to proceed via a reactive derivative of carboxylic acid (2). The amount of carboxylic acid (2) or a reactive derivative thereof to be used is generally about 0.2-5 mol, preferably about 0.5-2 mol, per 1 mol of compound (3). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides, aromatic organic bases and the like or a mixed solvent thereof and the like are preferable. When an acidic substance is released by the reaction, the reaction can be performed in the presence of a neutralizing agent to remove the substance from the reaction system. As such neutralizing agent, basic salts, organic bases and the like are used. For example, basic salts, organic bases and the like can also be used to promote the reaction. While the reaction time varies depending on the reagent and solvent to be used, it is generally 10 min-72 hr, preferably 30 min 24 hr. The reaction temperature is generally 0-100° C., preferably 0-70° C.

(step A-2)

Compound (6) can be produced by reacting compound (4) with carboxylic acid (5) or a reactive derivative thereof. The reaction may be performed in the same manner as in step A-1.

(Step A-3)

Compound (7) can be produced by subjecting compound (6) to an intramolecular cyclization reaction. The reaction can be performed according to a production method of an oxadiazole ring known per se, or a method analogous thereto and, for example, a method using a dehydrating agent can be used. Examples of the dehydrating agent include diphosphorus pentoxide, phosphorus oxychloride, phosphorus pentachloride, phosgene, N,N'-dicyclohexylcarbodiimide, alumina, polyphosphoric acid, acetic anhydride, acetyl chloride, sodium dioxide, thionyl chloride, methanesulfonyl chloride, p-toluenesulfonyl chloride, trifluoroacetic anhydride or complexes of triphenylphosphine and halogenated hydrocarbons such as carbon tetrachloride, carbon tetrabromide and the like, and the like. The amount of the dehydrating agent to be used is not less than about 1-100 mol, per 1 mol of compound (6). This reaction is advantageously performed without solvent or using a solvent inert to the reaction. Such solvent is not particularly limited as long as the reaction proceeds and, for example, a solvent such as ethers, halogenated hydrocarbons, esters, ketones, nitriles and the like or a mixed solvent thereof and the like are preferable. While the reaction time varies depending on the reagent and solvent to be used, it is generally 10 min-30 hr, preferably 1 hr-10 hr. The reaction temperature is generally 0-150° C., preferably 0-100° C.

(Step A-4)

Compound (8) can be produced by converting the leaving group $LG^1$ of compound (7) to an amino group, which is then subjected to an intramolecular cyclization reaction. The conversion method of the leaving group $LG^1$ to amino group can be performed according to a method known per se, or a method analogous thereto and, for example, a method which comprises substituting the leaving group LG$^1$ with phthalimide and deprotecting the phthalic acid, a method which comprises substituting the leaving group LG$^1$ with an azide group and reducing the azide group, and the like can be used. The intramolecular cyclization reaction is advantageously performed using a solvent inert to the reaction. Such solvent is not particularly limited as long as the reaction proceeds and, for example, a solvent such as alcohols, ethers, aromatic hydrocarbons, saturated hydrocarbons, amides, halogenated hydrocarbons, sulfoxides, organic acids, inorganic acids, water and the like, or a mixed solvent thereof and the like are preferable. While the reaction time varies depending on the reagent and solvent to be used, it is generally 10 min-72 hr, preferably 30 min-24 hr. The reaction temperature is generally 0-250° C., preferably 20-150° C.

(Step A-5)

Compound (I-1') can be produced by reacting compound (8) with a compound represented by R$^1$-LG$^2$ in the presence of a base.

Examples of the base include inorganic bases, basic salts, organic bases, metal alkoxides, alkali metal hydrides and the like. The amount of the base to be used is about 1-10 mol, preferably about 1-2 mol, per 1 mol of compound (8). The amount of R$^1$-LG$^2$ to be used is about 1-10 mol, preferably about 1-2 mol, per 1 mol of compound (8). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. The reaction is also preferably performed in an inactive gas stream such as argon gas, nitrogen gas and the like. While the reaction time varies depending on the reagent and solvent to be used, it is generally 10 min-100 hr, preferably 10 min-24 hr. The reaction temperature is generally −100-100° C., preferably −78-50° C.

Compound (I-1') can also be produced by reacting compound (8) with a corresponding carbonyl compound in the presence of a base. Examples of the base include inorganic bases, basic salts, organic bases, metal alkoxides, alkali metal hydrides and the like. The amount of the base to be used is about 1-mol, preferably about 1-2 mol, per 1 mol of compound (8). Examples of the carbonyl compound include paraformaldehyde, acetaldehyde, acetone and the like. The amount of the carbonyl compound to be used is about 1-10 mol, preferably about 1-2 mol, per 1 mol of compound (8). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. The reaction is also preferably performed in an inactive gas stream such as argon gas, nitrogen gas and the like. While the reaction time varies depending on the reagent and solvent to be used, it is generally 10 min-100 hr, preferably 10 min-24 hr. The reaction temperature is generally −100-100° C., preferably −78-50° C.

Compound (I-1') can also be produced by reacting compound (8) with oxygen in the presence of a base. Examples of the base include inorganic bases, basic salts, organic bases, metal alkoxides, alkali metal hydrides and the like. The amount of the base to be used is about 1-10 mol, preferably about 1-2 mol, per 1 mol of compound (8). The amount of oxygen to be used is not less than about 1-100 mol, per 1 mol of compound (8). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 10 min-24 hr. The reaction temperature is generally −100-100° C., preferably −78-50° C.

Compound (I-1) can be further converted to a desired compound by a known substituent conversion reaction, condensation reaction, oxidation reaction, reduction reaction and the like, conducted individually or by a combination of two or more thereof. These reactions can be carried out, for example, according to the method described in Shin Jikken Kagaku Koza (Courses in Experimental Chemistry), vols. 14 and 15 (edited by the Chemical Society of Japan); ORGANIC FUNCTIONAL GROUP PREPARATIONS, 2nd edition, Academic Press (ACADEMIC PRESS, INC.), 1989; Comprehensive Organic Transformations (VCH Publishers Inc.), 1989, and the like, or a method analogous thereto. For example, when —R$^1$ is a hydroxy group, the group can be converted to a desired alkoxy group by reacting with the corresponding alkyl halide.

Compounds (2), (3), (4), (5), (6), (7) and (8) may be commercially available products, or can also be produced according to a method known per se or a method analogous thereto. Compound (5) can also be produced according to the method described in Tetrahedron Letters, vol. 44, page 365 (2003), Tetrahedron, vol. 58, page 7663 (2002) and the like, or a method analogous thereto.

Production Method B:

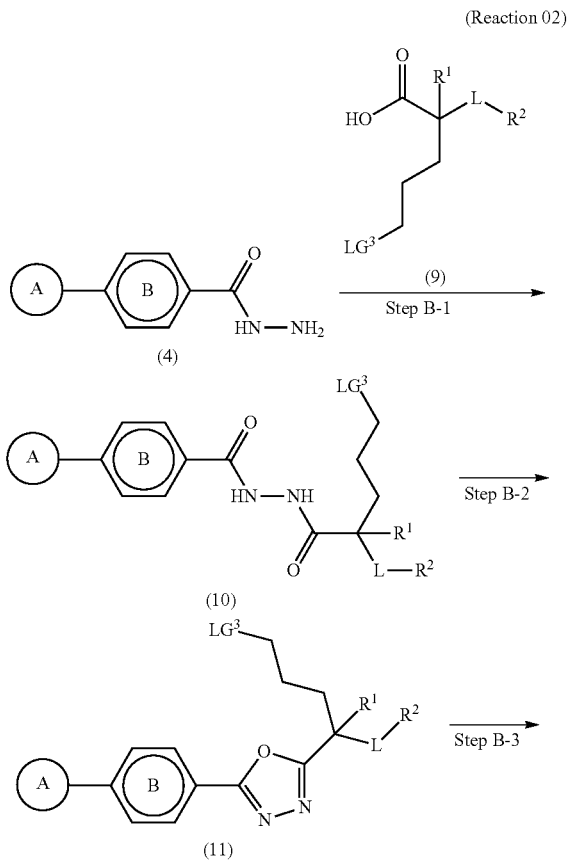

-continued

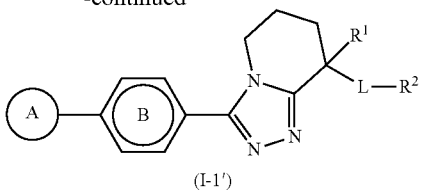

(I-1')

wherein each symbol is as defined above.

Compound (I-1') can be produced according to a series of reaction steps from step B-1 to step B-3. In the above-mentioned reaction scheme, a structure wherein n is 0 is shown as an example. When n is 1-6, the corresponding starting compound wherein $R^3$ in the number of n has been introduced can be used, or $R^3$ in the number of n may be introduced into predetermined positions during the production step.

(Step B-1)

Compound (10) can be produced by reacting compound (4) with carboxylic acid (9) or a reactive derivative thereof. The reaction may be performed in the same manner as in step A-2.

(Step B-2)

Compound (11) can be produced by subjecting compound (10) to an intramolecular cyclization reaction. The reaction may be performed in the same manner as in step A-3.

(Step B-3)

Compound (I-1') can be produced by converting the leaving group $LG^3$ of compound (11) to an amino group, which is then subjected to an intramolecular cyclization reaction. The reaction may be performed in the same manner as in step A-4.

Compounds (4), (9), (10) and (11) may be commercially available products, or can also be produced by a method known per se or a method analogous thereto.

step C-4. Compound (14) can be produced from compound (12) according to step C-1, and Compound (17) can be produced from compound (12) according to step C-3.

(Step C-1)

Compound (14) can be produced by reacting compound (12) with compound (13) in the presence of a base. Examples of the base include inorganic bases, basic salts, organic bases, metal alkoxides, alkali metal hydrides, organic lithiums and the like. The amount of the base to be used is about 1-10 mol, preferably about 1-2 mol, per 1 mol of compound (12). The amount of compound (13) to be used is about 1-10 mol, preferably about 1-2 mol, per 1 mol of compound (12). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 10 min-24 hr. The reaction temperature is generally –100-100° C., preferably –78-50° C.

(Step C-2)

Compound (9) can be produced by reacting compound (14) with compound (15) in the presence of a base. The reaction may be performed in the same manner as in step C-1.

(Step C-3)

Compound (17) can be produced by reacting compound (12) with compound (16) in the presence of a base. The reaction may be performed in the same manner as in step C-1.

(Step C-4)

Compound (9) can be produced reacting compound (17) with compound (18) in the presence of a base. The reaction may be performed in the same manner as in step C-1.

Production Method C:

(Reaction 03)

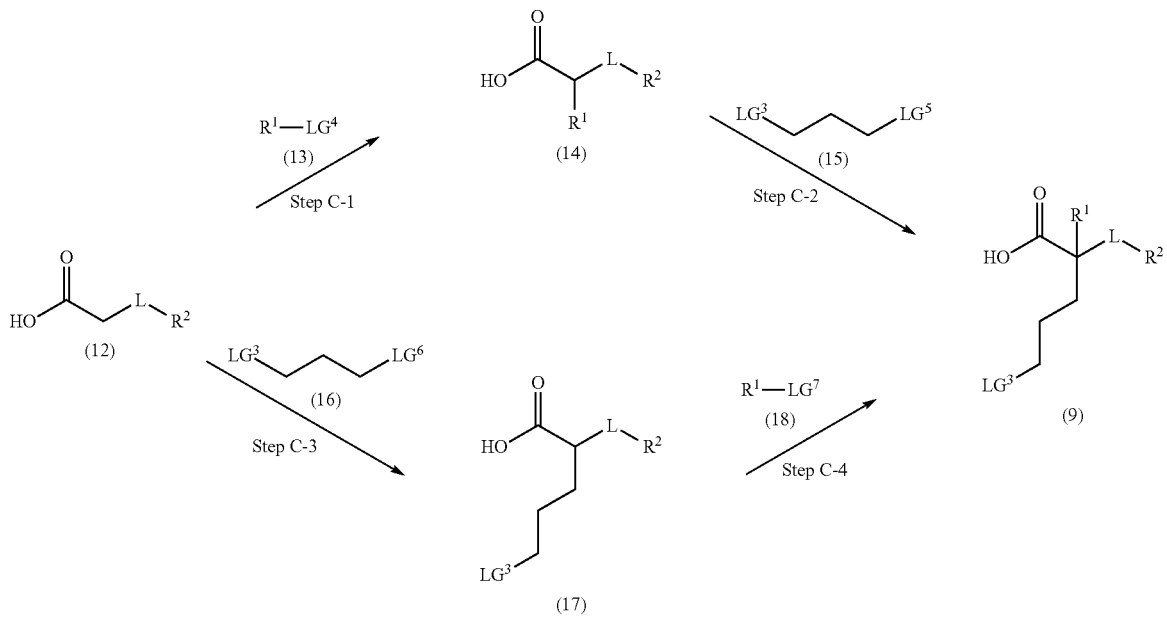

wherein each symbol is as defined above.

Compound (9) can be produced from compound (14) according to step C-2, or from compound (17) according to Compounds (12), (13), (14), (15), (16), (17) and (18) may be commercially available products, or can also be produced by a method known per se or a method analogous thereto.

Production Method D:

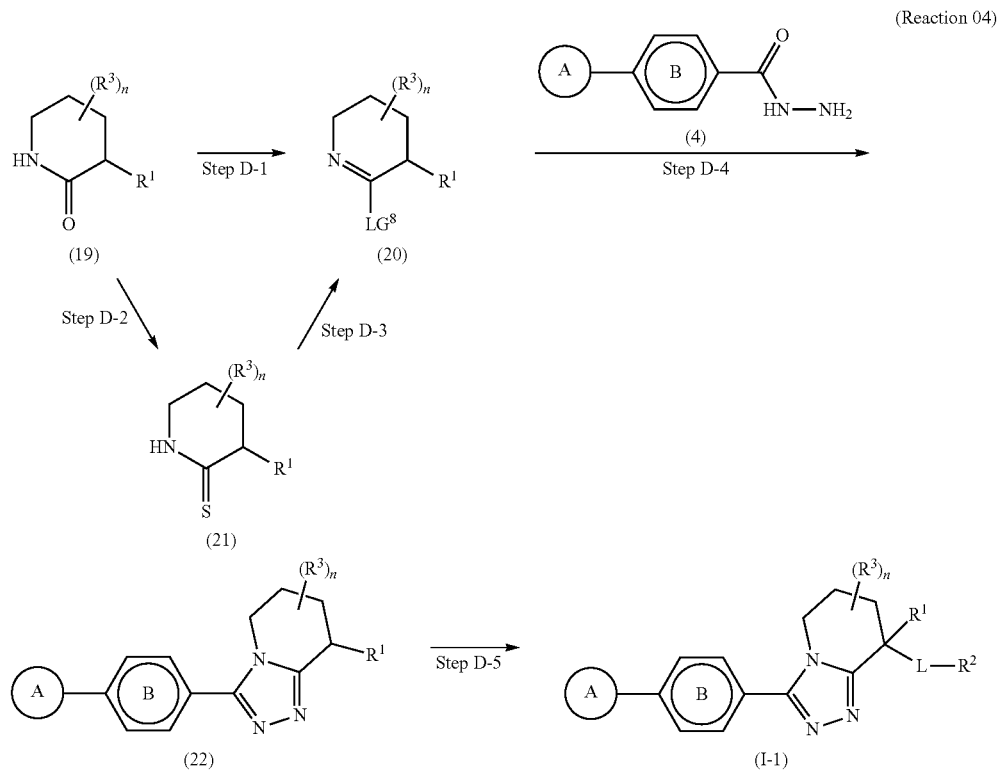

wherein each symbol is as defined above.

Compound (I-1) can be produced from compound (20) according to a series of reaction steps from step D-4 to step D-5. Compound (20) can be produced from compound (19) according to step D-1, or from compound (21) according to step D-3. Compound (21) can be produced from compound (19) according to step D-2.

(Step D-1)

Compound (20) can be produced by reacting compound (19) with an alkylating agent. Examples of the alkylating agent include trimethyloxonium tetrafluoroborate, triethyloxonium tetrafluoroborate and the like. The amount of the alkylating agent to be used is about 1-10 mol, preferably about 1-2 mol, per 1 mol of compound (19). This reaction is advantageously performed using a solvent inert to the reaction. Such solvent is not particularly limited as long as the reaction proceeds and, for example, a solvent such as ethers, aromatic hydrocarbons, saturated hydrocarbons, halogenated hydrocarbons, nitriles, sulfoxides and the like or a mixed solvent thereof and the like are preferable. While the reaction time varies depending on the reagent and solvent to be used, it is generally 10 min-100 hr, preferably 10 min-24 hr. The reaction temperature is generally –100-100° C., preferably 0-100° C.

Compound (20) can also be produces by reacting compound (19) with a halogenating agent. Examples of the halogenating agent include phosphorus oxychloride, thionyl chloride and the like. The amount of the halogenating agent to be used is not less than about 1-100 mol, per 1 mol of compound (19). This reaction is advantageously performed without solvent or using a solvent inert to the reaction. Such solvent is not particularly limited as long as the reaction proceeds and, for example, a solvent such as ethers, aromatic hydrocarbons, saturated hydrocarbons, halogenated hydrocarbons, nitriles, sulfoxides and the like or a mixed solvent thereof and the like are preferable. While the reaction time varies depending on the reagent and solvent to be used, it is generally 10 min -100 hr, preferably 10 min-24 hr. The reaction temperature is generally 0-250° C., preferably 20-150° C.

(Step D-2)

Compound (21) can be produced by reacting compound (19) with a thiocarbonylating agent. Examples of the thiocarbonylating agent include Lawesson's reagent and the like. The amount of the thiocarbonylating agent to be used is about 0.5-10 mol, preferably about 0.5-2 mol, per 1 mol of compound (19). This reaction is advantageously performed using a solvent inert to the reaction. Such solvent is not particularly limited as long as the reaction proceeds and, for example, a solvent such as ethers, aromatic hydrocarbons, saturated hydrocarbons, halogenated hydrocarbons, nitriles, sulfoxides and the like or a mixed solvent thereof and the like are preferable. While the reaction time varies depending on the reagent and solvent to be used, it is generally 10 min -100 hr, preferably 10 min-24 hr. The reaction temperature is generally 0-250° C., preferably 20-150° C.

(Step D-3)

to Compound (20) can be produced by reacting compound (21) with an alkylating agent. Examples of the alkylating agent include iodomethane, iodoethane and the like. The amount of the alkylating agent to be used is about 1-10 mol, preferably about 1-2 mol, per 1 mol of compound (21). This reaction is advantageously performed using a solvent inert to the reaction. Such solvent is not particularly limited as long as the reaction proceeds and, for example, a solvent such as ethers, aromatic hydrocarbons, saturated hydrocarbons, halogenated hydrocarbons, nitriles, sulfoxides, esters, ketones and the like or a mixed solvent thereof and the like are preferable. While the reaction time varies depending on the reagent and solvent to be used, it is generally 10 min-100 hr, preferably 10 min-24 hr. The reaction temperature is generally –100-100° C., preferably 0-100° C.

(Step D-4)

Compound (22) can be produced by reacting compound (20) with compound (4). The amount of compound (4) to be used is about 1-10 mol, preferably about 1-2 mol, per 1 mol of compound (20). This reaction is advantageously performed using a solvent inert to the reaction. Such solvent is not particularly limited as long as the reaction proceeds and, for example, a solvent such as ethers, aromatic hydrocarbons, saturated hydrocarbons, halogenated hydrocarbons, nitriles, sulfoxides, alcohols and the like or a mixed solvent thereof and the like are preferable. While the reaction time varies depending on the reagent and solvent to be used, it is generally 10 min-100 hr, preferably 10 min-24 hr. The reaction temperature is generally 20-250° C., preferably 20-150° C.

(Step D-5)

Compound (I-1) can be produced by reacting compound (22) with a compound represented by $LG^9$-$R^2$ in the presence of a base. The reaction may be performed in the same manner as in step A-5.

Compound (I-1) can also be produced by reacting compound (22) with a carbonyl compound in the presence of a base. The reaction may be performed in the same manner as in step A-5.

Compound (I-1) can also be produced by reacting compound (22) with oxygen in the presence of a base. The reaction may be performed in the same manner as in step A-5.

Compound (I-1) can also be produced by reacting compound (22) with a halogenating agent in the presence of a base. Examples of the base include inorganic bases, basic salts, organic bases, metal alkoxides, alkali metal hydrides and the like. The amount of the base to be used is about 1-10 mol, preferably about 1-2 mol, per 1 mol of compound (22). Examples of the halogenating agent include halogen, N-bromosuccinimide (NBS), N-chlorosuccinimide (NCS), N-fluoro-N'-chloromethyltriethylenediamine bis(tetrafluoroborate) and the like. The amount of the halogenating agent to be used is about 1-10 mol, preferably about 1-2 mol, per 1 mol of compound (22). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 10 min-24 hr. The reaction temperature is generally −100-100° C., preferably −78-50° C.

Compound (I-1) can also be produced by reacting compound (22) with a chlorinating agent. Examples of the chlorinating agent include sulfuryl chloride and the like. The amount of the chlorinating agent to be used is about 1-10 mol, preferably about 1-5 mol, per 1 mol of compound (22). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 10 min-24 hr. The reaction temperature is generally −100-100° C., preferably −78-50° C.

Compound (I-1) can be further converted to a desired compound by a known substituent conversion reaction, condensation reaction, oxidation reaction, reduction reaction and the like, conducted individually or by a combination of two or more thereof. These reactions can be carried out, for example, according to the method described in Shin Jikken Kagaku Koza (Courses in Experimental Chemistry), vols. 14 and 15(edited by the Chemical Society of Japan); ORGANIC FUNCTIONAL GROUP PREPARATIONS, 2nd edition, Academic Press (ACADEMIC PRESS, INC.), 1989; Comprehensive Organic Transformations (VCH Publishers Inc.), 1989, and the like, or a method analogous thereto. For example, when $R^1$ is an optionally substituted $C_{1-6}$ alkoxycarbonyl group, the group can be converted to the desired tertiary alcohol group by reacting with Grignard reagent, and when -L-$R^2$ is a halogen atom, a desired Compound (I-1), which is a compound wherein -L- is —O— can be obtained by a converting reaction using the corresponding compound represented by $R^2$—OH.

Compounds (4), (19), (20), (21) and (22) may be commercially available products, or can also be produced by a method known per se or a method analogous thereto.

Production Method E:

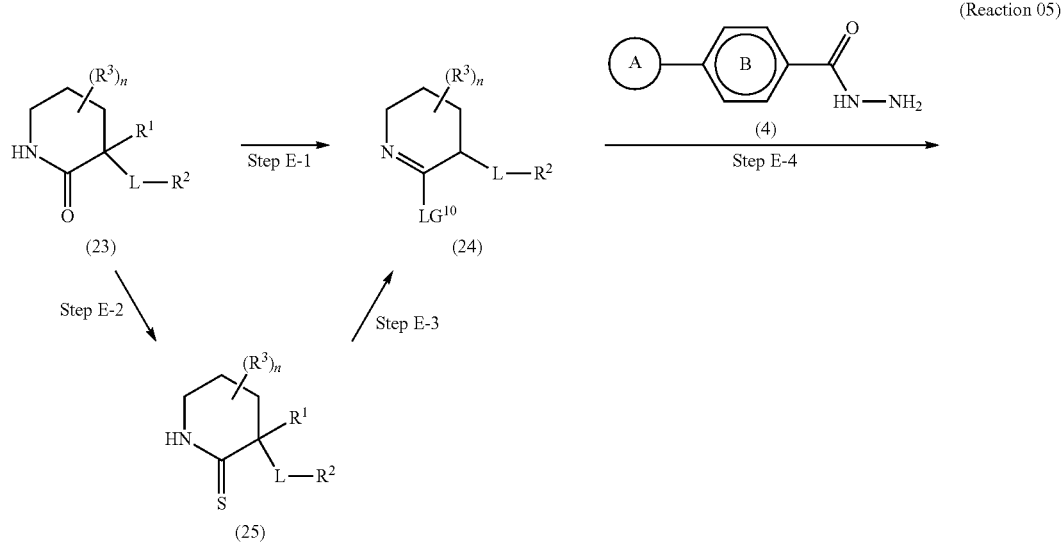

(Reaction 05)

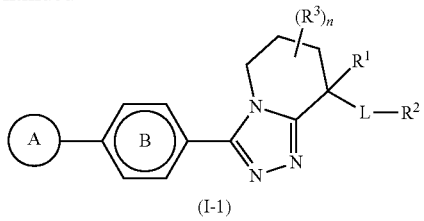

(I-1)

wherein each symbol is as defined above.

Compound (I-1) can be produced from compound (24) according to step E-4. Compound (24) can be produced from compound (23) according to step E-1, or from compound (25) according to step E-3. Compound (25) can be produced from compound (23) according to step E-2.

(Step E-1)

Compound (24) can be produced by reacting compound (23) with an alkylating agent. The reaction may be performed in the same manner as in step D-1.

Compound (24) can also be produced by reacting compound (23) with a halogenating agent. The reaction may be performed in the same manner as in step D-1.

(Step E-2)

Compound (25) can be produced by reacting compound (23) with a thiocarbonylating agent. The reaction may be performed in the same manner as in step D-2.

(Step E-3)

Compound (24) can be produced by reacting compound (25) with an alkylating agent. The reaction may be performed in the same manner as in step D-3.

(Step E-4)

Compound (I-1) can be produced by reacting compound (24) with compound (4). The reaction may be performed in the same manner as in step D-4.

Compound (I-1) can be further converted to a desired compound by a known substituent conversion reaction, condensation reaction, oxidation reaction, reduction reaction and the like, conducted individually or by a combination of two or more thereof. These reactions can be carried out, for example, according to the method described in Shin Jikken Kagaku Koza (Courses in Experimental Chemistry), vols. 14 and 15(edited by the Chemical Society of Japan); ORGANIC FUNCTIONAL GROUP PREPARATIONS, 2nd edition, Academic Press (ACADEMIC PRESS, INC.), 1989; Comprehensive Organic Transformations (VCH Publishers Inc.), 1989, and the like, or a method analogous thereto. For example, when $R^1$ is an optionally substituted $C_{1-6}$ alkoxycarbonyl group, the group can be converted to a desired tertiary alcohol group by reacting with the corresponding Grignard reagent, and when -L-$R^2$ is a halogen atom, a desired Compound (I-1), which is a compound wherein -L- is —O— can be obtained by a converting reaction using the corresponding compound represented by $R^2$—OH.

Compounds (4), (23), (24) and (25) may be commercially available products, or can also be produced by a method known per se or a method analogous thereto. Compound (23) can also be produced according to the method described in JOURNAL OF THE AMERICAN CHEMICAL SOCIETY, page 737 (1959) and the like, or a method analogous thereto.

Production Method F:

(Reaction 06)

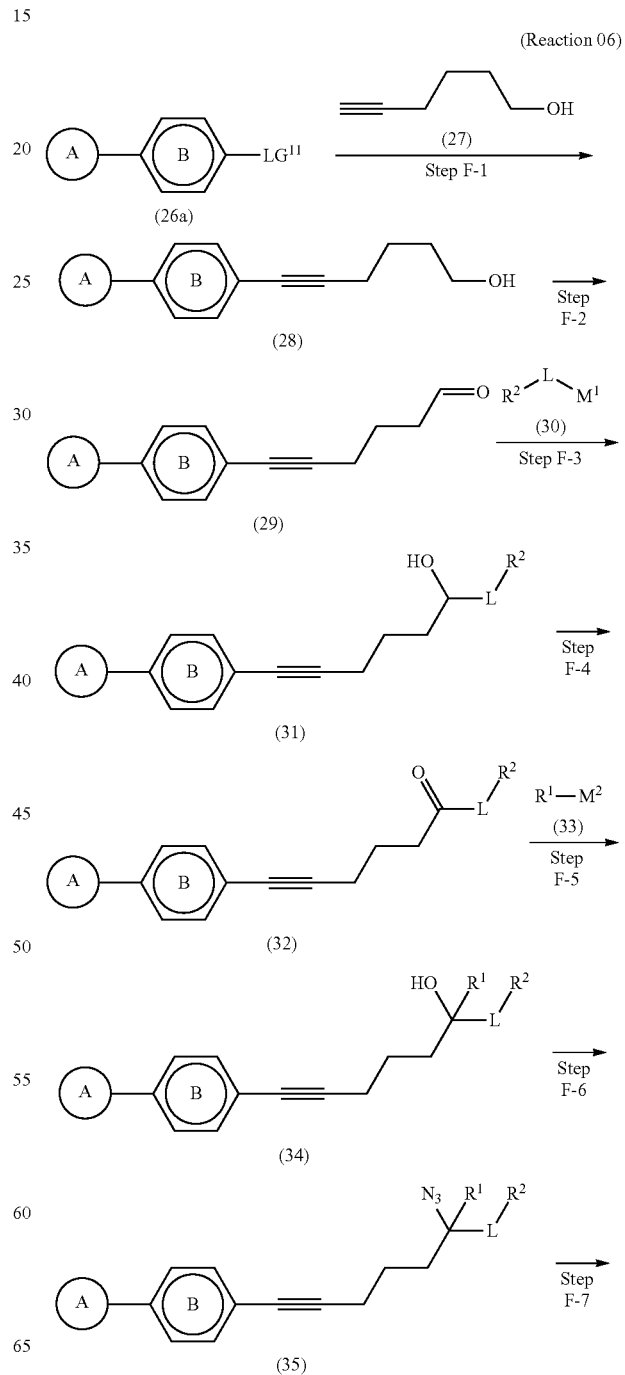

-continued

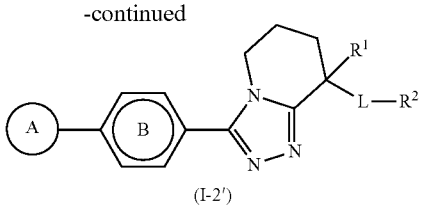

(I-2')

wherein each of $M^1$ and $M^2$ is a moiety consisting of an magnesium atom and a halogen atom (e.g., a bromine atom) of a Grignard reagent, or a lithium atom moiety of an organic lithium reagent; and other symbols are as defined above.

In compounds (1), a compound (to be referred to as compound (I-2)) wherein partial structure (1):

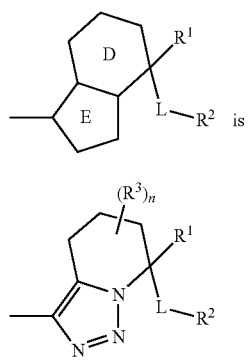

can be produced from compound (26a) according to a series of reaction steps from step F-1 to step F-7. In the above-mentioned reaction scheme, a structure wherein n is 0 is shown as an example. When n is 1-6, the corresponding starting compound wherein $R^3$ in the number of n has been introduced can be used, or $R^3$ in the number of n may be introduced into predetermined positions during the production step.

(Step F-1)

Compound (28) can be produced by condensing compound (26a) with 5-hexyn-1-ol (27) in the presence of an organic base and a metal catalyst. The amount of the organic base to be used is not less than about 1 mol, per 1 mol of compound (26a), and an organic base can also be used as a solvent. Examples of the metal catalyst include a combination of a palladium compound [e.g., dichlorobis(triphenylphosphine) palladium(II), palladium(II) acetate, tetrakis(triphenylphosphine)palladium(0), dichlorobis(triethylphosphine)palladium(II), tris(dibenzylideneacetone)dipalladium(0), 1,1'-bis (diphenylphosphino)ferrocene palladium(II) chloride, a complex with palladium(II) acetate and 1,1'-bis(diphenylphosphino)ferrocene etc.] with a copper compound [e.g., copper(I) iodide etc.]. The amount of the metal catalyst to be used is about 0.000001-5 mol, preferably about 0.0001-1 mol, per 1 mol of compound (26a). When a metal catalyst unstable to oxygen is used in this reaction, for example, the reaction is preferably performed in an inactive gas stream such as argon gas, nitrogen gas and the like. This reaction is advantageously performed without solvent or using a solvent inert to the reaction. Such solvent is not particularly limited as long as the reaction proceeds and, for example, a solvent such as organic bases, alcohols, ethers, aromatic hydrocarbons, saturated hydrocarbons, amides, halogenated hydrocarbons, nitriles, esters, water and the like or a mixed solvent thereof and the like are preferable. While the reaction time varies depending on the reagent and solvent to be used, it is generally 10 min-100 hr, preferably 10 min -24 hr. The reaction temperature is generally 0-250° C., preferably 20-150° C. In addition, microwave may be irradiated to promote the reaction.

(Step F-2)

Compound (29) can be produced by subjecting compound (28) to an oxidization reaction. The oxidation reaction may be performed according to, for example, a method described in Shin Jikken Kagaku Koza (Courses in Experimental Chemistry), vols. 14, 15 (The Chemical Society of Japan ed.); ORGANIC FUNCTIONAL GROUP PREPARATIONS, 2nd edition, Academic Press (ACADEMIC PRESS, INC.), 1989; Comprehensive Organic Transformations (VCH Publishers Inc.), 1989 and the like.

(Step F-3)

Compound (31) can be produced by reacting compound (29) with organic metal reagent (30). Examples of the organic metal reagent include Grignard reagents, organic lithium reagents and the like. The amount of the organic metal reagent to be used is about 1-10 mol, preferably about 1-2 mol, per 1 mol of compound (29). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 10 min-24 hr. The reaction temperature is generally –100-100° C., preferably –78-50° C.

(Step F-4)

Compound (32) can be produced by subjecting compound (31) to an oxidization reaction. The oxidation reaction may be performed according to, for example, a method described in Shin Jikken Kagaku Koza (Courses in Experimental Chemistry), vols. 14, 15 (The Chemical Society of Japan ed.); ORGANIC FUNCTIONAL GROUP PREPARATIONS, 2nd edition, Academic Press (ACADEMIC PRESS, INC.), 1989; Comprehensive Organic Transformations (VCH Publishers Inc.), 1989 and the like.

(Step F-5)

Compound (34) can be produced by reacting compound (32) with organic metal reagent (33). The reaction may be performed in the same manner as in step F-3.

(Step F-6)

Compound (35) can be produced by reacting compound (34) with an azidation agent in the presence of acid. Examples of the acid include Lewis acids, inorganic acids, organic acids and the like. The amount of the acid to be used is about 0.1-20 mol, preferably about 1-5 mol, per 1 mol of compound (34). Examples of the azidation agent include trimethylsilylazide, sodium azide and the like. The amount of the azidation agent to be used is about 1-20 mol, preferably about 1-5 mol, per 1 mol of compound (34). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 10 min-24 hr. The reaction temperature is generally 0-250° C., preferably 20-150° C.

(Step F-7)

Compound (I-2') can be produced by subjecting compound (35) to an intramolecular cyclization reaction. This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 10 min-24 hr. The reaction temperature is generally 0-250° C., preferably 20-150° C.

Compound (I-2') can also be directly produced from compound (34) according to step F-6.

Compounds (26a), (27), (28), (29), (30), (31), (32), (33), (34) and (35) may be commercially available products, or can also be produced by a method known per se or a method analogous thereto. Compound (26a) is encompassed in the below-mentioned compound (26), and can also be produced according to the following production method H. Compound (30) and compound (33) can also be produced according to the method described in Shin Jikken Kagaku Koza (Courses in Experimental Chemistry), vol. 12 (The Chemical Society of Japan ed.) and the like, or a method analogous thereto.

Production Method G:

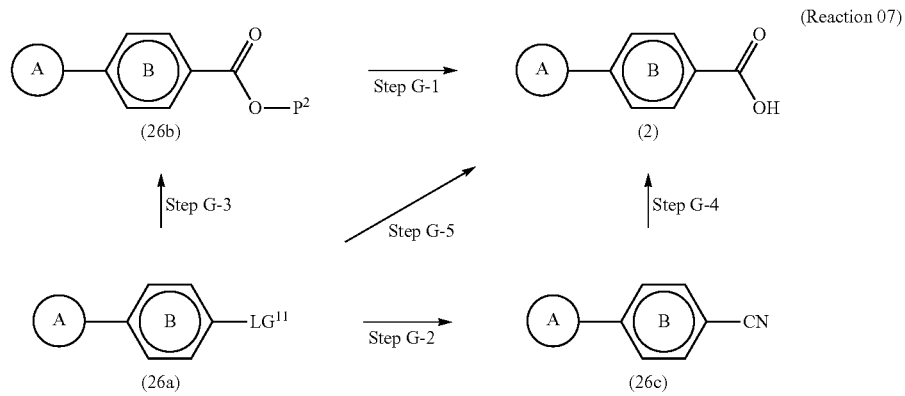

(Reaction 07)

wherein each symbol is as defined above.

Compound (2) can be produced from compound (26b) according to step G-1, from compound (26c) according to step G-4, or from compound (26a) according to step G-5. Compound (26b) can be produced from compound (26a) according to step G-3, and compound (26c) can be produced from compound (26a) according to step G-2.

(Step G-1)

Compound (2) can be produced by removing a protecting group of compound (26b). Removal of a protecting group can be performed according to a method known per se, for example, the method described in Wiley-Interscience Inc., 1999, "Protective Groups in Organic Synthesis, 3rd Ed." (Theodora W. Greene, Peter G. M. Wuts) and the like.

(Step G-4)

Compound (2) can be produced by subjecting compound (26c) to hydrolysis. The reaction can also be performed in the presence of an acid or a base to promote the reaction. Examples of the acid include acid chlorides such as acetyl chloride and the like, inorganic acids, organic acids, Lewis acids and the like. Examples of the base include inorganic bases, basic salts, organic bases, metal alkoxides and the like. The amount of the acid to be used is about 0.01-100 mol, preferably about 0.1-20 mol, per 1 mol of compound (26c). The amount of the base to be used is about 0.01-100 mol, preferably about 0.1-20 mol, per 1 mol of compound (26c). The solvent is not particularly limited as long as the reaction proceeds and, for example, water or a mixed solvent of water and alcohols, ethers, aromatic hydrocarbons, saturated hydrocarbons, amides, halogenated hydrocarbons, sulfoxides, ketones, aromatic organic bases or the like is preferable. While the reaction time varies depending on the reagent and solvent to be used, it is generally 10 min-50 hr, preferably 30 min-20 hr. The reaction temperature is generally 0-200° C., preferably 0-140° C.

(Step G-5)

Compound (2) can be produced by reacting compound (26a) with carbon dioxide in the presence of a base. The amount of the carbon dioxide to be used is not less than about 1 mol, per 1 mol of compound (26a), and the reaction can also be performed in a carbon dioxide stream. Dry ice can also be used as a carbon dioxide source. Examples of the base include alkali metal hydrides, metal amides, organic lithiums and the like. The amount of the base to be used is about 1-2 mol, preferably about 1-1.5 mol, per 1 mol of compound (26a). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min -100 hr, preferably 30 min-24 hr. The reaction temperature is generally −100-100° C., preferably −78-50° C.

Compound (2) can also be produced by reacting compound (26a) with carbon monoxide in the presence of a metal catalyst and water. The amount of carbon monoxide to be used is not less than about 1 mol, per 1 mol of compound (26a), and the reaction can also be performed in a carbon monoxide stream. The amount of water to be used is not less than about 1 mol, per 1 mol of compound (26a), and water can also be used as a solvent. As the metal catalyst, palladium compound [e.g., palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, a complex of palladium(II) acetate with 1,1'-bis(diphenylphosphino)ferrocene etc.] are preferable. The reaction is generally performed in the presence of a base. Examples of the base include inorganic bases, organic bases, basic salts and the like. The amount of the metal catalyst to be used is about 0.000001-5.0 mol, preferably about 0.0001-1.0 mol, per 1 mol of compound (26a). The amount of the base to be used is about 1.0-20 mol, preferably about 1-5 mol, per 1 mol of compound (26a). This reaction is advantageously performed using a solvent inert to the reaction. Such solvent is not particularly limited as long as the reaction proceeds and, for example, a solvent such as alcohols, ethers, aromatic hydrocarbons, saturated hydrocarbons, amides, halogenated hydrocarbons, nitriles, esters and the like or a mixed solvent thereof and the like are preferable. While the reaction time varies depending on the reagent and solvent to be used, it is generally 1 min-200 hr, preferably 5 min-100 hr. The reaction temperature is −10-200° C., preferably 0-100° C. In addition, microwave may be irradiated to promote the reaction.

(Step G-3)

Compound (26b) can be produced by reacting compound (26a) with alkyl chlorocarbonate or dialkyl carbonate in the presence of a base. Examples of the alkyl chlorocarbonate include methyl chlorocarbonate, ethyl chlorocarbonate and the like. Examples of the dialkyl carbonate include dimethyl carbonate, diethyl carbonate and the like. The amount of alkyl chlorocarbonate or dialkyl carbonate to be used is about 1-10 mol, preferably about 1-2 mol, per 1 mol of compound (26a). Examples of the base include alkali metal hydrides, metal amides, organic lithiums and the like. The amount of the base to be used is about 1-2 mol, preferably about 1-1.5 mol, per 1 mol of compound (26a). This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 30 min-24 hr. The reaction temperature is generally −100-100° C., preferably −78-50° C.

Compound (26b) can also be produced by reacting compound (26a) with carbon monoxide in the presence of a metal catalyst and an alcohol. The amount of carbon monoxide to be used is not less than about 1 mol, per 1 mol of compound (26a), and the reaction can be performed in a carbon monoxide stream. Examples of the alcohol include methanol, ethanol and the like. The amount of the alcohol to be used is not less than about 1 mol, per 1 mol of compound (26a), and an alcohol can also be used as a solvent. As the metal catalyst, palladium compounds [e.g., palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium (0), 1,1'-bis(diphenylphosphino)ferrocene palladium(II) chloride, a complex of palladium(II) acetate with 1,1'-bis (diphenylphosphino)ferrocene etc.] are preferable. The reaction is generally performed in the presence of a base. Examples of the base include inorganic bases, organic bases, basic salts and the like. The amount of the metal catalyst to be used is about 0.000001-5.0 mol, preferably about 0.0001-1.0 mol, per 1 mol of compound (26a). The amount of the base to be used is about 1.0-20 mol, preferably about 1-5 mol, per 1 mol of compound (26a). This reaction is advantageously performed using a solvent inert to the reaction. Such solvent is not particularly limited as long as the reaction proceeds and, for example, a solvent such as alcohols, ethers, aromatic hydrocarbons, saturated hydrocarbons, amides, halogenated hydrocarbons, nitriles, esters and the like or a mixed solvent thereof and the like are preferable. While the reaction time varies depending on the reagent and solvent to be used, it is generally 1 min-200 hr, preferably 5 min-100 hr. The reaction temperature is −10-200° C., preferably 0-100° C. In addition, microwave may be irradiated to promote the reaction.

(Step G-2)

Compound (26c) can be produced by reacting compound (26a) with cyanide in the presence of a metal catalyst. Examples of the cyanide include sodium cyanide, potassium cyanide, zinc cyanide, potassium hexacyanoferrate(II) and the like. The amount of cyanide to be used is about 0.8-10 mol, preferably about 1-5 mol, per 1 mol of compound (26a). As the metal catalyst, metal complexes having various ligands are used, and examples thereof include palladium compounds [e.g., palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis (diphenylphosphino)ferrocene palladium(II) chloride, a complex of palladium(II) acetate with 1,1'-bis(diphenylphosphino)ferrocene etc.], nickel compounds [e.g., tetrakis(triphenylphosphine)nickel(0), bis(triethylphosphine)nickel(II) chloride, bis(triphenylphosphine)nickel(II) chloride etc.], copper compounds [e.g., copper oxide, copper(I) iodide, copper sulfate, copper(II) chloride etc.] and the like. The amount of the metal catalyst to be used is about 0.0001-5 mol, preferably about 0.001-1 mol, per 1 mol of compound (26a). This reaction is preferably performed in the presence of a base. Examples of the base include inorganic bases, organic bases, metal alkoxides, alkali metal hydrides, metal amides, basic salts and the like. The amount of the base to be used is about 1.0-20 mol, preferably about 1-5 mol, per 1 mol of compound (26a). In this reaction, zinc can be also used as an additive. The amount of zinc to be used is about 0.0001-5 mol, preferably about 0.001-1 mol, per 1 mol of compound (26a). When a metal catalyst unstable to oxygen is used in this reaction, for example, the reaction is preferably performed in an inactive gas stream such as argon gas, nitrogen gas and the like. This reaction is advantageously performed using a solvent inert to the reaction. Such solvent is not particularly limited as long as the reaction proceeds and, for example, a solvent such as alcohols, ethers, aromatic hydrocarbons, saturated hydrocarbons, amides, nitriles, sulfoxides, esters, water and the like or a mixed solvent thereof and the like are preferable. While the reaction time varies depending on the reagent and solvent to be used, it is generally 10 min-100 hr, preferably 30 min-50 hr. The reaction temperature is −10-250° C., preferably 50-150° C. In addition, microwave may be irradiated to promote the reaction.

Compounds (26a), (26b), and (26c) may be commercially available products, or can also be produced by a method known per se or a method analogous thereto. In addition, compounds (26a), (26b) and (26c) are encompassed in the below-mentioned compound (26), and can also be produced according to the following production method H.

Production Method of Compound (26), and, for Example, Compounds (26d), (26e), (26f), (26g), (26h) etc. of Compound (26)

Compound (26d) is, of compound (26), a compound wherein ring A is an oxazole ring (which is bonded to ring B at the 5-position of the oxazole ring), compounds (26e) and (26f) are, of compound (26), compounds wherein ring A is an oxazole ring optionally having $C_{1-6}$ alkyl group(s) optionally having substituent(s) (which is bonded to ring B at the 5-position of the oxazole ring), compound (26g) is, of compound (26), a compound wherein ring A is a 1,2,4-triazole ring optionally having $C_{1-6}$ alkyl group(s) optionally having substituent(s) (which is bonded to ring B at the 1-position of the triazole ring), and compound (26h) is, of compound (26), a compound wherein ring A is an imidazole ring optionally having $C_{1-6}$ alkyl group(s) optionally having substituent(s) (which is bonded to ring B at the 1-position of the imidazole ring).

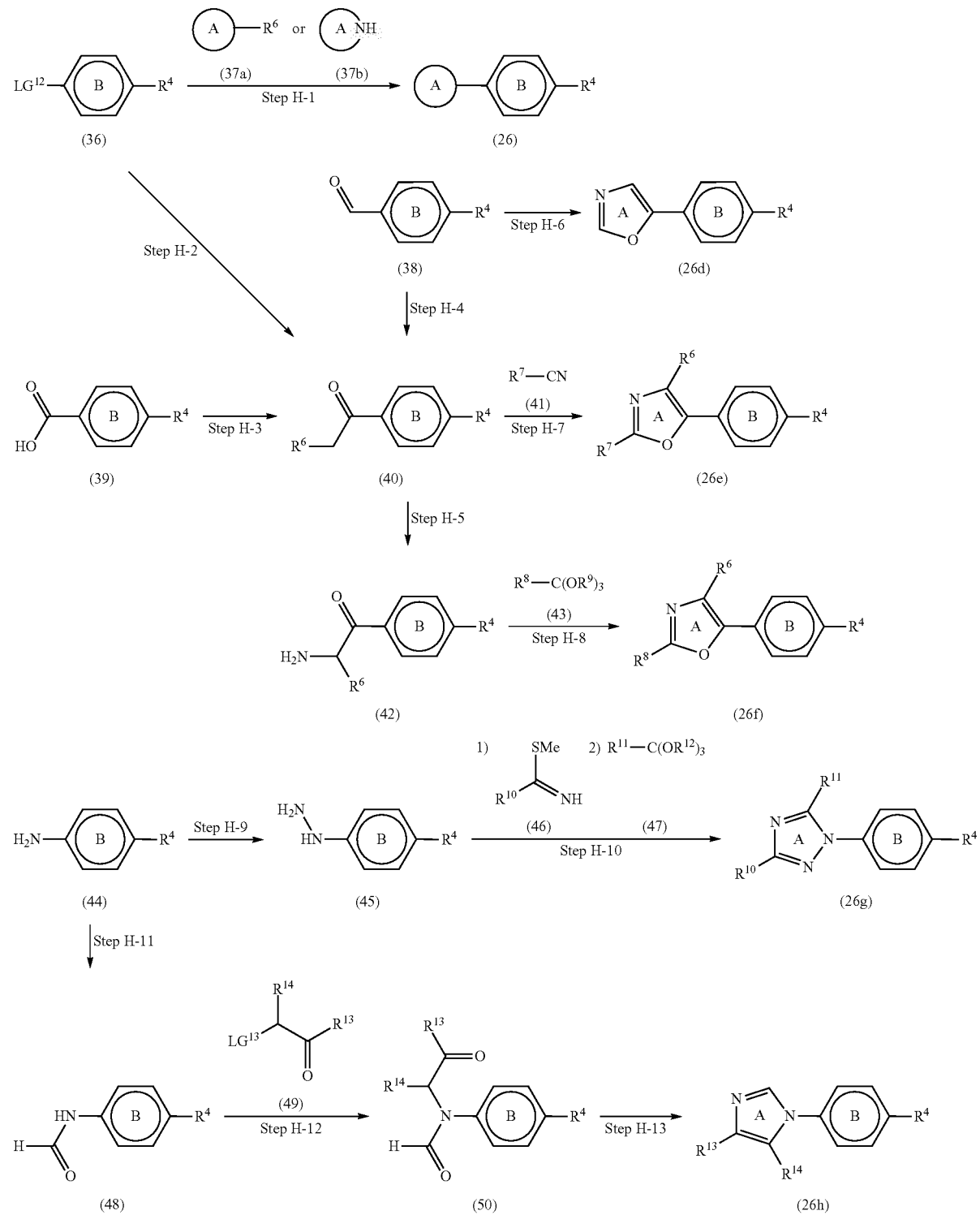

wherein —$R^4$ is a substituent such as —$COOP^2$, -$LG^{11}$, —CN and the like; $R^5$ is a boranyl group optionally having substituent(s), a tri-$C_{1-6}$ alkylstannyl group, a hydrogen atom and the like; each of $R^6$-$R^{14}$ is a $C_{1-6}$ alkyl group optionally having substituent(s) or a hydrogen atom; and other symbols are as defined above.

Compound (26) can be produced from compound (36) according to step H-1.

(Step H-1)

Compound (26) can be produced by condensing compound (36) with compound (37a). As the "boranyl group optionally having substituent(s)" for $R^5$, a dihydroxyboranyl group, a 4,4,5,5-tetramethyl-1,3,2-dioxaborolan-2-yl group and the like are preferable, and as the "tri-$C_{1-6}$ alkylstannyl group" for $R^5$, a tributylstannyl group and the like are preferable. The condensation reaction is performed by reacting compound (36) with compound (37a) in the presence of a metal catalyst. As the metal catalyst, palladium compounds [e.g., palladium (II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, a complex of palladium(II) acetate with 1,1'-bis(diphenylphosphino)ferrocene etc.] are preferable. The reaction is generally performed in the presence of a base. Examples of the base include inorganic bases, basic salts and the like. The amount of compound (37a) to be used is about 0.1-10 mol, preferably about 0.8-2 mol, per 1 mol of compound (36). The amount of the metal catalyst to be used is about 0.000001-5.0 mol, preferably about 0.0001-1.0 mol, per 1 mol of compound (36). The amount of the base to be used is about 1-20 mol, preferably about 1-5 mol, per 1 mol of compound (36). When a metal catalyst unstable to oxygen is used in these reactions, for example, the reaction is preferably performed in an inactive gas stream such as argon gas, nitrogen gas and the like. This reaction is advantageously performed using a solvent inert to the reaction. Such solvent is not particularly limited as long as the reaction proceeds and, for example, a solvent such as alcohols, ethers, aromatic hydrocarbons, saturated hydrocarbons, amides, halogenated hydrocarbons, nitriles, esters, water and the like or a mixed solvent thereof and the like are preferable. While the reaction time varies depending on the reagent and solvent to be used, it is generally 1 min-200 hr, preferably 5 min-100 hr. The reaction temperature is –10-250° C., preferably 0-150° C. In addition, microwave may be irradiated to promote the reaction.

Compound (26) can also be produced by condensing compound (36) with compound (37b) in the presence of a metal catalyst. As the metal catalyst, metal complexes having various ligands are used, and examples thereof include palladium compounds [e.g., palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, a complex of palladium(II) acetate with 1,1'-bis(diphenylphosphino)ferrocene, a complex of tris(dibenzylideneacetone)dipalladium(0) with 2-dicyclohexylphosphino-2'-(N,N-dimethylamino)biphenyl (DavePhos) or 2-dicyclohexylphosphino-2',4',6'-triisopropylbiphenyl (XPhos) etc.], nickel compounds [e.g., tetrakis(triphenylphosphine)nickel(0), bis(triethylphosphine)nickel(II) chloride, bis(triphenylphosphine)nickel(II) chloride etc.], rhodium compounds [e.g., tris(triphenylphosphine)rhodium(III) chloride etc.], cobalt compounds, copper compounds [e.g., copper oxide, copper(I) iodide, copper sulfate, copper (II) chloride etc.], platinum compounds and the like. Of them, palladium compounds and copper compounds are preferable. The amount of compound (37b) to be used is about 0.8-10 mol, preferably about 1-3 mol, per 1 mol of compound (36). The amount of the metal catalyst to be used is about 0.0001-5 mol, preferably about 0.001-1 mol, per 1 mol of compound (36). This reaction is preferably performed in the presence of a base. Examples of the base include inorganic bases, organic bases, metal alkoxides, alkali metal hydrides, metal amides and the like. The amount of the base to be used is about 1-20 mol, preferably about 1-5 mol, per 1 mol of compound (36). When a metal catalyst unstable to oxygen is used in this reaction, for example, the reaction is preferably performed in an inactive gas stream such as argon gas, nitrogen gas and the like. This reaction is advantageously performed using a solvent inert to the reaction. Such solvent is not particularly limited as long as the reaction proceeds and, for example, a solvent such as alcohols, ethers, aromatic hydrocarbons, saturated hydrocarbons, amides, nitriles, sulfoxides, esters, water and the like or a mixed solvent thereof and the like are preferable. While the reaction time varies depending on the reagent and solvent to be used, it is generally 10 min-100 hr, preferably 30 min-50 hr. The reaction temperature is –10-250° C., preferably 50-150° C. In addition, microwave may be irradiated to promote the reaction.

Compound (26) can also be produced by condensing compound (36) with compound (37b). The amount of compound (37b) to be used is about 1-20 mol, preferably about 1-5 mol, per 1 mol of compound (36). The reaction can also be performed in the presence of a base to promote the reaction. Examples of the base include inorganic bases, basic salts, organic bases, metal alkoxides, alkali metal hydrides, metal amides, organic lithiums and the like. The amount of the base to be used is about 1-20 mol, preferably about 1-3 mol, per 1 mol of compound (36). This reaction is advantageously performed using a solvent inert to the reaction. Such solvent is not particularly limited as long as the reaction proceeds and, for example, a solvent such as alcohols, ethers, aromatic hydrocarbons, saturated hydrocarbons, amides, halogenated hydrocarbons, nitriles, sulfoxides, esters, ketones, aromatic organic bases, water and the like or a mixed solvent thereof and the like are preferable. While the reaction time varies depending on the reagent and solvent to be used, it is generally 10 min-100 hr, preferably 30 min-50 hr. The reaction temperature is generally 0-250° C., preferably 0-200° C. In addition, microwave may be irradiated to promote the reaction.

Compound (26d) can be produced from compound (38) according to step H-6, compound (26e) can be produced from compound (40) according to step H-7, and compound (26f) can be produced from compound (42) according to step H-8.

(Step H-6)

Compound (26d) can be produced by subjecting compound (38) to a condensation reaction with 1-[(isocyanomethyl)sulfonyl]-4-methylbenzene in the presence of a base. Examples of the base include inorganic bases, basic salts, organic bases, metal alkoxides and the like. The amount of the base to be used is about 0.8-20 mol, preferably about 1-5 mol, per 1 mol of compound (38). The amount of 1-[(isocyanomethyl)sulfonyl]-4-methylbenzene to be used is about 0.8-20 mol, preferably about 1-5 mol, per 1 mol of compound (38). This reaction is advantageously performed using a solvent inert to the reaction. Such solvent is not particularly limited as long as the reaction proceeds and, for example, a solvent such as alcohols, ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-50 hr, preferably 1 hr-24 hr. The reaction temperature is generally −20-200° C., preferably 0-100° C.

(Step H-7)

Compound (26e) can be produced by subjecting compound (40) and compound (41) to a condensation reaction in the presence of an oxidant and an acid. Examples of the oxidant include organic peracids such as perbenzoic acid, m-chloroperbenzoic acid (MCPBA), peracetic acid and the like, perchlorates such as lithium perchlorate, silver perchlorate, tetrabutylammonium perchlorate and the like, periodates such as iodobenzene diacetate, sodium periodate, Dess-Martin periodinane, o-iodooxybenzoic acid (IBX) and the like, manganates such as manganese dioxide, potassium permanganate and the like, leads such as lead tetraacetate and the like, chromates such as pyridinium chlorochromate, pyridinium dichromate and the like, inorganic nitrogen compounds such as acyl nitrate, dinitrogen tetraoxide and the like, halogen compounds such as halogen, N-bromosuccinimide (NBS), N-chlorosuccinimide (NCS) and the like, sulfuryl chloride, chloramine T, oxygen, hydrogen peroxide and the like. The amount of the oxidant to be used is about 0.8-20 mol, preferably about 1-5 mol, per 1 mol of compound (40). Examples of the acid include inorganic acids, organic acids, Lewis acids and the like. The amount of the acid to be used is about 0.8-20 mol, preferably about 1-10 mol, per 1 mol of compound (40). Examples of compound (41) include $C_{1-6}$ alkylnitriles such as acetonitrile, propionitrile and the like, and the like. The amount of compound (41) to be used is not less than about 0.8 mol, per 1 mol of compound (40), and compound (41) can also be used as a solvent. The solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 30 min-48 hr. The reaction temperature is generally −20-200° C., preferably −10-100° C.

(Step H-8)

Compound (26f) can be produced by subjecting compound (42) and compound (43) to a condensation reaction. The reaction can also be performed in the presence of an acid to promote the reaction. Examples of the acid include inorganic acids, organic acids, Lewis acids and the like. The amount of the acid to be used is about 0.001-10 mol, preferably about 0.1-2 mol, per 1 mol of compound (42). Examples of compound (43) include ortho acid esters such as trimethyl orthoacetate, triethyl orthopropionate, trimethyl orthoformate and the like, and the like. The amount of compound (43) to be used is not less than about 0.8 mol, per 1 mol of compound (42), and compound (43) can also be used as a solvent. This reaction is advantageously performed using a solvent inert to the reaction. Such solvent is not particularly limited as long as the reaction proceeds and, for example, a solvent such as alcohols, ethers, aromatic hydrocarbons, saturated hydrocarbons, amides, halogenated hydrocarbons, nitriles, sulfoxides, aromatic organic bases and the like or a mixed solvent thereof and the like are preferable. While the reaction time varies depending on the reagent and solvent to be used, it is generally 10 min -50 hr, preferably 1 hr-24 hr. The reaction temperature is generally −20-200° C., preferably 0-100° C.

Compounds (26d), (26e) and (26f) can also be produced according to a method known per se, for example, the method described in Bioorganic & Medicinal Chemistry Letters, vol. 13, page 2059 (2003) and the like, or a method analogous thereto.

Compound (40) can be produced from compound (36) according to step H-2, from compound (38) according to step H-4, or from compound (39) according to step H-3. Compound (42) can be produced from compound (40) according to step H-5.

(Step H-2)

As step H-2, for example, a method which comprises subjecting compound (36) and tributyl(1-ethoxyvinyl)tin etc. to a condensation reaction, and the like can be used.

(Step H-4)

As step H-4, for example, a method which comprises adding a Grignard reagent represented by $R^6CH_2MgBr$ and the like to an aldehyde group of compound (38), which is then subjected to an oxidation reaction, and the like can be used.

(Step H-3)

As step H-3, for example, a method which comprises converting a carboxy group of compound (39) to a Weinreb amide, which is then subjected to a reaction with a Grignard reagent represented by $R^6CH_2MgBr$ etc., and the like can be used. As the convert reaction of a carboxy group to a Weinreb amide, reaction of compound (39) with N,O-dimethylhydroxylamine hydrochloride can be used. The reaction may be performed in the same manner as in step A-1. The subsequent reaction with a Grignard reagent represented by $R^6CH_2MgBr$ etc. can be performed according to, for example, a method described in Shin Jikken Kagaku Koza (Courses in Experimental Chemistry), vols. 14, 15 (The Chemical Society of Japan ed.); ORGANIC FUNCTIONAL GROUP PREPARATIONS, 2nd edition, Academic Press (ACADEMIC PRESS, INC.), 1989; Comprehensive Organic Transformations (VCH Publishers Inc.), 1989 and the like.

(Step H-5)

As step H-5, for example, a method which comprises reacting compound (40), which is ketone, with a halogenating agent to give α-haloketone, which is then subjected to a reaction with an amination agent etc., and the like can be used.

These reaction can be performed according to, for example, a method described in Shin Jikken Kagaku Koza (Courses in Experimental Chemistry), vols. 14, 15 (The Chemical Society of Japan ed.); ORGANIC FUNCTIONAL GROUP PREPARATIONS, 2nd edition, Academic Press (ACADEMIC PRESS, INC.), 1989; Comprehensive Organic Transformations (VCH Publishers Inc.), 1989 and the like.

Compound (26g) can be produced from compound (44) according to a series of reaction steps of step H-9 and step H-10.

(Step H-10)

Compound (26g) can be produced by condensing compound (45) with compound (46), which is then subjected to a condensation reaction with compound (47). Examples of compound (46) include alkyl imidothioates methyl ethanimidothioate hydroiodide, methyl propanimidothioate hydrochloride and the like, and compound (46) can be produced according to a method known per se, for example, the method described in Indian Journal of Chemistry, Section B: Organic Chemistry Including Medicinal Chemistry, vol. 21, page 272 (1982) and the like, or a method analogous thereto. The amount of compound (46) to be used is about 0.8-10 mol, preferably about 1-5 mol, per 1 mol of compound (45). The solvent in the condensation reaction between compound (45) and compound (46) is not particularly limited as long as the reaction proceeds and, for example, a solvent such as alcohols, ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 5 min-100 hr, preferably 10 min-24 hr. The reaction temperature is generally −20-200° C., preferably −10-100° C. The condensation reaction with compound (47) may be performed in the same manner as in step H-8.

(Step H-9)

Compound (45) can be produced by reacting compound (44) with nitrite in the presence of an acid, which is then subjected to a reduction reaction. Examples of the acid include inorganic acids, organic acids, Lewis acids and the like. The amount of the acid to be used is not less than about 0.01 mol, per 1 mol of compound (44), and an acid can also be used as a solvent. Examples of nitrites include nitrite salts such as sodium nitrite, potassium nitrite and the like, nitrite esters such as isoamyl nitrite and the like, and the like. The amount of nitrite to be used is about 0.8-10 mol, preferably about 1-5 mol, per 1 mol of compound (44). Examples of the reducing agent include reducing agents such as tin chloride and the like, and the like. The amount of the reducing agent to be used is about 0.8-20 mol, preferably about 1-10 mol, per 1 mol of compound (44). The solvent in the reaction with nitrite is not particularly limited as long as the reaction proceeds and, for example, a solvent such as inorganic acids, organic acids, alcohols, ethers, amides, nitriles, sulfoxides, water and the like or a mixed solvent thereof and the like are preferable. While the reaction time varies depending on the reagent and solvent to be used, it is generally 5 min-100 hr, preferably 10 min-24 hr. The reaction temperature is generally −30-100° C., preferably −20-80° C. The solvent in the reduction reaction is not particularly limited as long as the reaction proceeds and, for example, a solvent such as inorganic acids, organic acids, alcohols, ethers, amides, nitriles, sulfoxides and the like or a mixed solvent thereof and the like are preferable. While the reaction time varies depending on the reagent and solvent to be used, it is generally 5 min-100 hr, preferably 10 min-24 hr. The reaction temperature is generally −30-100° C., preferably −20-80° C.

Compound (26h) can be produced from compound (44) according to a series of reaction steps of step H-11, step H-12 and step H-13.

(Step H-11)

Compound (48) can be produced by reacting compound (44) with a formylation reagent. Examples of the formylation reagent include N,N-dimethylformamide, N-formylpiperidine, N-formylmorpholine, formates such as ethyl formate and the like, a mixture of formic acid and acetic anhydride, and the like. The amount of the formylation reagent to be used is about 1-100 mol, preferably about 1-30 mol, per 1 mol of compound (44). This reaction is advantageously performed using a solvent inert to the reaction. Such solvent is not particularly limited as long as the reaction proceeds and, for example, a solvent such as ethers, halogenated hydrocarbons, aromatic hydrocarbons, saturated hydrocarbons and the like or a mixed solvent thereof and the like are preferable. While the reaction time varies depending on the reagent and solvent to be used, it is generally 30 min-50 hr, preferably 30 min-24 hr. The reaction temperature is generally 0-200° C., preferably 0-150° C.

(Step H-12)

Compound (50) can be produced by reacting compound (48) with alkylating agent (49) in the presence of a base. Examples of the base include inorganic bases, basic salts, organic bases, metal amides and the like. The amount of the base to be used is about 1-5 mol, preferably about 1-2 mol, per 1 mol of compound (48). The amount of alkylating agent (49) to be used is about 1-5 mol, preferably about 1-2 mol, per 1 mol of compound (48). For example, sodium iodide, potassium iodide and the like can be preferably added to promote the reaction. This reaction is advantageously performed using a solvent inert to the reaction. Such solvent is not particularly limited as long as the reaction proceeds and, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min -100 hr, preferably 30 min-24 hr. The reaction temperature is generally −20-200° C., preferably −10-150° C.

(Step H-13)

Compound (26h) can be produced by subjecting compound (50) to a heat treatment in an acetic acid solvent in the presence of ammonium acetate. The amount of ammonium acetate to be used is about 3-50 mol, preferably about 5-30 mol, per 1 mol of compound (50). The reaction time is generally 10 min-100 hr, preferably 30 min-24 hr. The reaction temperature is generally 0-100° C., preferably 50-100° C.

Compound (26) can also be produced according to a method known per se, for example, the method described in European journal of organic chemistry, vol. 13, p. 2970 (2006), Synthetic communications, vol. 36, page 2927 (2006), Journal of organic chemistry, vol. 44, page 4160 (1979), Journal of the chemical society, page 4251 (1954), WO 2008/77649 and the like, or a method analogous thereto.

Compounds (26), (26d), (26e), (26f), (26g) and (26h) can be further converted to a desired compound by a known substituent conversion reaction, condensation reaction, oxidation reaction, reduction reaction and the like, conducted individually or by a combination of two or more thereof. These reactions can be carried out, for example, according to the method described in Shin Jikken Kagaku Koza (Courses in Experimental Chemistry), vols. 14 and 15 (edited by the Chemical Society of Japan); ORGANIC FUNCTIONAL GROUP PREPARATIONS, 2nd edition, Academic Press (ACADEMIC PRESS, INC.), 1989; Comprehensive Organic Transformations (VCH Publishers Inc.), 1989, and the like or a method analogous thereto. For example, when ring A has one or two halogen atoms, one or two of the halogen atom(s) can be converted to a $C_{1-6}$ alkyloxy group by reacting with a $C_{1-6}$ alkyloxide according to a method known per se, or a method analogous thereto.

Compounds (36), (37a), (37b), (38), (39), (40), (41), (42), (43), (44), (45), (46), (47), (48), (49) and (50) may be commercially available products, or can also be produced by a method known per se or a method analogous thereto.

The compound of the present invention can be produced as any one configuration isomer or stereoisomer, or a mixture thereof. These isomers can be obtained as single products according to synthesis method, separation method (e.g., concentration, solvent extraction, column chromatography, recrystallization etc.), optical resolution method (e.g., fractional recrystallization, chiral column method, diastereomer method etc.) and the like known per se. They can also be converted to a desired isomer by heating, an acid catalyst, a transition metal complex, a metal catalyst, a radical catalyst, photoirradiation, a strong base catalyst and the like according to the method described in Shin Jikken Kagaku Koza (New Experimental Chemistry Course), vol. 14, pp. 251-253 (edited by the Chemical Society of Japan), Jikken Kagaku Kouza, $4^{th}$ Ed. vol. 19, pp. 273-274 (edited by the Chemical Society of Japan) and the like or a method analogous thereto.

Among the aforementioned compounds (2)-(50), those having a configurational isomer can be isolated and purified by, for example, a conventional separation means such as extraction, recrystallization, distillation, chromatography and the like, when isomerization occurs, whereby a pure compound can be produced. In addition, isomerization of double bond may be promoted by heating, acid catalyst, transition metal complex, metal catalyst, radical species catalyst, photoirradiation or strong base catalyst and the like according to the method described in Shin Jikken Kagaku Koza (New Experimental Chemistry Course), vol. 14, pp. 251-253 (edited by the Chemical Society of Japan), Jikken Kagaku Koza (Courses in Experimental Chemistry), 4th Ed., vol. 19, pp. 273-274 (edited by the Chemical Society of Japan) and the like or a method analogous thereto, whereby a corresponding pure isomer can be obtained. While the compound of the present invention has a stereoisomer depending on the kind of the substituent, not only the isomer itself but also a mixture thereof are encompassed in the present invention. In the above-mentioned reaction steps, where desired, the compound of the present invention can be produced by a known hydrolysis, deprotection, acylation reaction, alkylation reaction, hydrogenation reaction, oxidation reaction, reduction reaction, carbon chain extension reaction or substituent exchange reaction, condensation reaction and the like, conducted individually or by a combination of two or more thereof. These reactions can be carried out, for example, according to the method described in Shin Jikken Kagaku Koza (New Experimental Chemistry Course), vols. 14 and 15 (edited by the Chemical Society of Japan); ORGANIC FUNCTIONAL GROUP PREPARATIONS, 2nd edition, Academic Press (ACADEMIC PRESS, INC.), 1989; Comprehensive Organic Transformations (VCH Publishers Inc.), 1989, and the like.

The compound of the present invention can be isolated and purified by a known means, for example, phase transfer, concentration, solvent extraction, fractional distillation, liquid conversion, crystallization, recrystallization, chromatography and the like.

When the compound of the present invention is obtained as a free compound, it can be converted into a desired salt by a method known per se or a modification thereof; conversely, when compound (1) is obtained as a salt, it can be converted into a free form or another desired salt by a method known per se or a modification thereof.

When the compound of the present invention has an isomer such as optical isomer, stereoisomer, positional isomer, rotational isomer and the like, any one isomer and a mixture thereof are also encompassed in the compound of the present invention. For example, when an optical isomer is present in the compound of the present invention, an optical isomer resolved from a racemate is also encompassed in the compound of the present invention. These isomers can be obtained as single products by synthesis method and separation method (e.g., concentration, solvent extraction, column chromatography, recrystallization etc.), optical resolution method (e.g., fractional recrystallization, chiral column method, diastereomer method etc.) and the like known per se.

The compound of the present invention may be a crystal, and both single crystal form and a crystalline mixture are encompassed in the compound of the present invention. The crystal can be produced by crystallization by a crystallization method known per se. The compound of the present invention may be a pharmaceutically acceptable cocrystal or cocrystal salt. Here, the cocrystal and cocrystal salt mean crystalline substances consisting of two or more kinds of distinctive solids at room temperature, each having different physical properties (e.g., structure, melting point, melting heat, hygroscopicity, dissolution property and stability etc.). The cocrystal and cocrystal salt can be produced by a cocrystallization method known per se.

The compound of the present invention may be a solvate (e.g., hydrate etc.) or a non-solvate (e.g., non-hydrate etc.), all of which are also encompassed in the compound of the present invention.

A compound labeled with an isotope (e.g., $^3$H, $^{11}$C, $^{14}$C, $^{18}$F, $^{35}$S, $^{125}$I etc.) and a deuterium converter are also encompassed in the compound of the present invention. The compound of the present invention, which is labeled or substituted with an isotope, can be used, for example, as a tracer (PET tracer) used for positron-emission tomography (PET), and is useful in the field of medical diagnosis etc.

A prodrug of the compound of the present invention means a compound which is converted to the compound of the present invention with a reaction due to an enzyme, gastric acid, etc. under the physiological condition in the living body, that is, a compound which is converted to the compound of the present invention by oxidation, reduction, hydrolysis, etc. according to an enzyme; and a compound which is converted to the compound of the present invention by hydrolysis etc. due to gastric acid, etc.

A prodrug of the compound of the present invention may be a compound obtained by subjecting an amino group in the compound of the present invention to an acylation, alkylation or phosphorylation (e.g., a compound obtained by subjecting an amino group in the compound of the present invention to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxyl group in the compound of the present invention to an acylation, alkylation, phosphorylation or boration (e.g., a compound obtained by subjecting a hydroxyl group in the compound of the present invention to an acetylation, palmitoylation, propanoylation, pivaloylation, succinylation, fumarylation, alanylation or dimethylaminomethylcarbonylation, etc.); a compound obtained by subjecting a carboxy group in the compound of the present invention to an esterification or amidation (e.g., a compound obtained by subjecting a carboxy group in the compound of the present invention to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from the compound of the present invention by a method known per se.

A prodrug for the compound of the present invention may also be one which is converted into the compound of the present invention under a physiological condition, such as those described in IYAKUHIN no KAIHATSU (Development of Pharmaceuticals), Vol. 7 (Design of Molecules), p. 163-198 (HIROKAWA SHOTEN).

The compound of the present invention or a prodrug thereof has a superior amyloid β production inhibitory activity, shows low toxicity (e.g., acute toxicity, chronic toxicity, genetic toxicity, reproductive toxicity, cardiotoxicity, drug interaction, carcinogenicity etc.) and shows superior stability and disposition (absorbability, distribution, metabolism, excretion etc.), and therefore, is useful as a pharmaceutical product. Since the compound of the present invention or a prodrug thereof has an action to inhibit amyloid β production in a mammal (e.g., mouse, rat, hamster, rabbit, cat, dog, bovine, sheep, monkey, human etc.), it can be used as a prophylactic or therapeutic drug for diseases possibly related to amyloid β production. Examples of the "diseases possibly related to amyloid β production" include neurodegenerative diseases (e.g., senile dementia, Alzheimer's disease, Parkinson's disease etc.), memory disorders (e.g., senile dementia, mild cognitive impairment (MCI), amnesia etc.), ischemic central nervous disorders (e.g., cerebral amyloid angiopathy (CAA) etc.), Down's disease and the like.

The compound of the present invention or a prodrug thereof is preferably useful as an amyloid β production inhibitor, or a prophylactic drug or a therapeutic drug for mild cognitive impairment or Alzheimer's disease.

A medicament containing the compound of the present invention or a prodrug thereof (hereinafter to be referred to as the "medicament of the present invention") is obtained as, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, films (e.g., orally disintegrable films, oral cavity mucosa patch film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparations, pulmonary preparation (inhalant), eye drop and the like by using the compound of the present invention or a prodrug thereof alone or along with a pharmacologically acceptable carrier according to a method known per se as a production method of pharmaceutical preparations (e.g., the method described in the Japanese Pharmacopoeia etc.). It can be safely administered orally or parenterally (e.g., intravenous, intramuscular, subcutaneous, intraorgan, intranasal, intradermal, instillation, intracerebral, rectal, vaginal, intraperitoneal, intratumor, tumor proximal administration, direct administration to a lesion and the like).

The content of the compound of the present invention or a prodrug thereof in the medicament of the present invention is about 0.01-100 wt % of the whole medicament. While the dose of the medicament of the present invention varies depending on the subject of administration, administration route, disease, symptom and the like, it is, for example, about 0.001-about 100 mg/kg body weight, preferably about 0.005-about 50 mg/kg body weight, more preferably about 0.01-about 2 mg/kg body weight as the amount of the compound of the present invention or a prodrug thereof, which is the active ingredient, for the treatment of, for example, Alzheimer's disease by oral administration to an adult patient. This amount is desirably administered in about 1 to 3 portions a day according to the symptom.

Examples of the pharmacologically acceptable carrier include various organic or inorganic carrier substances conventionally used as preparation materials. For example, suitable amounts of additives such as excipient, lubricant, binder and disintegrant for solid preparations, or solvent, solubilizing agent, suspending agent, isotonicity agent, buffer and soothing agent for liquid preparations and the like, and where necessary, conventional preservative, antioxidizing agent, colorant, sweetening agent, adsorbent, wetting agent and the like can be used appropriately.

Examples of the excipient include lactose, sucrose, D-mannitol, starch, cornstarch, crystalline cellulose, light anhydrous silicic acid and the like. Examples of the lubricant include magnesium stearate, calcium stearate, talc, colloidal silica and the like. Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose, sodium carboxymethylcellulose and the like. Examples of the disintegrant include starch, carboxymethylcellulose, calcium carboxymethylcellulose, croscarmellose sodium, sodium carboxymethyl starch, L-hydroxypropylcellulose and the like. Examples of the solvent include water for injection, alcohol, propylene glycol, macrogol, sesame oil, corn oil, olive oil and the like. Examples of the solubilizing agents include polyethylene glycol, propylene glycol, D-mannitol, benzyl benzoate, ethanol, trisaminomethane, cholesterol, triethanolamine, sodium carbonate, sodium citrate and the like. Examples of the suspending agent include surfactants such as stearyltriethanolamine, sodium lauryl sulfate, lauryl aminopropionate, lecithin, benzalkonium chloride, benzethonium chloride, glyceryl monostearate etc.; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose etc., and the like. Examples of the isotonicity agent include glucose, D-sorbitol, sodium chloride, glycerol, D-mannitol and the like. Example of the buffer include buffer such as phosphate, acetate, carbonate, citrate etc., and the like. Examples of the soothing agent include benzyl alcohol and the like. Examples of the preservative include p-hydroxybenzoates, chlorobutanol, benzyl alcohol, phenethyl alcohol, dehydroacetic acid, sorbic acid and the like. Examples of the antioxidizing agent include sulfite, ascorbic acid, α-tocopherol and the like.

When the compound of the present invention or a prodrug thereof is applied to each of the above-mentioned diseases, it can be used in appropriate combination with a medicament or a treatment method generally employed for the disease.

In the following, a combined use of the compound of the present invention or a prodrug thereof with a concomitant drug is referred to as "the combination agent of the present invention".

Examples of such concomitant drug include acetylcholinesterase inhibitors (e.g., donepezil, rivastigmine, galanthamine etc.), inhibitors of amyloid β protein production, secretion, accumulation, coagulation and/or deposition, β-secretase inhibitors, amyloid β protein coagulation inhibitors, amyloid β vaccine, amyloid β antibody, amyloid β degrading enzyme etc., brain function activation drugs (e.g., idebenone, memantine, vinpocetine etc.), therapeutic drugs for abnormal behavior, wandering and the like which are developed with the progression of dementia (e.g., sedative, antianxiety agent etc.), drugs for suppression of progression of Alzheimer's disease (Alzhemed etc.), apoptosis inhibitors, neuronal differentiation regeneration promoters, anti-parkinsonian drugs (e.g., L-DOPA, deprenyl, carbidopa+levodopa, pergolide, ropinirole, cabergoline, pramipexole, entacapone, lazabemide etc.), therapeutic agents for amyotrophic lateral sclerosis (e.g., riluzole etc., neurotrophic factor etc.), antidepressants (e.g., fluoxetine, sertraline, paroxetine, venlafaxine, nefazodone, reboxetine, mirtazapine, imipramine hydrochloride, duloxetine, escitalopram, mifepristone, doxepin etc.), antianxiety drugs (e.g., alprazolam, bromazepam, chlordiazepoxide, diazepam, etizolam, flutoprazepam, lorazepam etc.), antiepileptic drugs (e.g., lamotrigine etc.), sleep inducing agents (e.g., GABA system sleep inducing agents such as brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol etc.; non-GABA system sleep inducing agents such as eplivaserin, pruvanserin, diphenhydramine, trazodone, doxepin etc., ramelteon etc.), therapeutic agents for narcolepsy, therapeutic agents for schizophrenia (e.g., olanzapine, risperidone, quetiapine, iloperidone, etc.), anti-obesity drugs, non-steroidal anti-inflammatory drugs (e.g., indomethacin, ibuprofen, acetylsalicylic acid, diclofenac, naproxen, piroxicam etc.), COX-2 inhibitors (e.g., celecoxib, rofecoxib etc.), cerebral circulation and metabolism improvement drugs (e.g., nicergoline, ibudilast, ifenprodil etc.), disease-modified anti-rheumatic drugs (DMARDs), anti-cytokine drugs (TNF inhibitor, MAP kinase inhibitor etc.), steroid drugs (e.g., dexamethasone, hexestrol, cortisone acetate etc.), therapeutic agents for incontinence•frequent urination (e.g., flavoxate hydrochloride, oxybutynin hydrochloride, propiverine hydrochloride etc.), therapeutic drugs for osteoporosis, hypolipidemic agents (e.g., simvastatin, fluvastatin, pravastatin, atorvastatin, etc.), antihypertensive agents (e.g., captopril, delapril, enalapril, nifedipine, nicardipine, amlodipine, alprenolol, propranolol, metoprolol, losartan, valsartan, candesartan, etc.), therapeutic agents for diabetes (e.g., pioglitazone, rosiglitazone, metformin, glibenclamide, nateglinide, voglibose, etc.), antiplatelet agents (e.g., ticlopidine, heparin, urokinase, alteplase, tisokinase, nasaruplase, cilostazol, etc.), antioxidizing agents (e.g., linolenic acid, ascorbic acid, icosapentaenoic acid, docosahexaenoic acid, tocopherol, etc.), vitamins (e.g., tocopherol, ascorbic acid, etc.), sex hormones (e.g., estrogen, estrone, estradiol, etc.), anticonvulsants (e.g., carbamazepine, valproic acid, clonazepam, vigabatrin, lamotrigine, gabapentin, etc.) and the like.

By combining the compound of the present invention or a prodrug thereof and a concomitant drug, a superior effect such as (1) the dose can be reduced as compared to single administration of the compound of the present invention or a prodrug thereof, or a concomitant drug,
(2) the concomitant drug can be selected according to the condition of patients (mild case, severe case and the like),
(3) the period of treatment can be set longer by selecting a concomitant drug having different action mechanism from the compound of the present invention or a prodrug thereof,
(4) a sustained treatment effect can be designed by selecting a concomitant drug having different action mechanism from the compound of the present invention or a prodrug thereof,
(5) a synergistic effect can be afforded by a combined use of the compound of the present invention or a prodrug thereof, and a concomitant drug, and the like, can be achieved.

The combination agent of the present invention has low toxicity, and for example, the compound of the present invention or a prodrug thereof, and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules, solutions, emulsions, suspensions, injections, suppositories, sustained release preparations (e.g., sublingual tablet, microcapsule etc.), plasters, orally disintegrating tablets, orally disintegrating films and the like, which can be safely administered orally or parenterally (e.g., subcutaneous, topical, rectal, intravenous administrations etc.).

Examples of the pharmacologically acceptable carriers usable for the production of the combination agent of the present invention include various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations and the like, and where necessary, conventional preservative, antioxidizing agent, colorant, sweetening agent, adsorbent, wetting agent and the like can be used appropriately.

When using the combination agent of the present invention, the administration time of the compound of the present invention or a prodrug thereof, and the concomitant drug is not restricted, and the compound of the present invention or a prodrug thereof or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that the compound of the present invention and the concomitant drug are combined in administration. Examples of such administration mode include the following:

(1) administration of a single preparation obtained by simultaneously processing the compound of the present invention or a prodrug thereof and the concomitant drug, (2) simultaneous administration of two kinds of preparations of the compound of the present invention or a prodrug thereof and the concomitant drug, which have been separately produced, by the same administration route, (3) administration of two kinds of preparations of the compound of the present invention or a prodrug thereof and the concomitant drug, which have been separately produced, by the same administration route in a staggered manner, (4) simultaneous administration of two kinds of preparations of the compound of the present invention or a prodrug thereof and the concomitant drug, which have been separately produced, by different administration routes, (5) administration of two kinds of preparations of the compound of the present invention or a prodrug thereof and the concomitant drug, which have been separately produced, by different administration routes in a staggered manner (e.g., administration in the order of the compound of the present invention or a prodrug thereof and the concomitant drug, or in the reverse order) and the like.

The compounding ratio of the compound of the present invention or a prodrug thereof to the concomitant drug in the combination agent of the present invention can be appropriately selected depending on an administration subject, administration route, diseases and the like.

For example, the content of the compound of the present invention or a prodrug thereof in the combination agent of the present invention varies depending on the form of a preparation, and usually about 0.01 to 100 wt %, preferably about 0.1 to 50 wt %, further preferably about 0.5 to 20 wt %, based on the whole preparation.

While the content of the concomitant drug in the combination agent of the present invention varies depending on the form of a preparation, it is usually about 0.01 to 100 wt %, preferably about 0.1 to 50 wt %, further preferably about 0.5 to 20 wt %, based on the whole preparation.

While the content of the additives such as carrier and the like in the combination agent of the present invention varies depending on the form of a preparation, it is generally about 1 to 99.99 wt %, preferably about 10 to 90 wt %, based on the whole preparation.

Similar contents can be employed for individual preparations of the compound of the present invention or a prodrug thereof and the concomitant drug.

EXAMPLES

The present invention is further explained in detail in the following by referring to Examples, Experimental Examples and Formulation Examples. However, the examples do not limit the present invention. The present invention may be modified without departing from the scope of the invention.

In the following Examples, the "room temperature" means generally about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

In the following Examples, the following abbreviations are used.

THF: tetrahydrofuran
DMF: N,N-dimethylformamide
DMSO: dimethylsulfoxide
ESI: electrospray method
APCI: atmospheric pressure chemical ionization
[M+H]$^+$: molecular ion peak
M: molar concentration
N: normality
TBAF: tetrabutylammonium fluoride
WSC: 1-ethyl-3-(3-dimethylaminopropyl)carbodiimide hydrochloride
HOBt: 1-hydroxybenzotriazole monohydrate
IPE: diisopropylether
HATU: 2-(7-azabenzotriazol-1-yl)-1,1,3,3-tetramethyluronium hexafluorophosphate
HPLC: high performance liquid chromatography
SFC: supercritical fluid chromatography $^1$H NMR (proton nuclear magnetic resonance spectrum) was measured by Fourier-transform type NMR. For the analysis, ACD/SpecManager (trade name) and the like were used. Peaks with very mild protons such as hydroxyl group, amino group and the like are note described.

MS (mass spectrum) was measured by LC/MS (liquid chromatography mass spectrometer). As the ionization method, ESI (ElectroSpray Ionization) method, or APCI (Atmospheric Pressure Chemical Ionization) method was used. The data indicates those found. Generally, a molecular ion peak is observed. In the case of a compound having a tert-butoxycarbonyl group (—Boc), a peak after elimination of a tert-butoxycarbonyl group or tert-butyl group may be observed as a fragment ion. In the case of a compound having a hydroxyl group (—OH), a peak after elimination of H$_2$O may be observed as a fragment ion. In the case of a salt, a molecular ion peak or fragment ion peak of free form is generally observed.

The unit of the sample concentration (c) in optical rotation ([α]$_D$) is g/100 mL.

The elemental analysis value (Anal.) shows those calculated (Calcd) and those found (Found).

Example 1

2-{8-(4-chloro-3-fluorophenoxy)-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol A) ethyl 8-(4-chloro-3-fluorophenoxy)-3-[6-methoxy-5-(4-methyl-1H-imidazol-1-yl)pyridin-2-yl]-5,6,7,8-tetrahydro[1,2,4]triazolo[4,3-a]pyridine-8-carboxylate A mixture of ethyl 8-chloro-3-[6-methoxy-5-(4-methyl-1H-imidazol-1-yl)pyridin-2-yl]-5,6,7,8-tetrahydro[1,2,4]triazolo[4,3-a]pyridine-8-carboxylate (200 mg), 4-chloro-3-fluorophenol (73.8 mg) and potassium carbonate (66.3 mg) in DMF (2 mL) was stirred at 100° C. for 2 hr. The reaction mixture was cooled to room temperature, saturated aqueous ammonium chloride solution was added, and the mixture was extracted with ethyl acetate. The extract was washed with water and saturated brine, and dried over anhydrous magnesium sulfate and the solvent was evaporated under reduced pressure. The residue was purified by silica gel column chromatography (NH, ethyl acetate/hexane) to give the title compound (73.5 mg).
$^1$H NMR (300 MHz, CDCl$_3$) δ 1.26-1.36 (3H, m), 2.19-2.30 (1H, m), 2.33 (3H, s), 2.39-2.56 (2H, m), 2.61-2.73 (1H, m), 4.09 (3H, s), 4.27-4.56 (3H, m), 4.92-5.03 (1H, m), 6.95-7.05 (2H, m), 7.09 (1H, dd, J=10.4, 2.7 Hz), 7.18-7.26 (1H, m), 7.71 (1H, d, J=8.0 Hz), 7.88 (1H, d, J=1.4 Hz), 8.09 (1H, d, J=8.0 Hz).

B) 2-{8-(4-chloro-3-fluorophenoxy)-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol To a mixture of ethyl 8-(4-chloro-3-fluorophenoxy)-3-[6-methoxy-5-(4-methyl-1H-imidazol-1-yl)pyridin-2-yl]-5,6,7,8-tetrahydro[1,2,4]triazolo[4,3-a]pyridine-8-carboxylate (70.2 mg) in THF (1.3 mL) was added methylmagnesium bromide (1M THF solution, 670 μL) at room temperature, and the mixture was stirred at room temperature for 1 hr. Saturated aqueous ammonium chloride solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, ethyl acetate/hexane) to give the title compound (40.4 mg).
$^1$H NMR (300 MHz, CDCl$_3$) δ 1.22-1.32 (3H, m), 1.57-1.66 (3H, m), 1.99-2.10 (1H, m), 2.13-2.25 (2H, m), 2.32 (3H, s), 2.39-2.50 (1H, m), 4.09 (3H, s), 4.22-4.35 (1H, m), 4.90-5.08 (2H, m), 6.56 (1H, d, J=7.6 Hz), 6.69 (1H, dd, J=10.6, 2.7 Hz), 7.02 (1H, s), 7.10 (1H, t, J=8.7 Hz), 7.73 (1H, d, J=8.0 Hz), 7.88 (1H, s), 8.09 (1H, d, J=8.0 Hz).

Example 2

2-{8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol A) ethyl 8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridine-8-carboxylate A mixture of ethyl 8-chloro-3-[6-methoxy-5-(4-methyl-1H-imidazol-1-yl)pyridin-2-yl]-5,6,7,8-tetrahydro[1,2,4]triazolo[4,3-a]pyridine-8-carboxylate (200 mg), 4-fluoro-3-(trifluoromethyl)phenol (91 mg) and potassium carbonate (199 mg) in DMF (2 mL) was stirred at 100° C. for 2 hr. The reaction mixture was cooled to room temperature, saturated aqueous ammonium chloride solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, ethyl acetate/hexane) to give the title compound (108 mg). $^1$H NMR (300 MHz, CDCl$_3$) δ 1.21-1.38 (3H, m), 2.21-2.31 (1H, m), 2.33 (3H, s), 2.42-2.71 (3H, m), 4.10 (3H, s), 4.29-4.53 (3H, m), 4.95-5.07 (1H, m), 6.96-7.18 (2H, m), 7.32 (1H, dd, J=5.9, 3.2 Hz), 7.46 (1H, dt, J=9.1, 3.2 Hz), 7.72 (1H, d, J=8.0 Hz), 7.91 (1H, d, J=1.4 Hz), 8.08 (1H, d, J=8.0 Hz).

B) 2-{8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol To a mixture of ethyl 8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridine-8-carboxylate (103.1 mg) in THF (1.8 mL) was added methylmagnesium bromide (1M THF solution, 920 μL) at room temperature, and the mixture was stirred at room temperature for 1 hr. Saturated aqueous ammonium chloride solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, ethyl acetate/hexane) to give the title compound (31.5 mg).
$^1$H NMR (300 MHz, CDCl$_3$) δ 1.22-1.30 (3H, m), 1.57-1.64 (3H, m), 1.96-2.09 (1H, m), 2.14-2.29 (2H, m), 2.32 (3H, s), 2.40-2.51 (1H, m), 4.09 (3H, s), 4.29 (1H, ddd, J=13.7, 12.0, 5.3 Hz), 4.92-5.09 (2H, m), 6.85-6.97 (2H, m), 7.00-7.12 (2H, m), 7.73 (1H, d, J=8.0 Hz), 7.88 (1H, s), 8.03 (1H, d, J=8.0 Hz).

Example 3

8-(4-chlorophenyl)-3-[3-methoxy-4-(2-methyl-1,3-oxazol-5-yl)phenyl]-8-methyl-5,6,7,8-tetrahydro[1,2,4]triazolo[4,3-a]pyridine A)
4-bromo-2-fluoro-N-methoxy-N-methylbenzamide To a mixture of 4-bromo-2-fluorobenzoic acid (10 g) in DMF (4.0 mL) were added N,O-dimethoxyhydroxylamine monohydrochloride (5.3 g), HOBt (8.0 g), N-ethyldiisopropylamine (23 mL) and WSC (11 g), and the mixture was stirred at room temperature for 9 hr, and then at 40° C. for 38 hr. The reaction mixture was allowed to cool to room temperature, saturated aqueous sodium hydrogen carbonate solution was added, and the mixture was extracted with ethyl acetate. The extract was washed with 1N aqueous sodium hydroxide solution, water and saturated brine, and dried over anhydrous magnesium sulfate, and the solvent was evaporated under reduced pressure to give the title compound (13 g). $^1$H NMR (300 MHz, CDCl$_3$) δ 3.35 (3H, s), 3.55 (3H, brs), 7.29-7.40 (3H, m).

B) 1-(4-bromo-2-fluorophenyl)ethanone

To a mixture of 4-bromo-2-fluoro-N-methoxy-N-methylbenzamide (13 g) in THF (4.0 mL) was added dropwise methylmagnesium bromide (3-Methylether solution, 30 ml) at 0° C., and the mixture was stirred at room temperature for 3 hr. Saturated aqueous ammonium chloride solution was added to the reaction mixture, and the mixture was extracted with ethyl acetate. The extract was washed with water and saturated brine, and dried over anhydrous magnesium sulfate, and the solvent was evaporated under reduced pressure to give the title compound (10g).
$^1$H NMR (300 MHz, CDCl$_3$) δ 2.63 (3H, d, J=5.3 Hz), 7.31-7.44 (2H, m), 7.77 (1H, t, J=8.0 Hz).

C) 5-(4-bromo-2-fluorophenyl)-2-methyl-1,3-oxazole

To a suspension of iodobenzene diacetate (6.7 g) in acetonitrile (100 mL) was added dropwise trifluoromethanesulfonic acid (3.7 mL), and the mixture was stirred at room temperature for 30 min. A mixture of 1-(4-bromo-2-fluorophenyl)ethanone (6.7 g) in acetonitrile (20 mL) was added to the reaction mixture, and the mixture was heated under reflux for 2 hr. The reaction mixture was allowed to cool to room temperature, and neutralized with saturated aqueous sodium hydrogen carbonate solution, and the solvent was evaporated under reduced pressure. The residue was extracted with ethyl acetate, the extract was washed with saturated brine and dried over anhydrous magnesium sulfate, and the solvent was evaporated under reduced pressure. The residue was purified by silica gel column chromatography (ethyl acetate/hexane) to give the title compound (2.6 g).
$^1$H NMR (300 MHz, CDCl$_3$) δ 2.54 (3H, s), 7.31-7.40 (3H, m), 7.52-7.65 (1H, m).

D) 3-methoxy-4-(2-methyl-1,3-oxazol-5-yl)benzoic acid

Under a nitrogen atmosphere, a mixture of zinc cyanide(II) (41.3 g), 5-(4-bromo-2-fluorophenyl)-2-methyl-1,3-oxazole (150 g), tris(dibenzylideneacetone)dipalladium(0) (10.8 g), 1,1'-bis(diphenylphosphino)ferrocene (13.0 g), zinc powder (4.60 g) and N,N-dimethylacetamide (600 mL) was stirred to at 120° C. for 1 hr. The reaction mixture was diluted with ethyl acetate (1.4 L), aqueous ammonia (20%, 100 mL) and water (700 mL) were added, and the mixture was filtered through celite. The organic layer was separated, and the aqueous layer was extracted with ethyl acetate. The combined organic layers were is washed with water and saturated brine, and dried over anhydrous sodium sulfate, and the solvent was evaporated under reduced pressure. To a mixture of the residue in DMF (880 mL) was added dropwise sodium methoxide (28% methanol solution, 170 g) at 0° C., the mixture was stirred at room temperature for 4 hr, and ice water (300 g) was added. The resulting solid was collected by filtration, washed with water, and added to 6N hydrochloric acid (1.3 L). The reaction mixture was heated under reflux for 2 days, and allowed to cool to room temperature. The resulting solid was collected by filtration, washed with water, subjected to azeotropic distillation with toluene and dried under reduced pressure to give the title compound (93.0 g).
$^1$H NMR (300 MHz, DMSO-d$_6$) δ 2.49 (3H, s), 3.98 (3H, s), 7.52 (1H, s), 7.56-7.65(2H, m), 7.71-7.76 (1H, m), 13.10 (1H, brs).

E) 3-methoxy-4-(2-methyl-1,3-oxazol-5-yl)benzohydrazide

N,N'-Carbonyldiimidazole (115 g) was added to a suspension of 3-methoxy-4-(2-methyl-1,3-oxazol-5-yl)benzoic acid (83.0 g) in THF (1 L) at room temperature, and the mixture was stirred for 1 hr. The reaction mixture was cooled to −10° C., hydrazine monohydrate (173 mL) was added, and the mixture was stirred at room temperature for 16 hr. The solvent in the reaction mixture was evaporated under reduced pressure, and water was added to the residue. The resultant solid was collected by filtration, washed with water, dried under reduced pressure, and washed with IPE to give the title compound (85.8 g). $^1$H NMR (300 MHz, DMSO-$d_6$) δ 2.48 (3H, s), 3.97 (3H, s), 4.53 (2H, brs), 7.44-7.58 (3H, m), 7.68 (1H, d, J=8.0 Hz), 9.85 (1H, s).

F) 2-(4-chlorophenyl)propanoic acid

Under a nitrogen atmosphere, to a mixture of (4-chlorophenyl)acetic acid (13.6 g) in THF (140 mL) was added n-butyllithium (1.6 M hexane solution, 100 mL) at −60° C. to −70° C., and the mixture was allowed to warm to 0° C. A mixture of methyl iodide (4.96 mL) in THF (40 mL) was added to the reaction mixture at 0° C.-10° C., and the mixture was stirred at room temperature for 12 hr. The reaction mixture was extracted with 1N aqueous sodium hydroxide solution (2×100 mL), and the extract was acidified with 3N hydrochloric acid (100 mL). The mixture was extracted with ethyl acetate (3×100 mL), the extract was dried over magnesium sulfate, and the solvent was evaporated under reduced pressure. The residue was purified by silica gel column chromatography (ethyl acetate/hexane) to give the title compound (13.3 g).
$^1$H NMR (300 MHz, CDCl$_3$) δ 1.49 (3H, d, J=7.2 Hz), 3.71 (1H, q, J=7.2 Hz), 7.22-7.25 (2H, m), 7.27-7.31 (2H, m).

G) 5-chloro-2-(4-chlorophenyl)-2-methylpentanoic acid

Under a nitrogen atmosphere, to a mixture of 2-(4-chlorophenyl)propanoic acid (13.3 g) in THF (140 mL) was added n-butyllithium (1.6M hexane solution, 90.3 mL) at −60° C. to −70° C., and the mixture was allowed to warm to −20° C. 1-Bromo-3-chloropropane (11.4 g) was added to the reaction mixture at −20° C. to 10° C., and the mixture was stirred at room temperature for 12 hr. The reaction mixture was extracted with 1N aqueous sodium hydroxide solution (2×100 mL), and the extract was acidified with 3N hydrochloric acid (100 mL). The mixture was extracted with ethyl acetate (3×100 mL), the extract was dried over magnesium sulfate, and the solvent was evaporated under reduced pressure. The residue was purified by silica gel column chromatography (ethyl acetate/hexane) to give the title compound (15.7 g).
$^1$H NMR (300 MHz, CDCl$_3$) δ 1.58 (3H, s), 1.55-1.78 (2H, m), 2.07-2.11 (2H, m), 3.47-3.52 (2H, m), 7.30 (4H, m).

H) N'-[5-chloro-2-(4-chlorophenyl)-2-methylpentanoyl]-3-methoxy-4-(2-methyl-1,3-oxazol-5-yl) benzohydrazide To a mixture of 5-chloro-2-(4-chlorophenyl)-2-methylpentanoic acid (6.34 g), 3-methoxy-4-(2-methyl-1,3-oxazol-5-yl)benzohydrazide (5.0 g) and triethylamine (6.78 mL) in DMF (50 mL) was added HATU (9.23 g) at 0° C., and the mixture was stirred at room temperature for 14 hr. The reaction mixture was diluted with ethyl acetate (50 mL), water (150 mL) and saturated brine (50 mL), and the mixture was extracted with ethyl acetate. The extract was washed with saturated brine (4×50 mL), and dried over anhydrous magnesium sulfate, and the solvent was evaporated under reduced pressure. The residue was purified by silica gel column chromatography (ethyl acetate/hexane) to give the title compound (8.19 g). $^1$H NMR (300 MHz, CDCl$_3$) δ 1.54-1.82 (2H, m), 1.66 (3H, s), 2.14-2.23 (2H, m), 2.54 (3H, s), 3.52 (2H, t, J=6.3 Hz), 3.90 (3H, s), 7.35-7.37 (6H, m), 7.48 (1H, s), 7.69 (1H, d, J=8.4 Hz), 7.95 (1H, d, J=4.2 Hz), 9.35 (1H, d, J=4.5 Hz).

I) 8-(4-chlorophenyl)-3-[3-methoxy-4-(2-methyl-1, 3-oxazol-5-yl)phenyl]-8-methyl-5,6,7,8-tetrahydro [1,2,4]triazolo[4,3-a]pyridine To a mixture of N'-[5-chloro-2-(4-chlorophenyl)-2-methylpentanoyl]-3-methoxy-4-(2-methyl-1,3-oxazol-5-yl)benzohydrazide (4.0 g) and carbon tetrachloride (1.57 mL) in acetonitrile (25 mL) was added triphenylphosphine (8.56 g), and the mixture was stirred at 80° C. for 1 hr. The reaction mixture was diluted with ethyl acetate and saturated aqueous sodium hydrogen carbonate solution, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane). Another lot synthesized similarly was combined and the mixture was dissolved in diethyl ether. The insoluble material was removed by filtration. The solvent in the filtrate was evaporated under reduced pressure, and the residue was purified by silica gel column chromatography (ethyl acetate/hexane). To a mixture of the purified product in DMSO (50 mL) was added sodium azide (1.88 g), and the mixture was stirred at 70° C. for 18 hr. The reaction mixture was diluted with ethyl acetate, water and saturated brine, and the mixture was extracted with ethyl acetate. The extract was washed with saturated brine, and dried over anhydrous magnesium sulfate, and the solvent was evaporated under reduced pressure. To a mixture of the residue in THF (50 mL)/water (5 mL) was added triphenylphosphine (7.60 g), and the mixture was stirred at 60° C. for 2.5 hr. The solvent in the reaction mixture was evaporated under reduced pressure. Acetic acid (25 mL) was added to the residue, and the mixture was stirred under heating with reflux for 1 hr. The reaction mixture was diluted with ethyl acetate and saturated aqueous sodium hydrogen carbonate solution, and the mixture was extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (3.80 g).
$^1$H NMR (300 MHz, CDCl$_3$) δ1.77-1.91 (4H, m), 1.98-2.12 (2H, m), 2.42-2.50 (1H, m), 2.57 (3H, s), 3.97-4.20 (5H, m), 7.17-7.20 (2H, m), 7.30 (3H, m), 7.50-7.51 2H, m), 7.84 (1H, d, J=8.4 Hz).

Example 4 optically active 8-(4-chlorophenyl)-3-[3-methoxy-4-(2-methyl-1,3-oxazol-5-yl)phenyl]-8-methyl-5,6,7,8-tetrahydro[1,2,4]triazolo[4,3-a]pyridine A racemate (3.77 g) of 8-(4-chlorophenyl)-3-[3-methoxy-4-(2-methyl-1,3-oxazol-5-yl)phenyl]-8-methyl-5,6,7,8-tetrahydro[1,2,4]triazolo[4,3-a]pyridine was separated by HPLC (column: CHIRALCEL IC LF001 (trade name), 50 mm ID×500 mm L, manufactured by DAICEL CHEMICAL INDUSTRIES, LTD., mobile phase: ethanol=100%) to give the title compound (1.85 g) having a shorter retention time.

¹H NMR (300 MHz, CDCl₃) δ 1.78-1.92 (4H, m), 1.94-2.09 (2H, m), 2.37-2.49 (1H, m), 2.55 (3H, s), 3.93-4.09 (4H, m), 4.11-4.22 (1H, m), 7.13-7.21 (2H, m), 7.28 (3H, m), 7.46-7.51 (2H, m), 7.82 (1H, d, J=8.0 Hz).

Example 5 optically active 8-(4-chlorophenyl)-3-[3-methoxy-4-(2-methyl-1,3-oxazol-5-yl)phenyl]-8-methyl-5,6,7,8-tetrahydro[1,2,4]triazolo[4,3-a]pyridine A racemate (3.77 g) of 8-(4-chlorophenyl)-3-[3-methoxy-4-(2-methyl-1,3-oxazol-5-yl)phenyl]-8-methyl-5,6,7,8-tetrahydro[1,2,4]triazolo[4,3-a]pyridine was separated by HPLC (column: CHIRALCEL IC LF001 (trade name), 50 mm ID×500 mm L, manufactured by DAICEL CHEMICAL INDUSTRIES, LTD., mobile phase: ethanol=100%) to give the title compound (1.89 g) having a longer retention time.
¹H NMR (300 MHz, CDCl₃) δ 1.74-1.92 (4H, m), 1.93-2.08 (2H, m), 2.36-2.49 (1H, m), 2.55 (3H, s), 3.94-4.06 (4H, m), 4.10-4.21 (1H, m), 7.13-7.21 (2H, m), 7.28 (3H, m), 7.49 (2H, d, J=2.5 Hz), 7.82 (1H, d, J=8.2 Hz).

Example 8

3-[3-methoxy-4-(2-methyl-1,3-oxazol-5-yl)phenyl]-8-methyl-8-[4-(trifluoromethyl)phenyl]-5,6,7,8-tetrahydro[1,2,4]triazolo[4,3-a]pyridine A) 3-[3-methoxy-4-(2-methyl-1,3-oxazol-5-yl)phenyl]-8-[4-(trifluoromethyl)phenyl]-5,6,7,8-tetrahydro[1,2,4]triazolo[4,3-a]pyridine The title compound was obtained in the same manner as in Example 3.
¹H NMR (300 MHz, CDCl₃) δ 1.94-2.26 (3H, m), 2.34-2.47 (1H, m), 2.56 (3H, s), 4.05 (3H, s), 4.16-4.24 (2H, m), 4.47-4.57 (1H, m), 7.29 (1H, dd, J=8.1, 1.7 Hz), 7.34-7.39 (2H, m), 7.47-7.53 (2H, m), 7.57-7.63 (2H, m), 7.85 (1H, d, J=7.9 Hz).

B) 3-[3-methoxy-4-(2-methyl-1,3-oxazol-5-yl)phenyl]-8-methyl-8-[4-(trifluoromethyl)phenyl]-5,6,7,8-tetrahydro[1,2,4]triazolo[4,3-a]pyridine To a mixture of 3-[3-methoxy-4-(2-methyl-1,3-oxazol-5-yl)phenyl]-8-[4-(trifluoromethyl)phenyl]-5,6,7,8-tetrahydro[1,2,4]triazolo[4,3-a]pyridine (175 mg) in DMF (1.8 mL) was added sodium hydride (60%, 17.2 mg) at 0° C., and the mixture was stirred for 30 min. Methyl iodide (0.0446 mL) was added to the reaction mixture, and the mixture was stirred at room temperature for 1 hr. Water was added to the reaction mixture, and the mixture was extracted with ethyl acetate. The extract was dried over anhydrous magnesium sulfate, and the solvent was evaporated under reduced pressure. The residue was purified by silica gel column chromatography (ethyl acetate/hexane) to give the title compound (32.2 mg).
¹H NMR (300 MHz, CDCl₃) δ 1.60-2.21 (6H, m), 2.40-2.66 (4H, m), 3.92-4.29 (5H, m), 7.14-7.70 (7H, m), 7.84 (1H, d, J=7.9 Hz).

Example 9

8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-ol A) 8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridine The title compound was obtained in the same manner as in Example 3.
¹H NMR (300 MHz, CDCl₃) δ 1.93-2.25 (3H, m), 2.29-2.44 (1H, m), 2.56 (3H, s), 4.05 (3H, s), 4.12-4.24 (2H, m), 4.36-4.49 (1H, m), 7.10 (1H, dd, J=8.2, 2.2 Hz), 7.28 (1H, dd, J=8.1, 1.5 Hz), 7.34 (1H, d, J=2.2 Hz), 7.42 (1H, d, J=8.2 Hz), 7.46-7.54 (2H, m), 7.84 (1H, d, J=8.1 Hz).

B) 8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-ol To a mixture of 8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridine (100 mg) in DMF (2 mL) was added sodium hydride (60%, 9.4 mg) at room temperature, and the mixture was stirred for 30 min in the air. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (40.3 mg).
¹H NMR (300 MHz, CDCl₃) δ 1.96-2.12 (2H, m), 2.34-2.36 (2H, m), 2.58 (3H, s), 4.06 (3H, s), 4.09-4.30 (3H, m), 7.23 (1H, dd, J=2.1 Hz, 8.4 Hz), 7.31 (1H, d, J=1.2 Hz), 7.41 (1H, d, J=8.1 Hz), 7.48 (1H, s), 7.53-7.54 (2H, m), 7.86 (1H, d, J=8.1 Hz).

Example 10

{8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methanol To a mixture of 8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridine (300 mg) in DMF (5 mL) was added sodium hydride (60%, 31.6 mg) under ice-cooling, and the mixture was stirred for 1 hr under a nitrogen atmosphere. Paraformaldehyde (39.6 mg) was added to the reaction mixture, and the mixture was stirred for 30 min. The reaction mixture was diluted with water, and the mixture was extracted with ethyl acetate. The extract was washed with water and saturated brine, and dried over anhydrous magnesium sulfate, and the solvent was evaporated under reduced pressure. The residue was purified by silica gel column chromatography (methanol/ethyl acetate) to give the title compound (42.5 mg).
¹H NMR (300 MHz, CDCl₃) δ 1.76-1.93 (1H, m), 2.03-2.20 (2H, m), 2.30-2.40 (1H, m), 2.56 (3H, s), 3.83-3.89 (1H, m), 3.95-4.03 (2H, m), 4.05 (3H, s), 4.13-4.26 (2H, m), 7.09 (1H, dd, J=8.5, 2.2 Hz), 7.29 (1H, dd, J=8.1, 1.5 Hz), 7.33 (1H, d, J=2.2 Hz), 7.41 (1H, d, J=8.5 Hz), 7.50 (1H, d, J=1.6 Hz), 7.51 (1H, s), 7.83 (1H, d, J=8.0 Hz).

Example 13

8-(cyclopropylmethyl)-3-[3-methoxy-4-(2-methyl-1,3-oxazol-5-yl)phenyl]-8-[4-(methylsulfonyl)phenyl]-5,6,7,8-tetrahydro[1,2,4]triazolo[4,3-a]pyridine To a mixture of 8-(cyclopropylmethyl)-3-[3-methoxy-4-(2-methyl-1,3-oxazol-5-yl)phenyl]-8-[4-(methylsulfanyl)phenyl]-5,6,7,8-tetrahydro[1,2,4]triazolo[4,3-a]pyridine (86.0 mg) in DMF (1 mL) was added monoperoxyphthalic acid magnesium salt hexahydrate (87.4 mg) at 0° C., and the mixture was stirred at room temperature for 2 hr. Monoperoxyphthalic acid magnesium salt hexahydrate (87.4 mg) was added to the reaction mixture at room temperature, and the mixture was stirred at room temperature for 2 hr. The reaction mixture was diluted with ethyl acetate, the mixture was washed with aqueous sodium thiosulfate solution (1M) and dried over anhydrous magnesium sulfate, and the solvent was evaporated under reduced pressure. The residue was purified by silica gel column chromatography (ethyl acetate) to give the title compound (27.8 mg).

$^1$H NMR (300 MHz, CDCl$_3$) δ 0.07-0.17 (1H, m), 0.43 (2H, d, J=8.0 Hz), 0.63-0.76 (1H, m, J=6.0 Hz), 1.78-1.94 (1H, m), 2.07-2.21 (2H, m), 2.33-2.46 (2H, m), 2.56 (3H, s), 2.73 (1H, dd, J=14.4, 3.2 Hz), 3.06 (3H, s), 3.99-4.20 (6H, m), 7.29 (1H, brs), 7.50 (2H, d, J=3.3 Hz), 7.69 (2H, d, J=8.5 Hz), 7.83 (1H, d, J=8.2 Hz), 7.90 (2H, d, J=8.2 Hz).

Example 16

8-(3,4-difluorophenyl)-8-ethyl-3-[3-methoxy-4-(2-methyl-1,3-oxazol-5-yl)phenyl]-5,6,7,8-tetrahydro[1,2,4]triazolo[4,3-a]pyridine A) 8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine The title compound was obtained in the same manner as in Example 3.
MS (ESI+): [M+H]$^+$423.1.

B) 8-(3,4-difluorophenyl)-8-ethyl-3-[3-methoxy-4-(2-methyl-1,3-oxazol-5-yl)phenyl]-5,6,7,8-tetrahydro[1,2,4]triazolo[4,3-a]pyridine To a mixture of 8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine (200 mg) in DMF (4 mL) was added sodium hydride (60%, 28.4 mg) at room temperature, and the mixture was stirred at 60° C. for 30 min under a nitrogen atmosphere. Ethyl iodide (45.2 μL) was added to the reaction mixture at room temperature, and the mixture was stirred at room temperature for 30 min. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (37.1 mg).

$^1$H NMR (300 MHz, CDCl$_3$) δ 1.14 (3H, t, J=7.0 Hz), 1.86-2.10 (2H, m), 2.34-2.53 (2H, m), 2.58 (3H, s), 3.40-3.64 (2H, m), 3.97-4.13 (4H, m), 4.24-4.36 (1H, m), 7.10-7.23 (2H, m), 7.29-7.41 (2H, m), 7.53 (2H, s), 7.87 (1H, d, J=8.0 Hz).

Example 17

8-(3,4-difluorophenyl)-8-ethoxy-3-[3-methoxy-4-(2-methyl-1,3-oxazol-5-yl)phenyl]-5,6,7,8-tetrahydro[1,2,4]triazolo[4,3-a]pyridine To a mixture of 8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine (200 mg) in DMF (4 mL) was added sodium hydride (60%, 28.4 mg) at room temperature, and the mixture was stirred at 60° C. for 30 min under a nitrogen atmosphere. Ethyl iodide (45.2 μL) was added to the reaction mixture at room temperature, and the mixture was stirred at room temperature for 30 min. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (31.6 mg).

$^1$H NMR (300 MHz, CDCl$_3$) δ 0.96 (3H, t, J=7.3 Hz), 1.80-1.95 (1H, m), 2.01-2.15 (2H, m), 2.22-2.34 (2H, m), 2.40-2.51 (1H, m), 2.57 (3H, s), 3.95-4.08 (4H, m), 4.12-4.21 (1H, m), 7.06-7.15 (2H, m), 7.21-7.26 (1H, m), 7.29 (1H, brs), 7.52 (2H, s), 7.84 (1H, d, J=8.0 Hz).

Example 21 optically active 8-(cyclopropylmethyl)-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine A racemate (230 mg) of 8-(cyclopropylmethyl)-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine was separated by HPLC (column: CHIRALPAK AD (JG001, trade name), 50 mm ID×500 mm L, manufactured by DAICEL CHEMICAL INDUSTRIES, LTD., mobile phase: hexane/ethanol=500/500(v/v)) to give the title compound (118 mg) having a shorter retention time.

Example 22 optically active 8-(cyclopropylmethyl)-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine A racemate (230 mg) of 8-(cyclopropylmethyl)-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine was separated by HPLC (column: CHIRALPAK AD (JG001, trade name), 50 mm ID×500 mm L, manufactured by DAICEL CHEMICAL INDUSTRIES, LTD., mobile phase: hexane/ethanol=500/500(v/v)) to give the title compound (110 mg) having a longer retention time.

Example 24

8-(3,4-difluorophenyl)-8-(methoxymethyl)-3-[3-methoxy-4-(2-methyl-1,3-oxazol-5-yl)phenyl]-5,6,7,8-tetrahydro[1,2,4]triazolo[4,3-a]pyridine Under an argon atmosphere, to a mixture of {8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridin-8-yl}methanol (260 mg) in DMF (2.9 mL) was added sodium hydride (60%, 27.6 mg) at 0° C., and the mixture was stirred for 30 min. Methyl iodide (0.0716 mL) was added to the reaction mixture, and the mixture was stirred at room temperature for 1 hr. Saturated aqueous ammonium chloride solution was added to the reaction mixture, and the mixture was extracted with ethyl acetate. The extract was dried over anhydrous magnesium sulfate, and the solvent was evaporated under reduced pressure. The residue was purified by silica gel column chromatography (ethyl acetate/hexane) to give the title compound (69.1 mg).

Example 30

8-[(3,4-dichlorobenzyl)oxy]-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine To a mixture of 8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine (100 mg) in DMF (2 mL) was added sodium hydride (60%, 14.2 mg), and the mixture was stirred at room temperature for 30 min in the air. Sodium hydride (60%, 14.2 mg) was added, and the mixture was further stirred at room temperature for 30 min in the air. 4-(Bromomethyl)-1,2-dichlorobenzene (85.2 mg) was added, and the mixture was stirred at room temperature for 2 hr. Water was added to the reaction mixture, and the mixture was extracted with ethyl acetate. The extract was washed with saturated aqueous sodium hydrogen carbonate solution, and dried over anhydrous magnesium sulfate, and the solvent was evaporated under reduced pressure. The residue was purified by silica gel column chromatography (ethyl acetate/hexane), and further recrystallized from ethyl acetate/hexane to give the title compound (64.8 mg).

$^1$H NMR (300 MHz, CDCl$_3$) δ 1.93-2.13 (2H, m), 2.47-2.54(2H, m), 2.57 (3H, s), 3.97-4.13 (4H, m), 4.23-4.28 (1H, m), 4.52-4.64 (2H, m), 7.02 (1H, d, J=6.9 Hz), 7.19 (1H, d, J=8.8 Hz), 7.22-7.30 (2H, m), 7.37 (3H, m), 7.44 (1H, s), 7.52 (1H, s), 7.86 (1H, d, J=8.0 Hz).

Example 31

(6RS,8RS)-8-(3,4-difluorophenyl)-8-(hydroxymethyl)-3-[3-methoxy-4-(2-methyl-1,3-oxazol-5-yl)phenyl]-5,6,7,8-tetrahydro[1,2,4]triazolo[4,3-a]pyridin-6-ol A) 2-{[tert-butyl(dimethyl)silyl]oxy}-3-chloropropyl 4-methylbenzenesulfonate To a mixture of 3-chloro-2-hydroxypropyl 4-methylbenzenesulfonate (17.4 g) and imidazole (13.4 g) in DMF (130 mL) was added tert-butyl(chloro)dimethylsilane (14.9 g), and the mixture was stirred for 64 hr. Saturated aqueous sodium hydrogen carbonate solution was added to the reaction mixture, and the mixture was extracted with hexane. The extract was dried over anhydrous magnesium sulfate, and the solvent was evaporated under reduced pressure. The residue was purified by silica gel column chromatography (ethyl acetate/hexane) to give the title compound (20.3 g).

$^1$H NMR (300 MHz, CDCl$_3$) δ 0.05 (3H, s), 0.08 (3H, s), 0.82-0.88 (9H, m), 2.46 (3H, s), 3.40-3.53 (2H, m), 3.94-4.10 (3H, m), 7.36 (2H, d, J=7.9 Hz), 7.75-7.85 (2H, m).

B) tert-butyl[2-chloro-1-(iodomethyl)ethoxy]dimethylsilane

To a mixture of 2-{[tert-butyl(dimethyl)silyl]oxy}-3-chloropropyl 4-methylbenzenesulfonate (20.3 g) in acetone (200 mL) was added sodium iodide (19.7 g), and the mixture was stirred at 80° C. for 3 hr. The reaction mixture was concentrated, water was added to the residue, and the mixture was extracted with hexane. The extract was dried over anhydrous magnesium sulfate, and the solvent was evaporated under reduced pressure. The residue was purified by silica gel column chromatography (ethyl acetate/hexane) to give the title compound (13.4 g).

$^1$H NMR (300 MHz, CDCl$_3$) δ 0.13 (3H, s), 0.14 (3H, s), 0.90-0.96 (9H, m), 3.29-3.40 (2H, m), 3.53-3.61 (2H, m), 3.65-3.75 (1H, m).

C) N'-[(3,4-difluorophenyl)acetyl]-3-methoxy-4-(2-methyl-1,3-oxazol-5-yl)benzohydrazide A mixture of 3-methoxy-4-(2-methyl-1,3-oxazol-5-yl) benzohydrazide (4.10 g), 3,4-difluorophenylacetic acid (3.15 g), HATU (7.57 g) and triethylamine (2.77 mL) in DMF (77 mL,) was stirred at room temperature for 16 hr. Water was added to the reaction mixture, and the resultant precipitate was collected by filtration and washed with hexane and acetone to give the title compound (4.69 g).

$^1$H NMR (300 MHz, DMSO-d$_6$) δ 2.50 (3H, s), 3.54-3.62 (2H, m), 4.00 (3H, s), 7.14-7.24 (1H, m), 7.34-7.47 (2H, m), 7.50-7.64 (3H, m), 7.75 (1H, d, J=8.7 Hz), 10.39 (2H, brs).

D) 2-(3,4-difluorobenzyl)-5-[3-methoxy-4-(2-methyl-1,3-oxazol-5-yl)phenyl]-1,3,4-oxadiazole A mixture of N'-[(3,4-difluorophenyl)acetyl]-3-methoxy-4-(2-methyl-1,3-oxazol-5-yl)benzohydrazide (4.69 g), carbon tetrachloride (2.24 mL) and triphenylphosphine (12.3 g) in acetonitrile (117 mL) was stirred at 80° C. for 2 hr. The mixture was allowed to cool to room temperature, the precipitate was filtered off, and the filtrate was concentrated. Water was added to the residue, and the mixture was extracted with ethyl acetate. The extract was dried over anhydrous magnesium sulfate, and the solvent was evaporated under reduced pressure. The residue was purified by silica gel column chromatography (ethyl acetate). Ethyl acetate was added to the obtained crude product, the precipitate was filtered off, and the filtrate was concentrated. Acetonitrile was added to the obtained residue, and the resultant precipitate was collected by filtration to give the title compound (2.41 g).

$^1$H NMR (300 MHz, CDCl$_3$) δ 2.55 (3H, s), 4.05 (3H, s), 4.26 (2H, s), 7.05-7.25 (3H, m), 7.53 (1H, s), 7.59-7.66 (2H, m), 7.83 (1H, d, J=7.9 Hz).

E) (6RS,8SR)-6-{[tert-butyl(dimethyl)silyl]oxy}-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine To a mixture of 2-(3,4-difluorobenzyl)-5-[3-methoxy-4-(2-methyl-1,3-oxazol-5-yl)phenyl]-1,3,4-oxadiazole (2.41 g) in DMF (45 mL) was added sodium hydride (60%, 264 mg) at 0° C., and the mixture was stirred for 10 min. tert-Butyl[2-chloro-1-(iodomethyl)ethoxy]dimethylsilane (2.52 g) was added to the reaction mixture, and the mixture was stirred at room temperature for 30 min. Saturated aqueous ammonium chloride solution was added to the reaction mixture, and the mixture was extracted with ethyl acetate. The extract was dried over anhydrous magnesium sulfate, and the solvent was evaporated under reduced pressure. The residue was purified by silica gel column chromatography (ethyl acetate/hexane). To a mixture of the purified product in DMSO (7.6 mL) was added sodium azide (199 mg), and the mixture was stirred at 100° C. for 10 hr. The reaction mixture was diluted with ethyl acetate/brine, and the mixture was extracted with ethyl acetate. The extract was dried over anhydrous magnesium sulfate, and the solvent was evaporated under reduced pressure. The residue was purified by silica gel column chromatography (ethyl acetate). To a mixture of the purified product in THF (46 mL) were added diphenylphosphino-polystyrene (1.99 mmol/g, 4.58 g) and water (4.6 mL), and the mixture was stirred at 80° C. for 2 hr. The reaction mixture was allowed to cool to room temperature, the precipitate was filtered off, and the filtrate was evaporated under reduced pressure. Toluene (46 mL) was added to the residue, and the mixture was stirred under heating with reflux for 1 hr. The reaction mixture was concentrated, and the residue was purified by silica gel column chromatography (ethyl acetate/hexane) to give the title compound (415 mg).

$^1$H NMR (300 MHz, CDCl$_3$) δ 0.04 (3H, s), 0.11 (3H, s), 0.85 (9H, s), 1.98-2.09 (1H, m), 2.32-2.43 (1H, m), 2.56 (3H, s), 4.01-4.20 (5H, m), 4.44-4.51 (1H, m), 4.59 (1H, dd, J=11.1, 5.8 Hz), 7.01-7.25 (4H, m), 7.44 (1H, d, J=1.5 Hz), 7.51 (1H, s), 7.86 (1H, d, J=8.3 Hz).

F) (6RS,8RS)-8-(3,4-difluorophenyl)-8-(hydroxymethyl)-3-[3-methoxy-4-(2-methyl-1,3-oxazol-5-yl)phenyl]-5,6,7,8-tetrahydro[1,2,4]triazolo[4,3-a]pyridin-6-ol To a mixture of (6RS,8SR)-6-{[tert-butyl(dimethyl)silyl]oxy}-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine (209 mg) in DMF (1.9 mL) was added sodium hydride (60%, 16.6 mg) at 0° C., and the mixture was stirred for 10 min. Paraformaldehyde (18.1 mg) was added to the reaction mixture, and the mixture was stirred at room temperature for 1 hr. Water was added to the reaction mixture, and the mixture was extracted with ethyl acetate. The extract was dried over anhydrous magnesium sulfate, and the solvent was evaporated under reduced pressure. To a mixture of the residue in THF (1.9 ml) was added TBAF (1M THF solution, 0.756 ml), and the mixture was stirred at room temperature for 15 min. Saturated aqueous sodium chloride solution was added to the reaction mixture, and the mixture was extracted with ethyl acetate. The extract was dried over anhydrous magnesium sulfate, and the solvent was evaporated under reduced pressure. The residue was washed with ethyl acetate to give the title compound (154 mg).

Example 32

2-{8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A) ethyl (3,4-difluorophenyl)acetate To a mixture of ethyl (3,4-difluorophenyl)acetate (9.70 g) in ethanol (100 mL) was added sulfuric acid (55 mg), and the mixture was heated under reflux overnight. The mixture was allowed to cool to room temperature, and the solvent was evaporated under reduced pressure. The residue was dissolved in ethyl acetate, and the mixture was washed with saturated aqueous sodium hydrogen carbonate solution and saturated brine, and dried over anhydrous sodium sulfate. The solvent was evaporated under reduced pressure to give the title compound (11.3 g).

$^1$H NMR (300 MHz, CDCl$_3$) δ 1.26 (3H, t, J=7.2 Hz), 3.56 (2H, s), 4.16 (2H, q, J=7.2 Hz), 6.94-7.02 (1H, m), 7.04-7.16 (2H, m).

B) diethyl (3,4-difluorophenyl)propanedioate

A mixture of ethyl (3,4-difluorophenyl)acetate (11.3 g) in THF (50 ml) was added to a mixture of sodium hydride (60%, 4.74 g), diethyl carbonate (34.2 mL) and THF (250 mL) at room temperature, and the mixture was heated under reflux for 2 hr. Saturated aqueous ammonium chloride solution was added to the reaction mixture, and the mixture was extracted with ethyl acetate. The extract was washed with saturated aqueous sodium hydrogen carbonate solution and saturated brine, and dried over anhydrous sodium sulfate, and the solvent was evaporated under reduced pressure. The residue was purified by silica gel column chromatography (ethyl acetate/hexane) to give the title compound (13.8 g).

$^1$H NMR (300 MHz, CDCl$_3$) δ 1.27 (6H, t, J=7.1 Hz), 4.16-4.29 (4H, m), 4.55 (1H, s), 7.08-7.20 (2H, m), 7.26-7.35 (1H, m).

C) diethyl (2-cyanoethyl)(3,4-difluorophenyl)propanedioate

Under an argon atmosphere, sodium ethoxide (20% ethanol solution, 1.7 g) was added to a mixture of diethyl (3,4-difluorophenyl)propanedioate (13.8 g) in tert-butylalcohol (50 mL) at room temperature, and the mixture was stirred at 40° C. for 30 min. Acrylonitrile (3.34 mL) was added to the reaction mixture at room temperature, and the mixture was stirred at room temperature overnight. Saturated aqueous ammonium chloride solution was added to the reaction mixture, and the mixture was extracted with ethyl acetate. The extract was washed with saturated aqueous sodium hydrogen carbonate solution and saturated brine, and dried over anhydrous sodium sulfate. The solvent was evaporated under reduced pressure to give the title compound (15.2 g).

$^1$H NMR (300 MHz, CDCl$_3$) δ 1.27 (6H, t, J=7.1 Hz), 2.29-2.38 (2H, m), 2.53-2.65 (2H, m), 4.21-4.33 (4H, m), 7.00-7.09 (1H, m), 7.15 (1H, dd, J=9.9, 8.2 Hz), 7.21-7.30 (1H, m).

D) ethyl 3-(3,4-difluorophenyl)-2-oxopiperidine-3-carboxylate

A mixture of diethyl (2-cyanoethyl) (3,4-difluorophenyl)propanedioate (15.2 g), Raney cobalt (75 g) and ammonia (2M ethanol solution, 150 mL) was stirred at room temperature for 3 days under a hydrogen atmosphere. The insoluble material was filtered off through celite, and the filtrate was concentrated under reduced pressure. The residue was washed with diisopropylether to give the title compound (10.5 g).

MS (ESI+): [M+H]$^+$284.3.

E) ethyl 3-(3,4-difluorophenyl)-2-thioxopiperidine-3-carboxylate

Under an argon atmosphere, Lawesson's reagent (1.00 g) was added to a suspension of ethyl 3-(3,4-difluorophenyl)-2-oxopiperidine-3-carboxylate (1.00 g) in toluene (20 ml) at room temperature. The reaction mixture was stirred at 110° C. for 4 hr, and allowed to cool to room temperature, and the solvent was evaporated under reduced pressure. The residue was purified by silica gel column chromatography (NH, ethyl acetate/hexane) to give the title compound (859 mg).

¹H NMR (300 MHz, CDCl₃) δ 1.29 (3H, t, J=7.1 Hz), 1.45-1.62 (1H, m), 1.77-1.91 (1H, m), 2.26-2.35 (1H, m), 2.63-2.75 (1H, m), 3.28-3.53 (2H, m), 4.26 (2H, q, J=7.1 Hz), 7.07-7.19 (2H, m), 7.23-7.32 (1H, m), 8.57 (1H, brs).

F) ethyl 8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine-8-carboxylate Methyl iodide (0.536 mL) was added to a mixture of ethyl 3-(3,4-difluorophenyl)-2-thioxopiperidine-3-carboxylate (859 mg) in acetonitrile (10 mL) at room temperature, and the reaction mixture was stirred at 50° C. overnight. The solvent was evaporated under reduced pressure, and ethanol (10 mL) and 3-methoxy-4-(2-methyl-1,3-oxazol-5-yl)benzohydrazide (710 mg) were added to the residue at room temperature. The reaction mixture was stirred at 90° C. overnight, saturated aqueous sodium hydrogen carbonate solution was added, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate) to give the title compound (970 mg).
MS (ESI+): [M+H]⁺495.2.

G) 2-{8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol Under an argon atmosphere, methylmagnesium bromide (1M THF solution, 1.0 mL) was added to a mixture of ethyl 8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine-8-carboxylate (100 mg) in THF (1 mL) under ice-cooling. The reaction mixture was stirred under ice-cooling for 1 hr, saturated aqueous ammonium chloride solution was added, and the mixture was extracted with ethyl acetate. The extract was washed with saturated aqueous sodium hydrogen carbonate solution and saturated brine, and dried over anhydrous sodium sulfate, and the solvent was evaporated under reduced pressure. The residue was purified by silica gel column chromatography (NH, ethyl acetate/hexane) to give the title compound (35.0 mg).
¹H NMR (300 MHz, CDCl₃) δ 1.15 (3H, s), 1.35 (3H, s), 1.77-1.93 (1H, m), 2.00-2.23 (2H, m), 2.55 (3H, s), 2.67-2.81 (1H, m), 3.92-4.18 (5H, m), 5.26 (1H, brs),7.03-7.18 (1H, m), 7.22-7.32 (2H, m), 7.35-7.44 (1H, m), 7.47-7.53 (2H, m), 7.82 (1H, d, J=8.0 Hz).

Example 34

8-(4-fluorophenyl)-3-[3-methoxy-4-(2-methyl-1,3-oxazol-5-yl)phenyl]-8-methyl-5,6,7,8-tetrahydro[1,2,4]triazolo[4,3-a]pyridine To a mixture of 8-(3-chloro-4-fluorophenyl)-3-[3-methoxy-4-(2-methyl-1,3-oxazol-5-yl)phenyl]-8-methyl-5,6,7,8-tetrahydro[1,2,4]triazolo[4,3-a]pyridine (80.0 mg) in methanol (1.8 mL) was added palladium hydroxide (8.0 mg), and the mixture was stirred for 5 days under a hydrogen stream. The catalyst was removed, and the filtrate was concentrated under reduced pressure. The residue was purified by silica gel column chromatography (methanol/ethyl acetate) to give the title compound (26.0 mg).
¹H NMR (300 MHz, CDCl₃) δ 1.90 (3H, s), 1.93-2.10 (3H, m), 2.36-2.50 (1H, m), 2.55 (3H, s), 3.94-4.09 (4H, m), 4.09-4.25 (1H, m), 6.91-7.06 (2H, m), 7.17-7.25 (2H, m), 7.27-7.30 (1H, m), 7.45-7.53 (2H, m), 7.83 (1H, d, J=8.0 Hz).

Example 38 optically active 8-(3,4-dichlorophenyl)-3-[3-methoxy-4-(2-methyl-1,3-oxazol-5-yl)phenyl]-8-methyl-5,6,7,8-tetrahydro[1,2,4]triazolo[4,3-a]pyridine A racemate (166 mg) of 8-(3,4-dichlorophenyl)-3-[3-methoxy-4-(2-methyl-1,3-oxazol-5-yl)phenyl]-8-methyl-5,6,7,8-tetrahydro[1,2,4]triazolo[4,3-a]pyridine was separated by HPLC (column: CHIRALCEL OD CA002 (trade name), 50 mm ID×500 mm L, manufactured by DAICEL CHEMICAL INDUSTRIES, LTD., mobile phase: hexane/ethanol=700/300) to give the title compound (56.6 mg) having a shorter retention time.
¹H NMR (300 MHz, CDCl₃) δ 1.76-1.93 (4H, m), 1.99-2.12 (2H, m), 2.39-2.50 (1H, m), 2.57 (3H, s), 3.97-4.09 (4H, m), 4.14-4.24 (1H, m), 7.12 (1H, dd, J=8.5, 2.2 Hz), 7.29-7.31 (1H, m), 7.35-7.42 (2H, m), 7.51 (2H, d, J=2.2 Hz), 7.84 (1H, d, J=8.2 Hz).

Example 39 optically active 8-(3,4-dichlorophenyl)-3-[3-methoxy-4-(2-methyl-1,3-oxazol-5-yl)phenyl]-8-methyl-5,6,7,8-tetrahydro[1,2,4]triazolo[4,3-a]pyridine A racemate (166 mg) of 8-(3,4-dichlorophenyl)-3-[3-methoxy-4-(2-methyl-1,3-oxazol-5-yl)phenyl]-8-methyl-5,6,7,8-tetrahydro[1,2,4]triazolo[4,3-a]pyridine was separated by HPLC (column: CHIRALCEL OD CA002 (trade name), 50 mm ID×500 mm L, manufactured by DAICEL CHEMICAL INDUSTRIES, LTD., mobile phase: hexane/ethanol=700/300) to give the title compound (58.4 mg) having a longer retention time.
¹H NMR (300 MHz, CDCl₃) δ 1.78-1.94 (4H, m), 1.97-2.12 (2H, m), 2.44 (1H, dd, J=13.6, 5.6 Hz), 2.57 (3H, s), 3.98-4.10 (4H, m), 4.14-4.24 (1H, m), 7.12 (1H, dd, J=8.6, 2.1 Hz), 7.30 (1H, d, J=1.1 Hz), 7.35-7.42 (2H, m), 7.51 (2H, d, J=2.2 Hz), 7.84 (1H, d, J=8.0 Hz).

Example 40

2-{8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}ethanol To a mixture of 8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridine (200 mg) in DMF (5 mL) was added sodium hydride (60%, 31.6 mg) under ice-cooling, and the mixture was stirred for 30 min under a nitrogen atmosphere. (2-Bromoethoxy)(tert-butyl)dimethylsilane (113 µL) was added to the reaction mixture, and the mixture was stirred at room temperature for 1 hr. The reaction mixture was diluted with water, and the mixture was extracted with ethyl acetate. The extract was washed with saturated brine, and dried over anhydrous magnesium sulfate, and the solvent was evaporated under reduced pressure. To a mixture of the residue in THF (2 mL) was added TBAF (1M THF solution, 439 µL), and the mixture was stirred at room temperature for 2 hr. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (NH, methanol/ethyl acetate) to give the title compound (26.9 mg).
$^1$H NMR (300 MHz, CDCl$_3$) δ 1.69-1.84 (1H, m), 1.94-2.20 (2H, m), 2.31-2.51 (3H, m), 2.56 (3H, s), 3.53-3.75 (2H, m), 3.93-4.10 (4H, m), 4.14-4.27 (1H, m), 5.58 (1H, d, J=8.5 Hz), 6.93 (1H, dd, J=8.5, 1.9 Hz), 7.19 (1H, d, J=1.4 Hz), 7.27-7.32 (1H, m), 7.40 (1H, d, J=8.5 Hz), 7.48-7.53 (2H, m), 7.84 (1H, d, J=8.0 Hz).

Example 41

1-{8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methanamine A) {8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methyl 4-methylbenzenesulfonate To a mixture of {8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methanol (178 mg) in pyridine (3 mL) was added 4-methylbenzenesulfonyl chloride under ice-cooling, and the mixture was stirred at room temperature for 4 hr. 4-Methylbenzenesulfonyl chloride (84 mg) was further added, and the mixture was stirred at room temperature for 2 hr, and at 50° C. overnight. Water was added to the reaction mixture, and the precipitated solid was collected by filtration. The solid was purified by silica gel column chromatography (methanol/ethyl acetate) to give the title compound (163 mg).
MS (ESI+): [M+H]$^+$638.9.

B) 1-{8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methanamine A mixture of {8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methyl 4-methylbenzenesulfonate (150 mg) and sodium azide (45.8 mg) in DMSO (2 mL) was stirred at 100° C. for 2 days. Water was added to the reaction mixture, and the precipitated solid was collected by filtration. The solid was dissolved in THF (2 mL)/water (2 mL), diphenylphosphino-polystyrene (1.99 mmol/g, 236 mg) was added, and the mixture was stirred at 60° C. overnight. The reaction mixture was filtered, and the solvent in the filtrate was evaporated under reduced pressure. The residue was recrystallized from hexane/ethyl acetate to give the title compound (55.5 mg).
$^1$H NMR (300 MHz, CDCl$_3$) δ 1.77-1.91 (1H, m), 2.01-2.13 (1H, m), 2.23 (1H, td, J=13.2, 2.6 Hz), 2.30-2.40 (1H, m), 2.56 (3H, s), 3.19 (1H, d, J=13.2 Hz), 3.42 (1H, d, J=13.4 Hz), 3.96-4.08 (4H, m), 4.12-4.22 (1H, m), 7.14 (1H, dd, J=8.4, 2.3 Hz), 7.29 (1H, dd, J=8.2, 1.4 Hz), 7.36-7.44 (2H, m), 7.50 (2H, s), 7.83 (1H, d, J=8.0 Hz).

Example 42

N-({8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methyl)acetamide To a mixture of 1-{8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methanamine (76.7 mg) and triethylamine (26.2 μL) in THF (1 mL) was added acetic anhydride under ice-cooling, and the mixture was stirred at room temperature for 2 hr. Water was added to the reaction mixture, and the precipitated solid was collected by filtration. The solid was purified by silica gel column chromatography (methanol/ethyl acetate) to give the title compound (59.6 mg).
$^1$H NMR (300 MHz, CDCl$_3$) δ 1.74-1.86 (1H, m), 1.89 (3H, s), 1.97-2.12 (2H, m), 2.33-2.44 (1H, m), 2.56 (3H, s), 3.58 (1H, dd, J=13.6, 3.7 Hz), 3.94-4.10 (4H, m), 4.16-4.27 (1H, m), 4.32 (1H, dd, J=13.6, 8.4 Hz), 7.03-7.13 (2H, m), 7.21 (1H, d, J=2.5 Hz), 7.31 (1H, dd, J=8.0, 1.4 Hz), 7.40 (1H, d, J=8.2 Hz), 7.52 (2H, s), 7.85 (1H, d, J=8.0 Hz).

Example 47 ethyl 8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridine-8-carboxylate A) ethyl 3-[3-methoxy-4-(2-methyl-1,3-oxazol-5-yl)phenyl]-5,6,7,8-tetrahydro[1,2,4]triazolo[4,3-a]pyridine-8-carboxylate A mixture of ethyl 2-oxo-3-piperidinecarboxylate (34.6 g), trimethyloxonium tetrafluoroborate (95%, 31.5 g) and acetonitrile (600 mL) was stirred at room temperature for 16 hr. 3-Methoxy-4-(2-methyl-1,3-oxazol-5-yl)benzohydrazide (50.0 g) was added to the reaction mixture at room temperature, and the mixture was heated under reflux for 24 hr, allowed to cool to room temperature and concentrated under reduced pressure. Saturated aqueous sodium hydrogen carbonate solution was added to the residue, the insoluble material was filtered off through celite, and the filtrate was extracted with ethyl acetate. The extract was washed with saturated brine, and dried over anhydrous sodium sulfate, and the solvent was evaporated under reduced pressure. The residue was crystallized from methanol/ethyl acetate to give the title compound (29.0 g).
MS (ESI+): [M+H]$^+$383.3.

B) ethyl 8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridine-8-carboxylate Ethyl 3-[3-methoxy-4-(2-methyl-1,3-oxazol-5-yl)phenyl]-5,6,7,8-tetrahydro[1,2,4]triazolo[4,3-a]pyridine-8-carboxylate (3.00 g) was added to a suspension of sodium hydride (60%, 340 mg) in DMF (5 ml) under ice-cooling. The reaction mixture was stirred for 30 min under ice-cooling, 3,4-difluorobenzyl bromide (1.53 g) was added under ice-cooling, and the mixture was stirred for 1 hr under ice-cooling. The reaction mixture was diluted with ethyl acetate, the mixture was washed with saturated aqueous ammonium chloride solution and saturated brine, and dried over anhydrous sodium sulfate, and the solvent was evaporated under reduced pressure. The residue was purified by silica gel column chromatography (methanol/ethyl acetate) to give the title compound (3.47 g).

Example 48

1-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}ethanone Methylmagnesium bromide (12% THF solution, 13 mL) was added to a mixture of ethyl 8-(3,4-difluorobenzyl)-3-[3- methoxy-4-(2-methyl-1,3-oxazol-5-yl)phenyl]-5,6,7,8-tetrahydro[1,2,4]triazolo[4,3-a]pyridine-8-carboxylate (1.60 g) in THF (16 mL) under ice-cooling. The reaction mixture was stirred under ice-cooling for 1 hr, and methylmagnesium bromide (12% THF solution, 13 mL) was added under ice-cooling. The reaction mixture was stirred under ice-cooling for 1 hr, saturated aqueous ammonium chloride solution and water were added, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane), and further recrystallized from ethyl acetate/hexane to give the title compound (121 mg).

Example 49

2-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol Methylmagnesium bromide (12% THF solution, 13 mL) was added to a mixture of ethyl 8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridine-8-carboxylate (1.60 g) in THF (16 mL) under ice-cooling. The reaction mixture was stirred under ice-cooling for 1 hr, and methylmagnesium bromide (12% THF solution, 13 mL) was added under ice-cooling. The reaction mixture was stirred under ice-cooling for 1 hr, saturated aqueous ammonium chloride solution and water were added, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (740 mg).

Example 50 optically active 2-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A racemate (720 mg) of 2-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol was to separated by HPLC (column: CHIRALCEL AD (trade name), 50 mm ID×500 mm L, mobile phase:hexane/2-propanol=400/600) to give the title compound (350 mg) having a shorter retention time.

Example 51 optically active 2-[8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl]propan-2-ol A racemate (720 mg) of 2-[8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl]propan-2-ol was separated by HPLC (column: CHIRALCEL AD (trade name), 50 mm ID×500 mm L, mobile phase: hexane/2-propanol=400/600) to give the title compound (345 mg) having a longer retention time.

Example 52

{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}methanol A mixture of ethyl 8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridine-8-carboxylate (180 mg) in THF (2 mL) was added to a suspension of lithium aluminum hydride (53.7 mg) in THF (2 mL) under ice-cooling. The reaction mixture was stirred for 10 min under ice-cooling, and sodium sulfate decahydrate (500 mg) was added under ice-cooling. The reaction mixture was filtered, and the solvent was evaporated under reduced pressure. The residue was purified by silica gel column chromatography (NH, ethyl acetate/hexane) to give the title compound (121 mg).

Example 53

{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}methyl acetate A catalytic amount of 4-dimethylaminopyridine was added to a mixture of {8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}methanol (80.0 mg), acetic anhydride (19.4 µL), triethylamine (28.6 µL) and THF (1 mL) under ice-cooling. The reaction mixture was stirred at room temperature for 1 hr, and diluted with ethyl acetate, and the mixture was washed with water and saturated brine, and dried over anhydrous sodium sulfate. The solvent was evaporated under reduced pressure, and the residue was purified by silica gel column chromatography (methanol/ethyl acetate) to give the title compound (72.5 mg).

Example 54

8-(3,4-difluorobenzyl)-8-(methoxymethyl)-3-[3-methoxy-4-(2-methyl-1,3-oxazol-5-yl)phenyl]-5,6,7,8-tetrahydro[1,2,4]triazolo[4,3-a]pyridine {8-(3,4-Difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}methanol (100 mg) was added to a suspension of sodium hydride (60%, 9.4 mg) in DMF (1 mL) under ice-cooling, and the mixture was stirred for 30 min. Methyl iodide (14.7 µL) was added to the reaction mixture under ice-cooling. The reaction mixture was stirred under ice-cooling for 1 hr, and diluted with ethyl acetate, and the mixture was washed with water and saturated brine, and dried over anhydrous sodium sulfate. The solvent was evaporated under reduced pressure, and the residue was purified by silica gel column chromatography (methanol/ethyl acetate) to give the title compound (80.0 mg).

Example 55

8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridine-8-carboxamide A mixture of ethyl 8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridine-8-carboxylate (100 mg), formamide (78.5 µL), sodium methoxide (28% methanol solution, 200 μL) and DMF (1 mL) was stirred at 70° C. for 30 min, and allowed to cool to room temperature. Saturated aqueous ammonium chloride solution was added. The precipitate was collected by filtration, washed with water and IPE, and dried under reduced pressure to give the title compound (80.4 mg).

Example 56

1-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}ethanol A suspension of 1-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}ethanone (85.0 mg) in THF (1 mL) was added to a suspension of lithium aluminum hydride (13.5 mg) in THF (1 mL) under ice-cooling. The reaction mixture was stirred for 10 min under ice-cooling, and sodium sulfate decahydrate (140 mg) was added under ice-cooling. The reaction mixture was stirred at room temperature for 1 hr and filtered, and the solvent was evaporated under reduced pressure. The residue was purified by silica gel column chromatography (NH, ethyl acetate/hexane) to give the title compound (61.4 mg).

Example 59

8-(3,4-difluorobenzyl)-3-[3-methoxy-4-(2-methyl-1,3-oxazol-5-yl)phenyl]-N-(2,2,2-trifluoroethyl)-5,6,7,8-tetrahydro[1,2,4]triazolo[4,3-a]pyridine-8-carboxamide To a mixture of ethyl 8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridine-8-carboxylate (200 mg) in THF (1 mL)/methanol (1 mL) was added 1N aqueous sodium hydroxide solution (0.39 ml) at room temperature, and the mixture was stirred at room temperature for 3 hr. The solvent in the reaction mixture was evaporated under reduced pressure. To a mixture of the residue, triethylamine (0.066 mL) and 2,2,2-trifluoroethylamine (0.037 mL) in DMF (2 mL) was added HATU (179 mg) at 0° C., and the mixture was stirred at 0° C. for 1 hr. The reaction mixture was diluted with ethyl acetate, the mixture was washed with saturated brine and dried over anhydrous magnesium sulfate, and the solvent was evaporated under reduced pressure. The residue was purified by silica gel column chromatography (ethyl acetate/hexane), and further recrystallized from ethyl acetate/methanol to give the title compound (69.0 mg).

$^1$H NMR (300 MHz, CDCl$_3$) δ 1.65-1.86 (2H, m), 1.94-2.06 (1H, m), 2.57 (3H, s), 2.68-2.79 (1H, m), 3.30 (1H, d, J=13.5 Hz), 3.60 (1H, d, J=13.5 Hz), 3.71-3.92(2H, m), 3.99-4.13 (5H, m), 6.78-6.86 (1H, m), 6.86-6.96 (1H, m), 6.97-7.09 (1H, m), 7.22 (1H, d, J=8.0 Hz), 7.47 (1H, s), 7.52 (1H, s), 7.84 (1H, d, J=8.0 Hz), 8.27 (1H, t, J=6.3 Hz).

Example 60

8-(3,4-difluorobenzyl)-3-[3-methoxy-4-(2-methyl-1,3-oxazol-5-yl)phenyl]-N-methyl-N-(2,2,2-trifluoroethyl)-5,6,7,8-tetrahydro[1,2,4]triazolo[4,3-a]pyridine-8-carboxamide To a mixture of 8-(3,4-difluorobenzyl)-3-[3-methoxy-4-(2-methyl-1,3-oxazol-5-yl)phenyl]-N-(2,2,2-trifluoroethyl)-5,6,7,8-tetrahydro[1,2,4]triazolo[4,3-a]pyridine-8-carboxamide (200 mg) in DMF (2 mL) was added sodium hydride (60%, 7.8 mg) at 0° C., and the mixture was stirred at room temperature for 1 hr. Methyl iodide (0.012 mL) was added to the reaction mixture at 0° C., and the mixture was stirred at room temperature for 3 hr. The reaction mixture was diluted with ethyl acetate, the mixture was washed with saturated brine and dried over anhydrous magnesium sulfate, and the solvent was evaporated under reduced pressure. The residue was purified by silica gel column chromatography (ethyl acetate/hexane), and further recrystallized from ethyl acetate/methanol to give the title compound (25.3 mg).

$^1$H NMR (300 MHz, CDCl$_3$) δ 1.63-1.76 (1H, m), 1.79-1.94 (1H, m), 1.98-2.11 (1H, m), 2.43-2.61 (4H, m), 2.92 (3H, s), 3.58-3.73 (2H, m), 3.84-4.02 (2H, m), 4.03-4.09 (4H, m), 4.32-4.51 (1H, m), 6.82-7.09 (3H, m), 7.18 (1H, d, J=8.0 Hz), 7.44 (1H, s), 7.52 (1H, s), 7.84 (1H, d, J=8.0 Hz).

Example 70

2-{8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A) ethyl 8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate A mixture of ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (200 mg), 4-chloro-3-fluorophenol (73.8 mg), potassium carbonate (199 mg) and DMF (2 mL) was stirred at 100° C. for 30 min, and allowed to cool to room temperature. Ethyl acetate and water were added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (127 mg).

MS (ESI+): [M+H]$^+$527.3.

B) 2-{8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol Under an argon atmosphere, methylmagnesium bromide (1M THF solution, 1.9 mL) was added to a suspension of ethyl 8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate (200 mg) in THF (2 mL) under ice-cooling. The reaction mixture was stirred for 2 hr under ice-cooling, saturated aqueous ammonium chloride solution was added, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane) to give the title compound (129 mg).

$^1$H NMR (300 MHz, CDCl$_3$) δ 1.28 (3H, s), 1.59 (3H, s), 2.02-2.18 (3H, m), 2.38-2.49 (1H, m), 2.56 (3H, s), 3.91-4.07 (4H, m), 4.20-4.30 (1H, m), 4.84 (1H, brs),6.52-6.66 (2H, m), 7.07-7.15 (1H, m), 7.23 (1H, dd, J=8.1, 1.5 Hz), 7.47 (1H, d, J=1.5 Hz), 7.51 (1H, s), 7.84 (1H, d, J=8.1 Hz).

Example 71

8-[(2-bromo-5-fluorobenzyl)oxy]-3-[3-methoxy-4-(2-methyl-1,3-oxazol-5-yl)phenyl]-N-methyl-N-(2,2,2-trifluoroethyl)-5,6,7,8-tetrahydro[1,2,4]triazolo[4,3-a]pyridine-8-carboxamide A) ethyl 8-[(2-bromo-5-fluorobenzyl)oxy]-3-[3-methoxy-4-(2-methyl-1,3-oxazol-5-yl)phenyl]-5,6,7,8-tetrahydro[1,2,4]triazolo[4,3-a]pyridine-8-carboxylate To a mixture of ethyl 3-[3-methoxy-4-(2-methyl-1,3-oxazol-5-yl)phenyl]-5,6,7,8-tetrahydro[1,2,4]triazolo[4,3-a]pyridine-8-carboxylate (1000 mg) in DMF (8 ml) was added sodium hydride (60%, 115 mg), and the mixture was stirred at room temperature for 1 hr in the air. Sodium hydride (60%, 115 mg) and 1-bromo-2-(bromomethyl)-4-fluorobenzene (1051 mg) were added, and the mixture was stirred at room temperature for 1 hr. Saturated aqueous ammonium chloride was added to the reaction mixture, and the mixture was extracted with ethyl acetate. The extract was washed successively with saturated aqueous sodium hydrogen carbonate solution and brine, and dried over anhydrous magnesium sulfate, and the solvent was evaporated under reduced pressure. The residue was purified by silica gel column chromatography (ethyl acetate/hexane) to give the title compound (920 mg).

$^1$H NMR (300 MHz, CDCl$_3$) δ 1.32 (3H, t, J=7.2 Hz), 2.02-2.64 (7H, m), 3.98-4.47 (7H, m), 4.78 (1H, d, J=13.0 Hz), 5.09 (1H, d, J=13.0 Hz), 6.83 (1H, td, J=8.3, 3.0 Hz), 7.13-7.35 (2H, m), 7.39-7.61 (3H, m), 7.84 (1H, d, J=7.9 Hz).

B) 8-[(2-bromo-5-fluorobenzyl)oxy]-3-[3-methoxy-4-(2-methyl-1,3-oxazol-5-yl)phenyl]-N-(2,2,2-trifluoroethyl)-5,6,7,8-tetrahydro[1,2,4]triazolo[4,3-a]pyridine-8-carboxamide In the same manner as in Example 59, the title compound was obtained from ethyl 8-[(2-bromo-5-fluorobenzyl)oxy]-3-[3-methoxy-4-(2-methyl-1,3-oxazol-5-yl)phenyl]-5,6,7,8-tetrahydro[1,2,4]triazolo[4,3-a]pyridine-8-carboxylate.

$^1$H NMR (300 MHz, CDCl$_3$) δ 2.18-2.43 (3H, m), 2.53-2.66 (4H, m), 3.78-3.97 (1H, m), 3.99-4.27 (6H, m), 4.58-4.70 (2H, m), 7.01 (1H, td, J=8.2, 2.5 Hz), 7.22-7.33 (2H, m), 7.36-7.46 (2H, m), 7.46-7.54 (1H, m), 7.82-7.89 (1H, m), 8.42 (1H, t, J=6.4 Hz).

C) 8-[(2-bromo-5-fluorobenzyl)oxy]-3-[3-methoxy-4-(2-methyl-1,3-oxazol-5-yl)phenyl]-N-methyl-N-(2,2,2-trifluoroethyl)-5,6,7,8-tetrahydro[1,2,4]triazolo[4,3-a]pyridine-8-carboxamide In the same manner as in Example 60, the title compound was obtained from 8-[(2-bromo-5-fluorobenzyl)oxy]-3-[3-methoxy-4-(2-methyl-1,3-oxazol-5-yl)phenyl]-N-(2,2,2-trifluoroethyl)-5,6,7,8-tetrahydro[1,2,4]triazolo[4,3-a]pyridine-8-carboxamide.

$^1$H NMR (300 MHz, CDCl$_3$) δ 2.09-2.67 (7H, m), 3.40 (3H, br s), 3.67-4.53 (7H, m), 4.77 (2H, s), 6.88 (1H, d, J=3.0 Hz), 7.20-7.33 (2H, m), 7.38-7.59 (3H, m), 7.85 (1H, d, J=7.9 Hz).

Example 73

8-(4-chlorophenyl)-3-[3-methoxy-4-(3-methyl-1H-1,2,4-triazol-1-yl)phenyl]-8-methyl-5,6,7,8-tetrahydro[1,2,4]triazolo[4,3-a]pyridine A) (4-bromo-2-fluorophenyl) hydrazine To a mixture of 4-bromo-2-fluoroaniline (5.0 g) in concentrated hydrochloric acid (25 mL) was added a mixture of sodium nitrite (1.9 g) in water (2.5 mL) at −20° C., and the mixture was stirred at 0° C. for 30 min. The reaction mixture was added dropwise to a mixture of tin chloride (19 g) in concentrated hydrochloric acid (25 mL) at −20° C., and the mixture was stirred at room temperature for 1 hr. The precipitate was collected by filtration, and washed with diethyl ether. The obtained solid was neutralized with 10% aqueous potassium carbonate solution, and ethyl acetate was added. The insoluble material was removed by filtration, the filtrate was extracted with ethyl acetate, the extract was washed with saturated brine and dried over anhydrous magnesium sulfate, and the solvent was evaporated under reduced pressure to give the title compound (3.4 g).

$^1$H NMR (300 MHz, CDCl$_3$) δ 3.56 (2H, br, s), 5.41 (1H, br, s), 7.02 (1H, t, J=9.0 Hz), 7.12 (1H, dd, J=10.9, 2.3 Hz), 7.16-7.23 (1H, m).

B) 1-(4-bromo-2-fluorophenyl)-3-methyl-1H-1,2,4-triazole

To a mixture of (4-bromo-2-fluorophenyl)hydrazine (3.4 g) in methanol (25 mL) was added methyl ethanimidothioate hydroiodide (3.6 g), and the mixture was stirred at room temperature for 40 min. The solvent was evaporated under reduced pressure. To a mixture of the obtained residue in toluene (20 mL) were added methyl orthoformate (15 mL) and pyridine (15 mL), and the mixture was stirred at 100° C. for 9 hr. The reaction mixture was allowed to cool to room temperature, and diluted with saturated aqueous sodium hydrogen carbonate solution, and the mixture was extracted with ethyl acetate. The extract was washed with saturated brine, the organic layer was dried over anhydrous magnesium sulfate, and the solvent was evaporated under reduced pressure. The residue was purified by silica gel column chromatography (ethyl acetate/hexane) to give the title compound (3.7 g).

$^1$H NMR (300 MHz, CDCl$_3$) δ 2.50 (3H, s), 7.40-7.51 (2H, m), 7.68-7.85 (1H, m), 8.52 (1H, d, J=3.0 Hz).

C) 3-fluoro-4-(3-methyl-1H-1,2,4-triazol-1-yl)benzonitrile

Under a nitrogen atmosphere, to a mixture of 1-(4-bromo-2-fluorophenyl)-3-methyl-1H-1,2,4-triazole (1.02 g), potassium carbonate (0.55 g) and potassium hexacyanoferrate(II) trihydrate (0.68 g) in DMF (4 mL)/ethanol (0.20 mL) was added palladium acetate (45 mg) at room temperature, and the mixture was stirred at 120° C. for 2 hr. The reaction mixture was allowed to cool to room temperature, and diluted with water and saturated brine, and the mixture was extracted with ethyl acetate. The extract was washed with saturated brine, the organic layer was dried over anhydrous magnesium sulfate, and the solvent was evaporated under reduced pressure. The residue was purified by silica gel column chromatography (ethyl acetate/hexane) to give the title compound (0.51 g).

¹H NMR (300 MHz, CDCl₃) δ 2.53 (3H, s), 7.59-7.64 (2H, m), 8.15 (1H, dd, J=8.1 Hz, 8.1 Hz), 8.68 (1H, d, J=2.7 Hz).

D) 3-methoxy-4-(3-methyl-1H-1,2,4-triazol-1-yl)benzonitrile

To a mixture of 3-fluoro-4-(3-methyl-1H-1,2,4-triazol-1-yl)benzonitrile (0.51 g) in DMF (10 mL) was added sodium methoxide (5M methanol solution, 1.51 mL) at room temperature, and the mixture was stirred at 50° C. for 2 hr. The reaction mixture was added to ice water, and the precipitated solid was collected by filtration, and washed with water to give the title compound (0.34 g).
¹H NMR (300 MHz, CDCl₃) δ 2.51 (3H, s), 4.03 (3H, s), 7.33 (1H, m), 7.42 (1H, dd, J=1.5 Hz, 8.4 Hz), 8.02 (1H, d, J=8.7 Hz), 8.82 (1H, s).

E) 3-methoxy-4-(3-methyl-1H-1,2,4-triazol-1-yl)benzoic acid

To 3-methoxy-4-(3-methyl-1H-1,2,4-triazol-1-yl)benzonitrile (0.34 g) was added 6N hydrochloric acid (3 mL) at room temperature, and the mixture was stirred at 120° C. overnight. The reaction mixture was allowed to cool to room temperature, and the precipitated solid was collected by filtration, and washed with water to give the title compound (0.34 g).
¹H NMR (300 MHz, DMSO-d₆) δ 2.36 (3H, s), 3.97 (3H, s), 7.66-7.72 (2H, m), 7.81 (1H, d, J=8.1 Hz), 8.95 (1H, s).

F) tert-butyl 2-{[3-methoxy-4-(3-methyl-1H-1,2,4-triazol-1-yl)phenyl]carbonyl}hydrazinecarboxylate To a mixture of 3-methoxy-4-(3-methyl-1H-1,2,4-triazol-1-yl)benzoic acid (0.15 g), tert-butyl hydrazinecarboxylate (0.17 g) and triethylamine (0.18 mL) in DMF (2 mL) was added HATU (0.49 g) at 0° C., and the mixture was stirred at 0° C. for 1 hr. The reaction mixture was diluted with ethyl acetate, the mixture was washed with saturated brine and dried over anhydrous magnesium sulfate, and the solvent was evaporated under reduced pressure. The residue was purified by silica gel column chromatography (ethyl acetate/hexane) to give the title compound (0.36 g).
¹H NMR (300 MHz, CDCl₃) δ 1.53 (9H, s), 2.50 (3H, s), 3.99 (3H, s), 6.71 (1H, br), 7.45 (1H, dd, J=1.2 Hz, 8.1 Hz), 7.60 (1H, s), 7.99 (1H, d, J=8.4 Hz), 8.34 (1H, br), 8.80 (1H, s).

G) 3-methoxy-4-(3-methyl-1H-1,2,4-triazol-1-yl)benzohydrazide dihydrochloride

To a mixture of tert-butyl 2-{[3-methoxy-4-(3-methyl-1H-1,2,4-triazol-1-yl)phenyl]carbonyl}hydrazinecarboxylate (0.22 g) in methanol (2 mL) was added hydrochloric acid (4-Methyl acetate solution, 1 mL) at room temperature, and the mixture was stirred at room temperature for 4 hr. The precipitated solid was collected by filtration, and washed with ethyl acetate to give the title compound (0.15 g).
¹H NMR (300 MHz, DMSO-d₆) δ 2.37 (3H, s), 4.01 (3H, s), 4.15 (4H, br), 7.68 (1H, dd, J=1.8 Hz, 8.7 Hz), 7.84 (1H, d, J=1.5 Hz), 7.87 (1H, d, J=8.1 Hz), 9.00 (1H, s), 11.95 (1H, s).

H) 8-(4-chlorophenyl)-3-[3-methoxy-4-(3-methyl-1H-1,2,4-triazol-1-yl)phenyl]-8-methyl-5,6,7,8-tetrahydro[1,2,4]triazolo[4,3-a]pyridine In the same manner as in Example 3, steps H to I, the title compound was obtained from 5-chloro-2-(4-chlorophenyl)-2-methylpentanoic acid and 3-methoxy-4-(3-methyl-1H-1,2,4-triazol-1-yl)benzohydrazide dihydrochloride.
¹H NMR (300 MHz, CDCl₃) δ1.78-1.94 (4H, m), 1.97-2.10 (2H, m), 2.41-2.55 (4H, m), 3.97-4.08 (4H, m), 4.11-4.21 (1H, m), 7.16-7.22 (2H, m), 7.30-7.35 (2H, m), 7.65 (1H, d, J=1.4 Hz), 7.95 (1H, d, J=8.2 Hz).

Example 74

8-(4-chlorophenyl)-3-[3-methoxy-4-(4-methyl-1H-imidazol-1-yl)phenyl]-8-methyl-5,6,7,8-tetrahydro[1,2,4]triazolo[4,3-a]pyridine A) methyl 4-(formylamino)-3-methoxybenzoate To formic acid (75 mL) was added dropwise acetic anhydride (50 mL) at room temperature, and the mixture was stirred at room temperature for 40 min. A mixture of methyl 4-amino-3-methoxybenzoate (25 g) in THF (100 mL) was added dropwise to the reaction mixture, and the mixture was stirred at room temperature for 1 hr. Ice water (700 mL) was added to the reaction mixture, and the precipitated solid was collected by filtration. The solid was washed with water (400 mL) to give the title compound (25.8 g).
¹H NMR (300 MHz, CDCl₃) δ 3.93 (3H, s), 3.97 (3H, s), 7.58 (1H, d, J=1.5 Hz), 7.70 (1H, dd, J=1.5 Hz, 8.4 Hz), 7.97 (1H, brs), 8.46 (1H, d, J=8.4 Hz), 8.52 (1H, d, J=0.9 Hz).

B) methyl 4-[formyl(2-oxopropyl)amino]-3-methoxybenzoate

To a mixture of methyl 4-(formylamino)-3-methoxybenzoate (25.8 g), cesium carbonate (80.4 g) and potassium iodide (2.04 g) in DMF (115 mL) was added dropwise chloroacetone (19.6 mL) at room temperature, and the mixture was stirred at room temperature for 3 hr. Cesium carbonate (40.2 g) and chloroacetone (9.8 mL) were added to the reaction mixture, and the mixture was stirred at room temperature for 2 hr. Ice water and ethyl acetate were added to the reaction mixture, and the organic layer was separated. To the aqueous layer was added ethyl acetate, and the organic layer was separated. The organic layers were combined, washed with saturated brine, and dried over anhydrous magnesium sulfate, and the solvent was evaporated under reduced pressure. The residue was purified by silica gel column chromatography (ethyl acetate/hexane) to give the title compound (32.6 g).
¹H NMR (300 MHz, CDCl₃) δ2.13-2.32 (3H, m), 3.84-4.05 (6H, m), 4.49 (2H, s), 7.21-7.44 (1H, m), 7.56-7.78 (2H, m), 8.33 (1H, s).

C) methyl 3-methoxy-4-(4-methyl-1H-imidazol-1-yl)benzoate

A mixture of methyl 4-[formyl(2-oxopropyl)amino]-3-methoxybenzoate (32.6 g) and ammonium acetate (47.5 g) in acetic acid (65.6 mL) was stirred at 140° C. for 1 hr. After completion of the reaction, ethyl acetate and saturated aqueous sodium hydrogen carbonate solution were added under ice-cooling, and the organic layer was separated. To the aqueous layer was added ethyl acetate, and the organic layer was separated. The organic layers were combined, washed with saturated brine, and dried over anhydrous magnesium sulfate, and the solvent was evaporated under reduced pressure. The residue was purified by silica gel column chromatography (methanol/ethyl acetate/hexane) to give the title compound (16.0 g).

$^1$H NMR (300 MHz, CDCl$_3$) δ 2.32 (3H, s), 3.95-3.96 (6H, m), 6.99 (1H, s), 7.33 (1H, d, J=8.4 Hz), 7.71-7.74 (2H, m), 7.80 (1H, s).

D) 3-methoxy-4-(4-methyl-1H-imidazol-1-yl)benzoic acid

A mixture of methyl 3-methoxy-4-(4-methyl-1H-imidazol-1-yl)benzoate (16.0 g) in 2N aqueous sodium hydroxide solution (65 mL) and methanol (100 mL) was stirred at room temperature for 1 hr, and the mixture was acidified with 6N hydrochloric acid (pH=3-4). Water was added to the reaction mixture, and the precipitate was collected by filtration. The solid was washed with ethyl acetate and water to give the title compound (8.07 g). To the filtrate was added saturated brine, and the mixture was extracted with ethyl acetate/2-propanol. The organic layers were combined, washed with saturated brine, and dried over anhydrous magnesium sulfate, and the solvent was evaporated under reduced pressure. The residue was washed with ethyl acetate to give the title compound (4.10 g).
MS (ESI+): [M+H]$^+$233.1.

E) tert-butyl 2-{[3-methoxy-4-(4-methyl-1H-imidazol-1-yl)phenyl]carbonyl}hydrazinecarboxylate To a mixture of 3-methoxy-4-(4-methyl-1H-imidazol-1-yl)benzoic acid (12.1 g) and tert-butyl hydrazinecarboxylate (7.61 g) in DMF (100 mL) was added diethyl phosphoryl cyanide (8.55 mL) at room temperature. After stirring at room temperature for 30 min, triethylamine (21.6 mL) was added, and the mixture was stirred overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (8.00 g).
$^1$H NMR (300 MHz, CDCl$_3$) δ 1.52 (9H, s), 2.28 (3H, s), 3.83 (3H, s), 6.80 (1H, br. s.), 6.90 (1H, s), 7.19 (1H, d, J=8.0 Hz), 7.42 (1H, d, J=8.2 Hz), 7.53 (1H, s), 7.72 (1H, s), 9.09 (1H, br. s.)

F) 3-methoxy-4-(4-methyl-1H-imidazol-1-yl)benzohydrazide dihydrochloride

To a mixture of tert-butyl 2-{[3-methoxy-4-(4-methyl-1H-imidazol-1-yl)phenyl]carbonyl}hydrazinecarboxylate (8.00 g) in ethyl acetate (50 mL) was added hydrogen chloride (4-Methyl acetate solution, 100 mL), and the mixture was stirred at room temperature overnight. Ethyl acetate was added to the reaction mixture, and the precipitate was collected by filtration. The solid was recrystallized from methanol/ethyl acetate to give the title compound (5.94 g).
MS (ESI+), found: 247.2.

G) 8-(4-chlorophenyl)-3-[3-methoxy-4-(4-methyl-1H-imidazol-1-yl)phenyl]-8-methyl-5,6,7,8-tetrahydro[1,2,4]triazolo[4,3-a]pyridine In the same manner as in Example 3, steps H to I, the title compound was obtained from 5-chloro-2-(4-chlorophenyl)-2-methylpentanoic acid and 3-methoxy-4-(4-methyl-1H-imidazol-1-yl)benzohydrazide dihydrochloride.
MS (ESI+): [M+H]$^+$434.2.

Example 75

2-{8-(3,4-difluorophenyl)-3-[3-methoxy-4-(4-methyl-1H-imidazol-1-yl)phenyl]-5,6,7,8-tetrahydro[1,2,4]triazolo[4,3-a]pyridin-8-yl}propan-2-ol A) 3-methoxy-4-(4-methyl-1H-imidazol-1-yl)benzohydrazide To a suspension of 3-methoxy-4-(4-methyl-1H-imidazol-1-yl)benzoic acid (5 g) in THF (60 mL) was added N,N'-carbonyldiimidazole (6.98 g) at room temperature, and the mixture was stirred at room temperature for 1 hr. The reaction mixture was cooled to −10° C., hydrazine monohydrate (10.44 mL) was added, and the mixture was stirred at room temperature for 2 hr. The solvent was evaporated under reduced pressure, and water was added. The precipitated solid was collected by filtration to give the title compound (0.70 g).
MS (ESI+): [M+H]$^+$247.3.

B) ethyl 3-(3,4-difluorophenyl)-2-(methylsulfanyl)-3,4,5,6-tetrahydropyridine-3-carboxylate Methyl iodide (0.520 ml,) was added to a mixture of ethyl 3-(3,4-difluorophenyl)-2-thioxopiperidine-3-carboxylate (500 mg) in acetonitrile (5 mL) at room temperature, and the mixture was stirred at 50° C. for 3 hr. The reaction mixture was diluted with ethyl acetate, the mixture was washed with saturated aqueous sodium hydrogen carbonate solution and saturated brine and dried over anhydrous sodium sulfate, and the solvent was evaporated under reduced pressure to give the title compound (530 mg).
MS (ESI+): [M+H]$^+$314.1.

C) ethyl 8-(3,4-difluorophenyl)-3-[3-methoxy-4-(4-methyl-1H-imidazol-1-yl)phenyl]-5,6,7,8-tetrahydro[1,2,4]triazolo[4,3-a]pyridine-8-carboxylate 3-Methoxy-4-(4-methyl-1H-imidazol-1-yl)benzohydrazide (236 mg) was added to a mixture of ethyl 3-(3,4-difluorophenyl)-2-(methylsulfanyl)-3,4,5,6-tetrahydropyridine-3-carboxylate (300 mg) in ethanol (3 mL) at room temperature, and the mixture was stirred at 90° C. for 2 days. The reaction mixture was diluted with ethyl acetate, the mixture was washed with water and saturated brine and dried over anhydrous sodium sulfate, and the solvent was evaporated under reduced pressure. The residue was purified by silica gel column chromatography (NH, ethyl acetate/hexane) to give the title compound (217 mg).
MS (ESI+): [M+H]$^+$494.2.

D) 2-{8-(3,4-difluorophenyl)-3-[3-methoxy-4-(4-methyl-1H-imidazol-1-yl)phenyl]-5,6,7,8-tetrahydro[1,2,4]triazolo[4,3-a]pyridin-8-yl}propan-2-ol In the same manner as in Example 32, step G, the title compound was obtained from ethyl 8-(3,4-difluorophenyl)-3-[3-methoxy-4-(4-methyl-1H-imidazol-1-yl)phenyl]-5,6,7,8-tetrahydro[1,2,4]triazolo[4,3-a]pyridine-8-carboxylate.

Example 80

2-{8-(3,4-difluorobenzyl)-3-[3-methoxy-4-(4-methyl-1H-imidazol-1-yl)phenyl]-5,6,7,8-tetrahydro[1,2,4]triazolo[4,3-a]pyridin-8-yl}propan-2-ol A) ethyl 3-(3,4-difluorobenzyl)-2-oxopiperidine-3-carboxylate Under a nitrogen atmosphere, to a mixture of ethyl 2-oxopiperidine-3-carboxylate (2.0 g) in DMF (20 mL) was added sodium hydride (60%, 0.47 g) at 0° C., and the mixture was stirred at 0° C. for 30 min. 4-(Bromomethyl)-1,2-difluorobenzene (1.50 mL) was added to the reaction mixture, and the mixture was stirred at room temperature overnight. The reaction mixture was diluted with ethyl acetate and saturated aqueous ammonium chloride solution, the mixture was washed with saturated brine and dried over anhydrous magnesium sulfate, and the solvent was evaporated under reduced pressure. The residue was purified by silica gel column chromatography (ethyl acetate/hexane) to give the title compound (2.82 g).

$^1$H NMR (300 MHz, CDCl$_3$) δ 1.30 (3H, t, J=7.1 Hz), 1.54-1.66 (1H, m), 1.69-1.92 (2H, m), 2.11 (1H, dd, J=11.4, 3.7 Hz), 2.99 (1H, d, J=13.7 Hz), 3.03-3.11 (1H, m), 3.21-3.32 (1H, m), 3.55 (1H, d, J=13.5 Hz), 4.11-4.34 (2H, m), 6.12 (1H, brs), 6.88-7.18 (3H, m).

B) ethyl 3-(3,4-difluorobenzyl)-2-thioxopiperidine-3-carboxylate

To a mixture of ethyl 3-(3,4-difluorobenzyl)-2-oxopiperidine-3-carboxylate (2.8 g) in toluene (50 ml) was added Lawesson's reagent (2.67 g) at room temperature, and the mixture was stirred at 100° C. overnight. The reaction mixture was diluted with ethyl acetate and saturated aqueous sodium hydrogen carbonate solution, the mixture was washed with saturated brine and dried over anhydrous magnesium sulfate, and the solvent was evaporated under reduced pressure. The residue was purified by silica gel column chromatography (ethyl acetate/hexane) to give the title compound (2.64 g).

$^1$H NMR (300 MHz, CDCl$_3$) δ 1.31 (3H, t, J=7.1 Hz), 1.46-1.57 (1H, m), 1.77-1.90 (1H, m), 1.90-2.12 (2H, m), 2.92-3.05 (1H, m), 3.27-3.39 (2H, m), 3.89 (1H, d, J=14.0 Hz), 4.25 (2H, q, J=7.1 Hz), 6.99-7.14 (2H, m), 7.24-7.34 (1H, m), 8.43 (1H, brs).

C) 2-{8-(3,4-difluorobenzyl)-3-[3-methoxy-4-(4-methyl-1H-imidazol-1-yl)phenyl]-5,6,7,8-tetrahydro[1,2,4]triazolo[4,3-a]pyridin-8-yl}propan-2-ol In the same manner as in Example 75, steps B to D, the title compound was obtained from 3-methoxy-4-(4-methyl-1H-imidazol-1-yl)benzohydrazide and ethyl 3-(3,4-difluorobenzyl)-2-thioxopiperidine-3-carboxylate.

$^1$H NMR (300 MHz, CDCl$_3$) δ 1.09 (3H, s), 1.42 (3H, s), 1.59-1.74 (1H, m), 1.80-2.08 (3H, m), 2.31 (3H, s), 2.84 (1H, d, J=13.2 Hz), 3.43-3.55 (1H, m), 3.65-3.79 (1H, m), 3.90-3.98 (4H, m), 5.09 (1H, brs), 6.53-6.70 (2H, m), 6.79-7.00 (2H, m), 7.05 (1H, d, J=7.7 Hz), 7.34 (1H, d, J=8.0 Hz), 7.46 (1H, s), 7.74 (1H, s).

Example 81

2-{8-fluoro-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A) ethyl 8-fluoro-3-[3-methoxy-4-(2-methyl-1,3-oxazol-5-yl)phenyl]-5,6,7,8-tetrahydro[1,2,4]triazolo[4,3-a]pyridine-8-carboxylate Under an argon atmosphere, ethyl 3-[3-methoxy-4-(2-methyl-1,3-oxazol-5-yl)phenyl]-5,6,7,8-tetrahydro[1,2,4]triazolo[4,3-a]pyridine-8-carboxylate (200 mg) was added to a suspension of sodium hydride (60%, 23 mg) in DMF (2 mL) under ice-cooling. The reaction mixture was stirred for 30 min under ice-cooling, N-fluoro-N'-chloromethyltriethylenediamine bis(tetrafluoroborate) (371 mg) was added under ice-cooling, and the mixture was stirred for 30 min under ice-cooling. The reaction mixture was poured into saturated aqueous ammonium chloride solution, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate) to give the title compound (127 mg).

MS (ESI+): [M+H]$^+$401.3.

B) 2-{8-fluoro-3-[3-methoxy-4-(2-methyl-1,3-oxazol-5-yl)phenyl]-5,6,7,8-tetrahydro[1,2,4]triazolo[4,3-a]pyridin-8-yl}propan-2-ol In the same manner as in Example 49, the title compound was obtained from ethyl 8-fluoro-3-[3-methoxy-4-(2-methyl-1,3-oxazol-5-yl)phenyl]-5,6,7,8-tetrahydro[1,2,4]triazolo[4,3-a]pyridine-8-carboxylate.

Example 82 ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate Under an argon atmosphere, ethyl 3-[3-methoxy-4-(2-methyl-1,3-oxazol-5-yl)phenyl]-5,6,7,8-tetrahydro[1,2,4]triazolo[4,3-a]pyridine-8-carboxylate (1.00 g) was added to a suspension of sodium hydride (60%, 115 mg) in DMF (10 mL) under ice-cooling. The reaction mixture was stirred for 20 min under ice-cooling, N-chlorosuccinimide (383 mg) was added under ice-cooling, and the mixture was stirred for 20 min under ice-cooling. The reaction mixture was diluted with ethyl acetate, the mixture was poured into saturated aqueous ammonium chloride solution, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate) to give the title compound (750 mg).

Example 86

8-[5-(3,4-dichlorophenyl)-1,3,4-oxadiazol-2-yl]-3-[3-methoxy-4-(2-methyl-1,3-oxazol-5-yl)phenyl]-8-methyl-5,6,7,8-tetrahydro[1,2,4]triazolo[4,3-a]pyridine A) ethyl 3-[3-methoxy-4-(2-methyl-1,3-oxazol-5-yl)phenyl]-8-methyl-5,6,7,8-tetrahydro[1,2,4]triazolo[4,3-a]pyridine-8-carboxylate To a mixture of ethyl 3-[3-methoxy-4-(2-methyl-1,3-oxazol-5-yl)phenyl]-5,6,7,8-tetrahydro[1,2,4]triazolo[4,3-a]pyridine-8-carboxylate (5.0 g) in DMF (50 mL) was added sodium hydride (60%, 576 mg) at 0° C., and the mixture was stirred at 0° C. for 30 min. Iodomethane (978 was added, and the mixture was stirred at 0° C. for 30 min. Water was added to the reaction mixture, and the mixture was extracted with ethyl acetate. The extract was washed with water, and dried over anhydrous magnesium sulfate, and the solvent was evaporated under reduced pressure. The residue was purified by silica gel column chromatography (NH, ethyl acetate/hexane) to give the title compound (3.40 g).

MS (ESI+): [M+H]$^+$397.1.

B) 3-[3-methoxy-4-(2-methyl-1,3-oxazol-5-yl)phenyl]-8-methyl-5,6,7,8-tetrahydro[1,2,4]triazolo[4,3-a]pyridine-8-carboxylic acid A mixture of ethyl 3-[3-methoxy-4-(2-methyl-1,3-oxazol-5-yl)phenyl]-8-methyl-5,6,7,8-tetrahydro[1,2,4]triazolo[4,3-a]pyridine-8-carboxylate (1.5 g), 1N aqueous sodium hydroxide solution (7.57 mL) and THF (8 mL) was stirred at room temperature for 16 hr. The reaction mixture was acidified with 1N hydrochloric acid, and the organic layer was evaporated under reduced pressure. The mixture was stirred at room temperature for 30 min, and the obtained solid was collected by filtration to give the title compound (1.36 g).
$^1$H NMR (300 MHz, CDCl$_3$) δ 1.84 (3H, s), 1.88-2.01 (1H, m), 2.01-2.28 (2H, m), 2.47-2.62 (4H, m), 4.02 (3H, s), 4.04-4.16 (2H, m), 7.23 (1H, dd, J=8.1, 1.5 Hz), 7.40 (1H, d, J=1.4 Hz), 7.50 (1H, s), 7.82 (1H, d, J=8.0 Hz).

C) 8-[5-(3,4-dichlorophenyl)-1,3,4-oxadiazol-2-yl]-3-[3-methoxy-4-(2-methyl-1,3-oxazol-5-yl)phenyl]-8-methyl-5,6,7,8-tetrahydro[1,2,4]triazolo[4,3-a]pyridine A mixture of 3-[3-methoxy-4-(2-methyl-1,3-oxazol-5-yl)phenyl]-8-methyl-5,6,7,8-tetrahydro[1,2,4]triazolo[4,3-a]pyridine-8-carboxylic acid (100 mg), 3,4-dichlorobenzohydrazide hydrochloride (79 mg) and triethylamine (114 μL) in DMF (1.5 ml) was stirred at room temperature for 4 hr. Water was added to the reaction mixture, and the mixture was extracted with ethyl acetate. The extract was washed with brine, and dried over anhydrous magnesium sulfate, and the solvent was evaporated under reduced pressure. The residue was dissolved in acetonitrile (1.5 ml), trichloroacetonitrile (114 μL) and triphenylphosphine (286 mg) were added, and the mixture was stirred at 70° C. for 2 hr. The solvent was evaporated under reduced pressure, and the residue was purified by silica gel column chromatography (NH, ethyl acetate/hexane) to give the title compound (38.8 mg).
$^1$H NMR (300 MHz, CDCl$_3$) δ 2.11 (3H, s), 2.13-2.27 (2H, m), 2.29-2.44 (1H, m), 2.55 (3H, s), 2.80-2.93 (1H, m), 4.03 (3H, s), 4.06-4.16 (1H, m), 4.19-4.30 (1H, m), 7.22-7.29 (1H, m), 7.45 (1H, d, J=1.5 Hz), 7.50 (1H, s), 7.58 (1H, d, J=8.3 Hz), 7.84 (1H, d, J=7.9 Hz), 7.89-7.95 (1H, m), 8.16 (1H, d, J=2.3 Hz).

Example 91

7-(3,4-dichlorophenyl)-3-[3-methoxy-4-(3-methyl-1H-1,2,4-triazol-1-yl)phenyl]-7-methyl-4,5,6,7-tetrahydro[1,2,3]triazolo[1,5-a]pyridine A) 1-(4-bromo-2-methoxyphenyl)-3-methyl-1H-1,2,4-triazole In the same manner as in Example 73, steps A and B, the title compound was obtained from 4-bromo-2-methoxyaniline.
$^1$H NMR (300 MHz, CDCl$_3$) δ 2.47 (3H, s), 3.93 (3H, s), 7.19-7.22 (2H, m), 7.64 (1H, d, J=8.1 Hz), 8.59 (1H, brs).

B) 6-[3-methoxy-4-(3-methyl-1H-1,2,4-triazol-1-yl)phenyl]hex-5-yn-1-ol

A mixture of 1-(4-bromo-2-methoxyphenyl)-3-methyl-1H-1,2,4-triazole (3.00 g), 5-hexyn-1-ol (2.45 mL), dichlorobis(triphenylphosphine)palladium(II) (786 mg), copper(I) iodide (213 mg) and triethylamine (110 mL) was stirred at 70° C. for 14 hr, allowed to cool to room temperature, and diluted with ethyl acetate, and the mixture was filtered through celite. The solvent was evaporated under reduced pressure, and the residue was purified by silica gel column chromatography (ethyl acetate/hexane) to give the title compound (2.80 g).
MS (ESI+): [M+H]$^+$ 286.3.

C) 6-[3-methoxy-4-(3-methyl-1H-1,2,4-triazol-1-yl)phenyl]hex-5-ynal

Dess-Martin reagent (4.99 g) was added to a mixture of 6-[3-methoxy-4-(3-methyl-1H-1,2,4-triazol-1-yl)phenyl]hex-5-yn-1-ol (2.80 g) in acetonitrile (30 mL) under ice-cooling, and the mixture was stirred at room temperature for 1 hr. Saturated aqueous sodium hydrogen carbonate solution and saturated aqueous sodium thiosulfate solution were added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (2.11 g).
MS (ESI+): [M+H]$^+$ 284.3.

D) 1-(3,4-dichlorophenyl)-6-[3-methoxy-4-(3-methyl-1H-1,2,4-triazol-1-yl)phenyl]hex-5-yn-1-ol 3,4-Dichlorophenylmagnesium bromide (0.5 M THF solution, 13 mL) was added dropwise to a mixture of 6-[3-methoxy-4-(3-methyl-1H-1,2,4-triazol-1-yl)phenyl]hex-5-ynal (900 mg) in THF (32 mL) at −78° C., and the mixture was stirred for 1 hr under ice-cooling and at room temperature for 14 hr. 3,4-Dichlorophenylmagnesium bromide (0.5M THF solution, 13 mL) was added to the reaction mixture under ice-cooling, and the mixture was stirred for 1 hr under ice-cooling. Saturated aqueous ammonium chloride solution was added, and the mixture was extracted with ethyl acetate. The extract was washed with saturated aqueous sodium hydrogen carbonate solution and saturated brine, and dried over anhydrous sodium sulfate, and the solvent was evaporated under reduced pressure. The residue was purified by silica gel column chromatography (ethyl acetate/hexane) to give the title compound (349 mg).
MS (ESI+): [M+H]$^+$ 430.1.

E) 1-(3,4-dichlorophenyl)-6-[3-methoxy-4-(3-methyl-1H-1,2,4-triazol-1-yl)phenyl]hex-5-yn-1-one Dess-Martin reagent (248 mg) was added to a mixture of 1-(3,4-dichlorophenyl)-6-[3-methoxy-4-(3-methyl-1H-1,2,4-triazol-1-yl)phenyl]hex-5-yn-1-ol (210 mg), acetonitrile (2.1 mL) and DMSO (200 μL) under ice-cooling, and the mixture was stirred at room temperature for 1 hr. Saturated aqueous sodium hydrogen carbonate solution and saturated aqueous sodium thiosulfate solution were added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (198 mg).
MS (ESI+): [M+H]$^+$ 428.2.

F) 2-(3,4-dichlorophenyl)-7-[3-methoxy-4-(3-methyl-1H-1,2,4-triazol-1-yl)phenyl]hept-6-yn-2-ol Methylmagnesium bromide (12% THF solution, 550 μL) was added to a mixture of 1-(3,4-dichlorophenyl)-6-[3-methoxy-4-(3-methyl-1H-1,2,4-triazol-1-yl)phenyl]hex-5-yn-1-one (198 mg) in THF (5 mL) under ice-cooling, and the mixture was stirred at room temperature for 30 min. Methylmagnesium bromide (12% THF solution, 550 µL) was added to the reaction mixture under ice-cooling, and the mixture was stirred for 15 min under ice-cooling. Saturated aqueous ammonium chloride solution was added, and the mixture was extracted with ethyl acetate. The extract was washed with saturated aqueous sodium hydrogen carbonate solution and saturated brine, and dried over anhydrous sodium sulfate, and the solvent was evaporated under reduced pressure. The residue was purified by silica gel column chromatography (NH, ethyl acetate/hexane) to give the title compound (177 mg).

MS (ESI+): [M+H]+444.2.

G) 7-(3,4-dichlorophenyl)-3-[3-methoxy-4-(3-methyl-1H-1,2,4-triazol-1-yl)phenyl]-7-methyl-4,5,6,7-tetrahydro[1,2,3]triazolo[1,5-a]pyridine Boron trifluoride-diethyl ether complex (75.3 µL) was added to a mixture of 2-(3,4-dichlorophenyl)-7-[3-methoxy-4-(3-methyl-1H-1,2,4-triazol-1-yl)phenyl]hept-6-yn-2-ol (88.0 mg), trimethylsilylazide (105 µL) and toluene (4 mL) under ice-cooling, and the mixture was stirred at room temperature for 30 min, at 70° C. for 15 min and at 110° C. for 6 hr, and allowed to cool to room temperature. The reaction mixture was diluted with ethyl acetate, the mixture was washed with saturated aqueous sodium hydrogen carbonate solution and saturated brine, and dried over anhydrous sodium sulfate, and the solvent was evaporated under reduced pressure. The residue was purified by silica gel column chromatography (ethyl acetate/hexane) to give the title compound (15.7 mg).

Example 92

2-{8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A) ethyl 8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate To a mixture of 3,4-difluorophenol (0.16 g) and potassium carbonate (0.50 g) in DMF (5 mL) was added ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (0.50 g) at room temperature, and the mixture was stirred at 100° C. for 30 min. The reaction mixture was allowed to cool to room temperature, and diluted with ethyl acetate and saturated aqueous ammonium chloride solution, the mixture was washed with saturated brine, and dried over anhydrous magnesium sulfate, and the solvent was evaporated under reduced pressure. The residue was purified by silica gel column chromatography (ethyl acetate/hexane) to give the title compound (0.27 g).

$^1$H NMR (300 MHz, CDCl$_3$) δ 1.31 (3H, t, J=7.1 Hz), 2.16-2.29 (1H, m), 2.34-2.52 (2H, m), 2.57 (3H, s), 2.65 (1H, dd, J=11.1, 5.6 Hz), 4.03 (3H, s), 4.06-4.19 (1H, m), 4.25-4.46 (3H, m), 6.89-7.14 (3H, m), 7.26-7.29 (1H, m), 7.48 (1H, d, J=1.1 Hz), 7.51 (1H, s), 7.84 (1H, d, J=8.0 Hz).

B) 2-{8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol Under a nitrogen atmosphere, to a mixture of ethyl 8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate (0.27 g) in THF (3 ml) was added methylmagnesium bromide (1M THF solution, 2.62 ml) at 0° C., and the mixture was stirred at 0° C. for 2 hr and at room temperature for 4 hr. The reaction mixture was diluted with ethyl acetate and saturated aqueous ammonium chloride solution, the mixture was washed with saturated brine and dried over anhydrous magnesium sulfate, and the solvent was evaporated under reduced pressure. The residue was purified by silica gel column chromatography (ethyl acetate/hexane), and further recrystallized from ethyl acetate/hexane to give the title compound (0.15 g).

$^1$H NMR (300 MHz, CDCl$_3$) δ 1.29 (3H, s), 1.61 (3H, s), 2.03-2.17 (3H, m), 2.37-2.49 (1H, m), 2.57 (3H, s), 3.94-4.09 (4H, m), 4.21-4.31 (1H, m), 4.86 (1H, brs), 6.52-6.60 (1H, m), 6.67 (1H, ddd, J=11.6, 6.9, 2.9 Hz), 6.83-6.96 (1H, m), 7.19-7.24 (1H, m), 7.48 (1H, d, J=1.1 Hz), 7.53 (1H, s), 7.85 (1H, d, J=8.0 Hz).

Example 99

2-{3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol A) ethyl 3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridine-8-carboxylate To a mixture of 3,4,5-trifluorophenol (0.19 g) and potassium carbonate (0.50 g) in DMF (5 mL) was added ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (0.50 g) at room temperature, and the mixture was stirred at 100° C. for 30 min. The reaction mixture was allowed to cool to room temperature, diluted with ethyl acetate and saturated aqueous ammonium chloride solution, the mixture was washed with saturated brine and dried over anhydrous magnesium sulfate, and the solvent was evaporated under reduced pressure. The residue was purified by silica gel column chromatography (NH, ethyl acetate/hexane) to give the title compound (0.28 g).

$^1$H NMR (300 MHz, CDCl$_3$) δ 1.31 (3H, t, J=7.1 Hz), 2.17-2.31 (1H, m), 2.34-2.52 (2H, m), 2.57 (3H, s), 2.65 (1H, dd, J=11.0, 5.5 Hz), 4.04 (3H, s), 4.07-4.19 (1H, m), 4.26-4.44 (3H, m), 6.96 (2H, dd, J=9.1, 6.0 Hz), 7.29 (1H, d, J=1.4 Hz), 7.49 (1H, d, J=1.1 Hz), 7.52 (1H, s), 7.85 (1H, d, J=8.0 Hz).

B) 2-{3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol Under a nitrogen atmosphere, to a mixture of ethyl 3[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridine-8-carboxylate (0.28 g) in THF (5 ml) was added methylmagnesium bromide (1M THF solution, 2.61 ml) at 0° C., and the mixture was stirred at room temperature for 4 hr. The reaction mixture was diluted with ethyl acetate and saturated aqueous ammonium chloride solution, the mixture was washed with saturated brine and dried over anhydrous magnesium sulfate, and the solvent was evaporated under reduced pressure. The residue was purified by silica gel column chromatography (NH, ethyl acetate/hexane), and further recrystallized from ethyl acetate/hexane to give the title compound (0.16 g).

¹H NMR (300 MHz, CDCl₃) δ 1.29 (3H, s), 1.59 (3H, s), 1.99-2.24 (3H, m), 2.38-2.49 (1H, m), 2.58 (3H, s), 3.97-4.09 (4H, m), 4.26-4.36 (1H, m), 4.90 (1H, brs), 6.49 (2H, dd, J=9.1, 6.0 Hz), 7.24 (1H, d, J=1.4 Hz), 7.47 (1H, d, J=1.4 Hz), 7.53 (1H, s), 7.86 (1H, d, J=8.0 Hz).

Example 103

2-{3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol A) ethyl 3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridine-8-carboxylate Ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (1.0 g) was added to a mixture of 3-(trifluoromethyl)phenol (408 mg), potassium carbonate (995 mg) and DMF (10 mL) at 90° C., and the mixture was stirred for 30 min. Saturated aqueous sodium hydrogen carbonate solution was added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (663 mg).
MS (ESI+): [M+H]⁺543.4.

B) 2-{3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol Methylmagnesium bromide (1 M THF solution, 5.81 mL) was added to a mixture of ethyl 3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridine-8-carboxylate (630 mg) in THF (7 mL) under ice-cooling, and the mixture was stirred for 1 hr. Saturated aqueous ammonium chloride solution was added, and the mixture was extracted with ethyl acetate. The extract was washed with saturated aqueous sodium hydrogen carbonate solution and saturated brine, and dried over anhydrous sodium sulfate, and the solvent was evaporated under reduced pressure. The residue was purified by silica gel column chromatography (NH, ethyl acetate/hexane) to give the title compound (270 mg).
¹H NMR (300 MHz, CDCl₃) δ 1.31 (3H, s), 1.64 (3H, s), 2.01-2.21 (3H, m), 2.46 (1H, dd, J=10.4, 3.6 Hz), 2.56 (3H, s), 3.91-4.02 (1H, m), 4.03 (3H, s), 4.18-4.30 (1H, m), 4.88 (1H, brs), 6.68 (1H, s), 7.14-7.32 (4H, m), 7.41 (1H, d, J=1.5 Hz), 7.52 (1H, s), 7.85 (1H, d, J=7.9 Hz).

Example 104

2-{3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl}propan-2-ol A) ethyl 3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridine-8-carboxylate Ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (1.0 g) was added to a mixture of 4-(trifluoromethyl)phenol (408 mg), potassium carbonate (995 mg) and DMF (10 ml) at 90° C., and the mixture was stirred for 30 min. Saturated aqueous sodium hydrogen carbonate solution was added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (520 mg).
MS (ESI+): [M+H]⁺543.4.

B) 2-{3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl}propan-2-ol Methylmagnesium bromide (1M THF solution, 4.75 ml) was added to a mixture of ethyl 3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridine-8-carboxylate (515 mg) in THF (7 mL) under ice-cooling, and the mixture was stirred for 1 hr. Saturated aqueous ammonium chloride solution was added, and the mixture was extracted with ethyl acetate. The extract was washed with saturated aqueous sodium hydrogen carbonate solution and saturated brine, and dried over anhydrous sodium sulfate, and the solvent was evaporated under reduced pressure. The residue was purified by basic silica gel column chromatography (NH, ethyl acetate/hexane) to give the title compound (250 mg).
¹H NMR (300 MHz, CDCl₃) δ 1.31 (3H, s), 1.61 (3H, s), 2.01-2.21 (3H, m), 2.40-2.53 (1H, m), 2.56 (3H, s), 3.90-4.04 (1H, m), 4.05 (3H, s), 4.16-4.31 (1H, m), 4.77 (1H, brs), 6.86 (2H, d, J=8.3 Hz), 7.22-7.28 (1H, m), 7.39 (2H, d, J=8.7 Hz), 7.49 (1H, d, J=1.5 Hz), 7.52 (1H, s), 7.85 (1H, d, J=7.9 Hz).

Example 108

8-[(3,4-difluorobenzyl)oxy]-3-[3-methoxy-4-(2-methyl-1,3-oxazol-5-yl)phenyl]-N-methyl-N-(2,2,2-trifluoroethyl)-5,6,7,8-tetrahydro[1,2,4]triazolo[4,3-a]pyridine-8-carboxamide A) ethyl 8-[(3,4-difluorobenzyl)oxy]-3-[3-methoxy-4-(2-methyl-1,3-oxazol-5-yl)phenyl]-5,6,7,8-tetrahydro[1,2,4]triazolo[4,3-a]pyridine-8-carboxylate To a mixture of ethyl 3-[3-methoxy-4-(2-methyl-1,3-oxazol-5-yl)phenyl]-5,6,7,8-tetrahydro[1,2,4]triazolo[4,3-a]pyridine-8-carboxylate (1000 mg) in DMF (15 ml) was added sodium hydride (60%, 115 mg), and the mixture was stirred at room temperature for 1 hr in the air. Sodium hydride (60%, 115 mg) and 4-(bromomethyl)-1,2-difluorobenzene (812 mg) were added, and the mixture was stirred at room temperature for 1 hr. Saturated aqueous ammonium chloride was added to the reaction mixture, and the mixture was extracted with ethyl acetate. The extract was washed with saturated aqueous sodium hydrogen carbonate solution and brine, and dried over anhydrous magnesium sulfate, and the solvent was evaporated under reduced pressure. The residue was purified by silica gel column chromatography (ethyl acetate/hexane) to give the title compound (1000 mg).
MS (ESI+): [M+H]⁺525.2.

B) 8-[(3,4-difluorobenzyl)oxy]-3-[3-methoxy-4-(2-methyl-1,3-oxazol-5-yl)phenyl]-N-(2,2,2-trifluoroethyl)-5,6,7,8-tetrahydro[1,2,4]triazolo[4,3-a]pyridine-8-carboxamide To a mixture of ethyl 8-[(3,4-difluorobenzyl)oxy]-3-[3-methoxy-4-(2-methyl-1,3-oxazol-5-yl)phenyl]-5,6,7,8-tetrahydro[1,2,4]triazolo[4,3-a]pyridine-8-carboxylate (400 mg) in THF-methanol (1/1, 8 mL) was added dropwise 2N aqueous sodium hydroxide solution (4 mL). The mixture was stirred at room temperature for 2 hr, and neutralized with 1N hydrochloric acid, and the solvent was evaporated under reduced pressure. The residue was dissolved in DMF (8 mL), and N,N-diisopropylethylamine (1.32 mL), 2,2,2-trifluoroethanamine hydrochloride (309 mg), 1-hydroxybenzotriazole monohydrate (113 mg) and N-ethyl-N'-(3-dimethylaminopropyl)carbodiimide hydrochloride (219 mg) were added. After stirring at room temperature overnight, saturated aqueous sodium hydrogen carbonate solution was added to the reaction mixture, and the mixture was extracted with ethyl acetate. The extract was dried over anhydrous sodium sulfate, and the solvent was evaporated under reduced pressure. The residue was purified by silica gel column chromatography (NH, ethyl acetate/hexane) to give the title compound (430 mg).

MS (ESI+): [M+H]$^+$578.2.

C) 8-[(3,4-difluorobenzyl)oxy]-3-[3-methoxy-4-(2-methyl-1,3-oxazol-5-yl)phenyl]-N-methyl-N-(2,2,2-trifluoroethyl)-5,6,7,8-tetrahydro[1,2,4]triazolo[4,3-a]pyridine-8-carboxamide To a mixture of 8-[(3,4-difluorobenzyl)oxy]-3-[3-methoxy-4-(2-methyl-1,3-oxazol-5-yl)phenyl]-N-(2,2,2-trifluoroethyl)-5,6,7,8-tetrahydro[1,2,4]triazolo[4,3-a]pyridine-8-carboxamide (200 mg) in DMF (5 mL) were added cesium carbonate (169 mg) and methyl iodide (0.026 mL) at room temperature. After stirring at room temperature for 2 hr, the reaction mixture was poured into water, and the mixture was extracted with ethyl acetate/THF (2/1). The extract was washed with brine, and dried over anhydrous sodium sulfate, and the solvent was evaporated under reduced pressure. The residue was purified by silica gel column chromatography (NH, ethyl acetate/hexane) to give the title compound (75 mg).

$^1$H NMR (300 MHz, CDCl$_3$) δ 2.13-2.41 (2H, m), 2.40-2.60 (5H, m), 3.31 (3H, br s), 3.86-4.45 (7H, m), 4.62-4.78 (2H, m), 7.00-7.31 (4H, m), 7.45 (1H, d, J=1.5 Hz), 7.51 (1H, s), 7.85 (1H, d, J=8.3 Hz).

Example 109

2-{8-(4-chloro-3-fluorophenoxy)-3-[3-methoxy-4-(4-methyl-1H-imidazol-1-yl)phenyl]-5,6,7,8-tetrahydro[1,2,4]triazolo[4,3-a]pyridin-8-yl}propan-2-ol A) ethyl 3-[3-methoxy-4-(4-methyl-1H-imidazol-1-yl)phenyl]-5,6,7,8-tetrahydro[1,2,4]triazolo[4,3-a]pyridine-8-carboxylate To a mixture of ethyl 2-oxopiperidine-3-carboxylate (1.86 g) in acetonitrile (20 mL) was added trimethyloxonium tetrafluoroborate (1.61 g) at room temperature, and the mixture was stirred at room temperature for 2 hr. 3-Methoxy-4-(4-methyl-1H-imidazol-1-yl)benzohydrazide (2.23 g) was added to the reaction mixture at room temperature, and the mixture was heated under reflux for 2 hr. The reaction mixture was allowed to cool to room temperature, and diluted with ethyl acetate and saturated aqueous sodium hydrogen carbonate solution, the mixture was washed with saturated brine, and dried over anhydrous magnesium sulfate, and the solvent was evaporated under reduced pressure. The residue was collected by filtration, and washed with ethyl acetate to give the title compound (1.32 g).

$^1$H NMR (300 MHz, CDCl$_3$) δ 1.34 (3H, t, J=7.1 Hz), 1.99-2.13 (1H, m), 2.17-2.29 (2H, m), 2.30-2.43 (4H, m), 3.94 (3H, s), 3.99-4.11 (1H, m), 4.13-4.34 (4H, m), 6.98 (1H, s), 7.22-7.26 (1H, m), 7.35-7.39 (1H, m), 7.54 (1H, d, J=1.4 Hz), 7.77 (1H, d, J=1.1 Hz).

B) ethyl 8-chloro-3-[3-methoxy-4-(4-methyl-1H-imidazol-1-yl)phenyl]-5,6,7,8-tetrahydro[1,2,4]triazolo[4,3-a]pyridine-8-carboxylate Under an argon atmosphere, to a mixture of ethyl 3-[3-methoxy-4-(4-methyl-1H-imidazol-1-yl)phenyl]-5,6,7,8-tetrahydro[1,2,4]triazolo[4,3-a]pyridine-8-carboxylate (1.32 g) in DMF (11 ml) was added sodium hydride (60%, 0.14 g) at 0° C., and the mixture was stirred at room temperature for 30 min. N-Chlorosuccinimide (0.46 g) was added to the reaction mixture at 0° C., and the mixture was stirred at room temperature for 30 min. The reaction mixture was diluted with ethyl acetate and saturated aqueous sodium hydrogen carbonate solution, the mixture was washed with saturated brine and dried over anhydrous magnesium sulfate, and the solvent was evaporated under reduced pressure. The residue was purified by silica gel column chromatography (ethyl acetate/hexane), and further recrystallized from ethyl acetate/hexane to give the title compound (0.15 g).

$^1$H NMR (300 MHz, CDCl$_3$) δ 1.40 (3H, t, J=7.1 Hz), 2.20-2.30 (1H, m), 2.33 (3H, s), 2.38-2.62 (2H, m), 2.73-2.86 (1H, m), 3.95 (3H, s), 4.04-4.16 (1H, m), 4.27 (1H, dt, J=12.3, 4.4 Hz), 4.42 (2H, q, J=7.0 Hz), 6.99 (1H, s), 7.24 (1H, d, J=1.6 Hz), 7.39 (1H, d, J=8.2 Hz), 7.56 (1H, d, J=1.4 Hz), 7.77 (1H, s).

C) 2-{8-(4-chloro-3-fluorophenoxy)-3-[3-methoxy-4-(4-methyl-1H-imidazol-1-yl)phenyl]-5,6,7,8-tetrahydro[1,2,4]triazolo[4,3-a]pyridin-8-yl}propan-2-ol In the same manner as in Example 92, steps A and B, the title compound was obtained from 4-chloro-3-fluorophenol and ethyl 8-chloro-3-[3-methoxy-4-(4-methyl-1H-imidazol-1-yl)phenyl]-5,6,7,8-tetrahydro[1,2,4]triazolo[4,3-a]pyridine-8-carboxylate.

$^1$H NMR (300 MHz, CDCl$_3$) δ 1.31 (3H, s), 1.61 (3H, brs), 2.04-2.18 (3H, m), 2.33(3H, s), 2.41-2.51 (1H, m), 3.94-4.06 (4H, m), 4.21-4.30 (1H, m), 4.77 (1H, brs), 6.56-6.65 (2H, m), 6.99 (1H, s), 7.13 (1H, t, J=8.8 Hz), 7.19-7.24 (1H, m),7.40 (1H, d, J=8.0 Hz), 7.56 (1H, d, J=1.4 Hz), 7.78 (1H, s).

Example 110 optically active 2-{8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A racemate (108 mg) of 2-{8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol was separated by HPLC (column: CHIRALCEL AD (trade name), 50 mm ID×500 mm L, mobile phase: hexane/2-propanol=600/400) to give the title compound (53 mg) having a longer retention time.

$^1$H NMR (300 MHz, CDCl$_3$) δ 1.38 (3H, s), 1.65-1.85 (4H, m), 2.09-2.22 (1H, m), 2.31-2.51 (2H, m), 2.55 (3H, s), 4.04 (3H, s), 4.10-4.21 (2H, m), 6.50-6.56 (1H, m), 6.61 (1H, dd,

J=10.2, 2.5 Hz), 7.11-7.18 (1H, m), 7.29 (1H, dd, J=8.1, 1.5 Hz), 7.44 (1H, s), 7.52 (1H, d, J=1.5 Hz), 7.72 (1H, d, J=8.1 Hz).

Example 111 optically active 2-{8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A racemate (108 mg) of 2-{8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol was separated by HPLC (column: CHIRALCEL AD (trade name), 50 mm ID×500 mm L, mobile phase: hexane/2-propanol=600/400) to give the title compound (53 mg) having a shorter retention time.

$^1$H NMR (300 MHz, CDCl$_3$) δ 1.35 (3H, s), 1.66 (3H, s), 1.73-1.91 (1H, m), 2.08-2.20 (1H, m), 2.30-2.45 (2H, m), 2.56 (3H, s), 4.01-4.25 (5H, m), 6.51-6.57 (1H, m), 6.61 (1H, dd, J=10.3, 2.6 Hz), 7.09-7.17 (1H, m), 7.28 (1H, dd, J=8.3, 1.6 Hz), 7.47 (1H, s), 7.51 (1H, d, J=1.6 Hz), 7.75 (1H, d, J=8.3 Hz).

Example 116

3-{8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}pentan-3-ol A) ethyl 8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate A mixture of ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (2000 mg), 3,4-difluorophenol (655 mg), potassium carbonate (1989 mg) and DMF (10 mL) was stirred at 90° C. for 30 min, and the mixture was allowed to cool to room temperature. Ethyl acetate and water were added to the reaction mixture, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (1240 mg).

MS (ESI+): [M+H]$^+$511.4.

B) 3-{8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}pentan-3-ol Under an argon atmosphere, ethylmagnesium bromide (1M THF solution, 11.8 mL) was added to a suspension of ethyl 8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate (1200 mg) in THF (12 mL) under ice-cooling. The reaction mixture was stirred under ice-cooling for 1 hr, saturated aqueous ammonium chloride solution was added, and the mixture was extracted with ethyl acetate. The extract was washed with water and saturated brine, and dried over anhydrous sodium sulfate, and the solvent was evaporated under reduced pressure. The residue was purified by silica gel column chromatography (NH, methanol/ethyl acetate) to give the title compound (230 mg).

$^1$H NMR (300 MHz, CDCl$_3$) δ 0.87 (3H, t, J=7.4 Hz), 1.14 (3H, t, J=7.6 Hz), 1.23-1.44 (1H, m), 1.58-1.81 (1H, m), 1.86-2.32 (5H, m), 2.37-2.50 (1H, m), 2.56 (3H, s), 3.89-4.07 (4H, m), 4.16-4.30 (1H, m), 4.72 (1H, brs), 6.52-6.60 (1H, m), 6.70 (1H, ddd, J=11.7, 7.0, 2.8 Hz), 6.88 (1H, q, J=9.1 Hz), 7.17-7.30 (1H, m), 7.44-7.55 (2H, m), 7.84 (1H, d).

Example 117

3-{8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-3-ol Under an argon atmosphere, ethylmagnesium bromide (1M THF solution, 11.8 mL) was added to a suspension of ethyl 8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate (1200 mg) in THF (12 mL) under ice-cooling. The reaction mixture was stirred under ice-cooling for 1 hr, saturated aqueous ammonium chloride solution was added, and the mixture was extracted with ethyl acetate. The extract was washed with water and saturated brine, and dried over anhydrous sodium sulfate, and the solvent was evaporated under reduced pressure. The residue was purified by silica gel column chromatography (NH, methanol/ethyl acetate) to give the title compound (400 mg).

$^1$H NMR (300 MHz, CDCl$_3$) δ1.00-1.22 (3H, m), 1.41-1.74 (2H, m), 1.98-2.22 (3H, m), 2.31-2.50 (1H, m), 2.56 (3H, s), 3.63 (1H, s), 3.97 (1H, ddd, J=12.5, 9.4, 5.7 Hz), 4.04 (3H, s), 4.20 (1H, dt, J=12.4, 4.2 Hz), 4.33-4.42 (1H, m), 6.56-6.65 (1H, m), 6.72 (1H, ddd, J=11.5, 6.8, 2.8 Hz), 6.96 (1H, q, J=9.1 Hz), 7.13-7.31 (1H, m), 7.44-7.53 (2H, m), 7.84 (1H, d, J=7.9 Hz).

Example 119

8-(4-chloro-3-fluorophenoxy)-3-[3-methoxy-4-(2-methyl-1,3-oxazol-5-yl)phenyl]-N-(2,2,2-trifluoroethyl)-5,6,7,8-tetrahydro[1,2,4]triazolo[4,3-a]pyridine-8-carboxamide To a mixture of ethyl 8-(4-chloro-3-fluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate (300 mg) in THF (1.5 mL)/methanol (1.5 mL) was added 1N aqueous sodium hydroxide solution (0.68 mL) at room temperature, and the mixture was stirred at room temperature for 1 hr. The solvent in the reaction mixture was evaporated under reduced pressure. To a mixture of the residue, triethylamine (0.16 mL) and 2,2,2-trifluoroethylamine hydrochloride (93 mg) in DMF (3 mL) was added HATU (260 mg) at 0° C., and the mixture was stirred at 0° C. for 1 hr. The reaction mixture was diluted with ethyl acetate, the mixture was washed with saturated brine and dried over anhydrous magnesium sulfate, and the solvent was evaporated under reduced pressure. The precipitated crystals were washed with IPE and dried to give the title compound (320 mg).

$^1$H NMR (300 MHz, CDCl$_3$) δ 2.16-2.32 (2H, m), 2.47-2.69 (5H, m), 2.80 (2H, s), 3.74-3.92 (1H, m), 4.02-4.29 (4H, m), 6.70-6.77 (1H, m), 6.82 (1H, dd, J=10.2, 2.6 Hz), 7.22-7.32 (2H, m), 7.46 (1H, d, J=1.1 Hz), 7.52 (1H, s), 7.86 (1H, d, J=8.3 Hz), 8.21 (1H, t, J=6.6 Hz).

Example 122

[Method A]

2-{(8R)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol A racemate (119 mg) of 2-{3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol was separated by HPLC (column: CHIRALPAK AD (trade name), 50 mm ID×500 mm L, mobile phase: hexane/2-propanol=700/300) to give the title compound (60 mg) having a shorter retention time.

$^1$H NMR (300 MHz, CDCl$_3$) δ 1.27 (3H, s), 1.57 (3H, s), 2.00-2.25 (3H, m), 2.42 (1H, d, J=12.4 Hz), 2.56 (3H, s), 3.93-4.10 (4H, m), 4.30 (1H, d, J=12.1 Hz), 4.89 (1H, brs), 6.47 (2H, dd, J=8.4, 6.5 Hz), 7.21-7.24 (1H, m), 7.41-7.55 (2H, m), 7.84 (1H, d, J=8.0 Hz).

[Method B]

2-{(8R)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol A) ethyl 3-chloro-2-oxopiperidine-3-carboxylate To a mixture of ethyl 2-oxopiperidine-3-carboxylate (30 g) in THF (300 mL) was added dropwise sulfuryl chloride (14.2 mL) at 0° C-5° C., and the mixture was stirred at room temperature for 18 hr. To the reaction mixture was added saturated aqueous sodium hydrogen carbonate solution (300 mL) at 0° C., and the mixture was stirred at room temperature for 30 min and extracted with ethyl acetate (300 mL×3). The extract was washed with saturated brine (300 mL), and dried over anhydrous magnesium sulfate, and the solvent was evaporated under reduced pressure. The residue was washed with hexane/ethyl acetate (5/1, 60 mL×2) to give the title compound (32.7 g).

MS (ESI+): [M+H]$^+$206.1.

B) ethyl 2-oxo-3-(3,4,5-trifluorophenoxy)piperidine-3-carboxylate

To a mixture of 3,4,5-trifluorophenol (14.4 g) and potassium carbonate (40.3 g) in DMF (200 mL) was added ethyl 3-chloro-2-oxopiperidine-3-carboxylate (20 g), and the mixture was stirred at 100° C. for 1 hr. To the reaction mixture were added water (200 mL) and saturated brine (200 mL) at 0° C., and the mixture was extracted with ethyl acetate. The extract was washed with saturated aqueous sodium hydrogen carbonate solution (200 mL), water (200 mL) and saturated brine (200 mL×2), and dried over anhydrous magnesium sulfate, and the solvent was evaporated under reduced pressure. The residue was purified by silica gel column chromatography (ethyl acetate/hexane) to give the title compound (24.61 g).

MS (ESI+): [M+H]$^+$318.1.

C) ethyl (3R)-2-oxo-3-(3,4,5-trifluorophenoxy)piperidine-3-carboxylate

A racemate (23.9 g) of ethyl 2-oxo-3-(3,4,5-trifluorophenoxy)piperidine-3-carboxylate was separated by HPLC (column: CHIRALPAK AD (trade name), 50 mm ID×500 mm L, manufactured by DAICEL CHEMICAL INDUSTRIES, LTD., mobile phase: hexane/ethanol=900/100) to give the title compound (11.7 g) having a shorter retention time.

MS (ESI+): [M+H]$^+$318.2.

D) ethyl (3S)-2-(methylsulfanyl)-3-(3,4,5-trifluorophenoxy)-3,4,5,6-tetrahydropyridine-3-carboxylate Lawesson's reagent (4.46 g) was added to a mixture of ethyl (3R)-2-oxo-3-(3,4,5-trifluorophenoxy)piperidine-3-carboxylate (5.00 g) in toluene (50 mL) at room temperature, and the mixture was stirred with heating at 100° C. for 1 hr. After cooling to room temperature, the reaction mixture was purified by silica gel column chromatography (NH, ethyl acetate/hexane) to give ethyl (3S)-2-thioxo-3-(3,4,5-trifluorophenoxy)piperidine-3-carboxylate (5.25 g). To a mixture of ethyl (3S)-2-thioxo-3-(3,4,5-trifluorophenoxy)piperidine-3-carboxylate (5.25 g) in acetonitrile (25 mL) was added methyl iodide (2.94 mL) at room temperature, and the mixture was stirred under a nitrogen atmosphere at 50° C. for 1 hr. The reaction mixture was concentrated under reduced pressure, to the residue was added 10% aqueous potassium carbonate solution, and the mixture was extracted with ethyl acetate. The extract was washed with saturated brine, dried over anhydrous sodium sulfate, and purified by silica gel column chromatography (NH, ethyl acetate) to give the title compound (5.65 g).

MS (ESI+): [M+H]$^+$348.1.

E) ethyl (8R)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridine-8-carboxylate To ethyl (3S)-2-(methylsulfanyl)-3-(3,4,5-trifluorophenoxy)-3,4,5,6-tetrahydropyridine-3-carboxylate (702 mg) and 3-methoxy-4-(2-methyl-1, 3-oxazol-5-yl)benzohydrazide (500 mg) was added acetic acid (3 mL), and the mixture was stirred at 100° C. for 3 hr. The reaction mixture was diluted with ethyl acetate, and the mixture was washed with 10% aqueous potassium carbonate solution and saturated brine, dried over anhydrous sodium sulfate, and purified by silica gel column chromatography (NH, ethyl acetate). The crudely-purified product was purified by silica gel column chromatography (ethyl acetate/hexane) to give the title compound (933 mg).

MS (ESI+): [M+H] +529.3.

F) 2-{(8R)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol To a mixture of methylmagnesium bromide (1 M THF solution, 6.81 mL) in THF (6 mL) was added a mixture of ethyl (8R)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridine-8-carboxylate (1 g) in THF (6 mL) at 0° C., and the mixture was stirred at room temperature for 3 hr. The reaction mixture was diluted with ethyl acetate and saturated aqueous ammonium chloride solution, the mixture was washed with saturated brine and dried over anhydrous magnesium sulfate, and the solvent was evaporated under reduced pressure. The residue was purified by silica gel column chromatography (NH, ethyl acetate) to give the title compound (0.63 g) as a solid.

[Method C]

2-{(8R)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol 2-{(8R)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol (57 g) was diluted with ethanol (170 ml,) at 60° C. and filtered. Water (170 mL) was added to the filtrate at 50° C., and the mixture was allowed to cool to room temperature and stirred for 30 min. The solid was collected by filtration, washed with ethanol (40 mL)/water (80 mL) and dried at 50° C. under reduced pressure to give the title compound (52.5 g) as crystals.

$^1$H NMR (300 MHz, CDCl$_3$) δ 1.27 (3H, s), 1.57 (3H, s), 1.99-2.23 (3H, m), 2.37-2.46 (1H, m), 2.56 (3H, s), 3.96-4.09 (4H, m), 4.25-4.35 (1H, m), 4.91 (1H, s), 6.42-6.54 (2H, m), 7.24 (1H, dd, J=8.0, 1.4 Hz), 7.45 (1H, d, J=1.3 Hz), 7.52 (1H, s), 7.85 (1H, d, J=8.1 Hz).

mp 188° C.

$[α]_D^{25}$ +6.9 (c 1.00, CH$_3$OH)

Anal. Calcd for C$_{26}$H$_{25}$F$_3$N$_4$O$_4$: C, 60.70; H, 4.90; N, 10.89. Found: C, 60.74; H, 4.93; N, 10.84.

Example 123

2-[(8S)-3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl]propan-2-ol A racemate (119 mg) of 2-{3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol was separated by HPLC (column: CHIRALCEL AD (trade name), 50 mm ID×500 mm L, mobile phase: hexane/2-propanol=700/300) to give the title compound (63 mg) having a longer retention time.

$^1$H NMR (300 MHz, CDCl$_3$) δ 1.27 (3H, brs), 1.57 (3H, brs), 1.97-2.24 (3H, m), 2.42 (1H, d, J=9.6 Hz), 2.56 (3H, brs), 4.04 (4H, brs), 4.29 (1H, d, J=9.3 Hz), 4.90 (1H, brs), 6.41-6.55 (2H, m), 7.17-7.24 (1H, m), 7.39-7.55 (2H, m), 7.84 (1H, d, J=7.1 Hz)

Example 124 optically active 2-{8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A racemate (116 mg) of 2-{8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol was separated by HPLC (column: CHIRALCEL AD (trade name), 50 mm ID×500 mm L, mobile phase: hexane/2-propanol=700/300) to give the title compound (45 mg) having a shorter retention time.

$^1$H NMR (300 MHz, CDCl$_3$) δ 1.29 (3H, s), 1.61 (3H, s), 2.04-2.19 (3H, m), 2.35-2.53 (1H, m), 2.57 (3H, s), 3.93-4.09 (4H, m), 4.20-4.31 (1H, m), 4.85 (1H, brs),6.52-6.59 (1H, m), 6.67 (1H, ddd, J=11.5, 6.9, 2.7 Hz), 6.82-6.97 (1H, m), 7.21-7.25 (1H, m), 7.48 (1H, s), 7.53 (1H, s), 7.85 (1H, d, J=8.0 Hz).

Example 125 optically active 2-{8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A racemate (116 mg) of 2-{8-(3,4-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol was separated by HPLC (column: CHIRALCEL AD (trade name), 50 mm ID×500 mm L, mobile phase: hexane/2-propanol=700/300) to give the title compound (59 mg) having a longer retention time.

$^1$H NMR (300 MHz, CDCl$_3$) δ 1.29 (3H, s), 1.61 (3H, s), 2.04-2.17 (3H, m), 2.36-2.52 (1H, m), 2.57 (3H, s), 3.92-4.08 (4H, m), 4.20-4.30 (1H, m), 4.85 (1H, brs),6.51-6.60 (1H, m), 6.67 (1H, ddd, J=11.5, 6.9, 2.7 Hz), 6.90 (1H, q, J=9.3 Hz), 7.22-7.26 (1H, m), 7.48 (1H, s), 7.53 (1H, s), 7.85 (1H, d, J=8.0 Hz).

Example 127

2-{8-[(4-chlorophenoxy)methyl]-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A) ethyl 8-[(4-chlorophenoxy)methyl]-3-[3-methoxy-4-(2-methyl-1,3-oxazol-5-yl)phenyl]-5,6,7,8-tetrahydro[1,2,4]triazolo[4,3-a]pyridine-8-carboxylate Under ice-cooling and an argon stream, to a mixture of ethyl 3-[3-methoxy-4-(2-methyl-1,3-oxazol-5-yl)phenyl]-5,6,7,8-tetrahydro[1,2,4]triazolo[4,3-a]pyridine-8-carboxylate (1000 mg) in DMF (15 mL) was added sodium hydride (60%, 115 mg), and the mixture was stirred at 0° C. for 30 min. 1-Chloro-4-(chloromethoxy)benzene (694 mg) was added, and the mixture was stirred at 0° C. for 1 hr. Saturated aqueous ammonium chloride was added to the reaction mixture, and the mixture was extracted with ethyl acetate. The extract was washed with saturated aqueous sodium hydrogen carbonate solution and brine, and dried over anhydrous magnesium sulfate, and the solvent was evaporated under reduced pressure. The residue was purified by silica gel column chromatography (ethyl acetate/hexane) to give the title compound (440 mg).

MS (ESI+): [M+H]$^+$ 523.4.

B) 2-{8-[(4-chlorophenoxy)methyl]-3-[3-methoxy-4-(2-methyl-1,3-oxazol-5-yl)phenyl]-5,6,7,8-tetrahydro[1,2,4]triazolo[4,3-a]pyridin-8-yl}propan-2-ol Under an argon atmosphere, methylmagnesium bromide (12% THF solution, 1.9 mL) was added to a suspension of ethyl 8-[(4-chlorophenoxy)methyl]-3-[3-methoxy-4-(2-methyl-1,3-oxazol-5-yl)phenyl]-5,6,7,8-tetrahydro[1,2,4]triazolo[4,3-a]pyridine-8-carboxylate (200 mg) in THF (2 mL) under ice-cooling. The reaction mixture was stirred under ice-cooling for 1 hr, saturated aqueous ammonium chloride solution was added, and the mixture was extracted with ethyl acetate. The extract was washed with water and saturated brine, and dried over anhydrous sodium sulfate, and the solvent was evaporated under reduced pressure. The residue was purified by silica gel column chromatography (NH, methanol/ethyl acetate) to give the title compound (65 mg).

$^1$H NMR (300 MHz, CDCl$_3$) δ 1.14 (3H, s), 1.39 (3H, s), 1.85-2.53 (4H, m), 2.56 (3H, s), 3.90-4.34 (5H, m), 4.41-4.66

(2H, m), 4.94 (1H, brs), 6.78 (2H, d, J=8.7 Hz), 7.07-7.37 (3H, m), 7.50 (2H, d, J=9.4 Hz), 7.85 (1H, d, J=7.9 Hz).

Example 130 optically active 2-{3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol A racemate (198 mg) of 2-{3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol was separated by HPLC (column: CHIRALCEL AD (trade name), 50 mm ID×500 mm L, mobile phase: hexane/2-propanol=600/400) to give the title compound (100 mg) having a shorter retention time.

$^1$H NMR (300 MHz, CDCl$_3$) δ 1.31 (3H, s), 1.64 (3H, s), 2.12 (3H, d, J=3.0 Hz), 2.45 (1H, d, J=6.6 Hz), 2.55 (3H, s), 3.92-4.06 (4H, m), 4.23 (1H, d, J=12.1 Hz), 4.90 (1H, brs), 6.67 (1H, s), 7.12-7.24 (4H, m), 7.40 (1H, s), 7.51 (1H, s), 7.84 (1H, d, J=8.0 Hz).

Example 131 optically active 2-{3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol A racemate (198 mg) of 2-{3-[3-methoxy-4-(2-methyl-1,3-oxazol-5-yl)phenyl]-8-[3-(trifluoromethyl)phenoxy]-5,6,7,8-tetrahydro[1,2,4]triazolo[4,3-a]pyridin-8-yl}propan-2-ol was separated by HPLC (column: CHIRALCEL AD (trade name), 50 mm ID×500 mm L, mobile phase: hexane/2-propanol=600/400) to give the title compound (100 mg) having a longer retention time.

$^1$H NMR (300 MHz, CDCl$_3$) δ 1.31 (3H, s), 1.64 (3H, s), 2.12 (3H, d, J=3.3 Hz), 2.41-2.50 (1H, m), 2.55 (3H, s), 3.92-4.06 (4H, m), 4.23 (1H, d, J=12.1 Hz), 4.89 (1H, brs), 6.67 (1H, s), 7.13-7.24 (4H, m), 7.40 (1H, s), 7.51 (1H, s), 7.84 (1H, d, J=8.0 Hz).

Example 132 optically active 2-{3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl}propan-2-ol A racemate (196 mg) of 2-[3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl]propan-2-ol was separated by HPLC (column: CHIRALCEL AD (trade name), 50 mm ID×500 mm L, mobile phase: hexane/2-propanol=500/500) to give the title compound (82.1 mg) having a shorter retention time.

$^1$H NMR (300 MHz, CDCl$_3$) δ 1.30 (3H, s), 1.62 (3H, s), 2.00-2.19 (3H, m), 2.46 (1H, d, J=14.6 Hz), 2.55 (3H, s), 3.91-4.08 (4H, m), 4.23 (1H, d, J=12.4 Hz), 4.80 (1H, brs), 6.85 (2H, d, J=8.2 Hz), 7.20-7.23 (1H, m), 7.38 (2H, d, J=8.2 Hz), 7.49 (2H, d, J=9.9 Hz), 7.83 (1H, d, J=8.0 Hz).

Example 133 optically active 2-{3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl}propan-2-ol A racemate (196 mg) of 2-{3-[3-methoxy-4-(2-methyl-1,3-oxazol-5-yl)phenyl]-8-[4-(trifluoromethyl)phenoxy]-5,6,7,8-tetrahydro[1,2,4]triazolo[4,3-a]pyridin-8-yl}propan-2-ol was separated by HPLC (column: CHIRALCEL AD (trade name), 50 mm ID×500 mm L, mobile phase: hexane/2-propanol=500/500) to give the title compound (81.3 mg) having a longer retention time.

$^1$H NMR (300 MHz, CDCl$_3$) δ 1.30 (3H, s), 1.62 (3H, s), 1.90-2.23 (3H, m), 2.46 (1H, d, J=14.3 Hz), 2.55 (3H, s), 3.90-4.09 (4H, m), 4.23 (1H, d, J=11.8 Hz), 4.82 (1H, brs), 6.85 (2H, d, J=8.0 Hz), 7.21-7.23 (1H, m), 7.38 (2H, d, J=8.2 Hz), 7.49 (2H, d, J=10.2 Hz), 7.83 (1H, d, J=8.0 Hz).

Example 134

2-{3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol A) N-(6-bromo-2-methoxypyridin-3-yl)formamide To formic acid (12 mL) was added acetic anhydride (12 mL) at 0° C., and the mixture was stirred at 0° C. for 30 min. 6-Bromo-2-methoxypyridin-3-amine (8.8 g) was gradually added to the reaction mixture at 0° C. over 10 min, and the mixture was stirred at 0° C. for 30 min. IPE (50 mL) and hexane (50 mL) were added to the reaction mixture, and the mixture was stirred at room temperature for 30 min. The obtained solid was collected by filtration to give the title compound (8.1 g).

$^1$H NMR (300 MHz, CDCl$_3$) δ 3.94-4.08 (3H, m), 7.07 (1H, d, J=8.2 Hz), 7.62 (1H, brs), 8.39-8.56 (2H, m).

B) 6-bromo-2-methoxy-3-(4-methyl-1H-imidazol-1-yl)pyridine

To a mixture of N-(6-bromo-2-methoxypyridin-3-yl)formamide (8.0 g), cesium carbonate (20.1 g) and potassium iodide (580 mg) in DMF (40 mL) was added 1-chloropropan-2-one (4.13 mL), and the mixture was stirred at room temperature for 3 hr. The solvent was evaporated under reduced pressure, water was added, and the mixture was extracted with ethyl acetate. The extract was washed with water and saturated brine, and dried over anhydrous magnesium sulfate, and the solvent was evaporated under reduced pressure. Acetic acid (50 mL) and ammonium acetate (26.7 g) were added to the residue, and the mixture was stirred at 130° C. for 3 hr. The reaction mixture was allowed to cool to room temperature, and the solvent was evaporated under reduced pressure. Water was added, and the mixture was neutralized with aqueous sodium hydroxide solution and extracted with ethyl acetate. The extract was dried over anhydrous magnesium sulfate, and the solvent was evaporated under reduced pressure. The residue was purified by silica gel column chromatography (ethyl acetate/hexane) to give the title compound (4.72 g).

$^1$H NMR (300 MHz, CDCl$_3$) δ 2.29 (3H, s), 4.02 (3H, s), 6.91 (1H, s), 7.15 (1H, d, J=7.7 Hz), 7.39 (1H, d, J=8.0 Hz), 7.71 (1H, s).

C) 6-methoxy-5-(4-methyl-1H-imidazol-1-yl)pyridine-2-carbonitrile

Under a nitrogen atmosphere, to a mixture of 6-bromo-2-methoxy-3-(4-methyl-1H-imidazol-1-yl)pyridine (25 g) and zinc cyanide (16.4 g) in DMF (250 mL) was added tetrakis(triphenylphosphine)palladium(0) (2.16 g) at room temperature, and the mixture was stirred at 120° C. for 2 hr. The reaction mixture was allowed to cool to room temperature, and diluted with ethyl acetate and 10% aqueous ammonia solution. The precipitate was collected by filtration, washed with ethyl acetate and dried to give the title compound (17.5 g)

MS (ESI+): $[M+H]^+$ 215.1.

D) sodium 6-methoxy-5-(4-methyl-1H-imidazol-1-yl)pyridine-2-carboxylate

To a mixture of 6-methoxy-5-(4-methyl-1H-imidazol-1-yl)pyridine-2-carbonitrile (17.5 g) in ethanol (300 ml) was added 8N aqueous sodium hydroxide solution (51.2 mL) at room temperature, and the mixture was stirred for 1 hr under reflux. The reaction mixture was allowed to cool to room temperature, and the precipitate was collected by filtration, washed with ethanol and dried to give the title compound (17.5 g).

MS (ESI+), found: 234.1.

E) benzyl 2-{[6-methoxy-5-(4-methyl-1H-imidazol-1-yl)pyridin-2-yl]carbonyl}hydrazinecarboxylate To a mixture of sodium 6-methoxy-5-(4-methyl-1H-imidazol-1-yl)pyridine-2-carboxylate (12.7 g), benzyl hydrazinecarboxylate (9.10 g) and HOBt (7.4 g) in DMF (2.50 mL) was added WSC (8.50 g) at 0° C., and the mixture was stirred at 0° C. for 1 hr. Saturated aqueous sodium hydrogen carbonate solution (200 ml), water (400 mL) and saturated brine solution (200 mL) were added to the reaction mixture at 0° C., and the mixture was extracted with ethyl acetate. The extract was washed with saturated brine, and dried over anhydrous magnesium sulfate, and the solvent was evaporated under reduced pressure. The residue was washed with ethyl acetate and dried to give the title compound (14.6 g).

MS (ESI+): $[M+H]^+$ 382.2.

F) 6-methoxy-5-(4-methyl-1H-imidazol-1-yl)pyridine-2-carbohydrazide

Under a nitrogen atmosphere, to a mixture of benzyl 2-{[6-methoxy-5-(4-methyl-1H-imidazol-1-yl)pyridin-2-yl]carbonyl}hydrazinecarboxylate (14.6 g) in methanol (150 mL) and THF (100 mL) was added 5% palladium-carbon (1.5 g) at room temperature, and the mixture was stirred at room temperature for 6 hr under a hydrogen atmosphere. Under a nitrogen atmosphere, the catalyst was filtered off, and the solvent in the filtrate was evaporated under reduced pressure. To a mixture of the residue in ethanol (200 mL) and THF (400 ml) was added 5% palladium-carbon (1.5 g) at room temperature, and the mixture was stirred at room temperature overnight under a hydrogen atmosphere. Under a nitrogen atmosphere, the catalyst was filtered off, and the solvent in the filtrate was evaporated under reduced pressure. The residue was collected by filtration, washed with ethyl acetate and dried to give the title compound (3.9 g). The solvent in the mother liquor was evaporated under reduced pressure, and the residue was collected by filtration, washed with ethyl acetate and dried to give the title compound (2.6 g).

MS (ESI+): $[M+H]^+$ 248.1.

G) ethyl 3-[6-methoxy-5-(4-methyl-1H-imidazol-1-yl)pyridin-2-yl]-5,6,7,8-tetrahydro[1,2,4]triazolo[4,3-a]pyridine-8-carboxylate To a mixture of ethyl 2-oxopiperidine-3-carboxylate (3.5 g) in acetonitrile (100 mL) was added trimethyloxonium tetrafluoroborate (3.0 g) at room temperature, and the mixture was stirred at room temperature for 2 hr. 6-Methoxy-5-(4-methyl-1H-imidazol-1-yl)pyridine-2-carbohydrazide (5.0 g) was added to the reaction mixture at room temperature, and the solvent was evaporated under reduced pressure. Methanol (100 mL) was added to the residue at room temperature, and the mixture was stirred for 2 hr under reflux. The solvent in the reaction mixture was evaporated under reduced pressure, acetonitrile (100 mL) was added to the residue at room temperature, and the mixture was stirred at 80° C. overnight. The solvent in the reaction mixture was evaporated under reduced pressure, the residue was diluted with ethyl acetate and saturated aqueous sodium hydrogen carbonate solution, the mixture was washed with saturated brine and dried over anhydrous magnesium sulfate, and the solvent was evaporated under reduced pressure. The residue of another lot synthesized similarly was combined, and the mixture was purified by silica gel column chromatography (methanol/ethyl acetate) to give the title compound (3.1 g).

MS (ESI+): $[M+H]^+$ 383.2.

H) ethyl 8-chloro-3-[6-methoxy-5-(4-methyl-1H-imidazol-1-yl)pyridin-2-yl]-5,6,7,8-tetrahydro[1,2,4]triazolo[4,3-a]pyridine-8-carboxylate Under a nitrogen atmosphere, to a mixture of ethyl 3-[6-methoxy-5-(4-methyl-1H-imidazol-1-yl)pyridin-2-yl]-5,6,7,8-tetrahydro[1,2,4]triazolo[4,3-a]pyridine-8-carboxylate (3.1 g) in DMF (30 mL) was added sodium hydride (60%, 0.34 g) at 0° C., and the mixture was stirred at room temperature for 30 min. N-Chlorosuccinimide (1.14 g) was added to the reaction mixture at 0° C., and the mixture was stirred at room temperature for 30 min. The reaction mixture was diluted with ethyl acetate and saturated aqueous sodium hydrogen carbonate solution, the mixture was washed with saturated brine and dried over anhydrous magnesium sulfate, and the solvent was evaporated under reduced pressure. The residue was purified by silica gel column chromatography (ethyl acetate) to give the title compound (1.9 g).

MS (ESI+): $[M+H]^+$ 417.1.

I) ethyl 3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridine-8-carboxylate To a mixture of 3,4,5-trifluorophenol (0.31 g) and potassium carbonate (0.80 g) in DMF (16 mL) was added ethyl 8-chloro-3-[6-methoxy-5-(4-methyl-1H-imidazol-1-yl)pyridin-2-yl]-5,6,7,8-tetrahydro[1,2,4]triazolo[4,3-a]pyridine-8-carboxylate (0.80 g) at room temperature, and the mixture was stirred at 100° C. for 30 min. The reaction mixture was allowed to cool to room temperature, and diluted with ethyl acetate and saturated aqueous ammonium chloride solution, the mixture was washed with saturated brine, and dried over anhydrous magnesium sulfate, and the solvent was evaporated under reduced pressure. The residue was purified by silica gel column chromatography (ethyl acetate/hexane) to give the title compound (0.42 g).

MS (ESI+): $[M+H]^+$ 529.2.

J) 2-{3-[6-methoxy-5-(4-methyl-1H-imidazol-1-yl) pyridin-2-yl]-8-(3,4,5-trifluorophenoxy)-5,6,7,8-tetrahydro[1,2,4]triazolo[4,3-a]pyridin-8-yl}propan-2-ol Under a nitrogen atmosphere, to a mixture of ethyl 3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridine-8-carboxylate (0.42 g) in THF (4 mL) was added methylmagnesium bromide (1M THF solution, 3.97 mL) at 0° C., and the mixture was stirred at room temperature for 30 min. The reaction mixture was diluted with ethyl acetate and saturated aqueous ammonium chloride solution, the mixture was washed with saturated brine and dried over anhydrous magnesium sulfate, and the solvent was evaporated under reduced pressure. The residue was purified by silica gel column chromatography (ethyl acetate/hexane) to give the title compound (0.30 g).
$^1$H NMR (300 MHz, CDCl$_3$) δ 1.25 (3H, s), 1.59 (3H, s), 1.99-2.08 (1H, m), 2.22-2.28 (2H, m), 2.33 (3H, s), 2.40-2.47 (1H, m), 4.12 (3H, s), 4.23-4.38 (1H, m), 4.95 (1H, brs), 5.06 (1H, d, J=12.9 Hz), 6.53 (2H, dd, J=8.8, 6.0 Hz), 7.07 (1H, s), 7.79 (1H, d, J=8.0 Hz), 8.12 (1H, d, J=8.0 Hz), 8.17 (1H, s).

Example 135

2-{8-(3,4-difluorophenoxy)-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol A) ethyl 8-(3,4-difluorophenoxy)-3-[6-methoxy-5-(4-methyl-1H-imidazol-1-yl)pyridin-2-yl]-5,6,7,8-tetrahydro[1,2,4]triazolo[4,3-a]pyridine-8-carboxylate To a mixture of 3,4-difluorophenol (59 mg) and potassium carbonate (0.18 g) in DMF (4 mL) was added ethyl 8-chloro-3-[6-methoxy-5-(4-methyl-1H-imidazol-1-yl)pyridin-2-yl]-5,6,7,8-tetrahydro[1,2,4]triazolo[4,3-a]pyridine-8-carboxylate (0.18 g) at room temperature, and the mixture was stirred at 100° C. for 30 min. The reaction mixture was cooled to room temperature, and diluted with ethyl acetate and saturated aqueous ammonium chloride solution, the mixture was washed with saturated brine, and dried over anhydrous magnesium sulfate, and the solvent was evaporated under reduced pressure. The residue was purified by silica gel column chromatography (ethyl acetate/hexane) to give the title compound (0.11 g).
MS (ESI+): [M+H]$^+$511.2.

B) 2-{8-(3,4-difluorophenoxy)-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol Under a nitrogen atmosphere, to a mixture of ethyl 8-(3,4-difluorophenoxy)-3-[6-methoxy-5-(4-methyl-1H-imidazol-1-yl)pyridin-2-yl]-5,6,7,8-tetrahydro[1,2,4]triazolo[4,3-a]pyridine-8-carboxylate (0.11 g) in THF (1 mL) was added methylmagnesium bromide (1M THF solution, 1.06 mL) at 0° C., and the mixture was stirred at room temperature for 30 min. The reaction mixture was diluted with ethyl acetate and saturated aqueous ammonium chloride solution, the mixture was washed with saturated brine and dried over anhydrous magnesium sulfate, and the solvent was evaporated under reduced pressure. The residue was purified by silica gel column chromatography (ethyl acetate/hexane), and recrystallized from ethyl acetate/hexane to give the title compound (9.8 mg).
$^1$H NMR (300 MHz, CDCl$_3$) δ 1.26 (3H, s), 1.61 (3H, s), 1.98-2.11 (1H, m), 2.15-2.23 (2H, m), 2.35 (3H, s), 2.39-2.49 (1H, m), 4.10 (3H, s), 4.21-4.34 (1H, m), 4.94 (1H, brs), 4.97-5.07 (1H, m), 6.51-6.58 (1H, m), 6.73 (1H, ddd, J=11.6, 6.9, 2.6 Hz), 6.82-6.93 (1H, m), 7.04 (1H, s), 7.74 (1H, d, J=8.0 Hz), 7.94 (1H, s), 8.10 (1H, d, J=8.0 Hz).

Example 140

2-{8-[(3,4-difluorophenyl)sulfanyl]-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A) ethyl 8-[(3,4-difluorophenyl)sulfanyl]-3-[3-methoxy-4-(2-methyl-1,3-oxazol-5-yl)phenyl]-5,6,7,8-tetrahydro[1,2,4]triazolo[4,3-a]pyridine-8-carboxylate To a mixture of ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (500 mg) and potassium carbonate (497 mg) in DMF (6.0 mL) was added 3,4-difluorobenzenethiol (0.133 mL), and the mixture was stirred at 100° C. for 4 hr. The reaction mixture was diluted with ethyl acetate, the mixture was washed with saturated brine and dried over anhydrous magnesium sulfate, and the solvent was evaporated under reduced pressure. The residue was purified by silica gel column chromatography (ethyl acetate/hexane) to give the title compound (491 mg).
MS (ESI+): [M+H]$^+$527.0.

B) 2-{8-[(3,4-difluorophenyl)sulfanyl]-3-[3-methoxy-4-(2-methyl-1,3-oxazol-5-yl)phenyl]-5,6,7,8-tetrahydro[1,2,4]triazolo[4,3-a]pyridin-8-yl}propan-2-ol In the same manner as in Example 92, step B, the title compound was obtained.

Example 141

2-{8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A) ethyl 8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate A mixture of ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (671 mg), 3,5-difluorophenol (220 mg), potassium carbonate (667 mg) and DMF (6 ml) was stirred at 100° C. for 1 hr, the reaction mixture was diluted with ethyl acetate, and the mixture was washed with saturated brine. The organic layer was dried over anhydrous magnesium sulfate, and purified by silica gel chromatography (NH, ethyl acetate). The solvent was evaporated under reduced pressure. The residue was purified by silica gel column chromatography (ethyl acetate/hexane) to give the title compound (317 mg).
MS (ESI+): [M+H]$^+$511.1.

B) 2-{8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol Under a nitrogen atmosphere, to a mixture of ethyl 8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridine-8-carboxylate (317 mg) in THF (6.2 mL) was added methylmagnesium bromide (1 M THF solution, 3.10 mL) at 0° C., and the mixture was stirred at room temperature for 30 min. The reaction mixture was diluted with saturated aqueous ammonium chloride solution, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, ethyl acetate/hexane) to give the title compound (254 mg).

Example 143

2-{8-[3-(difluoromethyl)-4-fluorophenoxy]-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A) ethyl 8-(4-fluoro-3-formylphenoxy)-3-[3-methoxy-4-(2-methyl-1,3-oxazol-5-yl)phenyl]-5,6,7,8-tetrahydro[1,2,4]triazolo[4,3-a]pyridine-8-carboxylate In the same manner as in Example 92, step A, the title compound was obtained.
MS (ESI+): [M+H]$^+$521.2.

B) ethyl 8-[3-(difluoromethyl)-4-fluorophenoxy]-3-[3-methoxy-4-(2-methyl-1,3-oxazol-5-yl)phenyl]-5,6,7,8-tetrahydro[1,2,4]triazolo[4,3-a]pyridine-8-carboxylate To a mixture of ethyl 8-(4-fluoro-3-formylphenoxy)-3-[3-methoxy-4-(2-methyl-1,3-oxazol-5-yl)phenyl]-5,6,7,8-tetrahydro[1,2,4]triazolo[4,3-a]pyridine-8-carboxylate (350 mg) in acetonitrile (1.7 mL) was added N,N-diethylaminosulfur trifluoride (1.8 mL) at 0° C. To the reaction mixture was added methanol (1 drop), and the mixture was stirred under a nitrogen atmosphere at room temperature over the weekend. To the reaction mixture was added 10% aqueous potassium carbonate solution at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) and silica gel chromatography (NH, ethyl acetate) to give the title compound (78 mg).
MS (ESI+): [M+H]$^+$543.2.

C) 2-{8-[3-(difluoromethyl)-4-fluorophenoxy]-3-[3-methoxy-4-(2-methyl-1,3-oxazol-5-yl)phenyl]-5,6,7,8-tetrahydro[1,2,4]triazolo[4,3-a]pyridin-8-yl}propan-2-ol In the same manner as in Example 92, step B, the title compound was obtained.

Example 144

2-{3-[3-methoxy-4-(1-methyl-1H-pyrazol-4-yl)phenyl]-8-(3,4,5-trifluorophenoxy)-5,6,7,8-tetrahydro[1,2,4]triazolo[4,3-a]pyridin-8-yl}propan-2-ol A) ethyl 3-methoxy-4-{[(trifluoromethyl)sulfonyl]oxy}benzoate To a mixture of ethyl 4-hydroxy-3-methoxybenzoate (5.00 g) in pyridine (20 mL) was added trifluoromethanesulfonic anhydride (4.60 mL) at 0° C., and the mixture was stirred for 1 hr under a nitrogen atmosphere. The reaction mixture was added to a mixture of 6N hydrochloric acid and ice, and the mixture was extracted with ethyl acetate. The organic layer was separated and washed with saturated aqueous sodium hydrogen carbonate solution, and dried over anhydrous magnesium sulfate, and the solvent was evaporated under reduced pressure to give the title compound (8.37 g).
MS (ESI+): [M+H]$^+$329.0.

B) ethyl 3-methoxy-4-(1-methyl-1H-pyrazol-4-yl)benzoate

In the same manner as in Example 174, step B, the title compound (6.07 g) was obtained from ethyl 3-methoxy-4-{[(trifluoromethyl)sulfonyl]oxy}benzoate (8.37 g) and 1-methyl-4-(4,4,5,5-tetramethyl-1,3,2-dioxaborolan-2-yl)-1H-pyrazole (5.00 g).
MS (ESI+): [M+H]$^+$261.1.

C) 3-methoxy-4-(1-methyl-1H-pyrazol-4-yl)benzoic acid

In the same manner as in Example 167, step B, the title compound was obtained.
MS (ESI+): [M+H]$^+$233.0.

D) 3-methoxy-4-(1-methyl-1H-pyrazol-4-yl)benzohydrazide

In the same manner as in Example 3, step E, the title compound was obtained.
MS (ESI+): [M+H]$^+$247.1.

E) ethyl 3-[3-methoxy-4-(1-methyl-1H-pyrazol-4-yl)phenyl]-5,6,7,8-tetrahydro[1,2,4]triazolo[4,3-a]pyridine-8-carboxylate In the same manner as in Example 47, step A, the title compound was obtained.
MS (ESI+): [M+H]$^+$382.4.

F) ethyl 8-chloro-3-[3-methoxy-4-(1-methyl-1H-pyrazol-4-yl)phenyl]-5,6,7,8-tetrahydro[1,2,4]triazolo[4,3-a]pyridine-8-carboxylate In the same manner as in Example 82, the title compound was obtained.
MS (ESI+): [M+H]$^+$416.1.

G) 2-[3-[3-methoxy-4-(1-methyl-1H-pyrazol-4-yl)phenyl]-8-(3,4,5-trifluorophenoxy)-5,6,7,8-tetrahydro[1,2,4]triazolo[4,3-a]pyridin-8-yl]propan-2-ol In the same manner as in Example 99, the title compound was obtained.

Example 147

2,2,2-trifluoro-1-{3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}ethanol A) {3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}methanol In the same manner as in Example 52, the title compound was obtained.
MS (ESI+): [M+H]$^+$487.2.

B) 3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridine-8-carbaldehyde In the same manner as in Example 91, step C, the title compound was obtained.
$^1$H NMR (300 MHz, CDCl$_3$) δ 2.07-2.50 (4H, m), 2.55 (3H, s), 3.99-4.15 (4H, m), 4.20-4.33 (1H, m), 6.73-6.86 (1H, m), 7.22-7.29 (2H, m), 7.43-7.53 (2H, m), 7.81-7.87 (1H, m), 10.05 (1H, s).

C) 2,2,2-trifluoro-1-{3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}ethanol To a mixture of 3-[3-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridine-8-carbaldehyde (150 mg) and (trifluoromethyl)trimethylsilane (0.137 mL) in THF (1.5 mL) was added TBAF (1M THF solution, 0.062 mL) under an argon atmosphere at room temperature. The reaction mixture was stirred at room temperature for 2 hr, 1N hydrochloric acid (3 mL) was added, and the mixture was stirred at room temperature overnight. The reaction mixture was diluted with saturated aqueous sodium hydrogen carbonate solution, and the mixture was extracted with ethyl acetate. The organic layer was separated, washed with saturated brine, and dried over anhydrous sodium sulfate, and the solvent was evaporated under reduced pressure. The residue was purified by silica gel column chromatography (NH, ethyl acetate/hexane), and further recrystallized from ethyl acetate/hexane to give the title compound (38.8 mg).

Example 150

(6RS, 8RS or 6RS, 8SR)-2-{8-(3,4-difluorophenoxy)-3-[3-methoxy-4-(2-methyl-1,3-oxazol-5-yl)phenyl]-6-methyl-5,6,7,8-tetrahydro[1,2,4]triazolo[4,3-a]pyridin-8-yl}propan-2-ol A) diethyl (2-cyanopropyl)propanedioate In the same manner as in Example 32, step C, the title compound (893 mg) was obtained from diethyl malonate (2.00 g) and 2-methylprop-2-enenitrile (1.0 mL).
$^1$H NMR (300 MHz, CDCl$_3$) δ 1.25-1.33 (6H, m), 1.37 (3H, d, J=7.1 Hz), 2.07-2.25 (2H, m), 2.70-2.84 (1H, m), 3.55-3.61 (1H, m), 4.14-4.31 (4H, m).

B) ethyl 5-methyl-2-oxopiperidine-3-carboxylate

In the same manner as in Example 32, step D, the title compound was obtained.
$^1$H NMR (300 MHz, CDCl$_3$) δ 0.99-1.06 (3H, m), 1.29 (3H, t, J=7.1 Hz), 1.63-2.28 (3H, m), 2.87-3.07 (1H, m), 3.24-3.48 (2H, m), 4.14-4.32 (2H, m), 6.21 (1H, brs).

C) ethyl 3-[3-methoxy-4-(2-methyl-1,3-oxazol-5-yl)phenyl]-6-methyl-5,6,7,8-tetrahydro[1,2,4]triazolo[4,3-a]pyridine-8-carboxylate In the same manner as in Example 47, step A, the title compound was obtained.
MS (ESI+): [M+H]$^+$397.2.

D) ethyl 8-chloro-3-[3-methoxy-4-(2-methyl-1,3-oxazol-5-yl)phenyl]-6-methyl-5,6,7,8-tetrahydro[1,2,4]triazolo[4,3-a]pyridine-8-carboxylate In the same manner as in Example 82, the title compound was obtained.
MS (ESI+): [M+H]$^+$431.2.

E) ethyl 8-(3,4-difluorophenoxy)-3-[3-methoxy-4-(2-methyl-1,3-oxazol-5-yl)phenyl]-6-methyl-5,6,7,8-tetrahydro[1,2,4]triazolo[4,3-a]pyridine-8-carboxylate In the same manner as in Example 92, step A, the title compound was obtained.
MS (ESI+): [M+H]$^+$525.2.

F) ethyl (6RS, 8RS or 6RS, 8SR)-8-(3,4-difluorophenoxy)-3-[3-methoxy-4-(2-methyl-1,3-oxazol-5-yl)phenyl]-6-methyl-5,6,7,8-tetrahydro[1,2,4]triazolo[4,3-a]pyridine-8-carboxylate Ethyl 8-(3,4-difluorophenoxy)-3-[3-methoxy-4-(2-methyl-1,3-oxazol-5-yl)phenyl]-6-methyl-5,6,7,8-tetrahydro[1,2,4]triazolo[4,3-a]pyridine-8-carboxylate (247 mg) was separated by HPLC (column: L-column2, mobile phase: water/acetonitrile (10 mM ammonium hydrogen carbonate-containing system)) to give the title compound (88.4 mg) having a shorter retention time.
MS (ESI+): [M+H]$^+$525.3.
$^1$H NMR (300 MHz, CDCl$_3$) δ 1.18 (3H, d, J=6.6 Hz), 1.24 (3H, t, J=7.1 Hz), 2.08 (1H, dd, J=13.3, 12.5 Hz), 2.38-2.52 (1H, m), 2.55 (3H, s), 2.62-2.70 (1H, m), 3.60 (1H, dd, J=12.1, 11.0 Hz), 4.03 (3H, s), 4.11-4.20 (1H, m), 4.28 (2H, q, J=7.1 Hz), 6.87-7.13 (3H, m), 7.22 (1H, dd, J=8.1, 1.6 Hz), 7.47-7.52 (2H, m), 7.83 (1H, d, J=8.1 Hz).

G) (6RS, 8RS or 6RS, 8SR)-2-{8-(3,4-difluorophenoxy)-3-[3-methoxy-4-(2-methyl-1,3-oxazol-5-yl)phenyl]-6-methyl-5,6,7,8-tetrahydro[1,2,4]triazolo[4,3-a]pyridin-8-yl}propan-2-ol In the same manner as in Example 92, step B, the title compound was obtained.
$^1$H NMR (300 MHz, CDCl$_3$) δ 1.06 (3H, d, J=6.8 Hz), 1.42 (3H, s), 1.59 (3H, s), 1.93 (1H, dd, J=14.8, 12.9 Hz), 2.11-2.26 (1H, m), 2.39-2.49 (1H, m), 2.56 (3H, s), 3.12 (1H, t, J=11.7 Hz), 3.94-4.02 (1H, m), 4.03 (3H, s), 4.63 (1H, s), 6.30-6.38 (1H, m), 6.44-6.53 (1H, m), 6.89-7.00 (1H, m), 7.08 (1H, dd, J=8.0, 1.5 Hz), 7.43 (1H, d, J=1.5 Hz), 7.52 (1H, s), 7.84 (1H, d, J=8.0 Hz).

Example 151

(6RS, 8SR or 6RS, 8RS)-2-{8-(3,4-difluorophenoxy)-3-[3-methoxy-4-(2-methyl-1,3-oxazol-5-yl)phenyl]-6-methyl-5,6,7,8-tetrahydro[1,2,4]triazolo[4,3-a]pyridin-8-yl}propan-2-ol A) ethyl (6RS, 8SR or 6RS, 8RS)-8-(3,4-difluorophenoxy)-3-[3-methoxy-4-(2-methyl-1,3-oxazol-5-yl)phenyl]-6-methyl-5,6,7,8-tetrahydro[1,2,4]triazolo[4,3-a]pyridine-8-carboxylate Ethyl 8-(3,4-difluorophenoxy)-3-[3-methoxy-4-(2-methyl-1,3-oxazol-5-yl)phenyl]-6-methyl-5,6,7,8-tetrahydro[1,2,4]triazolo[4,3-a]pyridine-8-carboxylate (247 mg) was separated by HPLC (column: L-column2, mobile phase: water/acetonitrile (10 mM ammonium hydrogen carbonate-containing system)) to give the title compound (94.0 mg) having a longer retention time.
MS (ESI+): [M+H]$^+$525.3.
$^1$H NMR (300 MHz, CDCl$_3$) δ 1.23 (3H, d, J=6.6 Hz), 1.29 (3H, t, J=7.1 Hz), 2.17 (1H, dd, J=13.7, 12.4 Hz), 2.55 (3H, s), 2.57-2.78 (2H, m), 3.64 (1H, t, J=12.1 Hz), 4.02 (3H, s), 4.22-4.43 (3H, m), 6.86-7.10 (3H, m), 7.20-7.27 (1H, m), 7.44 (1H, d, J=1.4 Hz), 7.50 (1H, s), 7.83 (1H, d, J=8.0 Hz).

B) (6RS, 8SR or 6RS, 8RS)-2-[8-(3,4-difluorophenoxy)-3-[3-methoxy-4-(2-methyl-1,3-oxazol-5-yl)phenyl]-6-methyl-5,6,7,8-tetrahydro[1,2,4]triazolo[4,3-a]pyridin-8-yl]propan-2-ol In the same manner as in Example 92, step B, the title compound was obtained.
$^1$H NMR (300 MHz, CDCl$_3$) δ 1.15 (3H, d, J=6.8 Hz), 1.25 (3H, s), 1.59 (3H, s), 1.82 (1H, dd, J=14.4, 12.5 Hz), 2.11-2.28 (1H, m), 2.31-2.40 (1H, m), 2.56 (3H, s), 3.54 (1H, t, J=12.5 Hz), 4.05 (3H, s), 4.22 (1H, dd, J=12.5, 4.9 Hz), 4.74 (1H, brs), 6.52-6.61 (1H, m), 6.61-6.71 (1H, m), 6.83-6.95 (1H, m), 7.23 (1H, dd, J=7.9, 1.5 Hz), 7.47 (1H, d, J=1.5 Hz), 7.52 (1H, s), 7.86 (1H, d, J=8.0 Hz).

Example 152

[Method A]

2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol A racemate (300 mg) of 2-{3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol was separated by SFC (column: CHIRALCEL ODH (trade name), 20 mm ID×250 mm L, manufactured by DAICEL CHEMICAL INDUSTRIES, LTD., mobile phase: carbon dioxide/2-propanol=770/230) to give the title compound (89.0 mg) having a shorter retention time.
$^1$H NMR (300 MHz, CDCl$_3$) δ 1.25 (3H, s), 1.59 (3H, s), 1.96-2.10 (1H, m), 2.20-2.28 (2H, m), 2.33 (3H, s), 2.38-2.48 (1H, m), 4.11 (3H, s), 4.30 (1H, ddd, J=13.7, 11.0, 6.3 Hz), 5.00 (1H, brs), 5.02-5.12 (1H, m), 6.53 (2H, dd, J=8.8, 6.0 Hz), 7.03 (1H, s), 7.74 (1H, d, J=8.0 Hz), 7.88 (1H, d, J=0.8 Hz), 8.08 (1H, d, J=8.0 Hz).

[Method B]

2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol A) ethyl (8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridine-8-carboxylate To ethyl (3S)-2-(methylsulfanyl)-3-(3,4,5-trifluorophenoxy)-3,4,5,6-tetrahydropyridine-3-carboxylate (702 mg) and 6-methoxy-5-(4-methyl-1H-imidazol-1-yl)pyridine-2-carbohydrazide (500 mg) was added acetic acid (3 ml), and the mixture was stirred at 100° C. for 3 hr. The reaction mixture was diluted with ethyl acetate, and the mixture was washed with 10% aqueous potassium carbonate solution and saturated brine, dried over anhydrous sodium sulfate, and purified by silica gel column chromatography (NH, ethyl acetate). The crudely-purified product was purified by silica gel column chromatography (methanol/ethyl acetate) to give the title compound (1.02 g).
MS (ESI+): [M+H]$^+$529.3.

B) 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol To a mixture of methylmagnesium bromide (1M THF solution, 35.9 mL) in THF (35 mL) was added a mixture of ethyl (8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridine-8-carboxylate (6.33 g) in THF (35 mL) at 0° C., and the mixture was stirred at room temperature for 2 hr. The reaction mixture was diluted with ethyl acetate and saturated aqueous ammonia chloride solution, the mixture was washed with saturated brine and dried over anhydrous magnesium sulfate, and the solvent was evaporated under reduced pressure. The residue was purified by silica gel column chromatography (NH, ethyl acetate/hexane), and further recrystallized from ethyl acetate/tert-butyl methyl ether/hexane to give the title compound (4.90 g).

Example 153

2-{(8S)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol A racemate (300 mg) of 2-{3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol was separated by SFC (column: CHIRALCEL ODH (trade name), 20 mm ID×250 mm L, manufactured by DAICEL CHEMICAL INDUSTRIES, LTD., mobile phase: carbon dioxide/2-propanol=770/230) to give the title compound (103 mg) having a longer retention time.
$^1$H NMR (300 MHz, CDCl$_3$) δ 1.25 (3H, s), 1.58 (3H, s), 1.95-2.10 (1H, m), 2.19-2.28 (2H, m), 2.33 (3H, s), 2.37-2.47 (1H, m), 4.10 (3H, s), 4.30 (1H, ddd, J=13.7, 10.9, 6.5 Hz), 5.00 (1H, brs), 5.02-5.13 (1H, m), 6.53 (2H, dd, J=8.8, 6.0 Hz), 7.03 (1H, s), 7.74 (1H, d, J=8.0 Hz), 7.88 (1H, d, J=1.1 Hz), 8.08 (1H, d, J=8.0 Hz).

Example 155 optically active 2-{8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A racemate (160 mg) of 2-[8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl]propan-2-ol was separated by SFC (column: CHIRALCEL IC (trade name), 20 mm ID×250 mm L, manufactured by DAICEL CHEMICAL INDUSTRIES, LTD., mobile phase: carbon dioxide/ethanol=740/260) to give the title compound (80 mg) having a shorter retention time.
$^1$H NMR (300 MHz, CDCl$_3$) δ 1.29 (3H, s), 1.59 (3H, s), 2.02-2.17 (3H, m), 2.40-2.47 (1H, m), 2.56 (3H, s), 3.91-4.08 (4H, m), 4.21-4.30 (1H, m), 4.81 (1H, brs),6.33 (2H, dd, J=8.7, 2.3 Hz), 6.49 (1H, tt, J=8.9, 2.3 Hz), 7.21-7.26 (1H, m), 7.47 (1H, d, J=1.5 Hz), 7.52 (1H, s), 7.85 (1H, d, J=7.9 Hz).

Example 156 optically active 2-{8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol A racemate (160 mg) of 2-{8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol was separated by SFC (column: CHIRALCEL IC (trade name), 20 mm ID×250 mm L, manufactured by DAICEL CHEMICAL INDUSTRIES, LTD., mobile phase: carbon dioxide/ethanol=740/260) to give the title compound (80 mg) having a longer retention time.
$^1$H NMR (300 MHz, CDCl$_3$) δ 1.29 (3H, s), 1.59 (3H, s), 2.02-2.17 (3H, m), 2.37-2.49 (1H, m), 2.56 (3H, s), 3.92-4.07 (4H, m), 4.20-4.30 (1H, m), 4.82 (1H, brs),6.33 (2H, dd, J=8.7, 2.3 Hz), 6.48 (1H, tt, J=8.9, 2.3 Hz), 7.21-7.26 (1H, m), 7.46 (1H, d, J=1.5 Hz), 7.52 (1H, s), 7.85 (1H, d, J=7.9 Hz).

Example 157 optically active 2-{8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol A racemate (210 mg) of 2-{8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol was separated by HPLC (column: CHIRALCEL IC (trade name), 50 mm ID×500 mm L, manufactured by DAICEL CHEMICAL INDUSTRIES, LTD., mobile phase: hexane/ethanol=300/700) to give the title compound (90.8 mg) having a shorter retention time.
$^1$H NMR (300 MHz, CDCl$_3$) δ 1.26 (3H, s), 1.62 (3H, brs), 1.98-2.11 (1H, m), 2.20-2.29 (2H, m), 2.33 (3H, s), 2.39-2.51 (1H, m), 4.10 (3H, s), 4.23-4.37 (1H, m),4.96 (1H, brs), 5.04 (1H, dd, J=13.9, 4.1 Hz), 6.87-6.98 (2H, m), 6.97-7.11 (2H, m), 7.73 (1H, d, J=7.9 Hz), 7.88 (1H, s), 8.04 (1H, d, J=7.9 Hz).

Example 158 optically active 2-{8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol A racemate (210 mg) of 2-{8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol was separated by HPLC (column: CHIRALCEL IC (trade name), 50 mm ID×500 mm L, manufactured by DAICEL CHEMICAL INDUSTRIES, LTD., mobile phase: hexane/ethanol=300/700) to give the title compound (54.9 mg) having a longer retention time.
$^1$H NMR (300 MHz, CDCl$_3$) δ 1.32 (3H, s), 1.68 (3H, s), 2.03-2.16 (1H, m), 2.22-2.56 (6H, m), 4.15 (3H, s), 4.35 (1H, ddd, J=13.7, 12.3, 5.4 Hz), 5.02 (1H, s),5.09 (1H, dd, J=13.7, 4.7 Hz), 6.91-7.02 (2H, m), 7.08 (1H, s), 7.09-7.16 (1H, m), 7.78 (1H, d, J=8.0 Hz), 7.93 (1H, d, J=0.8 Hz), 8.09 (1H, d, J=8.0 Hz).

Example 162

2-{3-[2-fluoro-5-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol A) 5-(4-chloro-5-fluoro-2-methoxyphenyl)-2-methyl-1,3-oxazole In the same manner as in Example 3, step C, the title compound was obtained.
MS (ESI+): [M+H]$^+$242.0.

B) 2-fluoro-5-methoxy-4-(2-methyl-1,3-oxazol-5-yl)benzonitrile

To a mixture of 5-(4-chloro-5-fluoro-2-methoxyphenyl)-2-methyl-1,3-oxazole (1.12 g) and zinc(II) cyanide (0.327 g) in DMF (10 mL) were added tris(dibenzylideneacetone)dipalladium(0) (212 mg) and 2-dicyclohexylphosphino-2'-(N,N-dimethylamino)biphenyl (182 mg) at room temperature, and the mixture was stirred overnight under a nitrogen atmosphere at 130° C. The reaction mixture was diluted with water, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (902 mg).
MS (ESI+): [M+H]$^+$233.1.

C) 2-fluoro-5-methoxy-4-(2-methyl-1,3-oxazol-5-yl)benzoic acid

In the same manner as in Example 73, step E, the title compound was obtained.
MS (ESI+): [M+H]$^+$252.1.

D) 2-fluoro-5-methoxy-4-(2-methyl-1,3-oxazol-5-yl)benzohydrazide

In the same manner as in Example 3, step E, the title compound was obtained.
MS (ESI+): [M+H]$^+$266.2.

E) ethyl 2-thioxo-3-(3,4,5-trifluorophenoxy)piperidine-3-carboxylate

In the same manner as in Example 32, step E, the title compound was obtained.
MS (ESI+): [M+H]$^+$334.0.

F) ethyl 3-[2-fluoro-5-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridine-8-carboxylate In the same manner as in Example 32, step F, the title compound (634 mg) was obtained from 2-fluoro-5-methoxy-4-(2-methyl-1,3-oxazol-5-yl)benzohydrazide (400 mg) and ethyl 2-thioxo-3-(3,4,5-trifluorophenoxy)piperidine-3-carboxylate (503 mg).
MS (ESI+): [M+H]$^+$547.3.

G) 2-{3-[2-fluoro-5-methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol In the same manner as in Example 32, step G, the title compound was obtained.

Example 163

2-{3-[3-fluoro-4-(3-methyl-1H-1,2,4-triazol-1-yl)phenyl]-8-(3,4,5-trifluorophenoxy)-5,6,7,8-tetrahydro[1,2,4]triazolo[4,3-a]pyridin-8-yl}propan-2-ol A) 3-fluoro-4-(3-methyl-1H-1,2,4-triazol-1-yl)benzonitrile To a mixture of 1-(4-bromo-2-fluorophenyl)-3-methyl-1H-1,2,4-triazole (5.5 g), tris(dibenzylideneacetone)dipalladium(0) (393 mg), 1,1'-bis(diphenylphosphino)ferrocene (476 mg) and zinc powder (169 mg) in N,N-dimethylacetamide (20 mL) was added zinc(II) cyanide (1.5 g) at room temperature, and the mixture was stirred at 120° C. for 1 hr. To the reaction mixture were added ethyl acetate, water and aqueous ammonia. The organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (3.84 g).
MS (ESI+): [M+H]$^+$ 203.1.

B) 2-{3-[3-fluoro-4-(3-methyl-1H-1,2,4-triazol-1-yl)phenyl]-8-(3,4,5-trifluorophenoxy)-5,6,7,8-tetrahydro[1,2,4]triazolo[4,3-a]pyridin-8-yl}propan-2-ol The title compound was obtained in the same manner as in Example 73, step E, Example 3, step E, and Example 32, steps E to G.

Example 165

2-{3-[4-(4-chloro-1H-imidazol-1-yl)-3-methoxyphenyl]-8-(3,4,5-trifluorophenoxy)-5,6,7,8-tetrahydro[1,2,4]triazolo[4,3-a]pyridin-8-yl}propan-2-ol A) methyl 4-fluoro-3-methoxybenzoate A mixture of 4-fluoro-3-methoxybenzoic acid (2.33 g) and sulfuric acid (0.2 ml) in methanol (20 mL) was heated under reflux for 10 hr, and allowed to cool to room temperature. The reaction mixture was neutralized with saturated aqueous sodium hydrogen carbonate solution, the solvent was evaporated under reduced pressure, and water was added to the residue. The resultant precipitate was collected by filtration to give the title compound (2.31 g).
$^1$H NMR (300 MHz, CDCl$_3$) δ 3.90 (3H, s), 3.93 (3H, s), 7.03-7.16 (1H, m), 7.57-7.69 (2H, m).

B) methyl 4-(4-bromo-1H-imidazol-1-yl)-3-methoxybenzoate

A mixture of methyl 4-fluoro-3-methoxybenzoate (2.13 g), 4-bromo-1H-imidazole (3.74 g) and potassium carbonate (4.80 g) in DMF (20 mL) was stirred at 100° C. overnight, and allowed to cool to room temperature, and ethyl acetate and water were added. The organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (0.580 g).
MS (ESI+): [M+H]$^+$311.0.

C) 4-(4-bromo-1H-imidazol-1-yl)-3-methoxybenzoic acid

A mixture of methyl 4-fluoro-3-methoxybenzoate (2.13 g), 4-bromo-1H-imidazole (3.74 g) and potassium carbonate (4.80 g) in DMF (20 mL) was stirred at 100° C. overnight, and allowed to cool to room temperature, and ethyl acetate and water were added. The aqueous layer was separated, and acidified with 6N hydrochloric acid (pH=3-4), and the resultant precipitate was collected by filtration to give the title compound (1.92 g).
MS (ESI+): [M+H]$^+$297.0.

D) methyl 4-(4-bromo-1H-imidazol-1-yl)-3-methoxybenzoate

To a mixture of 4-(4-bromo-1H-imidazol-1-yl)-3-methoxybenzoic acid (1.90 g) in toluene (20 mL) and methanol (5 mL) was added trimethylsilyldiazomethane (2M hexane solution, 3.84 mL) at 0° C., and the mixture was stirred at room temperature for 2 hr. To the reaction mixture was added trimethylsilyldiazomethane (2M hexane solution, 0.96 mL), the mixture was stirred for 1 hr, and the solvent was evaporated under reduced pressure. The residue was recrystallized from ethyl acetate/hexane to give the title compound (1.32 g).
MS (ESI+): [M+H]$^+$311.2.

E) methyl 4-(4-chloro-1H-imidazol-1-yl)-3-methoxybenzoate

A mixture of methyl 4-(4-bromo-1H-imidazol-1-yl)-3-methoxybenzoate (1.72 g) and copper(I) chloride (5.47 g) in DMSO (50 ml) was stirred at 120° C. overnight under a nitrogen atmosphere. To the reaction mixture were added water and ethyl acetate, and the mixture was filtered through celite. The organic layer of the filtrate was separated, washed with water and saturated brine, and dried over anhydrous magnesium sulfate, and the solvent was evaporated under reduced pressure. The residue was purified by silica gel column chromatography (ethyl acetate/hexane) to give the title compound (26 mg).
MS (ESI+): [M+H]$^+$267.0.

F) 4-(4-chloro-1H-imidazol-1-yl)-3-methoxybenzohydrazide

To a mixture of methyl 4-(4-chloro-1H-imidazol-1-yl)-3-methoxybenzoate (25.5 mg) in methanol (1 mL) was added hydrazine monohydrate (0.019 mL) at room temperature, the mixture was stirred at 60° C. overnight, and the solvent was evaporated under reduced pressure. The residue was washed with ethyl acetate to give the title compound (12.7 mg).
MS (ESI+): [M+H]$^+$267.0.

G) 2-{3-[4-(4-chloro-1H-imidazol-1-yl)-3-methoxyphenyl]-8-(3,4,5-trifluorophenoxy)-5,6,7,8-tetrahydro[1,2,4]triazolo[4,3-a]pyridin-8-yl}propan-2-ol In the same manner as in Example 32, steps F and G, the title compound was obtained.

Example 166

2-{3-[3-fluoro-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol A) 3-fluoro-4-(2-methyl-1,3-oxazol-5-yl)benzonitrile In the same manner as in Example 163, step A, the title compound (3.75 g) was obtained from 5-(4-bromo-2-fluorophenyl)-2-methyl-1,3-oxazole (5.00 g).
MS (ESI+): [M+H] 203.2.

B) 2-{3-[3-fluoro-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol In the same manner as in Example 73, step E, Example 3, step E, and Example 32, steps E to G, the title compound was obtained.

Example 167

2-[3-[3-(benzyloxy)-4-(2-methyl-1,3-oxazol-5-yl)phenyl]-8-(3,4-difluorophenoxy)-5,6,7,8-tetrahydro[1,2,4]triazolo[4,3-a]pyridin-8-yl]propan-2-ol A) 3-(benzyloxy)-4-(2-methyl-1,3-oxazol-5-yl)benzonitrile To a mixture of sodium hydride (60%, 2.1 g) in DMF (35 mL) was added benzylalcohol (5.61 g) at 0° C., and the mixture was stirred for 30 min. 3-Fluoro-4-(2-methyl-1,3-oxazol-5-yl)benzonitrile (3.50 g) was added to this reaction mixture at 0° C., and the mixture was stirred at room temperature for 1 hr, and diluted with water. The resultant precipitate was collected by filtration and washed with water to give the title compound (5.20 g).
MS (ESI+): [M+H]$^+$291.1

B) 3-(benzyloxy)-4-(2-methyl-1,3-oxazol-5-yl)benzoic acid

A mixture of 3-(benzyloxy)-4-(2-methyl-1,3-oxazol-5-yl)benzonitrile (3.00 g) and 8N aqueous sodium hydroxide solution (0.39 mL) in n-butylalcohol (15 mL) was stirred at 100° C. overnight, and allowed to cool to room temperature. The solvent was evaporated under reduced pressure, and the residue was acidified with 6N hydrochloric acid. The resultant precipitate was collected by filtration and washed with water to give the title compound (3.12 g).
MS (ESI+): [M+H]$^+$310.1.

C) 2-{3-[3-(benzyloxy)-4-(2-methyl-1,3-oxazol-5-yl)phenyl]-8-(3,4-difluorophenoxy)-5,6,7,8-tetrahydro[1,2,4]triazolo[4,3-a]pyridin-8-yl}propan-2-ol In the same manner as in Example 3, step E, and Example 32, steps E to G, the title compound was obtained from 3-(benzyloxy)-4-(2-methyl-1,3-oxazol-5-yl)benzoic acid.

Example 168

5-[8-(3,4-difluorophenoxy)-8-(1-hydroxy-1-methylethyl)-5,6,7,8-tetrahydro[1,2,4]triazolo[4,3-a]pyridin-3-yl]-2-(2-methyl-1,3-oxazol-5-yl)phenol A mixture of 2-{3-[3-(benzyloxy)-4-(2-methyl-1,3-oxazol-5-yl)phenyl]-8-(3,4-difluorophenoxy)-5,6,7,8-tetrahydro[1,2,4]triazolo[4,3-a]pyridin-8-yl}propan-2-ol (100 mg) and 5% palladium-carbon (100 mg) in methanol (1.5 mL) was stirred at room temperature for 45 min under a hydrogen atmosphere. The mixture was filtered through celite, and the solvent was evaporated under reduced pressure. The residue was purified by silica gel column chromatography (ethyl acetate/hexane) to give the title compound (58.1 mg).

Example 169

2-{8-(3,4-difluorophenoxy)-3-[3-ethoxy-4-(2-methyl-1,3-oxazol-5-yl)phenyl]-5,6,7,8-tetrahydro[1,2,4]triazolo[4,3-a]pyridin-8-yl}propan-2-ol To a mixture of 5-[8-(3,4-difluorophenoxy)-8-(1-hydroxy-1-methylethyl)-5,6,7,8-tetrahydro[1,2,4]triazolo[4,3-a]pyridin-3-yl]-2-(2-methyl-1,3-oxazol-5-yl)phenol (41.1 mg) and potassium carbonate (24 mg) in DMF (0.43 ml) was added iodoethane (60 µL) at room temperature, and the mixture was stirred overnight. To the reaction mixture was added ethyl acetate, the mixture was washed with saturated brine and dried over anhydrous magnesium sulfate, and the solvent was evaporated under reduced pressure. The residue was purified by silica gel column chromatography (NH, ethyl acetate/hexane) to give the title compound (38.1 mg).

Example 172

2-{3-[6-methoxy-5-(2-methyl-1,3-oxazol-5-yl)pyridin-2-yl]-8-(3,4,5-trifluorophenoxy)-5,6,7,8-tetrahydro[1,2,4]triazolo[4,3-a]pyridin-8-yl}propan-2-ol A) 2,6-dichloro-3-(2-methyl-1,3-oxazol-5-yl)pyridine In the same manner as in Example 3, steps A to C, the title compound was obtained from 2,6-dichloropyridine-3-carboxylic acid.
MS (ESI+): [M+H]$^+$229.0.

B) 6-chloro-2-methoxy-3-(2-methyl-1,3-oxazol-5-yl)pyridine

To a mixture of 2,6-dichloro-3-(2-methyl-1,3-oxazol-5-yl)pyridine (2.22 g) in methanol (25 mL) was added sodium methoxide (5M methanol solution, 1.9 mL) at room temperature, and the mixture was stirred under a nitrogen atmosphere over the weekend. The reaction mixture was concentrated and diluted with water, and the mixture was extracted with ethyl acetate. The organic layer was separated, and dried over anhydrous magnesium sulfate, and the solvent was evaporated under reduced pressure. The residue was purified by silica gel column chromatography (ethyl acetate/hexane), and separated by HPLC (column: Chiralpak AD, mobile phase: hexane/2-propanol) to give the title compound (867 mg).

MS (ESI+): [M+H]$^+$225.2.

$^1$H NMR (300 MHz, CDCl$_3$) δ 2.53 (3H, s), 4.10 (3H, s), 6.99 (1H, d, J=7.9 Hz), 7.42 (1H, s), 7.90 (1H, d, J=7.9 Hz).

C) 6-methoxy-5-(2-methyl-1,3-oxazol-5-yl)pyridine-2-carbonitrile

In the same manner as in Example 162, step B, the title compound was obtained.

MS (ESI+): [M+H]$^+$216.1.

D) 6-methoxy-5-(2-methyl-1,3-oxazol-5-yl)pyridine-2-carboxylic acid

In the same manner as in Example 167, step B, the title compound was obtained.

$^1$H NMR (300 MHz, DMSO-d$_6$) δ 2.52 (3H, s), 4.09 (3H, s), 7.61 (1H, s), 7.79 (1H, d, J=7.5 Hz), 8.13 (1H, d, J=7.9 Hz), 13.15 (1H, brs).

E) 2-{3-[6-methoxy-5-(2-methyl-1,3-oxazol-5-yl)pyridin-2-yl]-8-(3,4,5-trifluorophenoxy)-5,6,7,8-tetrahydro[1,2,4]triazolo[4,3-a]pyridin-8-yl}propan-2-ol In the same manner as in Example 73, step E, Example 3, step E, and Example 32, steps E to G, the title compound was obtained.

Example 174

2-{3-[3-methoxy-4-(2-methylpyridin-4-yl)phenyl]-8-(3,4,5-trifluorophenoxy)-5,6,7,8-tetrahydro[1,2,4]triazolo[4,3-a]pyridin-8-yl}propan-2-ol

A) 3-fluoro-4-(4,4,5,5-tetramethyl-1,3,2-dioxaborolan-2-yl)benzonitrile

A mixture of 4-bromo-3-fluorobenzonitrile (14.0 g), 1,1'-bis(diphenylphosphino)ferrocenepalladium(II) chloride (2.89 g), potassium acetate (20.6 g) and bis(pinacolato)diboron (26.7 g) in DMF (300 mL) was stirred at room temperature for 30 min under a nitrogen atmosphere, and at 85° C. overnight. The reaction mixture was allowed to cool to room temperature and diluted with water, and the mixture was extracted with ethyl acetate. The organic layer was separated, and dried over anhydrous magnesium sulfate, and the solvent was evaporated under reduced pressure. The residue was purified by silica gel column chromatography (ethyl acetate/hexane) to give the title compound (17.2 g).

$^1$H NMR (400 MHz, CDCl$_3$) δ 1.26 (12H, s), 7.32 (1H, dd, J=1.2, 8.4 Hz), 7.43 (1H, dd, J=1.2, 7.6 Hz), 7.84 (1H, dd, J=6.0, 7.6 Hz).

B) 3-fluoro-4-(2-methylpyridin-4-yl)benzonitrile

A mixture of 3-fluoro-4-(4,4,5,5-tetramethyl-1,3,2-dioxaborolan-2-yl)benzonitrile (14.0 g), 4-bromo-2-methylpyridine (5.84 mL), tetrakis(triphenylphosphine)palladium(0) (5.24 g) and 2N aqueous sodium carbonate solution (91 mL) in 1,2-dimethoxyethane (20 mL) was stirred at 80° C. for 30 min under a nitrogen atmosphere. The reaction mixture was allowed to cool to room temperature, and diluted with water, and the mixture was extracted with ethyl acetate. The organic layer was separated, and dried over anhydrous magnesium sulfate, and the solvent was evaporated under reduced pressure. The residue was purified by silica gel column chromatography (ethyl acetate/hexane) to give the title compound (6.41 g).

$^1$H NMR (400 MHz, CDCl$_3$) δ 2.65 (3H, s), 7.27 (1H, s), 7.32 (1H, s), 7.50 (1H, d, J=10.4 Hz), 7.57-7.58 (2H, m), 8.62 (1H, d, J=5.2 Hz).

C) 3-methoxy-4-(2-methylpyridin-4-yl)benzohydrazide dihydrochloride

In the same manner as in Example 73, steps D to G, the title compound was obtained.

MS (ESI+), found: 258.2.

D) 2-{3-[3-methoxy-4-(2-methylpyridin-4-yl)phenyl]-8-(3,4,5-trifluorophenoxy)-5,6,7,8-tetrahydro[1,2,4]triazolo[4,3-a]pyridin-8-yl}propan-2-ol In the same manner as in Example 32, steps F and G, the title compound was obtained.

Example 177

2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol monophosphate To a mixture of 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol (1.0 g) in 2-propanol (4 mL) was added a mixture of phosphoric acid (0.27 g) in 2-propanol (2 mL) at 50° C., and the mixture was stirred for 30 min. To the reaction mixture was added IPE (6 mL) at 50° C., and the mixture was stirred for 30 min. To the reaction mixture was added IPE (2 mL) at room temperature, and the mixture was stirred for 30 min. The crystals were collected by filtration, washed with IPE (2 mL) and dried to give the title compound (1.08 g).

$^1$H NMR (300 MHz, DMSO-d$_6$) δ 1.42 (6H, d, J=5.1 Hz), 2.02-2.44 (6H, m), 4.03 (3H, s), 4.15-4.32 (1H, m), 4.84 (1H, d, J=13.2 Hz), 6.73 (2H, dd, J=9.6, 6.2 Hz), 7.34 (1H, s), 7.94 (1H, d, J=7.9 Hz), 8.03 (1H, d, J=0.9 Hz), 8.04-8.08 (1H, m).

Anal. Calcd for C$_{25}$H$_{25}$N$_6$O$_3$F$_3$—H$_3$PO$_4$: C, 49.02; H, 4.61; N, 13.72.

Found: C, 48.80; H, 4.84; N, 13.16.

Example 178

2-{3-[4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol

A) ethyl 3-(4-(2-methyl-1,3-oxazol-5-yl)-3-{[(trifluoromethyl)sulfonyl]oxy}phenyl)-8-(3,4,5-trifluorophenoxy)-5,6,7,8-tetrahydro[1,2,4]triazolo[4,3-a]pyridine-8-carboxylate A mixture of ethyl 3-[3-hydroxy-4-(2-methyl-1,3-oxazol-5-yl)phenyl]-8-(3,4,5-trifluorophenoxy)-5,6,7,8-tetrahydro[1,2,4]triazolo[4,3-a]pyridine-8-carboxylate (235 mg), N-phenylbis(trifluoromethanesulfonimide) (245 mg) and triethylamine (0.127 mL) in DMF (1.8 mL) was stirred at room temperature for 2 hr under a nitrogen atmosphere. The reaction mixture was diluted with ethyl acetate, the mixture was washed with saturated brine and dried over anhydrous magnesium sulfate, and the solvent was evaporated under reduced pressure. The residue was purified by silica gel column chromatography (NH, ethyl acetate/hexane) to give the title compound (232 mg).

MS (ESI+): [M+H]$^+$647.2.

B) ethyl 3-[4-(2-methyl-1,3-oxazol-5-yl)phenyl]-8-(3,4,5-trifluorophenoxy)-5,6,7,8-tetrahydro[1,2,4]triazolo[4,3-a]pyridine-8-carboxylate In the same manner as in Example 168, the title compound was obtained.

MS (ESI+): [M+H]$^+$499.1.

C) 2-{3-[4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol In the same manner as in Example 92, step B, the title compound was obtained.

Example 181

2-{3-[3-methoxy-4-(2-methyl-1,3-oxazol-5-yl)phenyl]-8-[(3,4,5-trifluorophenyl)amino]-5,6,7,8-tetrahydro[1,2,4]triazolo[4,3-a]pyridin-8-yl}propan-2-ol A) ethyl 3-[3-methoxy-4-(2-methyl-1,3-oxazol-5-yl)phenyl]-8-[(3,4,5-trifluorophenyl)amino]-5,6,7,8-tetrahydro[1,2,4]triazolo[4,3-a]pyridine-8-carboxylate To 3,4,5-trifluoroaniline (2.1 g) was added ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (1 g) at room temperature, and the mixture was stirred at 100° C. overnight under a nitrogen atmosphere. The reaction mixture was diluted with saturated aqueous sodium hydrogen carbonate solution, and the mixture was extracted with ethyl acetate. The organic layer was separated, washed with water and saturated brine, and dried over anhydrous magnesium sulfate, and the solvent was evaporated under reduced pressure. The residue was purified by silica gel column chromatography (NH, ethyl acetate/hexane) to give the title compound (719 mg).

MS (ESI+): [M+H]$^+$528.2.

B) 2-{3-[3-methoxy-4-(2-methyl-1,3-oxazol-5-yl)phenyl]-8-[(3,4,5-trifluorophenyl)amino]-5,6,7,8-tetrahydro[1,2,4]triazolo[4,3-a]pyridin-8-yl}propan-2-ol In the same manner as in Example 92, step B, the title compound was obtained.

Example 182

3-[3-methoxy-4-(2-methyl-1,3-oxazol-5-yl)phenyl]-8-methyl-8-(3,4,5-trifluorophenoxy)-5,6,7,8-tetrahydro[1,2,4]triazolo[4,3-a]pyridine A) ethyl 1-(4-methoxybenzyl)-2-oxo-3-(3,4,5-trifluorophenoxy)piperidine-3-carboxylate To a mixture of sodium hydride (60%, 59.6 mg) in DMF (5 mL) was added ethyl 2-oxo-3-(3,4,5-trifluorophenoxy)piperidine-3-carboxylate (430 mg) at 0° C. under a nitrogen atmosphere, and the mixture was stirred for 30 min. To the reaction mixture was added 4-methoxybenzyl chloride (0.221 mL), the mixture was stirred at 0° C. for 30 min and diluted with saturated aqueous ammonium chloride solution, and the mixture was extracted with ethyl acetate. The organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (352 mg).

MS (ESI+): [M+H]$^+$438.2.

B) 1-(4-methoxybenzyl)-3-(3,4,5-trifluorophenoxy)piperidin-2-one

A mixture of ethyl 1-(4-methoxybenzyl)-2-oxo-3-(3,4,5-trifluorophenoxy)piperidine-3-carboxylate (352 mg) and 1N aqueous sodium hydroxide solution (1.6 mL) in THF (3 mL) was stirred at room temperature for 2 days, and acidified with 1N hydrochloric acid, and extracted with ethyl acetate. The organic layer was separated, washed with saturated brine, and dried over anhydrous magnesium sulfate, and the solvent was evaporated under reduced pressure. The residue was recrystallized from ethyl acetate/hexane, the white crystals were separated by filtration, and the filtrate was concentrated. A mixture of the residue and the white crystals in toluene (3 mL) was stirred at 100° C. for 1 hr, and the solvent was evaporated under reduced pressure to give the title compound (252 mg).

MS (ESI+): [M+H]$^+$366.2.

C) 1-(4-methoxybenzyl)-3-methyl-3-(3,4,5-trifluorophenoxy)piperidin-2-one

To a mixture of 1-(4-methoxybenzyl)-3-(3,4,5-trifluorophenoxy)piperidin-2-one (250 mg) in THF (5 mL) was added lithiumhexamethyl disilazide (1M THF solution, 0.821 mL) at −78° C. under a nitrogen atmosphere, and the mixture was stirred for 30 min. To the reaction mixture was added a mixture of methyl iodide in THF (1 mL), and the mixture was stirred at −78° C. for 30 min under a nitrogen atmosphere, and at room temperature for 2 hr. The reaction mixture was diluted with saturated aqueous ammonium chloride solution, and the mixture was extracted with ethyl acetate. The organic layer was separated, washed with saturated brine, and dried over anhydrous magnesium sulfate, and the solvent was evaporated under reduced pressure. The residue was purified by silica gel column chromatography (ethyl acetate/hexane) to give the title compound (89 mg).

MS (ESI+): [M+H]$^+$380.2.

D) 3-methyl-3-(3,4,5-trifluorophenoxy)piperidin-2-one

To a mixture of 1-(4-methoxybenzyl)-3-methyl-3-(3,4,5-trifluorophenoxy)piperidin-2-one (76.2 mg) in acetonitrile (1 mL) was added a mixture of cerium(IV) ammonium nitrate (275 mg) in water (1 mL) at room temperature, and the mixture was stirred overnight. Cerium(IV) ammonium nitrate (110 mg) was added, and the mixture was stirred at room temperature for 1 hr. The reaction mixture was diluted with ethyl acetate and saturated aqueous sodium hydrogen carbonate solution, and the insoluble material was removed by filtration. The organic layer was separated, washed with water and saturated brine, and dried over anhydrous magnesium sulfate, and the solvent was evaporated under reduced pressure. The residue was purified by silica gel column chromatography (NH, ethyl acetate) and silica gel column chromatography (ethyl acetate/hexane) to give the title compound (30.1 mg).

$^1$H NMR (300 MHz, CDCl$_3$) δ 1.56 (3H, s), 1.78-1.97 (2H, m), 2.01-2.17 (1H, m), 2.20-2.34 (1H, m), 3.28-3.50 (2H, m), 6.12 (1H, brs), 6.57-6.74 (2H, m).

E) 3-methyl-3-(3,4,5-trifluorophenoxy)piperidine-2-thione

In the same manner as in Example 32, step E, the title compound was obtained.

$^1$H NMR (300 MHz, CDCl$_3$) δ 1.72 (3H, s), 1.81-1.94 (1H, m), 1.94-2.08 (1H, m), 2.16 (1H, dd, J=12.9, 5.2 Hz), 2.26-2.39 (1H, m), 3.31-3.60 (2H, m), 6.56-6.82 (2H, m), 8.22 (1H, brs).

F) 3-[3-methoxy-4-(2-methyl-1,3-oxazol-5-yl)phenyl]-8-methyl-8-(3,4,5-trifluorophenoxy)-5,6,7,8-tetrahydro[1,2,4]triazolo[4,3-a]pyridine In the same manner as in Example 32, step F, the title compound (7.2 mg) was obtained from 3-methoxy-4-(2-methyl-1,3-oxazol-5-yl)benzohydrazide (25.7 mg) and 3-methyl-3-(3,4,5-trifluorophenoxy)piperidine-2-thione (28.6 mg).

Example 186

2-{3-[3-methoxy-4-(2-methyl-1,3-oxazol-5-yl)phenyl]-7-(3,4,5-trifluorophenoxy)-4,5,6,7-tetrahydro[1,2,3]triazolo[1,5-a]pyridin-7-yl}propan-2-ol A) 5-(4-bromo-2-methoxyphenyl)-2-methyl-1,3-oxazole To a mixture of 5-(4-bromo-2-fluorophenyl)-2-methyl-1,3-oxazole (10 g) in DMF (80 mL) was added sodium methoxide (28% methanol solution, 11.3 g) at 0° C., and the mixture was stirred at 80° C. for 2 hr under a nitrogen atmosphere. The reaction mixture was cooled to 0° C., and diluted with water, and the resultant solid was collected by filtration to give the title compound (10.4 g).
MS (ESI+): [M+H]$^+$268.0.

B) 5-[4-(5-chloropent-1-yn-1-yl)-2-methoxyphenyl]-2-methyl-1,3-oxazole

A mixture of 5-(4-bromo-2-methoxyphenyl)-2-methyl-1,3-oxazole (6.00 g), 5-chloropent-1-yne (4.74 mL), dichlorobis(triphenylphosphine)palladium(II) (1.57 g), copper(I) iodide (426 mg) and triethylamine (60 mL) was stirred at 70° C. for 3 hr, and diluted with ethyl acetate, and the mixture was filtered through celite. The solvent was evaporated under reduced pressure, and the residue was purified by silica gel column chromatography (ethyl acetate/hexane) to give the title compound (4.85 g).
MS (ESI+): [M+H]$^+$290.1.

C) ethyl 2-amino-7-[3-methoxy-4-(2-methyl-1,3-oxazol-5-yl)phenyl]hept-6-ynoate

A mixture of 5-[4-(5-chloropent-1-yn-1-yl)-2-methoxyphenyl]-2-methyl-1,3-oxazole (500 mg), ethyl N-(diphenylmethylene)glycinate (461 mg), potassium carbonate (1.2 g) and tetrabutylammonium iodide (637 mg) in acetonitrile (5 mL) was stirred at 80° C. overnight under an argon atmosphere. The reaction mixture was diluted with ethyl acetate, the mixture was washed with water and saturated brine, and dried over anhydrous sodium sulfate, and the solvent was evaporated under reduced pressure. Ethyl acetate was added to the residue, the insoluble material was separated by filtration, and the filtrate was concentrated. A mixture of the residue and 6N hydrochloric acid (0.5 mL) in acetonitrile (5 ml) was stirred at room temperature for 1 hr. To the reaction mixture was added saturated aqueous sodium hydrogen carbonate solution, and the mixture was extracted with ethyl acetate. The organic layer was separated, washed with water and saturated brine, and dried over anhydrous sodium sulfate, and the solvent was evaporated under reduced pressure. The residue was purified by silica gel column chromatography (ethyl acetate/hexane) to give the title compound (362 mg).
MS (ESI+): [M+H]$^+$357.2.

D) ethyl 2-azido-7-[3-methoxy-4-(2-methyl-1,3-oxazol-5-yl)phenyl]hept-6-ynoate

To a mixture of sodium azide (1.3 g), water (5 mL) and toluene (5 mL) was added trifluoromethanesulfonic anhydride (1.68 mL) at 0° C., and the mixture was stirred at room temperature for 30 min. To the reaction mixture was added saturated aqueous sodium hydrogen carbonate solution, and the mixture was extracted with toluene to give a solution of trifluoromethanesulfonyl azide in toluene. The solution of trifluoromethanesulfonyl azide in toluene was added to a mixture of ethyl 2-amino-7-[3-methoxy-4-(2-methyl-1,3-oxazol-5-yl)phenyl]hept-6-ynoeate (1.80 g), sodium hydrogen carbonate (1.7 g) and copper(II) sulfate pentahydrate in water (15 mL)/ethanol (45 mL), and the mixture was stirred at room temperature for 1 hr. The reaction mixture was diluted with ethyl acetate, washed with water and saturated brine, dried over anhydrous sodium sulfate, and the solvent was evaporated under reduced pressure. The residue was purified by silica gel column chromatography (ethyl acetate/hexane) to give the title compound (1.40 g).
MS (ESI+): [M+H]$^+$383.1.

E) ethyl 3-[3-methoxy-4-(2-methyl-1,3-oxazol-5-yl)phenyl]-4,5,6,7-tetrahydro[1,2,3]triazolo[1,5-a]pyridine-7-carboxylate A mixture of ethyl 2-azido-7-[3-methoxy-4-(2-methyl-1,3-oxazol-5-yl)phenyl]hept-6-ynoate (1.40 g) in chlorobenzene (28 mL) was stirred at 110° C. for 4 hr. The reaction mixture was purified by silica gel column chromatography (ethyl acetate/hexane) to give the title compound (1.34 g).
MS (ESI+): [M+H]$^+$383.1.

F) ethyl 7-chloro-3-[3-methoxy-4-(2-methyl-1,3-oxazol-5-yl)phenyl]-4,5,6,7-tetrahydro[1,2,3]triazolo[1,5-a]pyridine-7-carboxylate To a mixture of ethyl 3-[3-methoxy-4-(2-methyl-1,3-oxazol-5-yl)phenyl]-4,5,6,7-tetrahydro[1,2,3]triazolo[1,5-a]pyridine-7-carboxylate (1.00 g) in THF (52 mL) was added lithiumhexamethyl disilazide (1M THF solution, 3.14 mL) at −78° C. under an argon atmosphere. The reaction mixture was stirred at −78° C. for 20 min, and at 0° C. for 20 min. To the reaction mixture was added N-chlorosuccinimide (419 mg) at 0° C., and the mixture was stirred at room temperature for 30 min. The reaction mixture was diluted with ethyl acetate, the mixture was washed with water and saturated brine, and dried over anhydrous sodium sulfate, and the solvent was evaporated under reduced pressure. The residue was purified by silica gel column chromatography (ethyl acetate/hexane) to give the title compound (1.40 g).
MS (ESI+): [M+H]+417.1.

G) 2-{3-[3-methoxy-4-(2-methyl-1,3-oxazol-5-yl)phenyl]-7-(3,4,5-trifluorophenoxy)-4,5,6,7-tetrahydro[1,2,3]triazolo[1,5-a]pyridin-7-yl}propan-2-ol In the same manner as in Example 99, the title compound was obtained.

Example 187

2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol 1(+)-mandelate To a mixture of 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol (0.50 g) in ethanol (2 mL) was added a mixture of (+)-mandelic acid (148 mg) in ethanol (1 mL) at room temperature. To the reaction mixture was added hexane/IPE at room temperature, and the mixture was stirred for 3 hr. The crystals were collected by filtration and dried to give the title compound (0.55 g).
$^1$H NMR (300 MHz, DMSO-$d_6$) δ 1.42 (6H, d, J=5.1 Hz), 2.06-2.41 (6H, m), 4.03 (3H, s), 4.17-4.30 (1H, m), 4.79-4.89 (1H, m), 5.02 (2H, s), 6.74 (2H, dd, J=9.6, 6.4 Hz), 7.24-7.38 (4H, m), 7.39-7.44 (2H, m), 7.92-7.96 (1H, m), 8.01 (1H, d, J=0.9 Hz), 8.03-8.08 (1H, m).

Example 191 optically active 2-{3-[3-methoxy-4-(2-methyl-1,3-oxazol-5-yl)phenyl]-7-(3,4,5-trifluorophenoxy)-4,5,6,7-tetrahydro[1,2,3]triazolo[1,5-a]pyridin-7-yl}propan-2-ol A racemate (86 mg) of 2-{3-[3-methoxy-4-(2-methyl-1,3-oxazol-5-yl)phenyl]-7-(3,4,5-trifluorophenoxy)-4,5,6,7-tetrahydro[1,2,3]triazolo[1,5-a]pyridin-7-yl}propan-2-ol was separated by HPLC (column: CHIRALPAK AD (trade name), 50 mm ID×500 mm L, manufactured by DAICEL CHEMICAL INDUSTRIES, LTD., mobile phase: hexane/ethanol=800/200) to give the title compound (34 mg) having a shorter retention time.
$^1$H NMR (300 MHz, CDCl$_3$) δ 1.18 (3H, s), 1.48-1.65 (4H, m), 1.98-2.27 (2H, m), 2.43-2.59 (4H, m), 2.87 (1H, ddd, J=17.2, 11.9, 5.7 Hz), 3.22 (1H, dd, J=16.4, 3.2 Hz), 4.06 (3H, s), 4.54 (1H, s), 6.22-6.33 (2H, m), 7.22-7.29 (1H, m), 7.47 (1H, s), 7.59 (1H, d, J=1.5 Hz), 7.80 (1H, d, J=7.9 Hz).

Example 192 optically active 2-{3-[3-methoxy-4-(2-methyl-1,3-oxazol-5-yl)phenyl]-7-(3,4,5-trifluorophenoxy)-4,5,6,7-tetrahydro[1,2,3]triazolo[1,5-a]pyridin-7-yl}propan-2-ol A racemate (86 mg) of 2-{3-[3-methoxy-4-(2-methyl-1,3-oxazol-5-yl)phenyl]-7-(3,4,5-trifluorophenoxy)-4,5,6,7-tetrahydro[1,2,3]triazolo[1,5-a]pyridin-7-yl}propan-2-ol was separated by HPLC (column: CHIRALPAK AD (trade name), 50 mm ID×500 mm L, manufactured by DAICEL CHEMICAL INDUSTRIES, LTD., mobile phase: hexane/ethanol=800/200) to give the title compound (39 mg) having a longer retention time.
$^1$H NMR (300 MHz, CDCl$_3$) δ 1.18 (3H, s), 1.49-1.64 (4H, m), 1.99-2.11 (1H, m), 2.13-2.27 (1H, m), 2.42-2.59 (4H, m), 2.79-2.97 (1H, m), 3.16-3.29 (1H, m), 4.06 (3H, s), 4.52 (1H, s), 6.28 (2H, dd, J=8.5, 5.9 Hz), 7.21-7.30 (1H, m), 7.47 (1H, s), 7.60 (1H, d, J=1.1 Hz), 7.80 (1H, d, J=7.9 Hz).

Example 194

2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol 0.67 phosphate To 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol monophosphate (213.4 g) was added ethanol (350 mL), the mixture was dissolved at 60° C., and the insoluble material was removed by filtration. 2-Propanol (700 mL) was added to the filtrate at 60° C., and the mixture was stirred for 30 min, and at 0° C. for 30 min. The crystals were collected by filtration, washed with 2-propanol (250 mL) and dried at 60° C. under reduced pressure to give the title compound (184 g).
$^1$H NMR (300 MHz, DMSO-$d_6$) δ 1.42 (6H, d, J=5.3 Hz), 2.04-2.41 (6H, m), 4.03 (3H, s), 4.23 (1H, ddd, J=13.7, 9.9, 4.1 Hz), 4.78-4.89 (1H, m), 6.73 (2H, dd, J=9.5, 6.3 Hz), 7.33 (1H, t, J=1.0 Hz), 7.94 (1H, d, J=8.1 Hz), 8.02 (1H, d, J=1.3 Hz), 8.03-8.08 (1H, m).
Anal. Calcd for $C_{25}H_{25}N_6O_3F_3 \cdot 0.67H_3PO_4$: C, 51.76; H, 4.69; N, 14.49. Found: C, 51.38; H, 4.79; N, 14.31.

Example 195 ethyl 8-[6-(2-ethoxy-2-oxoethyl)-2,3,4-trifluorophenoxy]-3-[3-methoxy-4-(2-methyl-1,3-oxazol-5-yl)phenyl]-5,6,7,8-tetrahydro[1,2,4]triazolo[4,3-a]pyridine-8-carboxylate A) 2,3,4-trifluorophenyl acetate To a mixture of 2,3,4-trifluorophenol (5.2 g) and acetic anhydride (3.98 mL) in THF (50 mL) was added triethylamine (5.87 mL) at room temperature, and the mixture was stirred for 1 hr and concentrated under reduced pressure. Water and ethyl acetate were added to the residue, the organic layers were separated, and the aqueous layer was extracted with ethyl acetate. The combined organic layer was washed with saturated brine, and dried over anhydrous magnesium sulfate, and the solvent was evaporated under reduced pressure to give the title compound (6.70 g).
$^1$H NMR (300 MHz, CDCl$_3$) δ 2.39 (3H, s), 6.86-6.97 (1H, m), 6.98-7.10 (1H, m).

B) 1-(3,4,5-trifluoro-2-hydroxyphenyl)ethanone

A mixture of 2,3,4-trifluorophenyl acetate (6.70 g) and aluminum(III) chloride (14.10 g) was stirred at 170° C. for 30 min, and allowed to cool to 0° C. Water and 6N hydrochloric acid were added to the reaction mixture, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (5.50 g).
$^1$H NMR (300 MHz, CDCl$_3$) δ 2.64 (3H, d, J=5.2 Hz), 6.45 (1H, brs), 7.50 (1H, ddd, J=10.8, 6.0, 2.2 Hz).

C) 3,4,5-trifluoro-2-hydroxyphenyl)acetic acid

A mixture of 1-(3,4,5-trifluoro-2-hydroxyphenyl)ethanone (7.5 g), p-toluenesulfonic acid monohydrate (0.375 g), morpholine (10 mL) and sulfur (2.0 g) was stirred at 120° C. for 5 hr, and allowed to cool to room temperature, and hydrochloric acid (20 mL) and acetic acid (20 mL) were added to the reaction mixture. The reaction mixture was stirred at 100° C. for 3 hr, allowed to cool to room temperature, and extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (6.0 g).

$^1$H NMR (300 MHz, DMSO-$d_6$) δ 3.56 (2H, s), 7.03 (1H, ddd, J=11.2, 6.7, 2.2 Hz), 10.64 (1H, brs), 12.51 (1H, brs).

D) ethyl (3,4,5-trifluoro-2-hydroxyphenyl)acetate

A mixture of (3,4,5-trifluoro-2-hydroxyphenyl)acetic acid (6.0 g), sulfuric acid (0.016 mL) and ethanol (50 mL) was stirred at 80° C. overnight, neutralized with saturated aqueous sodium hydrogen carbonate solution, and concentrated under reduced pressure. The residue was purified by silica gel column chromatography (ethyl acetate/hexane) to give the title compound (5.6 g).

$^1$H NMR (300 MHz, CDCl$_3$) δ 1.29 (3H, t, J=7.1 Hz), 3.60 (2H, d, J=1.4 Hz), 4.20 (2H, q, J=7.1 Hz), 5.62-6.16 (1H, m), 6.78 (1H, ddd, J=10.4, 6.1, 2.5 Hz).

E) ethyl 8-[6-(2-ethoxy-2-oxoethyl)-2,3,4-trifluorophenoxy]-3-[3-methoxy-4-(2-methyl-1,3-oxazol-5-yl)phenyl]-5,6,7,8-tetrahydro[1,2,4]triazolo[4,3-a]pyridine-8-carboxylate To a mixture of ethyl (3,4,5-trifluoro-2-hydroxyphenyl)acetate (1.77 g) in ethanol (15 mL) was added sodium ethoxide (0.514 g) at room temperature under a nitrogen atmosphere, and the mixture was stirred for 30 min. To the reaction mixture was added ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate (3 g), the mixture was stirred at 80° C. overnight under a nitrogen atmosphere, and diluted with saturated aqueous ammonium chloride solution, and the mixture was extracted with ethyl acetate. The organic layer was separated, washed with saturated brine, and dried over anhydrous magnesium sulfate, and the solvent was evaporated under reduced pressure. The residue was purified by silica gel column chromatography (ethyl acetate/hexane) to give the title compound (2 g).

Example 197

2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol monogentisate To a mixture of 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol (0.50 g) in ethanol (1.5 ml) was added a mixture of gentisic acid (150 mg) in ethanol (1 mL) at room temperature. To the reaction mixture was added IPE/heptane at room temperature, and the mixture was stirred for 3 hr. The crystals were collected by filtration and dried to give the title compound (0.44 g).

$^1$H NMR (300 MHz, DMSO-$d_6$) δ 1.42 (6H, d, J=4.9 Hz), 2.06-2.44 (6H, m), 4.03 (3H, s), 4.16-4.30 (1H, m), 4.84 (1H, d, J=13.2 Hz), 6.68-6.82 (3H, m), 6.94 (1H, dd, J=8.8, 3.1 Hz), 7.15 (1H, d, J=3.0 Hz), 7.36 (1H, s), 7.95 (1H, d, J=8.1 Hz), 8.02-8.11 (2H, m).

Example compounds produced according to the abovementioned methods or a method analogous thereto are shown in the following Tables. MS in the Table means Found.

| Ex. No. | compound name | structure | MS |
|---|---|---|---|
| 1 | 2-{8-(4-chloro-3-fluorophenoxy)-3-[6-methoxy-5-(4-methyl-1H-imidazol-1-yl)pyridin-2-yl]-5,6,7,8-tetrahydro[1,2,4]-triazolo[4,3-a]pyridin-8-yl}propan-2-ol | 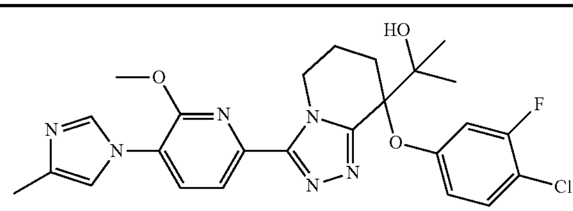 | 513.1 |
| 2 | 2-{8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]-triazolo[4,3-a]pyridin-8-yl}propan-2-ol | 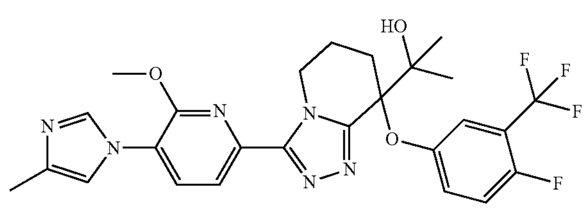 [SMILES: COc1nc(-c2nnc3n2CCCC3(Oc2ccc(F)c(C(F)(F)F)c2)C(C)(C)O)ccc1-n1cnc(C)c1] | 547.1 |
| 3 | 8-(4-chlorophenyl)-3-[3-methoxy-4-(2-methyl-1,3-oxazol-5-yl)phenyl]-8-methyl-5,6,7,8-tetrahydro[1,2,4]triazolo-[4,3-a]pyridine | 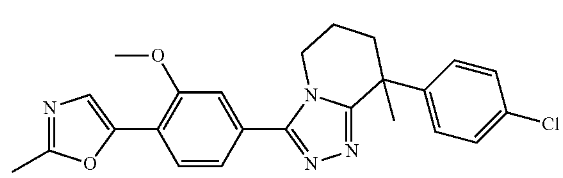 [SMILES: COc1cc(-c2nnc3n2CCCC3(C)c2ccc(Cl)cc2)ccc1-c1cnc(C)o1] | 435.2 |

-continued

| | | | |
|---|---|---|---|
| 4 | optically active 8-(4-chlorophenyl)-3-[3-methoxy-4-(2-methyl-1,3-oxazol-5-yl)phenyl]-8-methyl-5,6,7,8-tetrahydro[1,2,4]-triazolo[4,3-a]pyridine | 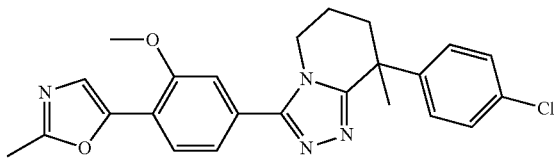 [SMILES: COc1cc(-c2nnc3n2CCCC3(C)c2ccc(Cl)cc2)ccc1-c1cnc(C)o1] | 435.3 |
| 5 | optically active 8-(4-chlorophenyl)-3-[3-methoxy-4-(2-methyl-1,3-oxazol-5-yl)phenyl]-8-methyl-5,6,7,8-tetrahydro[1,2,4]-triazolo[4,3-a]pyridine | 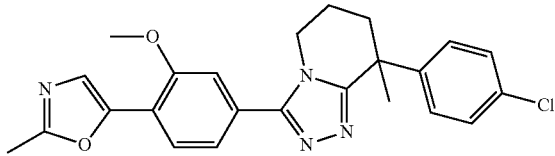 [SMILES: COc1cc(-c2nnc3n2CCCC3(C)c2ccc(Cl)cc2)ccc1-c1cnc(C)o1] | 435.3 |
| 6 | 8-(3-chlorophenyl)-3-[3-methoxy-4-(2-methyl-1,3-oxazol-5-yl)phenyl]-8-methyl-5,6,7,8-tetrahydro[1,2,4]triazolo-[4,3-a]pyridine | 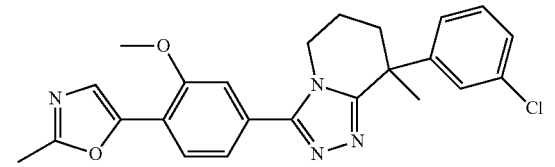 [SMILES: COc1cc(-c2nnc3n2CCCC3(C)c2cccc(Cl)c2)ccc1-c1cnc(C)o1] | 435.2 |
| 7 | 8-(2-chlorophenyl)-3-[3-methoxy-4-(2-methyl-1,3-oxazol-5-yl)phenyl]-8-methyl-5,6,7,8-tetrahydro-[1,2,4]triazolo[4,3-a]pyridine | 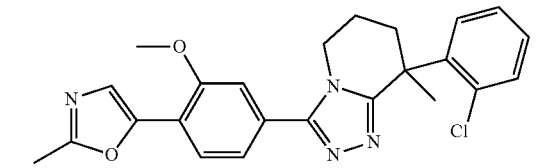 [SMILES: COc1cc(-c2nnc3n2CCCC3(C)c2ccccc2Cl)ccc1-c1cnc(C)o1] | 435.2 |
| 8 | 3-[3-methoxy-4-(2-methyl-1,3-oxazol-5-yl)phenyl]-8-methyl-8-[4-(trifluoromethyl)phenyl]-5,6,7,8-tetrahydro[1,2,4]-triazolo[4,3-a]pyridine | 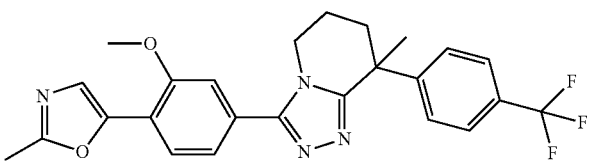 [SMILES: COc1cc(-c2nnc3n2CCCC3(C)c2ccc(C(F)(F)F)cc2)ccc1-c1cnc(C)o1] | 469.1 |
| 9 | 8-(3,4-dichlorophenyl)-3-[3-methoxy-4-(2-methyl-1,3-oxazol-5-yl)phenyl]-5,6,7,8-tetrahydro-[1,2,4]triazolo[4,3-a]pyridin-8-ol | 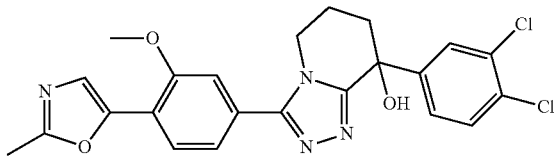 [SMILES: COc1cc(-c2nnc3n2CCCC3(O)c2ccc(Cl)c(Cl)c2)ccc1-c1cnc(C)o1] | 471.1 |
| 10 | {8-(3,4-dichlorophenyl)-3-[3-methoxy-4-(2-methyl-1,3-oxazol-5-yl)phenyl]-5,6,7,8-tetrahydro-[1,2,4]triazolo[4,3-a]pyridin-8-yl}methanol | 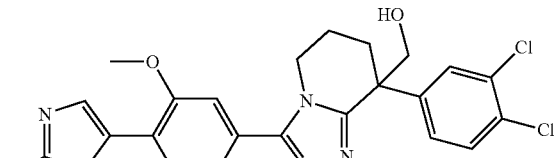 | 485.2 |
| 11 | 8-(3,4-difluorophenyl)-3-[3-methoxy-4-(2-methyl-1,3-oxazol-5-yl)phenyl]-8-methyl-5,6,7,8-tetrahydro-[1,2,4]triazolo[4,3-a]pyridine | 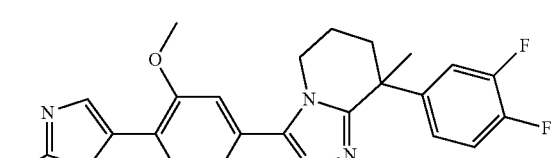 | 437.1 |
| 12 | 8-(cyclopropylmethyl)-3-[3-methoxy-4-(2-methyl-1,3-oxazol-5-yl)phenyl]-8-[4-(methylsulfanyl)-phenyl]-5,6,7,8-tetrahydro[1,2,4]-triazolo[4,3-a]pyridine | 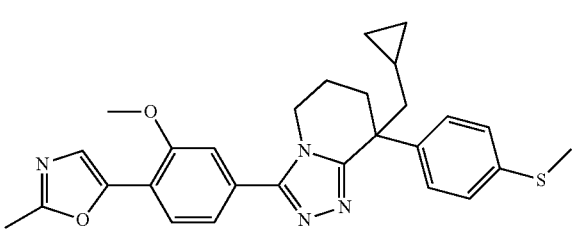 | 487.3 |

| | | | |
|---|---|---|---|
| 13 | 8-(cyclopropylmethyl)-3-[3-methoxy-4-(2-methyl-1,3-oxazol-5-yl)phenyl]-8-[4-(methylsulfonyl)-phenyl]-5,6,7,8-tetrahydro[1,2,4]triazolo-[4,3-a]pyridine | 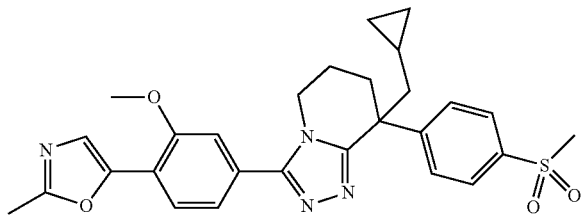 [SMILES: COc1cc(-c2nnc3n2CCCC3(CC2CC2)c2ccc(S(C)(=O)=O)cc2)ccc1-c1cnc(C)o1] | 519.4 |
| 14 | 8-(3,4-difluorobenzyl)-3-[3-methoxy-4-(2-methyl-1,3-oxazol-5-yl)phenyl]-8-[4-(methylsulfanyl)-phenyl]-5,6,7,8-tetrahydro[1,2,4]triazolo-[4,3-a]pyridine | 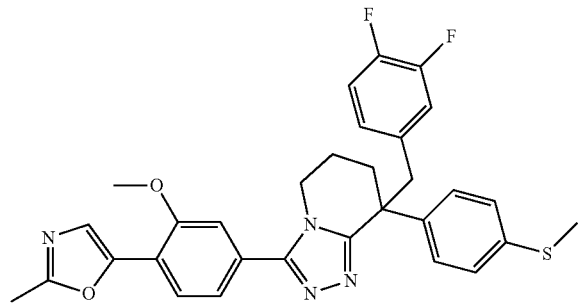 | 559.3 |
| 15 | 8-(3,4-difluorobenzyl)-3-[3-methoxy-4-(2-methyl-1,3-oxazol-5-yl)phenyl]-8-[4-(methylsulfonyl)-phenyl]-5,6,7,8-tetrahydro[1,2,4]triazolo-[4,3-a]pyridine | 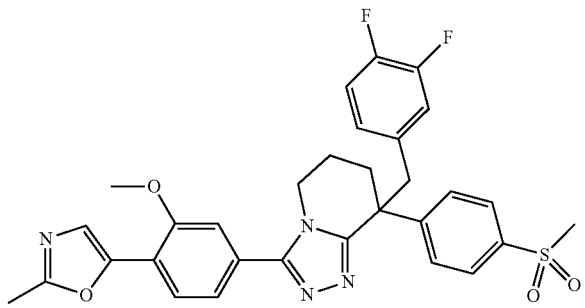 [SMILES: COc1cc(-c2nnc3n2CCCC3(Cc2ccc(F)c(F)c2)c2ccc(S(C)(=O)=O)cc2)ccc1-c1cnc(C)o1] | 591.4 |
| 16 | 8-(3,4-difluorophenyl)-8-ethyl-3-[3-methoxy-4-(2-methyl-1,3-oxazol-5-yl)phenyl]-5,6,7,8-tetrahydro[1,2,4]triazolo-[4,3-a]pyridine | 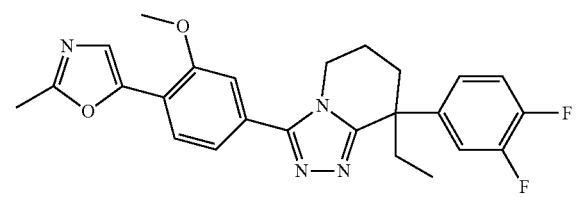 [SMILES: CCC1(c2ccc(F)c(F)c2)CCCn2c(-c3ccc(-c4cnc(C)o4)c(OC)c3)nnc21] | 451.4 |
| 17 | 8-(3,4-difluorophenyl)-8-ethoxy-3-[3-methoxy-4-(2-methyl-1,3-oxazol-5-yl)phenyl]-5,6,7,8-tetrahydro[1,2,4]triazolo-[4,3-a]pyridine | 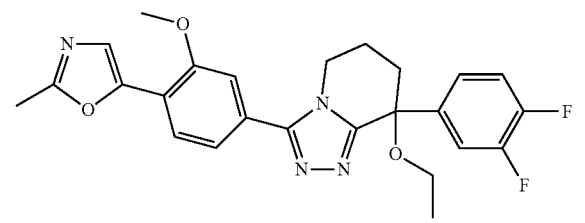 [SMILES: CCOC1(c2ccc(F)c(F)c2)CCCn2c(-c3ccc(-c4cnc(C)o4)c(OC)c3)nnc21] | 467.2 |
| 18 | {8-(3,4-difluorophenyl)-3-[3-methoxy-4-(2-methyl-1,3-oxazol-5-yl)phenyl]-5,6,7,8-tetrahydro[1,2,4]triazolo-[4,3-a]pyridin-8-yl}methanol | 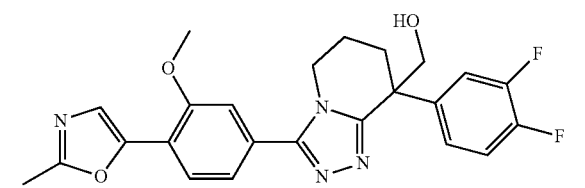 [SMILES: COc1cc(-c2nnc3n2CCCC3(CO)c2ccc(F)c(F)c2)ccc1-c1cnc(C)o1] | 453.2 |

| | | | |
|---|---|---|---|
| 19 | 8-(3,4-difluorophenyl)-3-[3-methoxy-4-(2-methyl-1,3-oxazol-5-yl)phenyl]-8-(1-methylethyl)-5,6,7,8-tetrahydro[1,2,4]triazolo[4,3-a]pyridine | 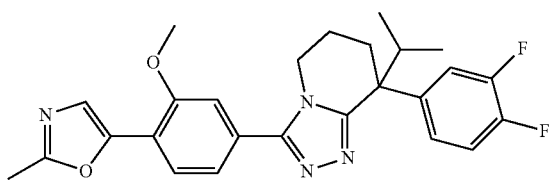 [SMILES: COc1cc(-c2nnc3n2CCCC3(c2ccc(F)c(F)c2)C(C)C)ccc1-c1cnc(C)o1] | 465.2 |
| 20 | 8-(cyclopropylmethyl)-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine | 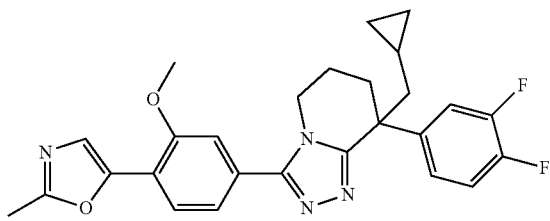 [SMILES: COc1cc(-c2nnc3n2CCCC3(CC2CC2)c2ccc(F)c(F)c2)ccc1-c1cnc(C)o1] | 477.2 |
| 21 | optically active 8-(cyclopropylmethyl)-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine | 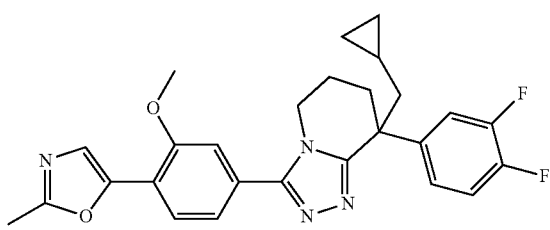 [SMILES: COc1cc(-c2nnc3n2CCCC3(CC2CC2)c2ccc(F)c(F)c2)ccc1-c1cnc(C)o1] | 477.1 |
| 22 | optically active 8-(cyclopropylmethyl)-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine | 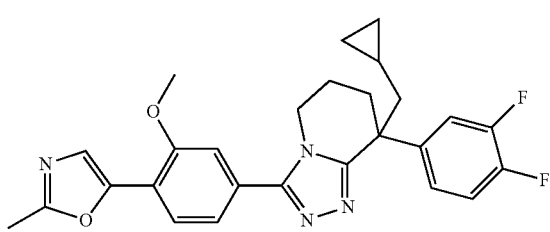 [SMILES: COc1cc(-c2nnc3n2CCCC3(CC2CC2)c2ccc(F)c(F)c2)ccc1-c1cnc(C)o1] | 477.2 |
| 23 | 8-(cyclopropylmethoxy)-8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridine | 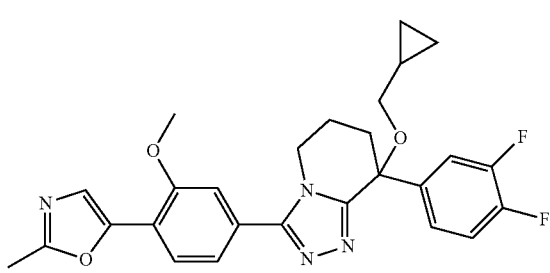 [SMILES: COc1cc(-c2nnc3n2CCCC3(OCC2CC2)c2ccc(F)c(F)c2)ccc1-c1cnc(C)o1] | 493.3 |
| 24 | 8-(3,4-difluorophenyl)-8-(methoxymethyl)-3-[3-methoxy-4-(2-methyl-1,3-oxazol-5-yl)phenyl]-5,6,7,8-tetrahydro[1,2,4]triazolo[4,3-a]pyridine | 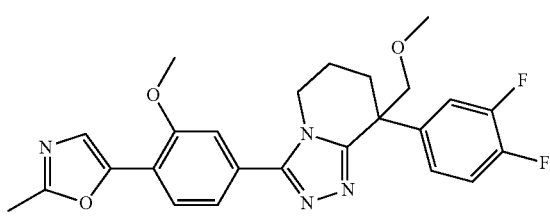 [SMILES: COCC1(c2ccc(F)c(F)c2)CCCn2c(-c3ccc(-c4cnc(C)o4)c(OC)c3)nnc21] | 467.2 |
| 25 | 8-(3,4-difluorophenyl)-3-[3-methoxy-4-(2-methyl-1,3-oxazol-5-yl)phenyl]-8-(2-methylbutyl)-5,6,7,8-tetrahydro[1,2,4]triazolo[4,3-a]pyridine | 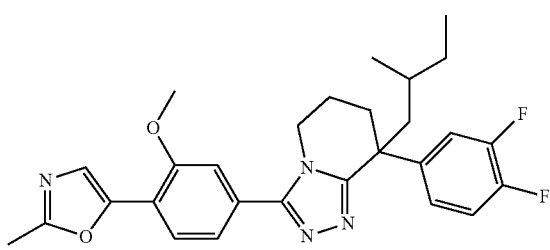 [SMILES: CCC(C)CC1(c2ccc(F)c(F)c2)CCCn2c(-c3ccc(-c4cnc(C)o4)c(OC)c3)nnc21] | 493.1 |

| | | | |
|---|---|---|---|
| 26 | 8-(3,4-difluorophenyl)-3-[3-methoxy-4-(2-methyl-1,3-oxazol-5-yl)phenyl]-8-(2-methylbutoxy)-5,6,7,8-tetrahydro[1,2,4]triazolo-[4,3-a]pyridine | 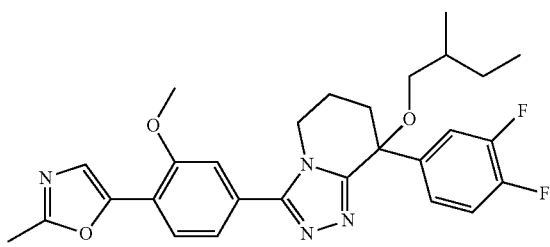 [SMILES: CCC(C)COC1(c2ccc(F)c(F)c2)CCCn2c(-c3ccc(-c4cnc(C)o4)c(OC)c3)nnc21] | 509.1 |
| 27 | 8-benzyl-8-(3,4-difluorophenyl)-3-[3-methoxy-4-(2-methyl-1,3-oxazol-5-yl)phenyl]-5,6,7,8-tetrahydro[1,2,4]triazolo-[4,3-a]pyridine | 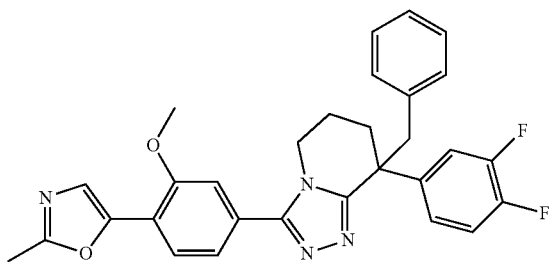 [SMILES: COc1cc(-c2nnc3n2CCCC3(Cc2ccccc2)c2ccc(F)c(F)c2)ccc1-c1cnc(C)o1] | 513.2 |
| 28 | 8-(benzyloxy)-8-(3,4-difluorophenyl)-3-[3-methoxy-4-(2-methyl-1,3-oxazol-5-yl)phenyl]-5,6,7,8-tetrahydro[1,2,4]triazolo-[4,3-a]pyridine | 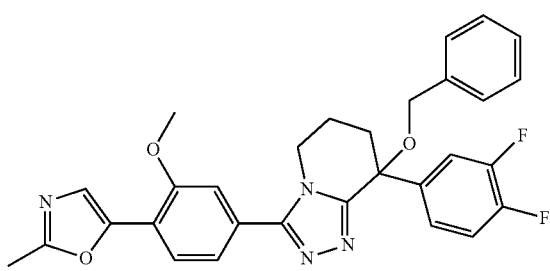 [SMILES: COc1cc(-c2nnc3n2CCCC3(OCc2ccccc2)c2ccc(F)c(F)c2)ccc1-c1cnc(C)o1] | 529.2 |
| 29 | 8-(3,4-difluorophenyl)-3-[3-methoxy-4-(2-methyl-1,3-oxazol-5-yl)phenyl]-8-propyl-5,6,7,8-tetrahydro[1,2,4]triazolo-[4,3-a]pyridine | 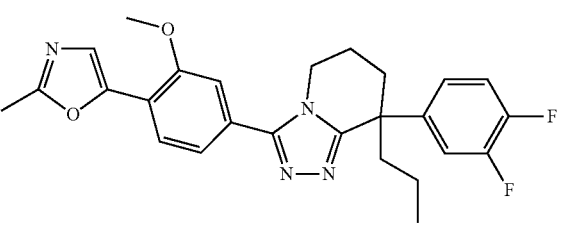 [SMILES: CCCC1(c2ccc(F)c(F)c2)CCCn2c(-c3ccc(-c4cnc(C)o4)c(OC)c3)nnc21] | 465.2 |
| 30 | 8-[(3,4-dichlorobenzyl)oxy]-8-(3,4-difluorophenyl)-3-[3-methoxy-4-(2-methyl-1,3-oxazol-5-yl)phenyl]-5,6,7,8-tetrahydro[1,2,4]triazolo-[4,3-a]pyridine | 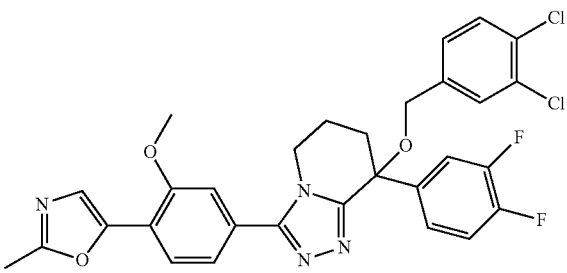 [SMILES: COc1cc(-c2nnc3n2CCCC3(OCc2ccc(Cl)c(Cl)c2)c2ccc(F)c(F)c2)ccc1-c1cnc(C)o1] | 597.6 |
| 31 | (6RS,8RS)-8-(3,4-difluorophenyl)-8-(hydroxymethyl)-3-[3-methoxy-4-(2-methyl-1,3-oxazol-5-yl)phenyl]-5,6,7,8-tetrahydro[1,2,4]triazolo-[4,3-a]pyridin-6-ol | 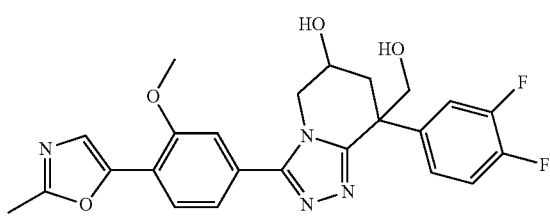 [SMILES: COc1cc(-c2nnc3n2CC(O)CC3(CO)c2ccc(F)c(F)c2)ccc1-c1cnc(C)o1] | 469.3 |

-continued

| | | | |
|---|---|---|---|
| 32 | 2-{8-(3,4-difluorophenyl)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol | 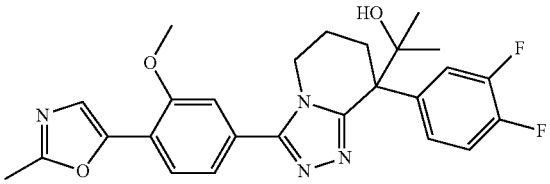 [SMILES: COc1cc(-c2nnc3n2CCCC3(c2ccc(F)c(F)c2)C(C)(C)O)ccc1-c1cnc(C)o1] | 481.1 |
| 33 | 8-(3-chloro-4-fluorophenyl)-3-[3-methoxy-4-(2-methyl-1,3-oxazol-5-yl)phenyl]-8-methyl-5,6,7,8-tetrahydro[1,2,4]triazolo[4,3-a]pyridine | 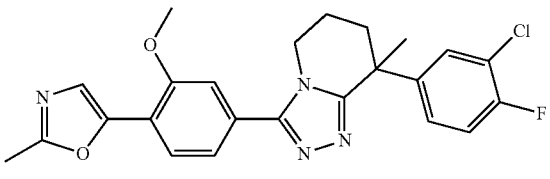 [SMILES: COc1cc(-c2nnc3n2CCCC3(C)c2ccc(F)c(Cl)c2)ccc1-c1cnc(C)o1] | 453.1 |
| 34 | 8-(4-fluorophenyl)-3-[3-methoxy-4-(2-methyl-1,3-oxazol-5-yl)phenyl]-8-methyl-5,6,7,8-tetrahydro[1,2,4]triazolo[4,3-a]pyridine | 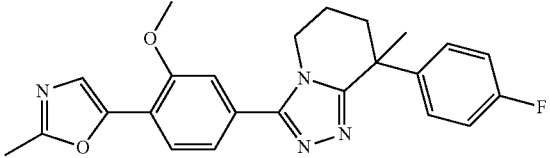 | 419.2 |
| 35 | 8-(4-chloro-3-fluorophenyl)-3-[3-methoxy-4-(2-methyl-1,3-oxazol-5-yl)phenyl]-8-methyl-5,6,7,8-tetrahydro[1,2,4]triazolo[4,3-a]pyridine | 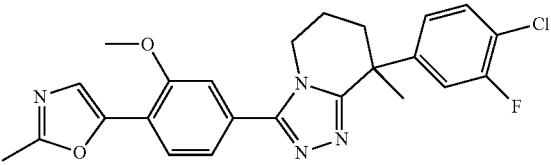 [SMILES: COc1cc(-c2nnc3n2CCCC3(C)c2ccc(Cl)c(F)c2)ccc1-c1cnc(C)o1] | 453.2 |
| 36 | 8-(3,4-dichlorophenyl)-8-methoxy-3-[3-methoxy-4-(2-methyl-1,3-oxazol-5-yl)phenyl]-5,6,7,8-tetrahydro[1,2,4]triazolo[4,3-a]pyridine | 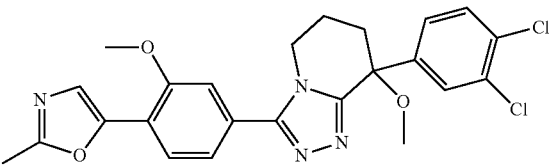 [SMILES: COc1cc(-c2nnc3n2CCCC3(OC)c2ccc(Cl)c(Cl)c2)ccc1-c1cnc(C)o1] | 485.1 |
| 37 | 8-(3,4-dichlorophenyl)-3-[3-methoxy-4-(2-methyl-1,3-oxazol-5-yl)phenyl]-8-methyl-5,6,7,8-tetrahydro[1,2,4]triazolo[4,3-a]pyridine | 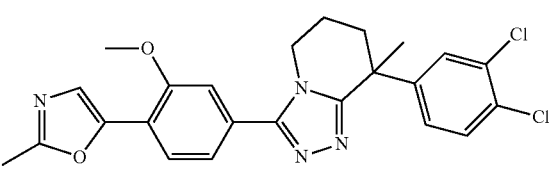 | 469.2 |
| 38 | optically active 8-(3,4-dichlorophenyl)-3-[3-methoxy-4-(2-methyl-1,3-oxazol-5-yl)phenyl]-8-methyl-5,6,7,8-tetrahydro[1,2,4]triazolo[4,3-a]pyridine | 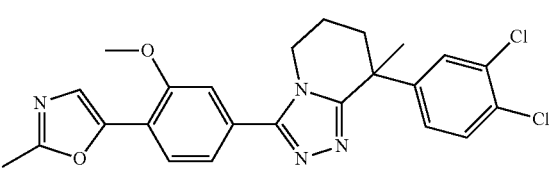 | 469.1 |
| 39 | optically active 8-(3,4-dichlorophenyl)-3-[3-methoxy-4-(2-methyl-1,3-oxazol-5-yl)phenyl]-8-methyl-5,6,7,8-tetrahydro[1,2,4]triazolo[4,3-a]pyridine | 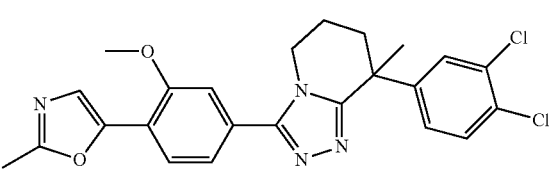 [SMILES: COc1cc(-c2nnc3n2CCCC3(C)c2ccc(Cl)c(Cl)c2)ccc1-c1cnc(C)o1] | 469.1 |
| 40 | 2-{8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}ethanol | 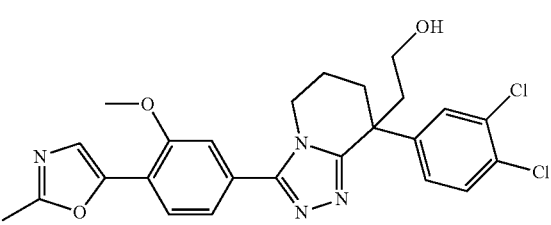 [SMILES: COc1cc(-c2nnc3n2CCCC3(CCO)c2ccc(Cl)c(Cl)c2)ccc1-c1cnc(C)o1] | 499.3 |

| | | | |
|---|---|---|---|
| 41 | 1-{8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methanamine | | 484.3 |
| 42 | N-({8-(3,4-dichlorophenyl)-3-[3-methoxy-4-(2-methyl-1,3-oxazol-5-yl)phenyl]-5,6,7,8-tetrahydro[1,2,4]triazolo[4,3-a]pyridin-8-yl}methyl)acetamide | | 526.3 |
| 43 | 8-[4-chloro-3-(trifluoromethyl)phenyl]-8-ethyl-3-[3-methoxy-4-(2-methyl-1,3-oxazol-5-yl)phenyl]-5,6,7,8-tetrahydro[1,2,4]triazolo[4,3-a]pyridine | | 517.1 |
| 44 | 8-[4-chloro-3-(trifluoromethyl)phenyl]-3-[3-methoxy-4-(2-methyl-1,3-oxazol-5-yl)phenyl]-5,6,7,8-tetrahydro[1,2,4]triazolo[4,3-a]pyridin-8-ol | | 505.1 |
| 45 | {8-[4-chloro-3-(trifluoromethyl)phenyl]-3-[3-methoxy-4-(2-methyl-1,3-oxazol-5-yl)phenyl]-5,6,7,8-tetrahydro[1,2,4]triazolo[4,3-a]pyridin-8-yl}methanol | | 519.2 |
| 46 | 8-(benzyloxy)-8-[4-chloro-3-(trifluoromethyl)phenyl]-3-[3-methoxy-4-(2-methyl-1,3-oxazol-5-yl)phenyl]-5,6,7,8-tetrahydro[1,2,4]triazolo[4,3-a]pyridine | | 595.4 |
| 47 | ethyl 8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridine-8-carboxylate | | 509.2 |

| | | | |
|---|---|---|---|
| 48 | 1-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}ethanone | 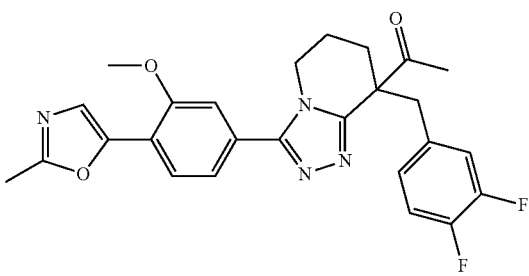 [SMILES: COc1cc(-c2nnc3n2CCCC3(Cc2ccc(F)c(F)c2)C(C)=O)ccc1-c1cnc(C)o1] | 479.3 |
| 49 | 2-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol | 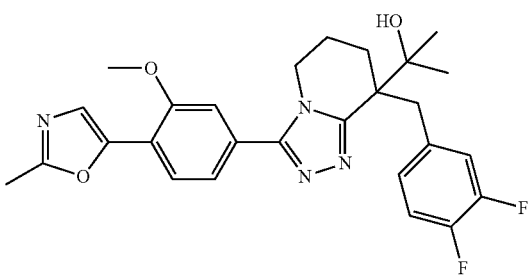 [SMILES: COc1cc(-c2nnc3n2CCCC3(Cc2ccc(F)c(F)c2)C(C)(C)O)ccc1-c1cnc(C)o1] | 495.1 |
| 50 | optically active 2-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol | 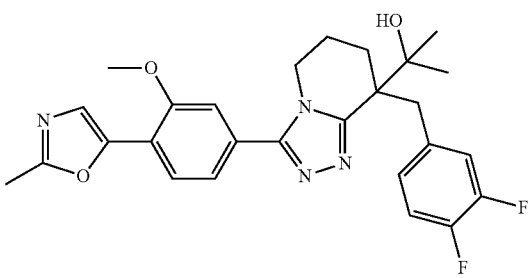 [SMILES: COc1cc(-c2nnc3n2CCCC3(Cc2ccc(F)c(F)c2)C(C)(C)O)ccc1-c1cnc(C)o1] | 495.2 |
| 51 | optically active 2-{8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol | 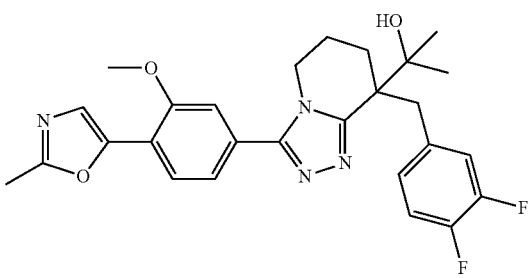 [SMILES: COc1cc(-c2nnc3n2CCCC3(Cc2ccc(F)c(F)c2)C(C)(C)O)ccc1-c1cnc(C)o1] | 495.2 |
| 52 | {8-(3,4-difluorobenzyl)-3-[3-methoxy-4-(2-methyl-1,3-oxazol-5-yl)phenyl]-5,6,7,8-tetrahydro[1,2,4]triazolo[4,3-a]pyridin-8-yl}methanol | 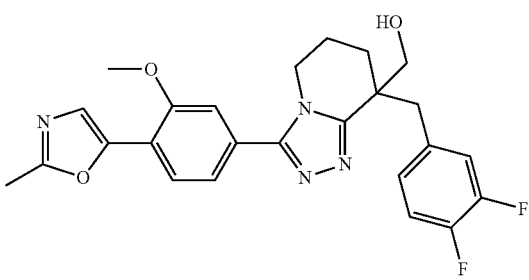 [SMILES: COc1cc(-c2nnc3n2CCCC3(CO)Cc2ccc(F)c(F)c2)ccc1-c1cnc(C)o1] | 467.0 |

-continued

| | | | |
|---|---|---|---|
| 53 | {8-(3,4-difluorobenzyl)-3-[3-methoxy-4-(2-methyl-1,3-oxazol-5-yl)phenyl]-5,6,7,8-tetrahydro[1,2,4]triazolo-[4,3-a]pyridin-8-yl}methyl acetate | 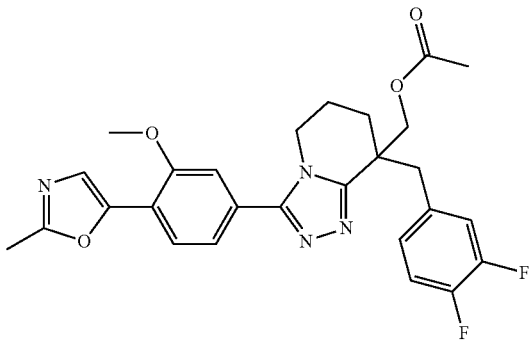 [SMILES: COc1cc(-c2nnc3n2CCCC3(COC(C)=O)Cc2ccc(F)c(F)c2)ccc1-c1cnc(C)o1] | 509.3 |
| 54 | 8-(3,4-difluorobenzyl)-8-(methoxymethyl)-3-[3-methoxy-4-(2-methyl-1,3-oxazol-5-yl)phenyl]-5,6,7,8-tetrahydro[1,2,4]triazolo-[4,3-a]pyridine | 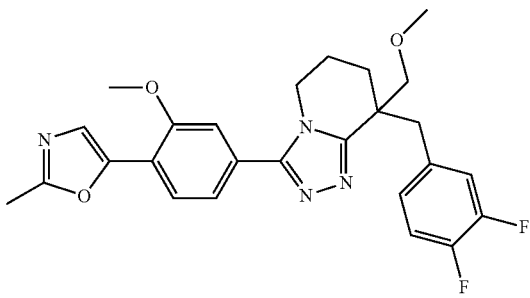 [SMILES: COCC1(Cc2ccc(F)c(F)c2)CCCn2c(-c3ccc(-c4cnc(C)o4)c(OC)c3)nnc21] | 481.1 |
| 55 | 8-(3,4-difluorobenzyl)-3-[3-methoxy-4-(2-methyl-1,3-oxazol-5-yl)phenyl]-5,6,7,8-tetrahydro[1,2,4]triazolo-[4,3-a]pyridine-8-carboxamide | 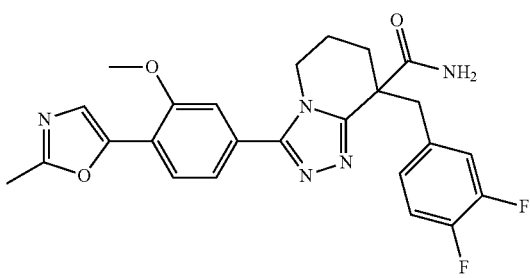 [SMILES: COc1cc(-c2nnc3n2CCCC3(Cc2ccc(F)c(F)c2)C(N)=O)ccc1-c1cnc(C)o1] | 480.4 |
| 56 | 1-{8-(3,4-difluorobenzyl)-3-[3-methoxy-4-(2-methyl-1,3-oxazol-5-yl)phenyl]-5,6,7,8-tetrahydro[1,2,4]triazolo-[4,3-a]pyridin-8-yl}ethanol | 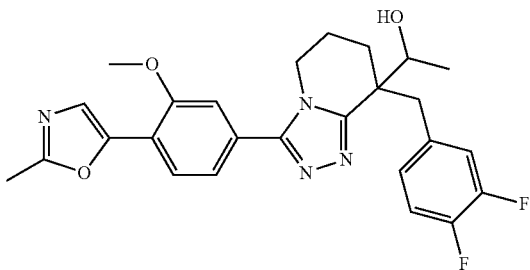 [SMILES: COc1cc(-c2nnc3n2CCCC3(Cc2ccc(F)c(F)c2)C(C)O)ccc1-c1cnc(C)o1] | 481.1 |
| 57 | 1-{8-(3,4-difluorobenzyl)-3-[3-methoxy-4-(2-methyl-1,3-oxazol-5-yl)phenyl]-5,6,7,8-tetrahydro[1,2,4]triazolo-[4,3-a]pyridin-8-yl}propan-1-one | 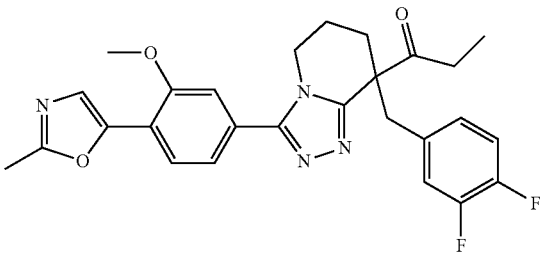 [SMILES: CCC(=O)C1(Cc2ccc(F)c(F)c2)CCCn2c(-c3ccc(-c4cnc(C)o4)c(OC)c3)nnc21] | 493.5 |

-continued

| | | | |
|---|---|---|---|
| 58 | 3-{8-(3,4-difluorobenzyl)-3-[3-methoxy-4-(2-methyl-1,3-oxazol-5-yl)phenyl]-5,6,7,8-tetrahydro[1,2,4]triazolo-[4,3-a]pyridin-8-yl}pentan-3-ol | 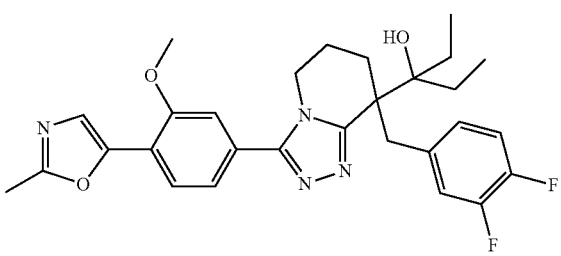 [SMILES: CCC(O)(CC)C1(Cc2ccc(F)c(F)c2)CCCn2c(-c3ccc(-c4cnc(C)o4)c(OC)c3)nnc21] | 523.6 |
| 59 | 8-(3,4-difluorobenzyl)-3-[3-methoxy-4-(2-methyl-1,3-oxazol-5-yl)phenyl]-N-(2,2,2-trifluoroethyl)-5,6,7,8-tetrahydro[1,2,4]triazolo-[4,3-a]pyridine-8-carboxamide | 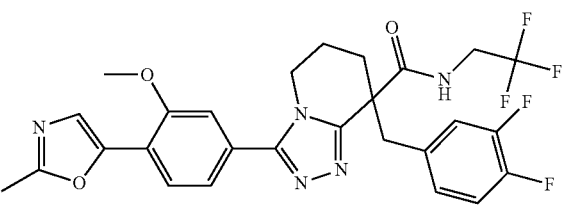 [SMILES: COc1cc(-c2nnc3n2CCCC3(Cc2ccc(F)c(F)c2)C(=O)NCC(F)(F)F)ccc1-c1cnc(C)o1] | 562.4 |
| 60 | 8-(3,4-difluorobenzyl)-3-[3-methoxy-4-(2-methyl-1,3-oxazol-5-yl)phenyl]-N-methyl-N-(2,2,2-trifluoroethyl)-5,6,7,8-tetrahydro[1,2,4]triazolo-[4,3-a]pyridine-8-carboxamide | 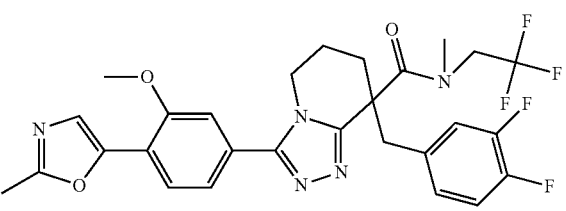 | 576.4 |
| 61 | 2-{3-[3-methoxy-4-(2-methyl-1,3-oxazol-5-yl)phenyl]-8-(2-methylbenzyl)-5,6,7,8-tetrahydro[1,2,4]triazolo[4,3-a]pyridin-8-yl}propan-2-ol | 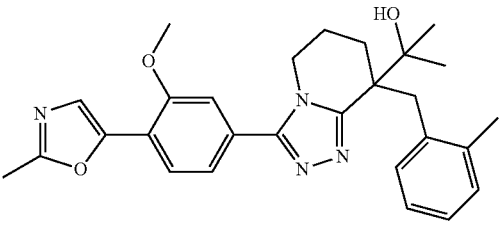 | 473.5 |
| 62 | 2-{8-(3-chlorobenzyl)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 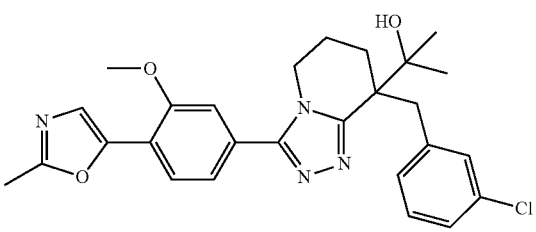 [SMILES: COc1cc(-c2nnc3n2CCCC3(Cc2cccc(Cl)c2)C(C)(C)O)ccc1-c1cnc(C)o1] | 493.4 |
| 63 | 2-{8-(4-chlorobenzyl)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 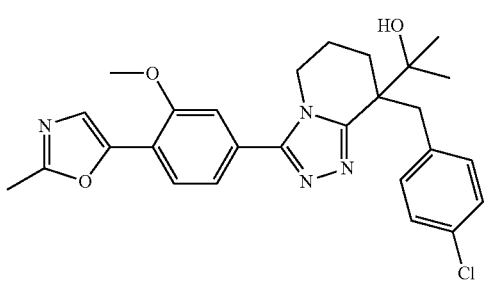 [SMILES: COc1cc(-c2nnc3n2CCCC3(Cc2ccc(Cl)cc2)C(C)(C)O)ccc1-c1cnc(C)o1] | 493.4 |

| | | | |
|---|---|---|---|
| 64 | 2-{3-[3-methoxy-4-(2-methyl-1,3-oxazol-5-yl)phenyl]-8-[2-(trifluoromethyl)benzyl]-5,6,7,8-tetrahydro[1,2,4]triazolo-[4,3-a]pyridin-8-yl}propan-2-ol | 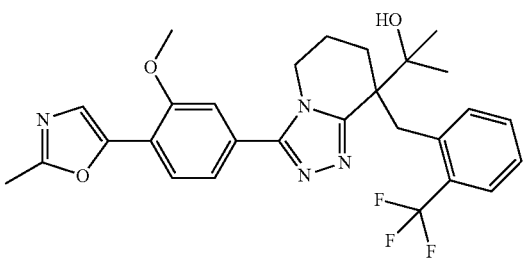 [SMILES: COc1cc(-c2nnc3n2CCCC3(Cc2ccccc2C(F)(F)F)C(C)(C)O)ccc1-c1cnc(C)o1] | 527.4 |
| 65 | 2-{8-(2,4-difluorobenzyl)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 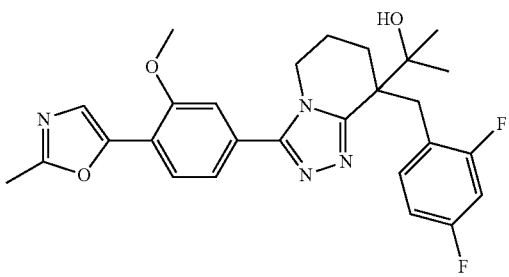 [SMILES: COc1cc(-c2nnc3n2CCCC3(Cc2ccc(F)cc2F)C(C)(C)O)ccc1-c1cnc(C)o1] | 495.2 |
| 66 | 2-{8-(4-chloro-3-fluorobenzyl)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 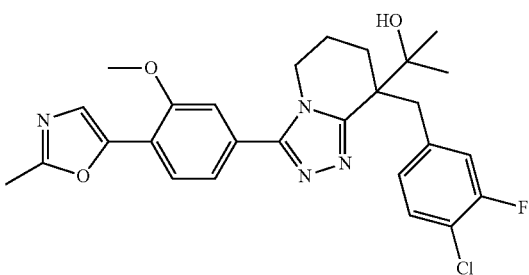 | 511.1 |
| 67 | 2-{3-[3-methoxy-4-(2-methyl-1,3-oxazol-5-yl)phenyl]-8-(2,3,4-trifluorobenzyl)-5,6,7,8-tetrahydro[1,2,4]triazolo-[4,3-a]pyridin-8-yl}propan-2-ol | 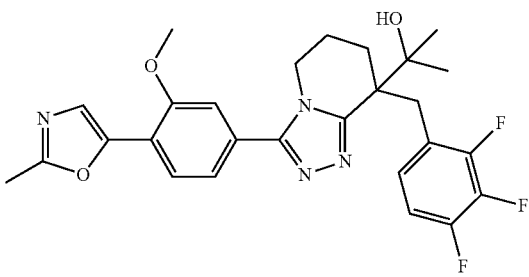 [SMILES: COc1cc(-c2nnc3n2CCCC3(Cc2ccc(F)c(F)c2F)C(C)(C)O)ccc1-c1cnc(C)o1] | 513.1 |
| 68 | 2-{8-(cyclopropylmethyl)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 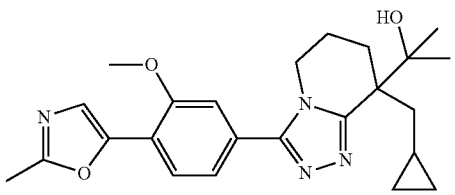 [SMILES: COc1cc(-c2nnc3n2CCCC3(CC2CC2)C(C)(C)O)ccc1-c1cnc(C)o1] | 423.1 |
| 69 | 2-{3-[3-methoxy-4-(2-methyl-1,3-oxazol-5-yl)phenyl]-8-(tetrahydro-2H-pyran-4-ylmethyl)-5,6,7,8-tetrahydro[1,2,4]triazolo-[4,3-a]pyridin-8-yl}propan-2-ol | 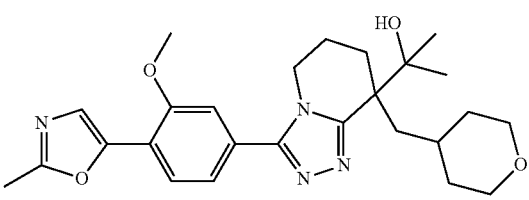 [SMILES: COc1cc(-c2nnc3n2CCCC3(CC2CCOCC2)C(C)(C)O)ccc1-c1cnc(C)o1] | 467.5 |

-continued

| # | Name | | |
|---|---|---|---|
| 70 | 2-{8-(4-chloro-3-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | | 513.1 |
| 71 | 8-[(2-bromo-5-fluorobenzyl)oxy]-3-[3-methoxy-4-(2-methyl-1,3-oxazol-5-yl)phenyl]-N-methyl-N-(2,2,2-trifluoroethyl)-5,6,7,8-tetrahydro[1,2,4]triazolo-[4,3-a]pyridine-8-carboxamide | | 652.3 |
| 72 | 8-[(2-bromo-4-fluorobenzyl)oxy]-3-[3-methoxy-4-(2-methyl-1,3-oxazol-5-yl)phenyl]-N-methyl-N-(2,2,2-trifluoroethyl)-5,6,7,8-tetrahydro[1,2,4]triazolo-[4,3-a]pyridine-8-carboxamide | | 652.3 |
| 73 | 8-(4-chlorophenyl)-3-[3-methoxy-4-(3-methyl-1H-1,2,4-triazol-1-yl)phenyl]-8-methyl-5,6,7,8-tetrahydro[1,2,4]triazolo-[4,3-a]pyridine | | 435.4 |
| 74 | 8-(4-chlorophenyl)-3-[3-methoxy-4-(4-methyl-1H-imidazol-1-yl)phenyl]-8-methyl-5,6,7,8-tetrahydro[1,2,4]triazolo-[4,3-a]pyridine | | 434.2 |
| 75 | 2-{8-(3,4-difluorophenyl)-3-[3-methoxy-4-(4-methyl-1H-imidazol-1-yl)phenyl]-5,6,7,8-tetrahydro[1,2,4]triazolo-[4,3-a]pyridin-8-yl}propan-2-ol | | 480.1 |

| | -continued | | |
|---|---|---|---|
| 76 | 8-(cyclopropylmethyl)-8-(3,4-difluorophenyl)-3-[3-methoxy-4-(4-methyl-1H-imidazol-1-yl)phenyl]-5,6,7,8-tetrahydro[1,2,4]triazolo[4,3-a]pyridine | | 476.3 |
| 77 | 8-(cyclopropylmethyl)-8-(3,4-difluorophenyl)-3-[3-methoxy-4-(3-methyl-1H-1,2,4-triazol-1-yl)phenyl]-5,6,7,8-tetrahydro[1,2,4]triazolo[4,3-a]pyridine | | 477.2 |
| 78 | 8-[4-chloro-3-(trifluoromethyl)phenyl]-8-(cyclopropylmethyl)-3-[3-methoxy-4-(4-methyl-1H-imidazol-1-yl)phenyl]-5,6,7,8-tetrahydro[1,2,4]triazolo[4,3-a]pyridine | | 542.3 |
| 79 | 8-[4-chloro-3-(trifluoromethyl)phenyl]-8-(cyclopropylmethyl)-3-[3-methoxy-4-(3-methyl-1H-1,2,4-triazol-1-yl)phenyl]-5,6,7,8-tetrahydro[1,2,4]triazolo[4,3-a]pyridine | | 543.1 |
| 80 | 2-{8-(3,4-difluorobenzyl)-3-[3-methoxy-4-(4-methyl-1H-imidazol-1-yl)phenyl]-5,6,7,8-tetrahydro[1,2,4]triazolo[4,3-a]pyridin-8-yl}propan-2-ol | | 494.0 |
| 81 | 2-{8-fluoro-3-[3-methoxy-4-(2-methyl-1,3-oxazol-5-yl)phenyl]-5,6,7,8-tetrahydro[1,2,4]triazolo[4,3-a]pyridin-8-yl}propan-2-ol | | 387.1 |
| 82 | ethyl 8-chloro-3-[3-methoxy-4-(2-methyl-1,3-oxazol-5-yl)phenyl]-5,6,7,8-tetrahydro[1,2,4]triazolo[4,3-a]pyridine-8-carboxylate | | 417.1 |
| 83 | 3-[3-methoxy-4-(2-methyl-1,3-oxazol-5-yl)phenyl]-N-(2-methoxyphenyl)-8-methyl-5,6,7,8-tetrahydro[1,2,4]triazolo[4,3-a]pyridine-8-carboxamide | | 474.4 |

| | | | |
|---|---|---|---|
| 84 | 3-[3-methoxy-4-(2-methyl-1,3-oxazol-5-yl)phenyl]-N-(3-methoxyphenyl)-8-methyl-5,6,7,8-tetrahydro[1,2,4]triazolo[4,3-a]pyridine-8-carboxamide | | 474.4 |
| 85 | 3-[3-methoxy-4-(2-methyl-1,3-oxazol-5-yl)phenyl]-N-(4-methoxyphenyl)-8-methyl-5,6,7,8-tetrahydro[1,2,4]triazolo[4,3-a]pyridine-8-carboxamide | | 474.4 |
| 86 | 8-[5-(3,4-dichlorophenyl)-1,3,4-oxadiazol-2-yl]-3-[3-methoxy-4-(2-methyl-1,3-oxazol-5-yl)phenyl]-8-methyl-5,6,7,8-tetrahydro[1,2,4]triazolo[4,3-a]pyridine | | 537.2 |
| 87 | N-(3,4-dichlorophenyl)-3-[3-methoxy-4-(2-methyl-1,3-oxazol-5-yl)phenyl]-8-methyl-5,6,7,8-tetrahydro[1,2,4]triazolo[4,3-a]pyridine-8-carboxamide | | 512.3 |
| 88 | 8-hydroxy-3-[3-methoxy-4-(2-methyl-1,3-oxazol-5-yl)phenyl]-N-(2-methylphenyl)-5,6,7,8-tetrahydro[1,2,4]triazolo[4,3-a]pyridine-8-carboxamide | | 460.3 |
| 89 | N-(3-fluorophenyl)-3-[3-methoxy-4-(2-methyl-1,3-oxazol-5-yl)phenyl]-8-methyl-5,6,7,8-tetrahydro[1,2,4]triazolo[4,3-a]pyridine-8-carboxamide | | 462.4 |
| 90 | 3-[3-methoxy-4-(2-methyl-1,3-oxazol-5-yl)phenyl]-8-methyl-N-[3-(trifluoromethyl)phenyl]-5,6,7,8-tetrahydro[1,2,4]triazolo[4,3-a]pyridine-8-carboxamide | | 512.5 |
| 91 | 7-(3,4-dichlorophenyl)-3-[3-methoxy-4-(3-methyl-1H-1,2,4-triazol-1-yl)phenyl]-7-methyl-4,5,6,7-tetrahydro[1,2,3]triazolo[1,5-a]pyridine | | 469.1 |

| | | | |
|---|---|---|---|
| 92 | 2-{8-(3,4-difluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 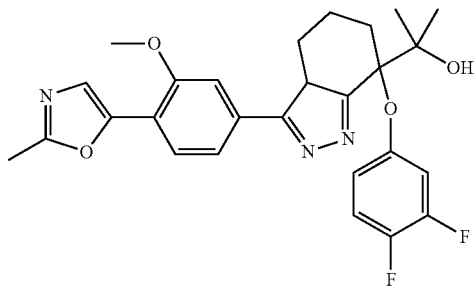 [SMILES: COc1cc(C2=NN=C3C2CCCC3(Oc2ccc(F)c(F)c2)C(C)(C)O)ccc1-c1cnc(C)o1] | 497.2 |
| 93 | 2-(3-[3-methoxy-4-(2-methyl-1,3-oxazol-5-yl)phenyl]-8-{[6-(trifluoromethyl)pyridin-3-yl]oxy}-5,6,7,8-tetrahydro[1,2,4]triazolo-[4,3-a]pyridin-8-yl)propan-2-ol | 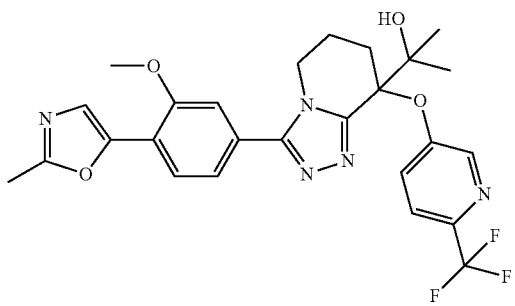 [SMILES: COc1cc(-c2nnc3n2CCCC3(Oc2ccc(C(F)(F)F)nc2)C(C)(C)O)ccc1-c1cnc(C)o1] | 530.2 |
| 94 | 2-chloro-4-({8-(1-hydroxy-1-methylethyl)-3-[3-methoxy-4-(2-methyl-1,3-oxazol-5-yl)phenyl]-5,6,7,8-tetrahydro[1,2,4]triazolo-[4,3-a]pyridin-8-yl}oxy)benzonitrile | 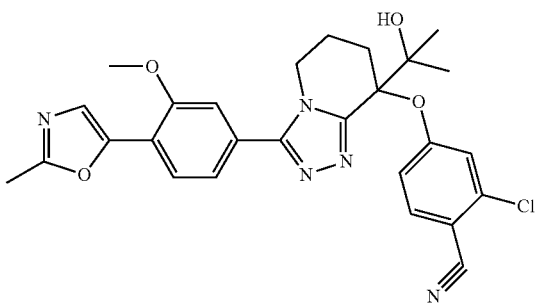 [SMILES: COc1cc(-c2nnc3n2CCCC3(Oc2ccc(C#N)c(Cl)c2)C(C)(C)O)ccc1-c1cnc(C)o1] | 520.2 |
| 95 | 2-(3-[3-methoxy-4-(2-methyl-1,3-oxazol-5-yl)phenyl]-8-{[5-(trifluoromethyl)pyridin-2-yl]oxy}-5,6,7,8-tetrahydro[1,2,4]triazolo-[4,3-a]pyridin-8-yl)propan-2-ol | 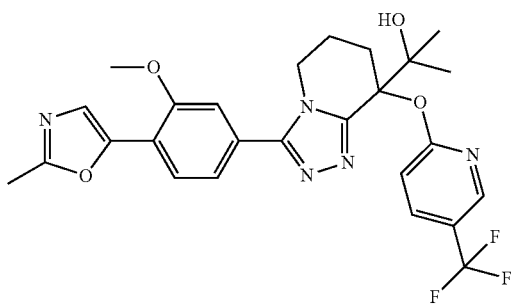 [SMILES: COc1cc(-c2nnc3n2CCCC3(Oc2ccc(C(F)(F)F)cn2)C(C)(C)O)ccc1-c1cnc(C)o1] | 530.3 |
| 96 | 2-{8-(2-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 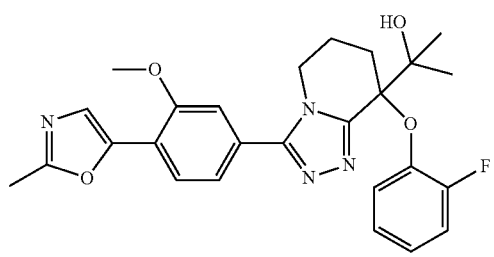 [SMILES: COc1cc(-c2nnc3n2CCCC3(Oc2ccccc2F)C(C)(C)O)ccc1-c1cnc(C)o1] | 479.4 |

| | | | |
|---|---|---|---|
| 97 | 2-{8-(3-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 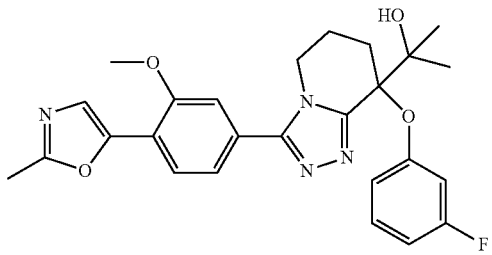 [SMILES: COc1cc(-c2nnc3n2CCCC3(Oc2cccc(F)c2)C(C)(C)O)ccc1-c1cnc(C)o1] | 479.2 |
| 98 | 2-{8-(4-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 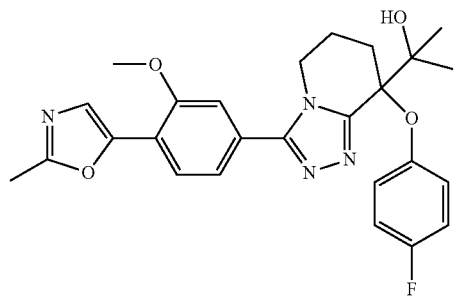 [SMILES: COc1cc(-c2nnc3n2CCCC3(Oc2ccc(F)cc2)C(C)(C)O)ccc1-c1cnc(C)o1] | 479.2 |
| 99 | 2-{3-[3-methoxy-4-(2-methyl-1,3-oxazol-5-yl)phenyl]-8-(3,4,5-trifluorophenoxy)-5,6,7,8-tetrahydro[1,2,4]triazolo-[4,3-a]pyridin-8-yl}propan-2-ol | 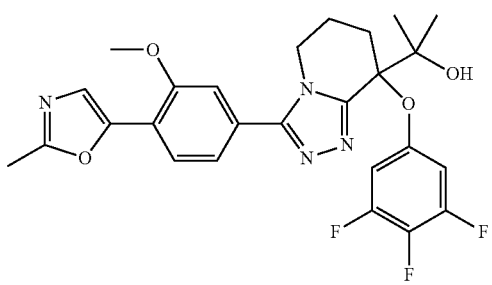 [SMILES: COc1cc(-c2nnc3n2CCCC3(Oc2cc(F)c(F)c(F)c2)C(C)(C)O)ccc1-c1cnc(C)o1] | 515.3 |
| 100 | ethyl 8-(4-chlorophenoxy)-3-[3-methoxy-4-(2-methyl-1,3-oxazol-5-yl)phenyl]-5,6,7,8-tetrahydro[1,2,4]triazolo-[4,3-a]pyridine-8-carboxylate | 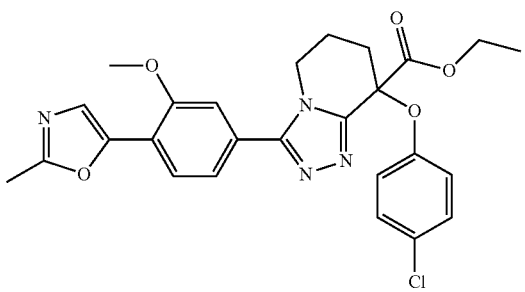 [SMILES: CCOC(=O)C1(Oc2ccc(Cl)cc2)CCCn2c(-c3ccc(-c4cnc(C)o4)c(OC)c3)nnc21] | 509.0 |
| 101 | 2-{8-(4-chlorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 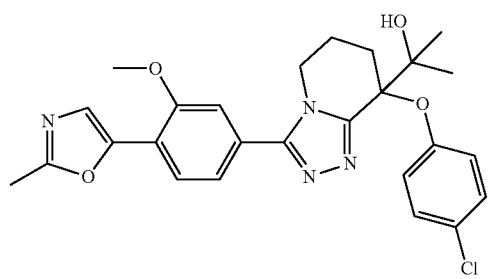 [SMILES: COc1cc(-c2nnc3n2CCCC3(Oc2ccc(Cl)cc2)C(C)(C)O)ccc1-c1cnc(C)o1] | 495.4 |

| | | | |
|---|---|---|---|
| 102 | 2-{3-[3-methoxy-4-(2-methyl-1,3-oxazol-5-yl)phenyl]-8-(4-methylphenoxy)-5,6,7,8-tetrahydro[1,2,4]triazolo-[4,3-a]pyridin-8-yl}propan-2-ol | 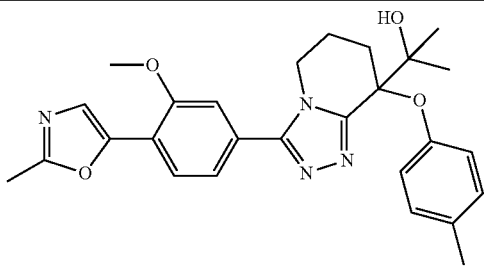 | 475.4 |
| 103 | 2-{3-[3-methoxy-4-(2-methyl-1,3-oxazol-5-yl)phenyl]-8-[3-(trifluoromethyl)phenoxy]-5,6,7,8-tetra-hydro[1,2,4]triazolo-[4,3-a]pyridin-8-yl}propan-2-ol | 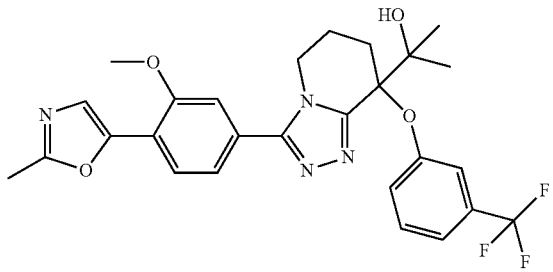 [SMILES: COc1cc(-c2nnc3n2CCCC3(Oc2cccc(C(F)(F)F)c2)C(C)(C)O)ccc1-c1cnc(C)o1] | 529.4 |
| 104 | 2-{3-[3-methoxy-4-(2-methyl-1,3-oxazol-5-yl)phenyl]-8-[4-(trifluoromethyl)phenoxy]-5,6,7,8-tetra-hydro[1,2,4]triazolo-[4,3-a]pyridin-8-yl}propan-2-ol | 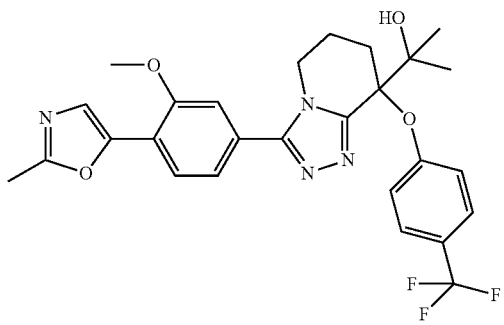 [SMILES: COc1cc(-c2nnc3n2CCCC3(Oc2ccc(C(F)(F)F)cc2)C(C)(C)O)ccc1-c1cnc(C)o1] | 529.4 |
| 105 | 2-{3-[3-methoxy-4-(2-methyl-1,3-oxazol-5-yl)phenyl]-8-[2-(trifluoromethyl)phenoxy]-5,6,7,8-tetra-hydro[1,2,4]triazolo-[4,3-a]pyridin-8-yl}propan-2-ol | 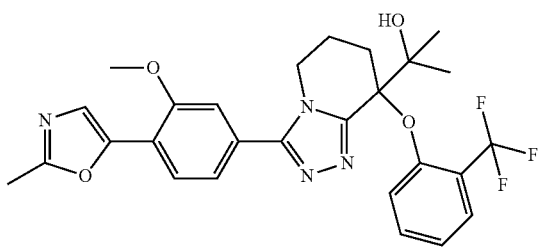 [SMILES: COc1cc(-c2nnc3n2CCCC3(Oc2ccccc2C(F)(F)F)C(C)(C)O)ccc1-c1cnc(C)o1] | 529.5 |
| 106 | ethyl 3-[3-methoxy-4-(4-methyl-1H-imidazol-1-yl)phenyl]-8-[3-(trifluoromethyl)phenyl]-5,6,7,8-tetrahydro[1,2,4]triazolo-[4,3-a]pyridine-8-carboxylate | 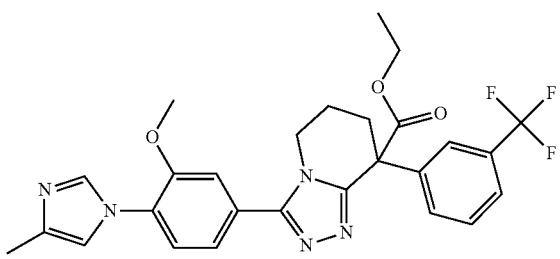 [SMILES: CCOC(=O)C1(c2cccc(C(F)(F)F)c2)CCCn2c(-c3ccc(-n4cnc(C)c4)c(OC)c3)nnc21] | 526.3 |
| 107 | 2-{8-[(3,4-difluorobenzyl)oxy]-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 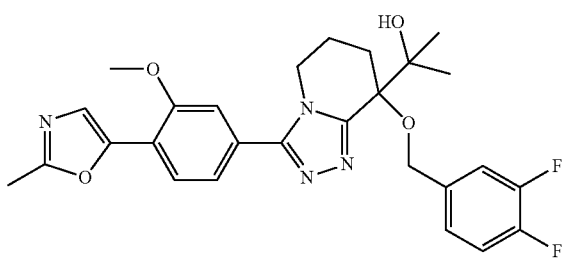 [SMILES: COc1cc(-c2nnc3n2CCCC3(OCc2ccc(F)c(F)c2)C(C)(C)O)ccc1-c1cnc(C)o1] | 511.4 |

| | | | |
|---|---|---|---|
| 108 | 8-[(3,4-difluorobenzyl)oxy]-3-[3-methoxy-4-(2-methyl-1,3-oxazol-5-yl)phenyl]-N-methyl-N-(2,2,2-trifluoroethyl)-5,6,7,8-tetrahydro[1,2,4]triazolo-[4,3-a]pyridine-8-carboxamide | 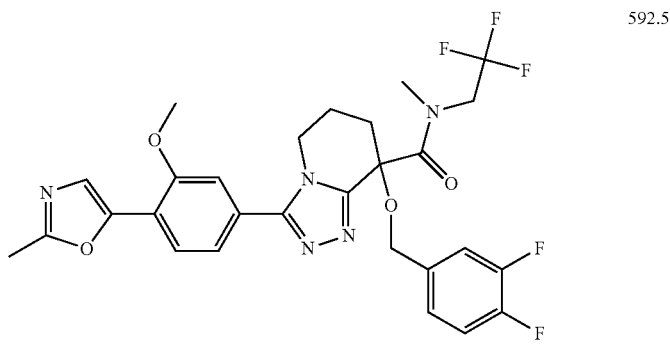 | 592.5 |
| 109 | 2-{8-(4-chloro-3-fluorophenoxy)-3-[3-methoxy-4-(4-methyl-1H-imidazol-1-yl)phenyl]-5,6,7,8-tetrahydro[1,2,4]triazolo-[4,3-a]pyridin-8-yl}propan-2-ol | 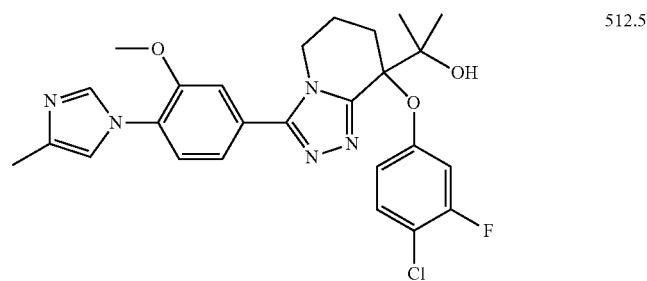 | 512.5 |
| 110 | optically active 2-{8-(4-chloro-3-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 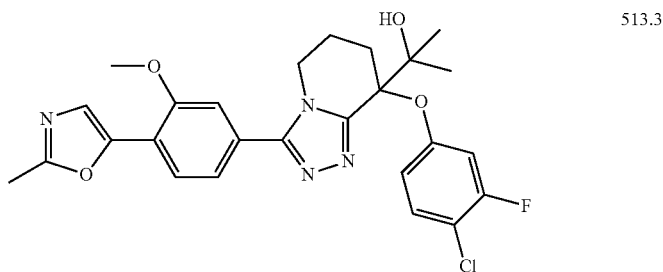 | 513.3 |
| 111 | optically active 2-{8-(4-chloro-3-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 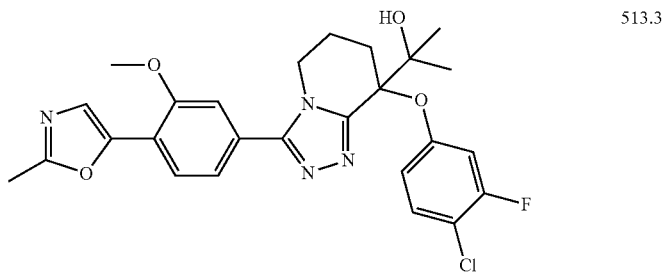 | 513.3 |
| 112 | {8-(3-chloro-4-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}methanol | 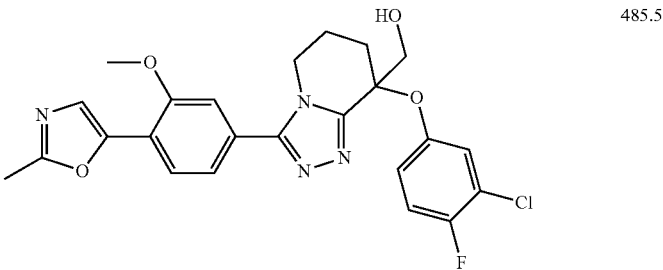 | 485.5 |

| | | | |
|---|---|---|---|
| 113 | 2-{3-[3-methoxy-4-(4-methyl-1H-imidazol-1-yl)phenyl]-8-[3-(trifluoromethyl)phenyl]-5,6,7,8-tetrahydro[1,2,4]triazolo-[4,3-a]pyridin-8-yl}propan-2-ol | 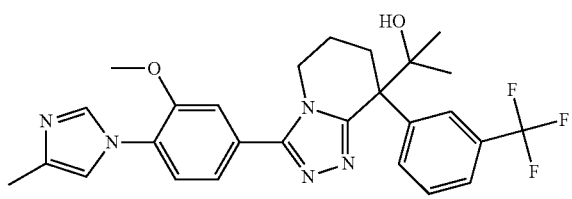 [SMILES: COc1cc(-c2nnc3n2CCCC3(c2cccc(C(F)(F)F)c2)C(C)(C)O)ccc1-n1cnc(C)c1] | 512.1 |
| 114 | 2-{8-(3-chloro-4-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 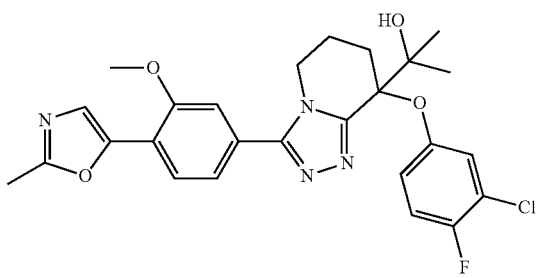 | 513.2 |
| 115 | 2-{8-[4-fluoro-3-(trifluoromethyl)phenoxy]-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 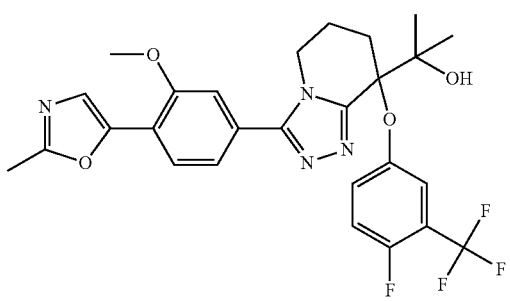 [SMILES: COc1cc(-c2nnc3n2CCCC3(Oc2ccc(F)c(C(F)(F)F)c2)C(C)(C)O)ccc1-c1cnc(C)o1] | 547.4 |
| 116 | 3-{8-(3,4-difluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}pentan-3-ol | 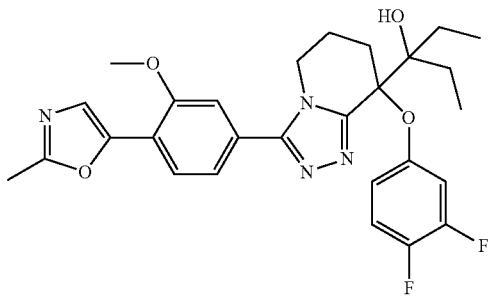 [SMILES: CCC(O)(CC)C1(Oc2ccc(F)c(F)c2)CCCn2c(-c3ccc(-c4cnc(C)o4)c(OC)c3)nnc21] | 525.5 |
| 117 | 1-{8-(3,4-difluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-1-ol | 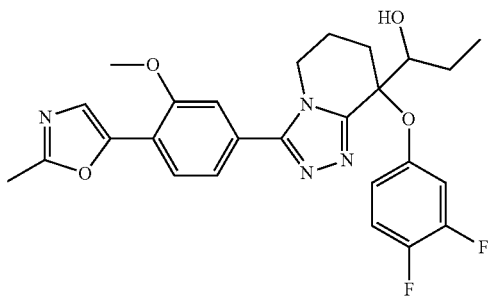 [SMILES: CCC(O)C1(Oc2ccc(F)c(F)c2)CCCn2c(-c3ccc(-c4cnc(C)o4)c(OC)c3)nnc21] | 497.4 |

| | | | |
|---|---|---|---|
| 118 | 8-(4-chloro-3-fluorophenoxy)-3-[3-methoxy-4-(2-methyl-1,3-oxazol-5-yl)phenyl]-8-[(3,3,4,4-tetrafluoropyrrolidin-1-yl)carbonyl]-5,6,7,8-tetrahydro[1,2,4]triazolo-[4,3-a]pyridine | 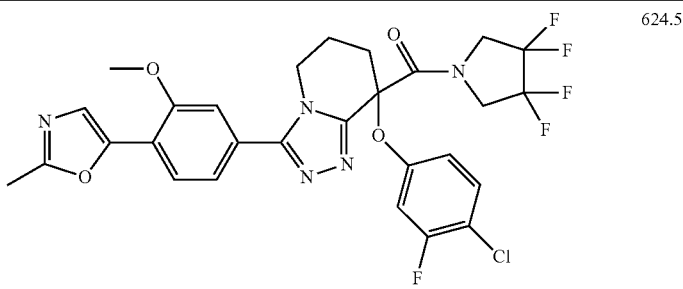 | 624.5 |
| 119 | 8-(4-chloro-3-fluorophenoxy)-3-[3-methoxy-4-(2-methyl-1,3-oxazol-5-yl)phenyl]-N-(2,2,2-trifluoroethyl)-5,6,7,8-tetrahydro[1,2,4]triazolo-[4,3-a]pyridine-8-carboxamide | 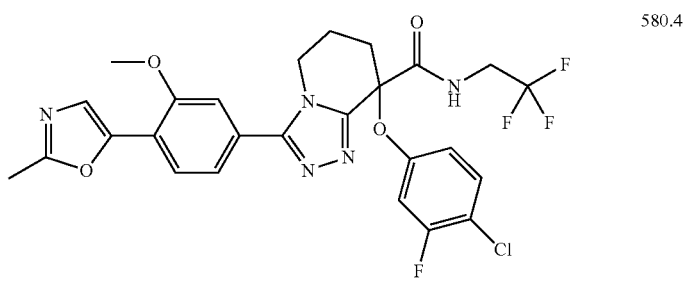 | 580.4 |
| 120 | 3-{8-(4-chloro-3-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}pentan-3-ol | 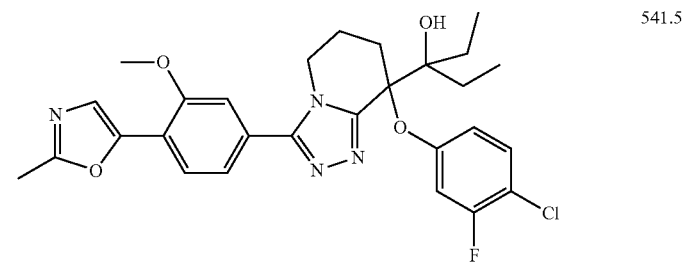 | 541.5 |
| 121 | 2-{8-(3,4-dichlorophenyl)-3-[3-methoxy-4-(4-methyl-1H-imidazol-1-yl)phenyl]-5,6,7,8-tetrahydro[1,2,4]triazolo-[4,3-a]pyridin-8-yl}propan-2-ol | 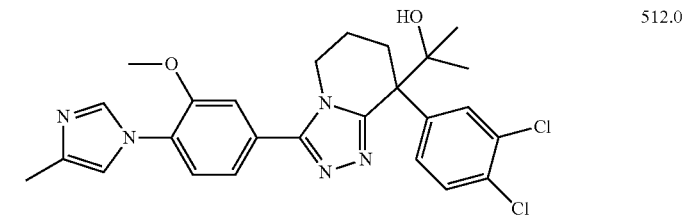 | 512.0 |
| 122 | 2-{(8R)-3-[3-methoxy-4-(2-methyl-1,3-oxazol-5-yl)phenyl]-8-(3,4,5-trifluorophenoxy)-5,6,7,8-tetrahydro[1,2,4]triazolo-[4,3-a]pyridin-8-yl}propan-2-ol | 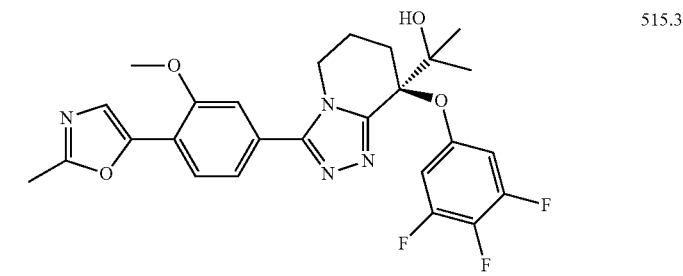 | 515.3 |
| 123 | 2-[(8S)-3-[3-methoxy-4-(2-methyl-1,3-oxazol-5-yl)phenyl]-8-(3,4,5-trifluorophenoxy)-5,6,7,8-tetrahydro[1,2,4]triazolo-[4,3-a]pyridin-8-yl]propan-2-ol | 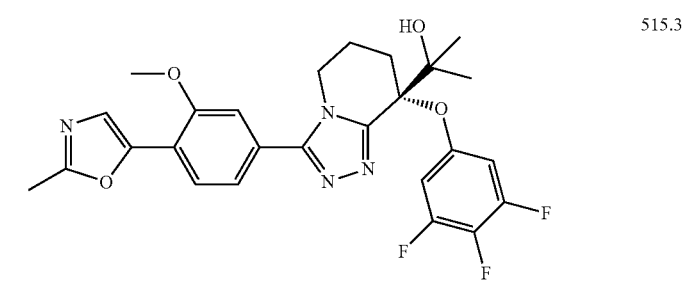 | 515.3 |

| | | | |
|---|---|---|---|
| 124 | optically active 2-{8-(3,4-difluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 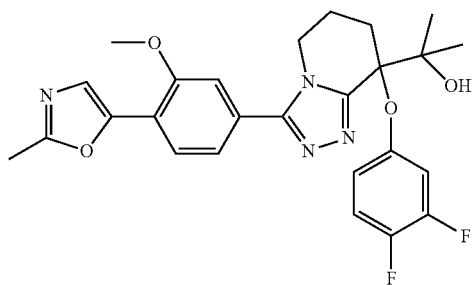 [SMILES: COc1cc(-c2nnc3n2CCCC3(Oc2ccc(F)c(F)c2)C(C)(C)O)ccc1-c1cnc(C)o1] | 497.3 |
| 125 | optically active 2-{8-(3,4-difluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 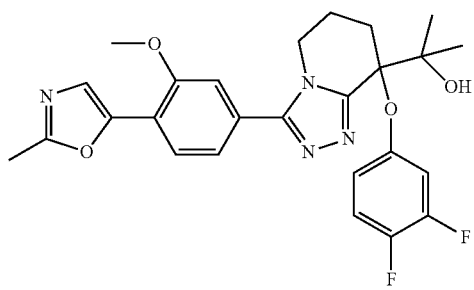 [SMILES: COc1cc(-c2nnc3n2CCCC3(Oc2ccc(F)c(F)c2)C(C)(C)O)ccc1-c1cnc(C)o1] | 497.3 |
| 126 | 2-{8-[3,5-bis(trifluoromethyl)phenoxy]-3-[3-methoxy-4-(4-methyl-1H-imidazol-1-yl)phenyl]-5,6,7,8-tetra-hydro[1,2,4]triazolo-[4,3-a]pyridin-8-yl}propan-2-ol | 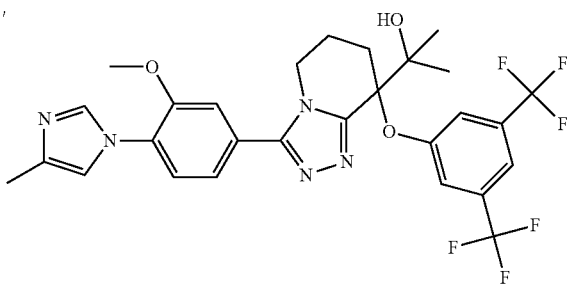 [SMILES: COc1cc(-c2nnc3n2CCCC3(Oc2cc(C(F)(F)F)cc(C(F)(F)F)c2)C(C)(C)O)ccc1-n1cnc(C)c1] | 596.1 |
| 127 | 2-{8-[(4-chlorophenoxy)methyl]-3-[3-methoxy-4-(2-methyl-1,3-oxazol-5-yl)phenyl]-5,6,7,8-tetrahydro[1,2,4]triazolo-[4,3-a]pyridin-8-yl}propan-2-ol | 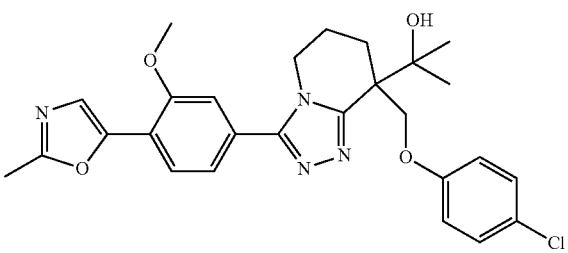 [SMILES: COc1cc(-c2nnc3n2CCCC3(COc2ccc(Cl)cc2)C(C)(C)O)ccc1-c1cnc(C)o1] | 509.4 |
| 128 | 2-{8-[4-chloro-3-(trifluoromethyl)phenoxy]-3-[3-methoxy-4-(4-methyl-1H-imidazol-1-yl)phenyl]-5,6,7,8-tetra-hydro[1,2,4]triazolo-[4,3-a]pyridin-8-yl}propan-2-ol | 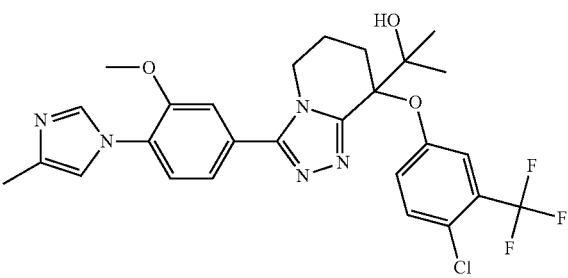 [SMILES: COc1cc(-c2nnc3n2CCCC3(Oc2ccc(Cl)c(C(F)(F)F)c2)C(C)(C)O)ccc1-n1cnc(C)c1] | 562.3 |

| | | | |
|---|---|---|---|
| 129 | 1-{8-(4-chloro-3-fluorophenoxy)-3-[3-methoxy-4-(2-methyl-1,3-oxazol-5-yl)phenyl]-5,6,7,8-tetrahydro[1,2,4]triazolo-[4,3-a]pyridin-8-yl}propan-1-ol | 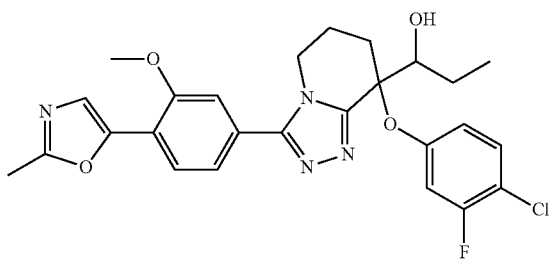 [SMILES: CCC(O)C1(Oc2ccc(Cl)c(F)c2)CCCn2c(-c3ccc(-c4cnc(C)o4)c(OC)c3)nnc21] | 513.4 |
| 130 | optically active 2-{3-[3-methoxy-4-(2-methyl-1,3-oxazol-5-yl)phenyl]-8-[3-(trifluoromethyl)phenoxy]-5,6,7,8-tetrahydro[1,2,4]triazolo-[4,3-a]pyridin-8-yl}propan-2-ol | 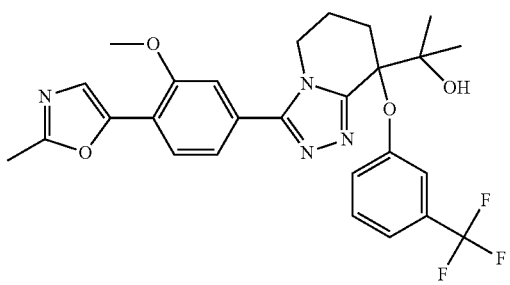 [SMILES: COc1cc(-c2nnc3n2CCCC3(Oc2cccc(C(F)(F)F)c2)C(C)(C)O)ccc1-c1cnc(C)o1] | 529.4 |
| 131 | optically active 2-{3-[3-methoxy-4-(2-methyl-1,3-oxazol-5-yl)phenyl]-8-[3-(trifluoromethyl)phenoxy]-5,6,7,8-tetrahydro[1,2,4]triazolo-[4,3-a]pyridin-8-yl}propan-2-ol | 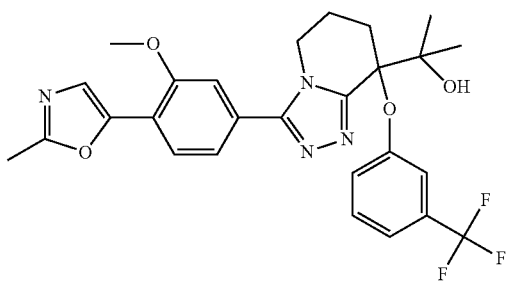 [SMILES: COc1cc(-c2nnc3n2CCCC3(Oc2cccc(C(F)(F)F)c2)C(C)(C)O)ccc1-c1cnc(C)o1] | 529.4 |
| 132 | optically active 2-{3-[3-methoxy-4-(2-methyl-1,3-oxazol-5-yl)phenyl]-8-[4-(trifluoromethyl)phenoxy]-5,6,7,8-tetrahydro[1,2,4]triazolo-[4,3-a]pyridin-8-yl}propan-2-ol | 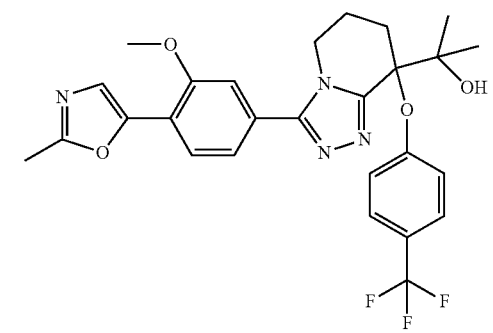 [SMILES: COc1cc(-c2nnc3n2CCCC3(Oc2ccc(C(F)(F)F)cc2)C(C)(C)O)ccc1-c1cnc(C)o1] | 529.3 |
| 133 | optically active 2-{3-[3-methoxy-4-(2-methyl-1,3-oxazol-5-yl)phenyl]-8-[4-(trifluoromethyl)phenoxy]-5,6,7,8-tetrahydro[1,2,4]-triazolo[4,3-a]pyridin-8-yl}propan-2-ol | 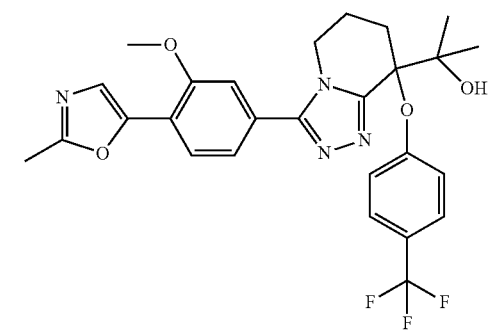 [SMILES: COc1cc(-c2nnc3n2CCCC3(Oc2ccc(C(F)(F)F)cc2)C(C)(C)O)ccc1-c1cnc(C)o1] | 529.3 |

-continued

| | | | | |
|---|---|---|---|---|
| 134 | 2-{3-[6-methoxy-5-(4-methyl-1H-imidazol-1-yl)pyridin-2-yl]-8-(3,4,5-trifluorophenoxy)-5,6,7,8-tetrahydro[1,2,4]triazolo-[4,3-a]pyridin-8-yl}propan-2-ol | 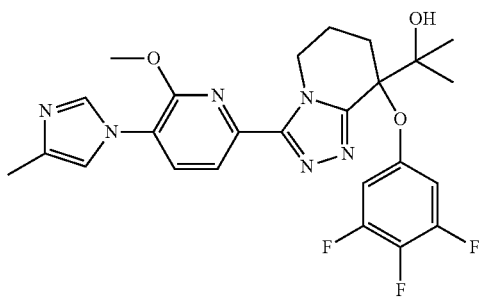 [SMILES: COc1nc(-c2nnc3n2CCCC3(Oc2cc(F)c(F)c(F)c2)C(C)(C)O)ccc1-n1cnc(C)c1] | | 515.3 |
| 135 | 2-{8-(3,4-difluorophenoxy)-3-[6-methoxy-5-(4-methyl-1H-imidazol-1-yl)pyridin-2-yl]-5,6,7,8-tetrahydro[1,2,4]triazolo-[4,3-a]pyridin-8-yl}propan-2-ol | 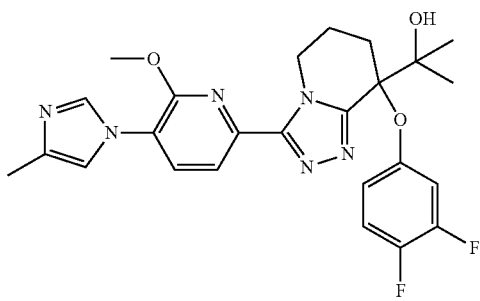 [SMILES: COc1nc(-c2nnc3n2CCCC3(Oc2ccc(F)c(F)c2)C(C)(C)O)ccc1-n1cnc(C)c1] | | 497.3 |
| 136 | ethyl 3-[3-methoxy-4-(2-methyl-1,3-oxazol-5-yl)phenyl]-8-phenyl-5,6,7,8-tetrahydro[1,2,4]triazolo-[4,3-a]pyridine-8-carboxylate | 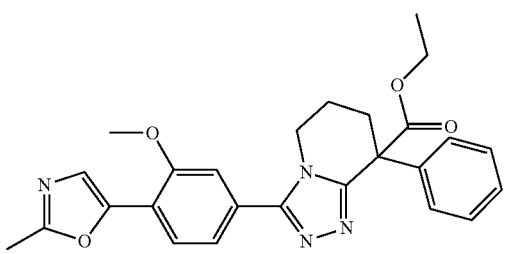 [SMILES: CCOC(=O)C1(c2ccccc2)CCCn2c(-c3ccc(-c4cnc(C)o4)c(OC)c3)nnc21] | | 459.1 |
| 137 | 2-{3-[3-methoxy-4-(2-methyl-1,3-oxazol-5-yl)phenyl]-8-phenyl-5,6,7,8-tetrahydro[1,2,4]triazolo-[4,3-a]pyridin-8-yl}propan-2-ol | 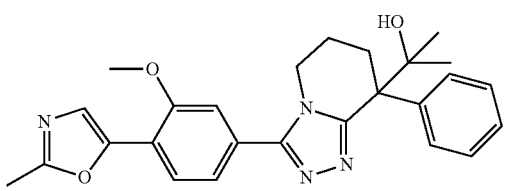 [SMILES: COc1cc(-c2nnc3n2CCCC3(c2ccccc2)C(C)(C)O)ccc1-c1cnc(C)o1] | | 445.3 |

| Ex. No. | compound name | structure | salt | MS |
|---|---|---|---|---|
| 138 | 2-{3-[3-methoxy-4-(3-methyl-1H-1,2,4-triazol-1-yl)phenyl]-8-(3,4,5-trifluorophenoxy)-5,6,7,8-tetrahydro-[1,2,4]triazolo[4,3-a]pyridin-8-yl}propan-2-ol | 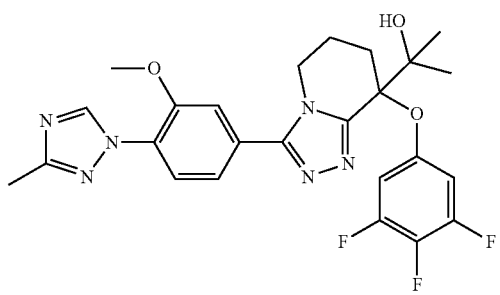 [SMILES: COc1cc(-c2nnc3n2CCCC3(Oc2cc(F)c(F)c(F)c2)C(C)(C)O)ccc1-n1cnc(C)n1] | | 515.2 |

| | | | |
|---|---|---|---|
| 139 | 2-{8-[4-chloro-3-(trifluoromethyl)-phenoxy]-3-[3-methoxy-4-(3-methyl-1H-1,2,4-triazol-1-yl)phenyl]-5,6,7,8-tetrahydro-[1,2,4]triazolo[4,3-a]pyridin-8-yl}propan-2-ol | 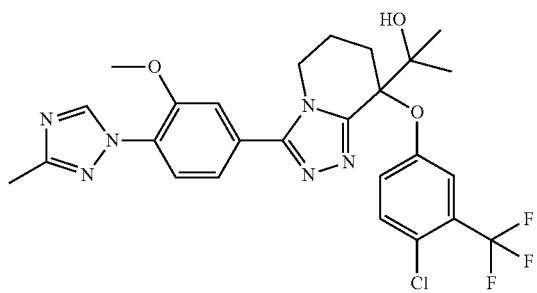 [SMILES: COc1cc(-c2nnc3n2CCCC3(Oc2ccc(Cl)c(C(F)(F)F)c2)C(C)(C)O)ccc1-n1cnc(C)n1] | 563.0 |
| 140 | 2-{8-[(3,4-difluoro-phenyl)sulfanyl]-3-[3-methoxy-4-(2-methyl-1,3-oxazol-5-yl)phenyl]-5,6,7,8-tetrahydro[1,2,4]-triazolo[4,3-a]pyridin-8-yl}propan-2-ol | 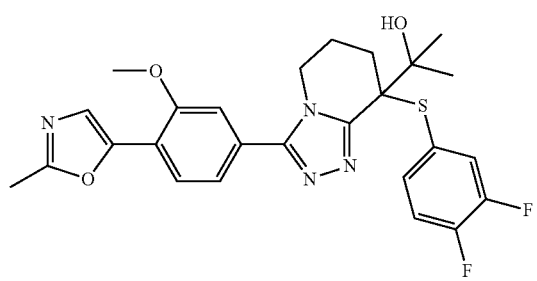 | 513.1 |
| 141 | 2-{8-(3,5-difluorophenoxy)-3-[3-methoxy-4-(2-methyl-1,3-oxazol-5-yl)phenyl]-5,6,7,8-tetrahydro[1,2,4]-triazolo[4,3-a]pyridin-8-yl}propan-2-ol | 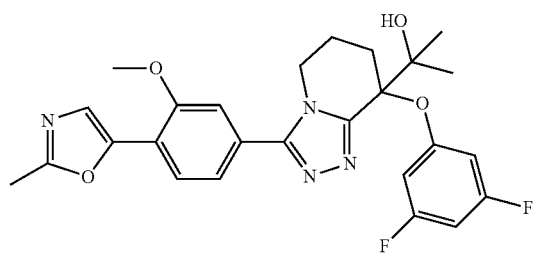 [SMILES: COc1cc(-c2nnc3n2CCCC3(Oc2cc(F)cc(F)c2)C(C)(C)O)ccc1-c1cnc(C)o1] | 497.0 |
| 142 | 2-{8-(3,4-dichloro-phenoxy)-3-[3-methoxy-4-(2-methyl-1,3-oxazol-5-yl)phenyl]-5,6,7,8-tetrahydro-[1,2,4]triazolo[4,3-a]pyridin-8-yl}propan-2-ol | 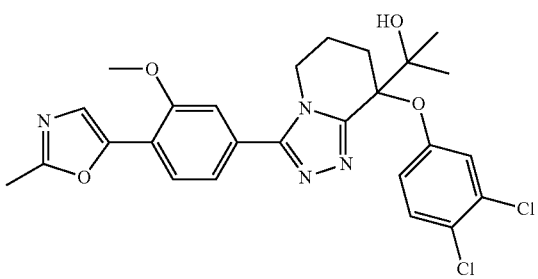 | 529.0 |
| 143 | 2-{8-[3-(difluoromethyl)-4-fluorophenoxy]-3-[3-methoxy-4-(2-methyl-1,3-oxazol-5-yl)phenyl]-5,6,7,8-tetrahydro[1,2,4]-triazolo[4,3-a]pyridin-8-yl}propan-2-ol | 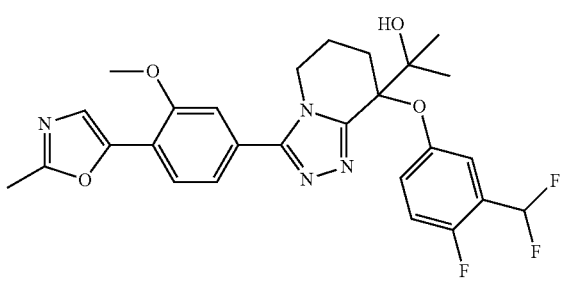 [SMILES: COc1cc(-c2nnc3n2CCCC3(Oc2ccc(F)c(C(F)F)c2)C(C)(C)O)ccc1-c1cnc(C)o1] | 529.1 |

| | | | |
|---|---|---|---|
| 144 | 2-{3-[3-methoxy-4-(1-methyl-1H-pyrazol-4-yl)phenyl]-8-(3,4,5-trifluorophenoxy)-5,6,7,8-tetrahydro[1,2,4]-triazolo[4,3-a]pyridin-8-yl}propan-2-ol | 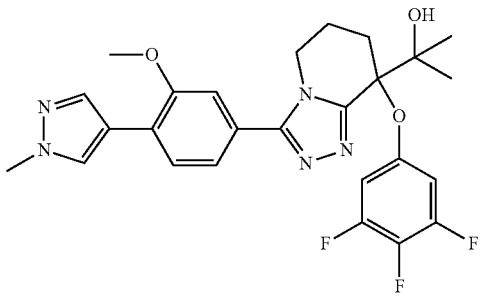 [SMILES: COc1cc(-c2nnc3n2CCCC3(Oc2cc(F)c(F)c(F)c2)C(C)(C)O)ccc1-c1cnn(C)c1] | 514.4 |
| 145 | 2-{8-(4-chloro-3-fluorophenoxy)-3-[6-methoxy-5-(4-methyl-1H-imidazol-1-yl)pyridin-2-yl]-5,6,7,8-tetrahydro[1,2,4]-triazolo[4,3-a]pyridin-8-yl}propan-2-ol | 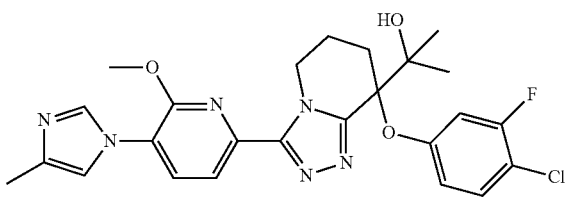 [SMILES: COc1nc(-c2nnc3n2CCCC3(Oc2ccc(Cl)c(F)c2)C(C)(C)O)ccc1-n1cnc(C)c1] | 513.1 |
| 146 | 2-{8-[4-fluoro-3-(trifluoromethyl)-phenoxy]-3-[6-methoxy-5-(4-methyl-1H-imidazol-1-yl)pyridin-2-yl]-5,6,7,8-tetrahydro[1,2,4]-triazolo[4,3-a]pyridin-8-yl}propan-2-ol | 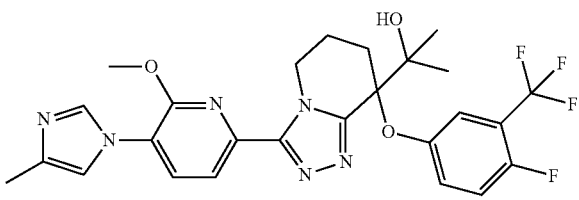 | 547.1 |
| 147 | 2,2,2-trifluoro-1-{3-[3-methoxy-4-(2-methyl-1,3-oxazol-5-yl)phenyl]-8-(3,4,5-trifluorophenoxy)-5,6,7,8-tetrahydro[1,2,4]-triazolo[4,3-a]pyridin-8-yl}ethanol | 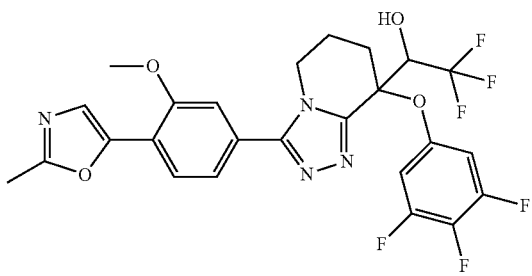 [SMILES: COc1cc(-c2nnc3n2CCCC3(Oc2cc(F)c(F)c(F)c2)C(O)C(F)(F)F)ccc1-c1cnc(C)o1] | 555.2 |
| 148 | 2-{8-[4-chloro-3-(trifluoromethyl)-phenoxy]-3-[6-methoxy-5-(4-methyl-1H-imidazol-1-yl)pyridin-2-yl]-5,6,7,8-tetrahydro[1,2,4]-triazolo[4,3-a]pyridin-8-yl}propan-2-ol | 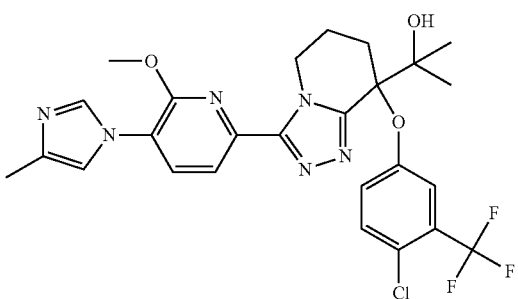 [SMILES: COc1nc(-c2nnc3n2CCCC3(Oc2ccc(Cl)c(C(F)(F)F)c2)C(C)(C)O)ccc1-n1cnc(C)c1] | 563.1 |
| 149 | 2-{8-[3-chloro-4-(difluoromethyl)-phenoxy]-3-[3-methoxy-4-(2-methyl-1,3-oxazol-5-yl)phenyl]-5,6,7,8-tetrahydro[1,2,4]-triazolo[4,3-a]pyridin-8-yl}propan-2-ol | 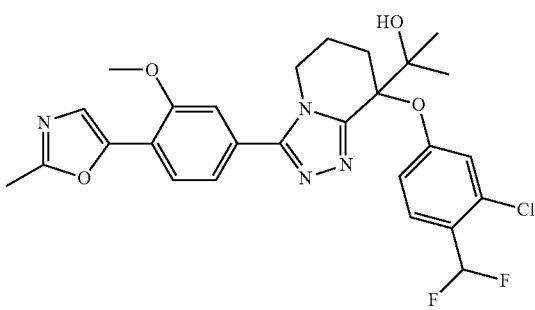 [SMILES: COc1cc(-c2nnc3n2CCCC3(Oc2ccc(C(F)F)c(Cl)c2)C(C)(C)O)ccc1-c1cnc(C)o1] | 545.1 |

| | | | |
|---|---|---|---|
| 150 | (6RS,8RS or 6RS,8SR)-2-{8-(3,4-difluorophenoxy)-3-[3-methoxy-4-(2-methyl-1,3-oxazol-5-yl)phenyl]-6-methyl-5,6,7,8-tetrahydro[1,2,4]-triazolo[4,3-a]pyridin-8-yl}propan-2-ol | 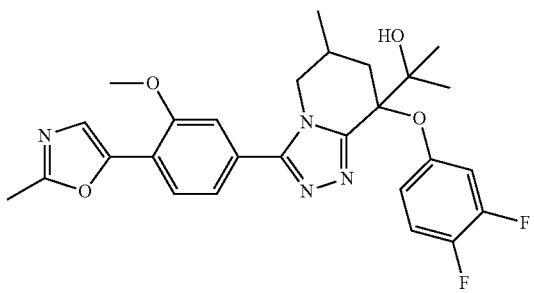 [SMILES: COc1cc(-c2nnc3n2CC(C)CC3(Oc2ccc(F)c(F)c2)C(C)(C)O)ccc1-c1cnc(C)o1] | 511.1 |
| 151 | (6RS,8SR or 6RS,8RS)-2-{8-{3,4-difluorophenoxy)-3-[3-methoxy-4-(2-methyl-1,3-oxazol-5-yl)phenyl]-6-methyl-5,6,7,8-tetrahydro[1,2,4]-triazolo[4,3-a]pyridin-8-yl}propan-2-ol | 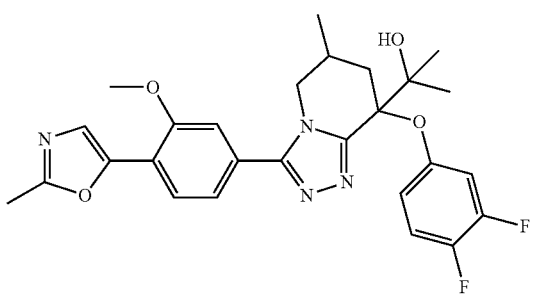 [SMILES: COc1cc(-c2nnc3n2CC(C)CC3(Oc2ccc(F)c(F)c2)C(C)(C)O)ccc1-c1cnc(C)o1] | 511.1 |
| 152 | 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]-triazolo[4,3-a]pyridin-8-yl}propan-2-ol | 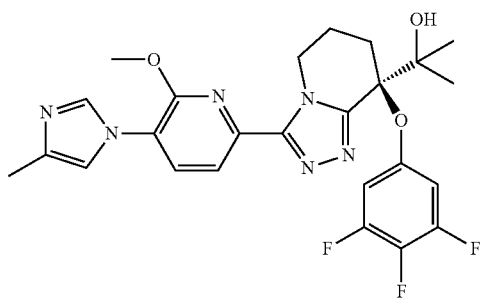 [SMILES: COc1nc(-c2nnc3n2CCC[C@]3(Oc2cc(F)c(F)c(F)c2)C(C)(C)O)ccc1-n1cnc(C)c1] | 515.1 |
| 153 | 2-{(8S)-3-[6-methoxy-5-(4-methyl-1H-imidazol-1-yl)pyridin-2-yl]-8-(3,4,5-trifluorophenoxy)-5,6,7,8-tetrahydro[1,2,4]-triazolo[4,3-a]pyridin-8-yl}propan-2-o | 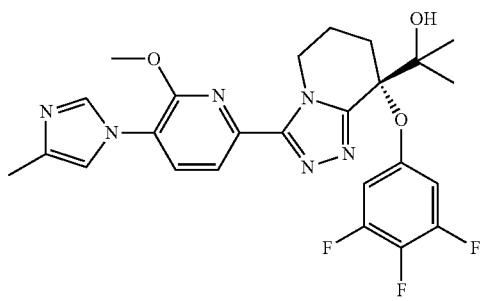 [SMILES: COc1nc(-c2nnc3n2CCC[C@@]3(Oc2cc(F)c(F)c(F)c2)C(C)(C)O)ccc1-n1cnc(C)c1] | 515.0 |
| 154 | 2-{8-[4-(difluoromethyl)-3,5-difluorophenoxy]-3-[3-methoxy-4-(2-methyl-1,3-oxazol-5-yl)phenyl]-5,6,7,8-tetrahydro[1,2,4]-triazolo[4,3-a]pyridin-8-yl}propan-2-ol | 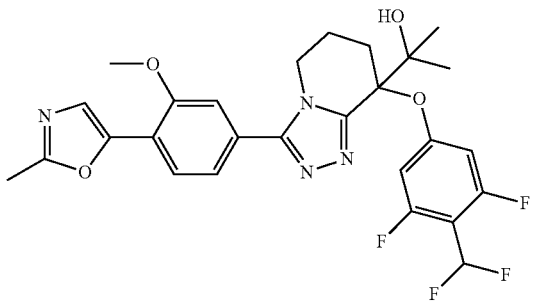 [SMILES: COc1cc(-c2nnc3n2CCCC3(Oc2cc(F)c(C(F)F)c(F)c2)C(C)(C)O)ccc1-c1cnc(C)o1] | 547.4 |

| | | | |
|---|---|---|---|
| 155 | optically active 2-{8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol | 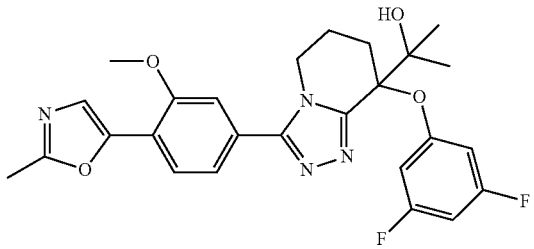 [SMILES: COc1cc(-c2nnc3n2CCCC3(Oc2cc(F)cc(F)c2)C(C)(C)O)ccc1-c1cnc(C)o1] | 497.0 |
| 156 | optically active 2-{8-(3,5-difluorophenoxy)-3-[3-methoxy-4-(2-methyl-1,3-oxazol-5-yl)phenyl]-5,6,7,8-tetrahydro[1,2,4]triazolo[4,3-a]pyridin-8-yl}propan-2-ol | 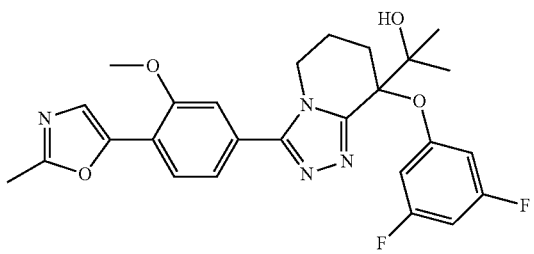 [SMILES: COc1cc(-c2nnc3n2CCCC3(Oc2cc(F)cc(F)c2)C(C)(C)O)ccc1-c1cnc(C)o1] | 497.3 |
| 157 | optically active 2-{8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol | 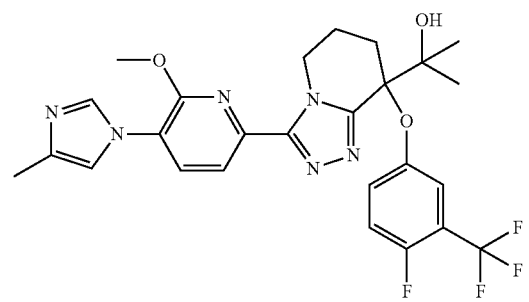 [SMILES: COc1nc(-c2nnc3n2CCCC3(Oc2ccc(F)c(C(F)(F)F)c2)C(C)(C)O)ccc1-n1cnc(C)c1] | 547.1 |
| 158 | optically active 2-{8-[4-fluoro-3-(trifluoromethyl)phenoxy]-3-[6-methoxy-5-(4-methyl-1H-imidazol-1-yl)pyridin-2-yl]-5,6,7,8-tetrahydro[1,2,4]triazolo[4,3-a]pyridin-8-yl}propan-2-ol | 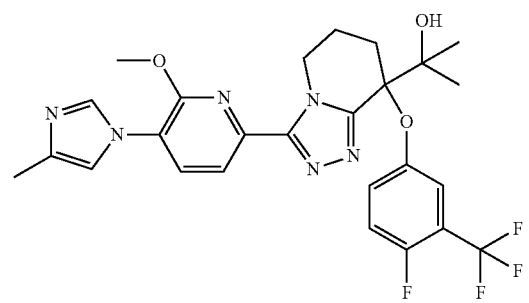 [SMILES: COc1nc(-c2nnc3n2CCCC3(Oc2ccc(F)c(C(F)(F)F)c2)C(C)(C)O)ccc1-n1cnc(C)c1] | 547.0 |
| 159 | 3-[3-methoxy-4-(2-methyl-1,3-oxazol-5-yl)phenyl]-N-(2,2,2-trifluoroethyl)-8-(3,4,5-trifluorophenoxy)-5,6,7,8-tetrahydro-[1,2,4]triazolo[4,3-a]pyridine-8-carboxamide | 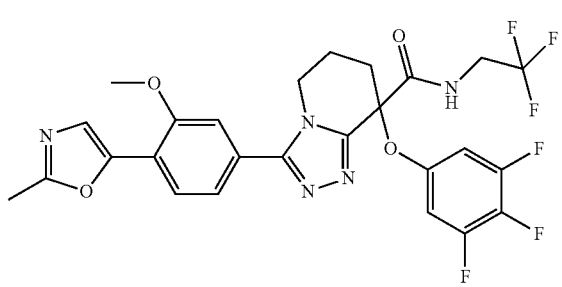 [SMILES: COc1cc(-c2nnc3n2CCCC3(Oc2cc(F)c(F)c(F)c2)C(=O)NCC(F)(F)F)ccc1-c1cnc(C)o1] | 582.2 |

| 160 | 3-[3-methoxy-4-(2-methyl-1,3-oxazol-5-yl)phenyl]-N-methyl-N-(2,2,2-trifluoro-ethyl)-8-(3,4,5-trifluorophenoxy)-5,6,7,8-tetrahydro-[1,2,4]triazolo[4,3-a]pyridine-8-carboxamide | 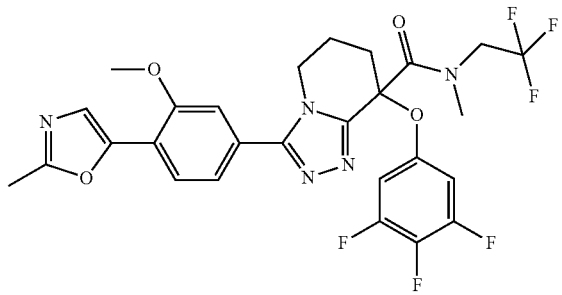 [SMILES: COc1cc(-c2nnc3n2CCCC3(Oc2cc(F)c(F)c(F)c2)C(=O)N(C)CC(F)(F)F)ccc1-c1cnc(C)o1] | 596.3 |
|---|---|---|---|
| 161 | 2-{8-(3,4-difluoro-phenoxy)-3-[2-fluoro-5-methoxy-4-(2-methyl-1,3-oxazol-5-yl)-phenyl]-5,6,7,8-tetrahydro[1,2,4]-triazolo[4,3-a]-pyridin-8-yl}propan-2-ol | 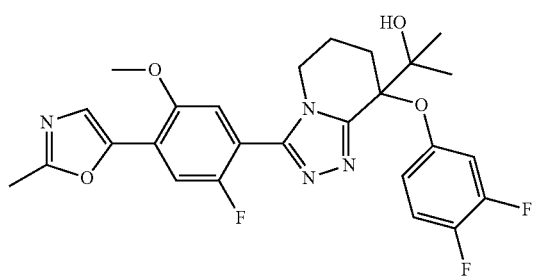 [SMILES: COc1cc(-c2nnc3n2CCCC3(Oc2ccc(F)c(F)c2)C(C)(C)O)c(F)cc1-c1cnc(C)o1] | 515.2 |
| 162 | 2-{3-[2-fluoro-5-methoxy-4-(2-methyl-1,3-oxazol-5-yl)phenyl]-8-(3,4,5-trifluorophenoxy)-5,6,7,8-tetrahydro[1,2,4]-triazolo[4,3-a]pyridin-8-yl}propan-2-ol | 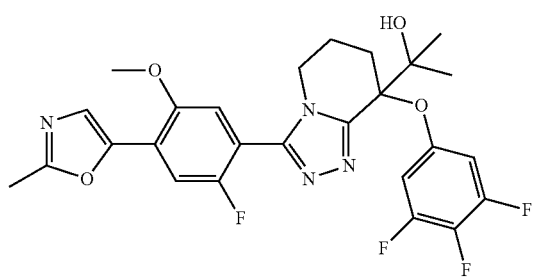 | 533.2 |
| 163 | 2-{3-[3-fluoro-4-(3-methyl-1H-1,2,4-triazol-1-yl)phenyl]-8-(3,4,5-trifluorophenoxy)-5,6,7,8-tetrahydro[1,2,4]-triazolo[4,3-a]pyridin-8-yl}propan-2-ol | 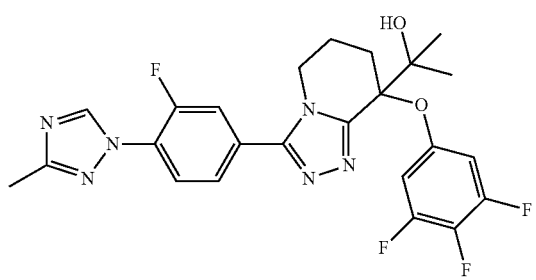 [SMILES: Cc1ncn(-c2ccc(-c3nnc4n3CCCC4(Oc3cc(F)c(F)c(F)c3)C(C)(C)O)cc2F)n1] | 503.3 |
| 164 | 2-{3-[6-methoxy-5-(4-methyl-1H-imidazol-1-yl)pyridin-2-yl]-8-[4-(trifluoromethyl)-phenoxy]-5,6,7,8-tetrahydro[1,2,4]-triazolo[4,3-a]pyridin-8-yl}propan-2-ol | 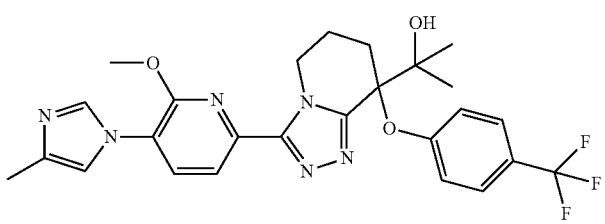 [SMILES: COc1nc(-c2nnc3n2CCCC3(Oc2ccc(C(F)(F)F)cc2)C(C)(C)O)ccc1-n1cnc(C)c1] | 529.4 |
| 165 | 2-{3-[4-(4-chloro-1H-imidazol-1-yl)-3-methoxyphenyl]-8-(3,4,5-trifluorophenoxy)-5,6,7,8-tetrahydro[1,2,4]-triazolo[4,3-a]pyridin-8-yl}propan-2-ol | 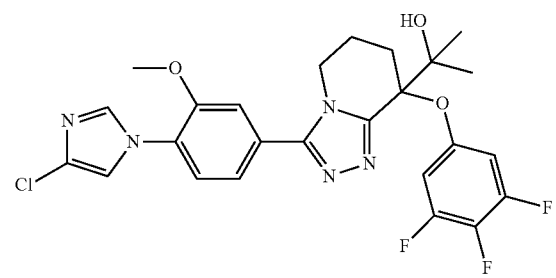 [SMILES: COc1cc(-c2nnc3n2CCCC3(Oc2cc(F)c(F)c(F)c2)C(C)(C)O)ccc1-n1cnc(Cl)c1] | 534.1 |

| | | | |
|---|---|---|---|
| 166 | 2-{3-[3-fluoro-4-(2-methyl-1,3-oxazol-5-yl)phenyl]-8-(3,4,5-trifluorophenoxy)-5,6,7,8-tetrahydro[1,2,4]-triazolo[4,3-a]pyridin-8-yl}propan-2-ol | 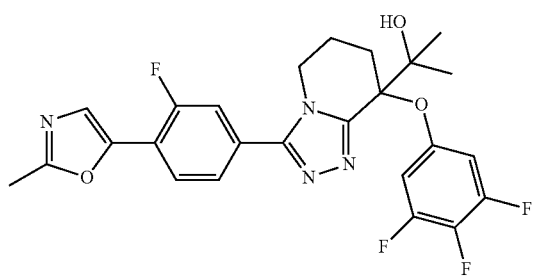 [SMILES: Cc1ncc(-c2ccc(-c3nnc4n3CCCC4(Oc3cc(F)c(F)c(F)c3)C(C)(C)O)cc2F)o1] | 503.2 |
| 167 | 2-{3-[3-(benzyloxy)-4-(2-methyl-1,3-oxazol-5-yl)phenyl]-8-(3,4-difluorophenoxy)-5,6,7,8-tetrahydro[1,2,4]-triazolo[4,3-a]pyridin-8-yl}propan-2-ol | 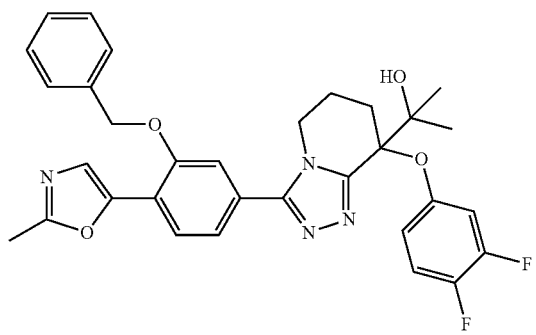 [SMILES: Cc1ncc(-c2ccc(-c3nnc4n3CCCC4(Oc3ccc(F)c(F)c3)C(C)(C)O)cc2OCc2ccccc2)o1] | 573.1 |
| 168 | 5-[8-(3,4-difluorophenoxy)-8-(1-hydroxy-1-methylethyl)-5,6,7,8-tetrahydro-[1,2,4]triazolo[4,3-a]pyridin-3-yl]-2-(2-methyl-1,3-oxazol-5-yl)phenol | 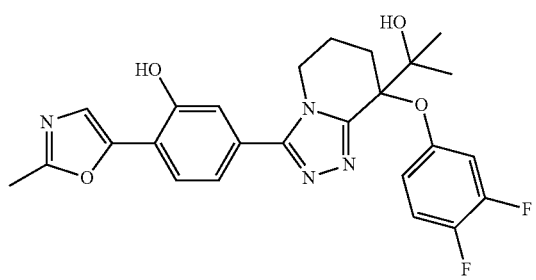 | 483.4 |
| 169 | 2-{8-(3,4-difluorophenoxy)-3-[3-ethoxy-4-(2-methyl-1,3-oxazol-5-yl)phenyl]-5,6,7,8-tetrahydro-[1,2,4]triazolo[4,3-a]pyridin-8-yl}propan-2-ol | 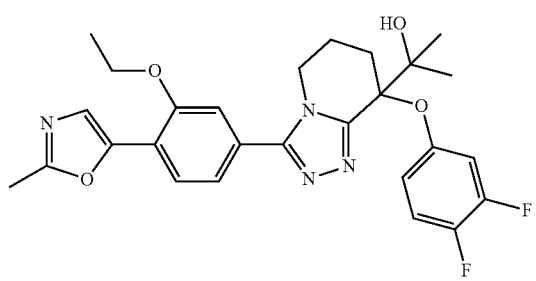 | 511.4 |
| 170 | 2-{8-(3,4-difluorophenoxy)-3-[4-(2-methyl-1,3-oxazol-5-yl)-3-(2,2,2-trifluoroethoxy)-phenyl]-5,6,7,8-tetrahydro-[1,2,4]triazolo[4,3-a]pyridin-8-yl}propan-2-ol | 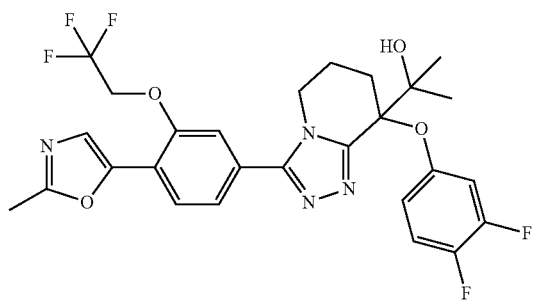 [SMILES: Cc1ncc(-c2ccc(-c3nnc4n3CCCC4(Oc3ccc(F)c(F)c3)C(C)(C)O)cc2OCC(F)(F)F)o1] | 565.3 |

| | | | |
|---|---|---|---|
| 171 | 2-{3-[6-methoxy-5-(4-methyl-1H-imidazol-1-yl)pyridin-2-yl]-8-[3-(trifluoromethyl)phenoxy]-5,6,7,8-tetrahydro[1,2,4]triazolo[4,3-a]pyridin-8-yl}propan-2-ol | | 529.1 |
| 172 | 2-{3-[6-methoxy-5-(2-methyl-1,3-oxazol-5-yl)pyridin-2-yl]-8-(3,4,5-trifluorophenoxy)-5,6,7,8-tetrahydro-[1,2,4]triazolo[4,3-a]pyridin-8-yl}propan-2-ol | | 516.4 |
| 173 | 2-{3-[3-(difluoromethoxy)-4-(2-methyl-1,3-oxazol-5-yl)phenyl]-8-(3,4-difluorophenoxy)-5,6,7,8-tetrahydro[1,2,4]-triazolo[4,3-a]pyridin-8-yl}propan-2-ol | | 533.1 |
| 174 | 2-{3-[3-methoxy-4-(2-methylpyridin-4-yl)phenyl]-8-(3,4,5-trifluorophenoxy)-5,6,7,8-tetrahydro[1,2,4]-triazolo[4,3-a]pyridin-8-yl}propan-2-ol | | 525.4 |
| 175 | 2-{3-[3-(2,2-difluoroethoxy)-4-(2-methyl-1,3-oxazol-5-yl)phenyl]-8-(3,4-difluorophenoxy)-5,6,7,8-tetrahydro[1,2,4]-triazolo[4,3-a]pyridin-8-yl}propan-2-ol | | 547.1 |
| 176 | 2-{3-[3-methoxy-4-(4-methyl-1H-imidazol-1-yl)phenyl]-8-(3,4,5-trifluorophenoxy)-5,6,7,8-tetrahydro[1,2,4]-triazolo[4,3-a]pyridin-8-yl}propan-2-ol | | 514.3 |

| | | | | |
|---|---|---|---|---|
| 177 | 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]triazolo[4,3-a]pyridin-8-yl}propan-2-ol | 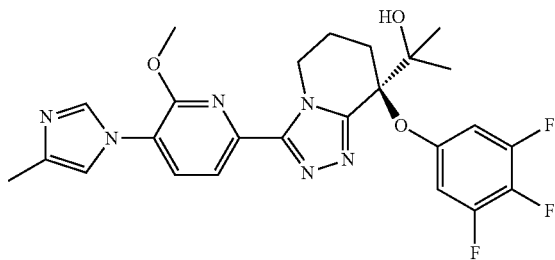 [SMILES: COc1nc(-c2nnc3n2CCC[C@]3(Oc2cc(F)c(F)c(F)c2)C(C)(C)O)ccc1-n1cnc(C)c1] | 1 phosphate | 515.2 |
| 178 | 2-{3-[4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol | 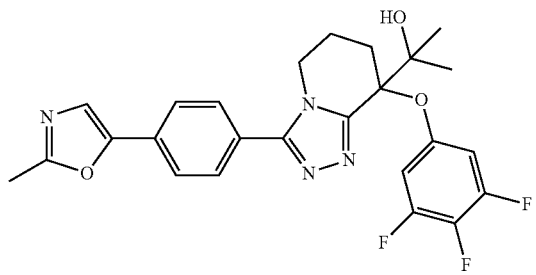 [SMILES: Cc1ncc(-c2ccc(-c3nnc4n3CCCC4(Oc3cc(F)c(F)c(F)c3)C(C)(C)O)cc2)o1] | | 485.3 |
| 179 | 2-{8-(3,4-difluorophenoxy)-3-[6-methoxy-5-(2-methyl-1,3-oxazol-5-yl)pyridin-2-yl]-5,6,7,8-tetrahydro[1,2,4]triazolo[4,3-a]pyridin-8-yl}propan-2-ol | 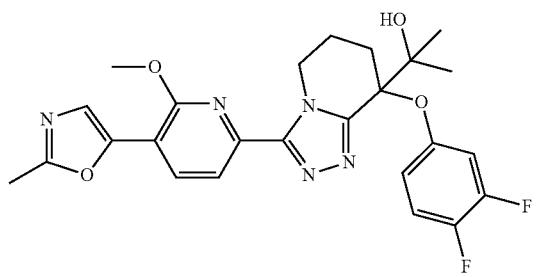 [SMILES: COc1nc(-c2nnc3n2CCCC3(Oc2ccc(F)c(F)c2)C(C)(C)O)ccc1-c1cnc(C)o1] | | 498.2 |
| 180 | 2-{8-(3,5-difluorophenoxy)-3-[6-methoxy-5-(2-methyl-1,3-oxazol-5-yl)pyridin-2-yl]-5,6,7,8-tetrahydro[1,2,4]triazolo[4,3-a]pyridin-8-yl}propan-2-ol | 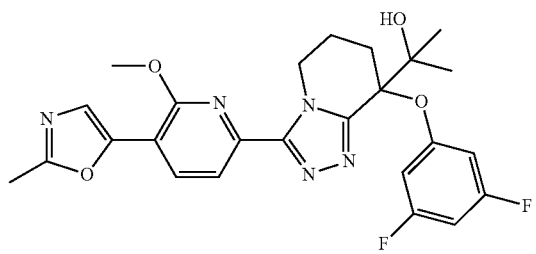 [SMILES: COc1nc(-c2nnc3n2CCCC3(Oc2cc(F)cc(F)c2)C(C)(C)O)ccc1-c1cnc(C)o1] | | 498.2 |
| 181 | 2-{3-[3-methoxy-4-(2-methyl-1,3-oxazol-5-yl)phenyl]-8-[(3,4,5-trifluorophenyl)amino]-5,6,7,8-tetrahydro[1,2,4]triazolo[4,3-a]pyridin-8-yl}propan-2-ol | 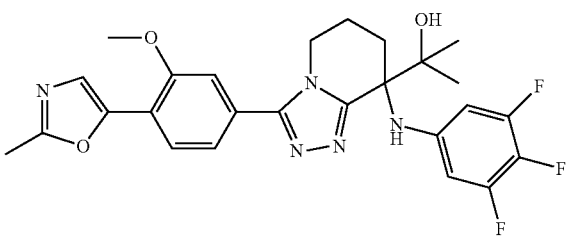 [SMILES: COc1cc(-c2nnc3n2CCCC3(Nc2cc(F)c(F)c(F)c2)C(C)(C)O)ccc1-c1cnc(C)o1] | | 514.3 |
| 182 | 3-[3-methoxy-4-(2-methyl-1,3-oxazol-5-yl)phenyl]-8-methyl-8-(3,4,5-trifluorophenoxy)-5,6,7,8-tetrahydro[1,2,4]triazolo[4,3-a]pyridine | 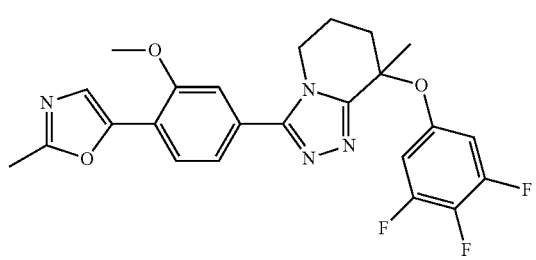 [SMILES: COc1cc(-c2nnc3n2CCCC3(C)Oc2cc(F)c(F)c(F)c2)ccc1-c1cnc(C)o1] | | 471.2 |

| | | | | |
|---|---|---|---|---|
| 183 | 2-{8-(3,4-dichlorophenyl)-3-[3-methoxy-4-(2-methyl-1,3-oxazol-5-yl)phenyl]-5,6,7,8-tetrahydro[1,2,4]-triazolo[4,3-a]pyridin-8-yl}propan-2-ol | | | 513.2 |
| 184 | 2-{7-(4-fluorophenoxy)-3-[3-methoxy-4-(2-methyl-1,3-oxazol-5-yl)phenyl]-4,5,6,7-tetrahydro[1,2,3]-triazolo[1,5-a]pyridin-7-yl}propan-2-ol | | | 479.2 |
| 185 | 2-{3-[3-methoxy-4-(2-methyl-1,3-oxazol-5-yl)phenyl]-8-(3,4,5-trifluorophenyl)-5,6,7,8-tetrahydro[1,2,4]-triazolo[4,3-a]pyridin-8-yl}propan-2-ol | | | 499.1 |
| 186 | 2-{3-[3-methoxy-4-(2-methyl-1,3-oxazol-5-yl)phenyl]-7-(3,4,5-trifluorophenoxy)-4,5,6,7-tetrahydro[1,2,3]-triazolo[1,5-a]pyridin-7-yl}propan-2-ol | | | 515.1 |
| 187 | 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]-triazolo[4,3-a]pyridin-8-yl}propan-2-ol | | 1(+)-mande-late | 515.2 |
| 188 | 2-{3-[6-methoxy-5-(4-methyl-1H-imidazol-1-yl)pyridin-2-yl]-8-(3,4,5-trifluorophenyl)-5,6,7,8-tetrahydro[1,2,4]-triazolo[4,3-a]pyridin-8-yl}propan-2-ol | | | 499.4 |

| | | | | |
|---|---|---|---|---|
| 189 | 2-{8-[4-chloro-3-(trifluoromethyl)-phenoxy]-3-[3-methoxy-4-(1-methyl-1H-pyrazol-4-yl)phenyl]-5,6,7,8-tetrahydro[1,2,4]-triazolo[4,3-a]pyridin-8-yl}propan-2-ol | 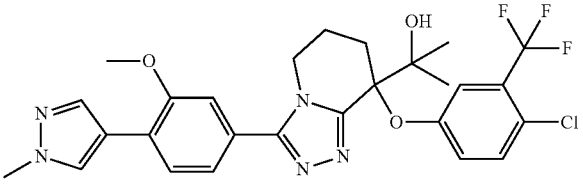 [SMILES: COc1cc(-c2nnc3n2CCCC3(Oc2ccc(Cl)c(C(F)(F)F)c2)C(C)(C)O)ccc1-c1cnn(C)c1] | | 562.3 |
| 190 | ethyl 3-[6-methoxy-5-(4-methyl-1H-imidazol-1-yl)pyridin-2-yl]-8-(3,4,5-trifluorophenoxy)-5,6,7,8-tetrahydro[1,2,4]-triazolo[4,3-a]pyridine-8-carboxylate | 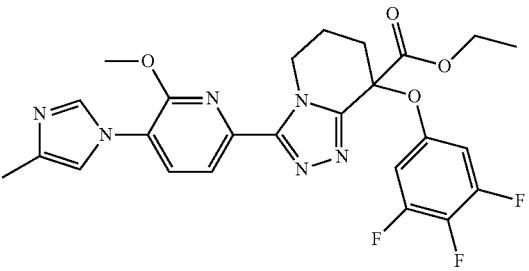 [SMILES: CCOC(=O)C1(Oc2cc(F)c(F)c(F)c2)CCCn2c(-c3ccc(-n4cnc(C)c4)c(OC)n3)nnc21] | | 529.3 |
| 191 | optically active 2-{3-[3-methoxy-4-(2-methyl-1,3-oxazol-5-yl)phenyl]-7-(3,4,5-trifluorophenoxy)-4,5,6,7-tetrahydro[1,2,3]-triazolo[1,5-a]pyridin-7-yl}propan-2-ol | 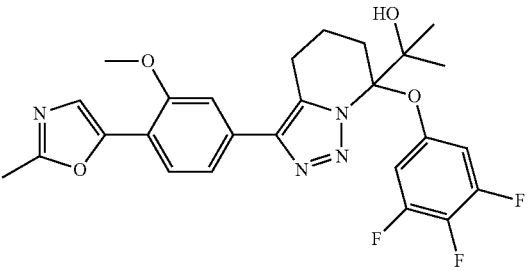 [SMILES: COc1cc(-c2nnn3c2CCCC3(Oc2cc(F)c(F)c(F)c2)C(C)(C)O)ccc1-c1cnc(C)o1] | | 515.3 |
| 192 | optically active 2-{3-[3-methoxy-4-(2-methyl-1,3-oxazol-5-yl)phenyl]-7-(3,4,5-trifluorophenoxy)-4,5,6,7-tetrahydro[1,2,3]-triazolo[1,5-a]pyridin-7-yl}propan-2-ol | 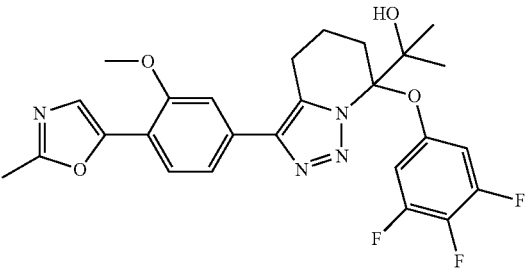 [SMILES: COc1cc(-c2nnn3c2CCCC3(Oc2cc(F)c(F)c(F)c2)C(C)(C)O)ccc1-c1cnc(C)o1] | | 515.3 |
| 193 | 1-{3-[3-methoxy-4-(2-methyl-1,3-oxazol-5-yl)phenyl]-8-(3,4,5-trifluorophenoxy)-5,6,7,8-tetrahydro[1,2,4]-triazolo[4,3-a]pyridin-8-yl}ethanone | 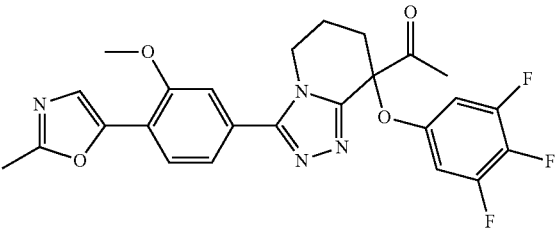 [SMILES: COc1cc(-c2nnc3n2CCCC3(Oc2cc(F)c(F)c(F)c2)C(C)=O)ccc1-c1cnc(C)o1] | | 499.2 |
| 194 | 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]-triazolo[4,3-a]pyridin-8-yl}propan-2-ol | 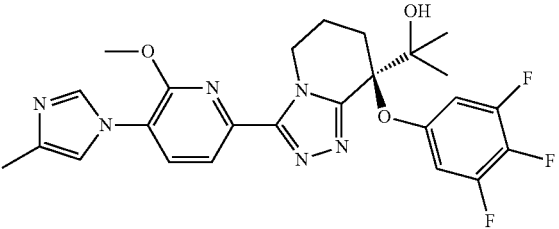 [SMILES: COc1nc(-c2nnc3n2CCC[C@]3(Oc2cc(F)c(F)c(F)c2)C(C)(C)O)ccc1-n1cnc(C)c1] | 0.67 phosphate | 515.2 |

| | | | |
|---|---|---|---|
| 195 | ethyl 8-[6-(2-ethoxy-2-oxoethyl)-2,3,4-trifluorophenoxy]-3-[3-methoxy-4-(2-methyl-1,3-oxazol-5-yl)phenyl]-5,6,7,8-tetrahydro[1,2,4]-triazolo[4,3-a]pyridine-8-carboxylate | 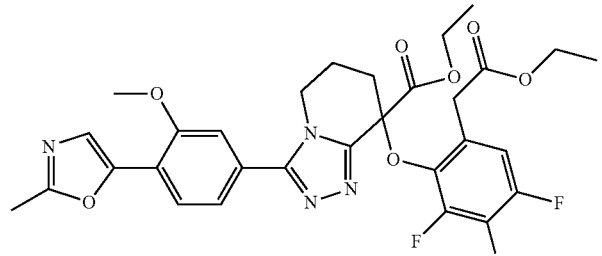 | 615.2 |
| 196 | 1-{3-[3-methoxy-4-(2-methyl-1,3-oxazol-5-yl)phenyl]-8-[(3,4,5-trifluorophenyl)-amino]-5,6,7,8-tetrahydro[1,2,4]-triazolo[4,3-a]pyridin-8-yl}ethanone | 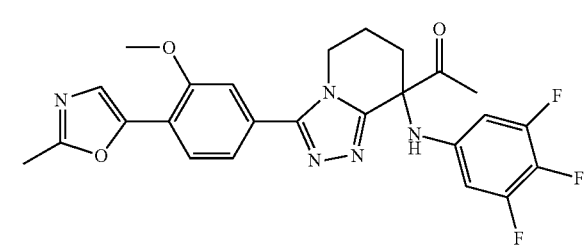 [SMILES: COc1cc(-c2nnc3n2CCCC3(Nc2cc(F)c(F)c(F)c2)C(C)=O)ccc1-c1cnc(C)o1] | 498.2 |
| 197 | 2-{(8R)-3-[6-methoxy-5-(4-methyl-1H-imidazol-1-yl)pyridin-2-yl]-8-(3,4,5-trifluorophenoxy)-5,6,7,8-tetrahydro[1,2,4]-triazolo[4,3-a]pyridin-8-yl}propan-2-ol | 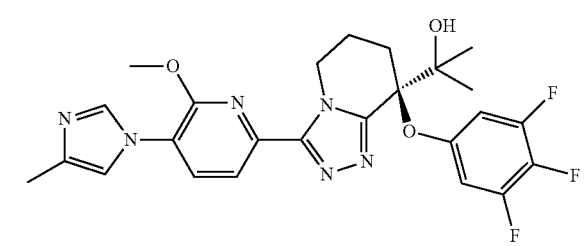 [SMILES: COc1nc(-c2nnc3n2CCC[C@]3(Oc2cc(F)c(F)c(F)c2)C(C)(C)O)ccc1-n1cnc(C)c1] 1 genti-sate | 515.2 |

Experimental Example 1

Measurement of Amyloid β Production Inhibition Rate Using Primary Nerve Cell

The primary nerve cells were collected from the cerebral cortex of rat fetus (CLEA Japan, Inc.: SD rat, fetal life 17 days of age), and suspended in a neurobasal medium containing B27 supplement, L-glutamine, penicillin-streptomycin (manufactured by Invitrogen) at 500,000 cells/mL. Then, the suspension was seeded in poly L-lysine-coated 96 well plate (manufactured by SUMITOMO BAKELITE) by 100 μL, and cultured at 37° C., 5% $CO_2$ for 7 days. The medium was completely removed, and a new neurobasal medium was added at 75 μL/well. Thereto was added (75 μL/well) a neurobasal medium supplemented with a 2-fold measurement concentration of an evaluation target compound, and the mixture was cultured for 3 days. The culture supernatant was collected from each well, diluted as appropriate, applied to sandwich ELISA between BNT77 antibody-BA27 antibody (for Aβ40) and sandwich ELISA between BNT77 antibody-BC05 antibody (for Aβ42), and the amounts of Aβ40 and Aβ42 were measured.

The amyloid β production inhibition rate (%) of the compound was calculated by the following formula. (1-(amyloid β production amount with addition of compound)/(amyloid β production amount without addition of compound))×100

The amyloid β production 50% inhibitory rate ($IC_{50}$ value) was calculated using the statistical analysis software (SAS Preclinical Package) as the concentration of the compound showing 50% inhibition when the amyloid β production amount without addition of the compound is 100%. In addition, a new neurobasal medium was added (75 μL/well) to the cells after collection of the culture supernatant, and the cells were left standing for about 30 min to reach room temperature. Cell-Titer Glo Luminescent Cell Viability Assay (manufactured by Promega) was added at 75 μL/well, and the plate was shaken for 2 min and reacted for about 10 min. Luminescence intensity was measured, and cytotoxicity was quantified using the amount of ATP as an index, whereby it was confirmed that amyloid β production inhibitory activity does not depend on the cytotoxicity. The test results are shown in Table 2.

TABLE 2

| Example No. | Aβ42 production inhibitory activity $IC_{50}$(nM) |
|---|---|
| 1 | 27 |
| 2 | 19 |
| 3 | 459 |
| 4 | 32 |
| 20 | 35 |
| 21 | 5 |
| 32 | 143 |
| 49 | 31 |
| 50 | 14 |
| 60 | 50 |
| 70 | 10 |
| 78 | 55 |
| 91 | 148 |
| 92 | 59 |
| 95 | 34 |
| 99 | 20 |
| 103 | 41 |
| 104 | 41 |
| 108 | 67 |
| 111 | 10 |
| 120 | 4 |
| 122 | 19 |
| 124 | 68 |

TABLE 2-continued

| Example No. | Aβ42 production inhibitory activity IC$_{50}$(nM) |
|---|---|
| 127 | 44 |
| 130 | 24 |
| 132 | 19 |
| 134 | 42 |
| 135 | 123 |
| 139 | 40 |
| 140 | 41 |
| 141 | 78 |
| 144 | 214 |
| 150 | 118 |
| 152 | 49 |
| 155 | 28 |
| 157 | 6 |
| 160 | 19 |
| 162 | 86 |
| 165 | 143 |
| 166 | 360 |
| 168 | 40 |
| 172 | 47 |
| 174 | 44 |
| 175 | 103 |
| 177 | 34 |
| 178 | 168 |
| 181 | 58 |
| 186 | 28 |
| 187 | 29 |
| 191 | 8 |
| 194 | 33 |
| 197 | 30 |

Experimental Example 2

Measurement of Amyloid β Production Inhibition Rate Using Primary Nerve Cell

[Animal]

C57BL/6J mice (7-10 weeks old) were purchased from CLEA Japan Inc. Mice were housed in groups and kept on a 12h-light; 12h-dark schedule. All mice were given ad libitum access to food and water.

[Test Compounds]

Each test compound was reconstituted in solubilization buffer ([DMSO (Wako)]: [10% Cremophor (Nakarai)+30% polyethylene glycol 400 (Wako)+60% 2 mol/L Citrate buffer (Wako)]=1:9) and orally administrated at 10 mg/kg.

[Aβ ELISA]

Hippocampi was isolated from animals, 3 hours after test compounds were orally administrated. Hippocampi were homogenized in ice-cold Tris-extraction buffer (50 mmol/L Tris-HCl, pH 7.2, 200 mmol/L sodium chloride, 2% protease-free bovine serum albumin, and 0.01% sodium merthiolate) containing protease inhibitor cocktails (Roche, Switzerland). After centrifugation at 15,000 rpm for 15 minutes, the supernatants were subjected to two-site sandwich ELISA to measure amount of soluble Aβ. Aβ42 was quantitated by two-site sandwich ELISA using BNT77, which recognizes Aβ11-28, as a capture antibody and BC05-HRP as a detector antibody, respectively. The test results are shown in Table 3.

TABLE 3

| Example No. | Aβ42 production inhibitory activity (% inhibition) |
|---|---|
| 1 | 40 |
| 2 | 48 |
| 21 | 39 |
| 92 | 32 |
| 99 | 34 |
| 103 | 42 |
| 104 | 36 |
| 111 | 46 |
| 120 | 21 |
| 122 | 54 |
| 124 | 41 |
| 127 | 21 |
| 130 | 59 |
| 132 | 58 |
| 134 | 31 |
| 139 | 22 |
| 141 | 46 |
| 144 | 31 |
| 152 | 57 |
| 155 | 56 |
| 157 | 61 |
| 162 | 26 |
| 172 | 35 |
| 186 | 22 |

Experimental Example 3

Measurement of CYP Inhibition Activity

Incubation mixtures are prepared in a total volume of 40 μL with final component concentrations as follows: 50 mmol/L phosphate buffer (pH 7.4), NADPH-generating system (5 mmol/L MgCl$_2$, 0.5 mmol/L β-NADP$^+$, 5 mmol/L glucose-6-phosphate, and 1.5 unit/mL glucose-6-phosphate dehydrogenase), CYP-expressing microsomes (2 nmol/L CYP2C8, 4 nmol/L CYP2C9, 2 nmol/L CYP2D6, or 10 nmol/L CYP3A4; BD Biosciences), substrates (2 μmol/L amodiaquine, 3 μmol/L diclofenac, 5 μmol/L bufuralol, or 25 μmol/L testosterone), and 10 μmol/L test compounds. The substrates and test compounds are dissolved in methanol and dimethylsulfoxide, respectively, and added to the incubation mixture with the final solvent concentration of 0.5%, respectively. Incubations are conducted at 27° C. for 60 minutes. Reactions are started by adding CYP-expressing microsomes and terminated by adding acetonitrile in equal amount. After centrifugation, aliquots of the supernatants are subjected to measurement of the LC/MS/MS. All incubations are conducted with one experiment performed in triplicate. The activities of CYP2C8, CYP2C9, CYP2D6 and CYP3A4 are determined by the peak of N-desethylamodiaquine, 4'-hydroxydiclofenac, 1'-hydroxybufuralol and 6β-hydroxytestosterone, respectively. The activities of test compounds are expressed as the percentage of activity remaining compared with a control sample containing no test compound. The inhibition values are obtained as following equation:

% inhibition=100×(1−Activity of test compound/Control activity)

Activity of test compound: activity of sample containing test compound

Control activity: activity of control sample containing no test compound

Experimental Example 4

Phototoxicity test

BALB/c 3T3 cells are cultured at 37° C., 5% CO$_2$ in DMEM supplemented with 10% fetal bovine serum, 50 IU/mL penicillin and 50 μg/mL streptomycin. Cells are seeded at 2.5×10$^3$ cells/well in 384-well white plate, and cultured in DMEM supplemented with 10% fetal bovine serum, 2 mM L-glutamine, 1 mM sodium pyruvate, 50 IU/mL penicillin and 50 μg/mL streptomycin for 1 day. Two 384-well plates per test compound in Earle's Balanced Salt Solution (EBSS) supplemented with 1 mM HEPES are pre-incubated with five different concentrations of the test compound for 1 h. One of the two plates is irradiated (+UV) for 60 minutes with 1.4-1.7 mW/cm² (5-6 J/cm²) whereas the other plate is kept in the dark. In both plates the treatment medium is replaced by the culture medium and after another 24 hr of culture the cell viability is determined by the cellular ATP content. The cellular ATP content is measured by Celltiter-Glo™ assay kit (Promega) according to the manufacture's instruction. ATP content is calculated by the following formula.

ATP content (% of control)=(RLU of test compound/RLU of 1% DMSO)×100.

The concentration responses obtained in the presence and in the absence of irradiation are compared at the $EC_{50}$ value, i.e. the concentration reducing cell viability to 50% compared to control containing 1% DMSO. To enable evaluation of the data, a Photo-Irritation-Factor (PIF) is calculated. PIF=$EC_{50}$(−UV)/$EC_{50}$(+UV). In some case, the differences of the ATP content (% of control) between the presence and the absence of irradiation in each test concentration are calculated, and strength of the phototoxic potential are compared by the maximum value (Delta Max).

Experimental Example 5

Cytotoxicity Test

HepG2 cells are cultured at 37° C., 5% $CO_2$ in DMEM supplemented with 10% fetal bovine serum, 50 IU/mL penicillin and 50 μg/mL streptomycin. Cells are seeded at 2×10⁴ cells/well in 96-well white plate, and cultured with test compounds in DMEM supplemented with 0.5% fetal bovine serum, 2 mM L-glutamine, 1 mM sodium pyruvate, 50 IU/mL penicillin and 50 μg/mL streptomycin for 1 day. The intracellular ATP content is measured by using ATPlite™-M (PerkinElmer) according to the manufacture's instruction. ATP content is calculated by the following formula.

ATP content (% of control)=(RLU of compound/RLU of 1% DMSO)×100.

In some case, Caspase-3/7 activity is measured by using Caspase-Glo™ 3/7 assay Kit (Promega) according to the manufacture's instruction. Caspase-3/7 activity is calculated (n=3) by the following formula.

Caspase-3/7 activity (%)=(RLU of compound−RLU of 1% DMSO)/(RLU of 30 μM Staurosporine−RLU of 1% DMSO)×100.

INDUSTRIAL APPLICABILITY

Since the compound of the present invention or a prodrug thereof shows a superior amyloid β production inhibitory activity, it can provide a clinically useful prophylactic or therapeutic drug for diseases such as mild cognitive impairment, Alzheimer's disease and the like. In addition, since the compound of the present invention or a prodrug thereof is superior in efficacy, low toxicity, stability, pharmacokinetics, CYP inhibition activity and the like, it is useful as a medicament.

This application is based on patent application Nos. 2010-197064 and 2011-143548 filed in Japan, the contents of which are encompassed in full herein.

The invention claimed is:

1. 2-{(8R)-3-[3-Methoxy-4-(2-methyl-1,3-oxazol-5-yl)phenyl]-8-(3,4,5-trifluorophenoxy)-5,6,7,8-tetrahydro[1,2,4]triazolo[4,3-a]pyridin-8-yl}propan-2-ol or a salt thereof.

* * * * *